United States Patent
Rava et al.

(10) Patent No.: US 12,139,760 B2
(45) Date of Patent: *Nov. 12, 2024

(54) METHODS FOR DETERMINING FRACTION OF FETAL NUCLEIC ACIDS IN MATERNAL SAMPLES

(71) Applicant: Verinata Health, Inc., San Diego, CA (US)

(72) Inventors: Richard P. Rava, Redwood City, CA (US); Yue-Jen Chuu, Cupertino, CA (US); Manjula Chinnappa, Foster City, CA (US); David A. Comstock, San Francisco, CA (US); Gabrielle Heilek, Mountain View, CA (US); Michael Hunkapiller, San Carlos, CA (US)

(73) Assignee: VERINATA HEALTH, INC., San Diego, CA (US)

( * ) Notice: Subject to any disclaimer, the term of this patent is extended or adjusted under 35 U.S.C. 154(b) by 1214 days.

This patent is subject to a terminal disclaimer.

(21) Appl. No.: 16/840,103

(22) Filed: Apr. 3, 2020

(65) Prior Publication Data

US 2020/0385810 A1 Dec. 10, 2020

Related U.S. Application Data

(63) Continuation of application No. 15/299,335, filed on Oct. 20, 2016, now Pat. No. 10,612,096, which is a continuation of application No. 13/461,582, filed on May 1, 2012, now Pat. No. 9,493,828, which is a continuation of application No. 12/958,347, filed on Dec. 1, 2010, now abandoned.

(60) Provisional application No. 61/455,849, filed on Oct. 26, 2010, provisional application No. 61/407,017, filed on Oct. 26, 2010, provisional application No. 61/360,837, filed on Jul. 1, 2010, provisional application No. 61/296,358, filed on Jan. 19, 2010.

(51) Int. Cl.
| | |
|---|---|
| *C12Q 1/6883* | (2018.01) |
| *C12Q 1/6827* | (2018.01) |
| *C12Q 1/6869* | (2018.01) |
| *C12Q 1/6886* | (2018.01) |
| *G16B 30/00* | (2019.01) |
| *G16B 30/10* | (2019.01) |

(52) U.S. Cl.
CPC ......... *C12Q 1/6883* (2013.01); *C12Q 1/6827* (2013.01); *C12Q 1/6869* (2013.01); *C12Q 1/6886* (2013.01); *G16B 30/00* (2019.02); *G16B 30/10* (2019.02); *C12Q 2537/143* (2013.01); *C12Q 2600/106* (2013.01); *C12Q 2600/156* (2013.01); *C12Q 2600/16* (2013.01)

(58) Field of Classification Search
CPC .. C12Q 1/6883; C12Q 1/6827; C12Q 1/6869; C12Q 1/6886; G16B 30/00
See application file for complete search history.

(56) References Cited

U.S. PATENT DOCUMENTS

| | | |
|---|---|---|
| 5,432,054 A | 7/1995 | Saunders et al. |
| 5,994,057 A | 11/1999 | Mansfield |
| 6,258,540 B1 | 7/2001 | Lo et al. |
| 6,440,705 B1 | 8/2002 | Stanton et al. |
| 6,440,706 B1 | 8/2002 | Vogelstein et al. |
| 6,555,315 B1 | 4/2003 | Short |
| 6,960,437 B2 | 11/2005 | Enzelberger et al. |
| 7,252,946 B2 | 8/2007 | Szasz |
| 7,332,277 B2 | 2/2008 | Dhallan |
| 7,645,576 B2 | 1/2010 | Lo et al. |
| 7,888,017 B2 | 2/2011 | Quake et al. |
| 8,008,018 B2 | 8/2011 | Quake et al. |
| 8,137,912 B2 | 3/2012 | Kapur et al. |
| 8,195,415 B2 | 6/2012 | Fan et al. |
| 8,318,430 B2 | 11/2012 | Chuu et al. |
| 8,532,936 B2 | 9/2013 | Rava |
| 9,493,828 B2 * | 11/2016 | Rava ................... C12Q 1/6827 |
| 10,612,096 B2 * | 4/2020 | Rava ................... C12Q 1/6886 |
| 2002/0142324 A1 | 10/2002 | Wang et al. |
| 2003/0022207 A1 | 1/2003 | Balasubramanian et al. |
| 2003/0044388 A1 | 3/2003 | Lo et al. |
| 2003/0064368 A1 | 4/2003 | Sakai et al. |
| 2003/0194704 A1 | 10/2003 | Penn et al. |
| 2004/0137470 A1 | 7/2004 | Dhallan |
| 2004/0209299 A1 | 10/2004 | Pinter et al. |
| 2005/0164241 A1 | 7/2005 | Hahn et al. |
| 2005/0221341 A1 | 10/2005 | Shimkets et al. |

(Continued)

FOREIGN PATENT DOCUMENTS

| | | |
|---|---|---|
| CA | 2693081 | 7/2008 |
| EP | 2334812 | 6/2011 |

(Continued)

OTHER PUBLICATIONS

Agarwal et al. (Commercial Landscape of noninvasive prenatal testing in the United States. Prenatal Design. Jun. 2013, vol. 33, No. 6, p. 521-531. (Year: 2013).*
Pollack, Andrew. (A Less Risky Down Syndrome Test is Developed. The New York Times. Oct. 17, 2011. 3 pages. (Year: 2011).*
U.S. Appl. No. 61/258,567, filed Nov. 5, 2009.
U.S. Appl. No. 61/259,075, filed Nov. 6, 2009.
U.S. Appl. No. 61/296,358, filed Jan. 19, 2010.
U.S. Appl. No. 61/360,837, filed Jul. 1, 2010.

(Continued)

*Primary Examiner* — Neil P Hammell
*Assistant Examiner* — Alexandra Geraldine Dace Denito
(74) *Attorney, Agent, or Firm* — Mueting Raasch Group

(57) ABSTRACT

The invention provides compositions and methods for determining the fraction of fetal nucleic acids in a maternal sample comprising a mixture of fetal and maternal nucleic acids. The fraction of fetal nucleic acids can be used in determining the presence or absence of fetal aneuploidy.

16 Claims, 7 Drawing Sheets

Specification includes a Sequence Listing.

(56) References Cited

U.S. PATENT DOCUMENTS

| | | |
|---|---|---|
| 2005/0252773 A1 | 11/2005 | McBride et al. |
| 2006/0046258 A1 | 3/2006 | Lapidus et al. |
| 2006/0121452 A1 | 6/2006 | Dhallan |
| 2006/0134599 A1 | 6/2006 | Toner et al. |
| 2006/0257895 A1 | 11/2006 | Pinkel et al. |
| 2006/0286558 A1 | 12/2006 | Novoradovskaya et al. |
| 2007/0134658 A1 | 6/2007 | Bohmer et al. |
| 2007/0207466 A1 | 9/2007 | Cantor et al. |
| 2008/0020390 A1 | 1/2008 | Mitchell et al. |
| 2008/0050739 A1 | 2/2008 | Stoughton et al. |
| 2008/0064098 A1 | 3/2008 | Allickson |
| 2008/0070792 A1 | 3/2008 | Stoughton et al. |
| 2008/0138809 A1 | 6/2008 | Kapur et al. |
| 2008/0193927 A1 | 8/2008 | Mann et al. |
| 2008/0220422 A1 | 9/2008 | Shoemaker et al. |
| 2008/0299562 A1 | 12/2008 | Oeth et al. |
| 2009/0026082 A1 | 1/2009 | Rothberg et al. |
| 2009/0029377 A1 | 1/2009 | Lo et al. |
| 2009/0087847 A1 | 4/2009 | Lo et al. |
| 2009/0098547 A1 | 4/2009 | Ghosh |
| 2009/0117542 A1 | 5/2009 | Maybruck et al. |
| 2009/0215042 A1 | 8/2009 | Sella-Tavor et al. |
| 2009/0270601 A1 | 10/2009 | Benner et al. |
| 2009/0291433 A1 | 11/2009 | Pollack et al. |
| 2009/0291443 A1 | 11/2009 | Stoughton et al. |
| 2009/0299645 A1 | 12/2009 | Colby et al. |
| 2009/0307181 A1 | 12/2009 | Colby et al. |
| 2009/0317817 A1 | 12/2009 | Oeth et al. |
| 2009/0317818 A1 | 12/2009 | Ehrich et al. |
| 2010/0068711 A1 | 3/2010 | Umansky et al. |
| 2010/0093835 A1 | 4/2010 | McSwiggen et al. |
| 2010/0112575 A1 | 5/2010 | Fan et al. |
| 2010/0112590 A1 | 5/2010 | Lo et al. |
| 2010/0138165 A1 | 6/2010 | Fan et al. |
| 2010/0167954 A1 | 7/2010 | Earnshaw et al. |
| 2010/0184043 A1 | 7/2010 | Mitchell et al. |
| 2010/0184075 A1 | 7/2010 | Cantor et al. |
| 2010/0216151 A1 | 8/2010 | Lapidus et al. |
| 2010/0216153 A1 | 8/2010 | Lapidus et al. |
| 2010/0285537 A1 | 11/2010 | Zimmerman |
| 2011/0003293 A1 | 1/2011 | Stoughton et al. |
| 2011/0105353 A1 | 5/2011 | Lo et al. |
| 2011/0118145 A1 | 5/2011 | Akmaev et al. |
| 2011/0177517 A1 | 7/2011 | Rava et al. |
| 2011/0201507 A1 | 8/2011 | Rava et al. |
| 2011/0224087 A1 | 9/2011 | Quake et al. |
| 2011/0230358 A1 | 9/2011 | Rava |
| 2011/0245085 A1 | 10/2011 | Rava |
| 2011/0312503 A1 | 12/2011 | Chuu et al. |
| 2011/0319272 A1 | 12/2011 | Fan |
| 2012/0010085 A1 | 1/2012 | Rava et al. |
| 2012/0034603 A1 | 2/2012 | Oliphant et al. |
| 2012/0034685 A1 | 2/2012 | Sparks et al. |
| 2012/0040859 A1 | 2/2012 | Sparks et al. |
| 2012/0094849 A1 | 4/2012 | Rava et al. |
| 2012/0100548 A1 | 4/2012 | Rava et al. |
| 2012/0149582 A1 | 6/2012 | Rava et al. |
| 2012/0149583 A1 | 6/2012 | Rava et al. |
| 2012/0184449 A1 | 7/2012 | Hixson et al. |
| 2012/0214678 A1 | 8/2012 | Rava et al. |
| 2012/0214680 A1 | 8/2012 | Oeth et al. |
| 2012/0237928 A1 | 9/2012 | Rava et al. |
| 2012/0238738 A1 | 9/2012 | Hendrickson |
| 2013/0029852 A1 | 1/2013 | Rava et al. |
| 2013/0034546 A1 | 2/2013 | Rava et al. |
| 2013/0096011 A1 | 4/2013 | Rava et al. |
| 2013/0103320 A1 | 4/2013 | Dzakula et al. |
| 2014/0038830 A1 | 2/2014 | Srinivasan et al. |
| 2014/0199691 A1 | 7/2014 | Chuu et al. |

FOREIGN PATENT DOCUMENTS

| | | |
|---|---|---|
| EP | 2496717 | 9/2012 |
| EP | 2513339 | 10/2012 |
| EP | 1981995 | 7/2013 |
| GB | 2479471 | 10/2011 |
| GB | 2479476 | 10/2011 |
| GB | 2479080 | 1/2012 |
| GB | 2484764 | 4/2012 |
| GB | 2485635 | 11/2012 |
| GB | 2485644 | 11/2012 |
| GB | 2485645 | 11/2012 |
| WO | 199619586 | 6/1996 |
| WO | 199814275 | 4/1998 |
| WO | 199839474 | 9/1998 |
| WO | 9844151 | 10/1998 |
| WO | 0018957 | 4/2000 |
| WO | 2003004677 | 1/2003 |
| WO | 2005010145 | 2/2005 |
| WO | 2006010610 | 2/2006 |
| WO | 2006028152 | 3/2006 |
| WO | 2006028153 | 3/2006 |
| WO | 2007092473 | 8/2007 |
| WO | 2007100911 | 9/2007 |
| WO | 2007147073 | 12/2007 |
| WO | 2007147074 | 12/2007 |
| WO | 2007147079 | 12/2007 |
| WO | 2009013492 | 1/2009 |
| WO | 2009013496 | 1/2009 |
| WO | 2009046445 | 4/2009 |
| WO | 2009114543 | 9/2009 |
| WO | 2010033578 | 3/2010 |
| WO | 2011051283 | 5/2011 |
| WO | 2011057094 | 5/2011 |
| WO | 2011090556 | 7/2011 |
| WO | 2011090557 | 7/2011 |
| WO | 2011090558 | 7/2011 |
| WO | 2011090559 | 7/2011 |
| WO | 2011091046 | 7/2011 |
| WO | 2011091063 | 7/2011 |
| WO | 2012019187 | 2/2012 |
| WO | 2012019193 | 2/2012 |
| WO | 2012019198 | 2/2012 |
| WO | 2012019200 | 2/2012 |
| WO | 2012071621 | 6/2012 |
| WO | 2012078792 | 6/2012 |
| WO | 2012088348 | 6/2012 |
| WO | 2012103031 | 8/2012 |
| WO | 2012108920 | 8/2012 |
| WO | 2012142334 | 10/2012 |
| WO | 2013015793 | 1/2013 |

OTHER PUBLICATIONS

U.S. Appl. No. 61/381,854, filed Nov. 10, 2010.
U.S. Appl. No. 61/407,017, filed Oct. 26, 2010.
U.S. Appl. No. 61/455,849, filed Oct. 26, 2010.
Ncbi: NCBI assay ID ss3206919 for rr560681, Sep. 5, 2001.
European Search Report for EP18160303.6, Jun. 19, 2018, 12 pages.
Combined Search and Examination Report in GB Patent Application No. 1118396.9, Mar. 16, 2012.
Combined Search and Examination Report in GB Patent Application No. 1118398.5, Mar. 16, 2012.
European Search Report in EP Patent Application No. 10825822.9, Feb. 22, 2012, 4 pages.
European Search Report in EP Patent Application No. 10830938.6, Feb. 22, 2012, 4 pages.
European Search Report in EP Patent Application No. 10830939.4, Feb. 22, 2012, 4 pages.
Examination Report in Australian Patent Application No. 2011207561, Aug. 29, 2013.
Examination Report in EP Patent Application No. 10825822.9, Oct. 17, 2012.
Examination Report in EP Patent Application No. 10825822.9, Apr. 10, 2013.
Examination Report in EP Patent Application No. 10825822.9, Mar. 19, 2012, 5.
Examination Report in EP Patent Application No. 10830938.6, Oct. 18, 2012.

(56) References Cited

OTHER PUBLICATIONS

Examination Report in EP Patent Application No. 10830938.6, Mar. 16, 2012.
Examination Report in EP Patent Application No. 10830938.6, Apr. 10, 2013.
Examination Report in EP Patent Application No. 10830939.4, Oct. 17, 2012.
Examination Report in EP Patent Application No. 10830939.4, Mar. 16, 2012.
Examination Report in EP Patent Application No. 10830939.4, Apr. 10, 2013.
Examination Report in EP Patent Application No. 11744148.5, Nov. 20, 2012.
Examination Report in EP Patent Application No. 11744148.5, Apr. 10, 2013.
Examination Report in GB Patent Application No. 1106394.8, Jun. 24, 2011.
Examination Report in GB Patent Application No. 1107268.3, Nov. 15, 2011.
Examination Report in GB Patent Application No. 1107268.3, Jul. 15, 2011.
Examination Report in GB Patent Application No. 1108794.7, Jul. 15, 2011.
Examination Report in GB Patent Application No. 1108795.4, Dec. 16, 2011.
Examination Report in GB Patent Application No. 1108795.4, Mar. 9, 2012.
Examination Report in GB Patent Application No. 1108795.4, Jul. 15, 2011.
Examination Report in GB Patent Application No. 1114713.9, Dec. 7, 2011.
Examination Report in GB Patent Application No. 1114713.9, Mar. 6, 2012.
Examination Report in GB Patent Application No. 1118396.9, Aug. 14, 2012.
Examination Report in GB Patent Application No. 1118398.5, Aug. 17, 2012.
Extended European Search Report in EP Patent Application No. 11175845.4, Nov. 17, 2011.
Extended European Search Report in EP Patent Application No. 11735131.2, Jun. 3, 2013.
Final Office Action in U.S. Appl. No. 12/958,353, filed Sep. 10, 2013.
Final Office Action in U.S. Appl. No. 12/958,356, filed Aug. 22, 2013.
Final Office Action in U.S. Appl. No. 13/364,809, filed Feb. 19, 2013.
Final Office Action in U.S. Appl. No. 13/365,134, filed Feb. 20, 2013.
Final Office Action in U.S. Appl. No. 13/365,240, filed Nov. 9, 2012.
International Search Report in PCT Application No. PCTUS2010058606, Feb. 28, 2011.
International Search Report in PCT Application No. PCT/US2010/058609, Apr. 4, 2011.
International Search Report in PCT Application No. PCT/US2010/058612, May 19, 2011.
International Search Report in PCT Application No. PCT/US2010/058614, Mar. 1, 2011.
International Search Report in PCT Application No. PCT/US2011/021729, Apr. 11, 2011.
International Search Report in PCT Application No. PCT/US2011/045412, Feb. 24, 2012.
International Search Report in PCT Application No. PCT/US2013/051399, Oct. 7, 2013.
Invitation to Pay Additional Fees in International Patent Application No. PCT/US2012/033391, Nov. 15, 2012.
Invitation to Pay Additional Fees in International Patent Application No. PCT/US2013/023887, Oct. 8, 2013.
Invitation to Pay Additional Fees in International Patent Application No. PCT/US2013/023909, Oct. 8, 2013.
Notice of Allowance in U.S. Appl. No. 12/696,509, filed Mar. 1, 2012.
Notice of Allowance in U.S. Appl. No. 13/452,083, filed Jul. 12, 2012.
Office Action for U.S. Appl. No. 13/482,964, filed Feb. 4, 2014.
Office Action in U.S. Appl. No. 13/191,366, filed Aug. 2, 2013.
Office Action in U.S. Appl. No. 12/393,833, filed Jun. 5, 2012.
Office Action in U.S. Appl. No. 12/958,352, filed Oct. 10, 2012.
Office Action in U.S. Appl. No. 12/958,352, filed Aug. 1, 2013.
Office Action in U.S. Appl. No. 12/958,353, filed Dec. 20, 2012.
Office Action in U.S. Appl. No. 12/958,356, filed Jan. 11, 2013.
Office Action in U.S. Appl. No. 13/323,683, filed Jun. 28, 2012.
Office Action in U.S. Appl. No. 13/333,832, filed May 23, 2012.
Office Action in U.S. Appl. No. 13/364,809, filed Aug. 10, 2012.
Office Action in U.S. Appl. No. 13/365,134, filed Aug. 15, 2012.
Office Action in U.S. Appl. No. 13/365,240, filed Jun. 3, 2012.
Office Action in U.S. Appl. No. 13/368,035, filed Mar. 13, 2012.
Search Report relating to claims 16-23, in part 24-31 in GB Patent Application No. 1114713.9, Apr. 17, 2012.
Search Report relating to claims 8-11, in part 12-15 in GB Patent Application No. 1114713.9, Apr. 17, 2012.
Amaral, et al., "Application of massive parallel sequencing to whole genome SNP discovery in the porcine genome", BMC Genomics, Biomed Central Ltd, London, UK, vol. 10, No. 1, Aug. 12, 2009, 374.
Angeloni, D., "Molecular analysis of deletions in human chromosome 3p21 and the role of resident cancer genes in disease", Briefings Functional Genomics, vol. 6(1), May 24, 2007, 19-39.
Ashoor, et al., "Chromosome-selective sequencing of maternal plasma cell-free DNA for first-trimester detection of trisomy 21 and trisomy 18", Am J Obstet Gynecol, 206(4), Apr. 2012, 322.e1-5.
Ashoor, et al., "Fetal Fraction in maternal plasma cell-free DNA at 11-13 weeks' gestation: effect of maternal and fetal factors", Fetal Diagn Ther, published online, A reference cited in the instructions, May 4, 2012, 7 pages.
Bauer, M. et al., "A prospective analysis of cell-free fetal DNA concentration in maternal plasma as an indicator for adverse pregnancy outcome", Prenatal Diagnosis, vol. 26, Jul. 11, 2006, 831-836.
Bentley, et al., "Accurate whole human genome sequencing using reversible terminator chemistry", Nature, vol. 456, 2008, 53-59.
Beroukhim, et al., "The landscape of somatic copy-No. alteration across human cancers", Nature, vol. 463, Feb. 2010, 899-905.
Bianchi, et al., "Genome-Wide Fetal Aneuploidy Detection by Maternal Plasma DNA Sequencing", Obstetrics and Gynecology, vol. 119, No. 5, May 5, 2012, 890-901.
Bianchi, et al., "Isolation of fetal DNA from nucleated erythrocytes in maternal blood", Medical Sciences, vol. 87, 1990, 3279-3283.
Bischoff, et al., "Cell-free fetal DNA and intact fetal cells in maternal blood circulation: implications for first and second trimester non-invasive prenatal diagnosis", Human Reproduction Updated, vol. 8, No. 6, Nov. 1, 2002, pp. 493-500.
Borsting, "Multiplex PCR, amplicon size and hybridization efficiency on the NanoChip electronic microarray", Int J. Legal Med. vol. 118, 2004, 75-82.
Botezatu, et al., "Genetic Analysis of DNA excreted in urine: a new approach for detecting specific genomic DNA sequences from cells dying in an organism", Clin Chem. 46(8 Pt1), Aug. 2000, 1078-84.
Bowcock, et al., "Exclusion of the Retinablastoma Gene and Chromosome 13q as the Site of a Primary Lesion for Human Breast Cancer", Am J Hum Genet, vol. 46, 1990, 12.
Braslavsky, et al., "Sequence information can be obtained from single DNA molecules", PNAS, 100(7), Apr. 1, 2003, 3960-3964.
Brosens, et al., "Deletion of chromosome 4q predicts outcome in stage II colon cancer patients", Analytical Cellular Pathology / Cellular Oncology 33, 2010, 95-104.
Brown, et al., "Chemical synthesis and cloning of a tyrosine tRNA gene", Methods Enzmol., vol. 68, 1979, 109.
Bruch, et al., "Trophoblast-like cells sorted from peripheral maternal blood using flow cytometry: A multiparametric study involving

(56) References Cited

OTHER PUBLICATIONS transmission electron microscopy and fetal DNA amplification", Prenatal Diagnosis, vol. 11, 1991, pp. 787-798.
Buck, et al., "Design Strategies and Performance of Custom DNA Sequencing Primers", Biotechniques vol. 27, 1999, 528-536.
Bustin, et al., "Pitfalls of Quantitative Real-Time Reverse-Transcription Polymerase Chain Reaction", J. Biomol. Tech., vol. 15, 2004, 155-166.
Butler, et al., "Short tandem repeat typing technologies used in human identity testing", Biotechniques 43(4), Oct. 2007, ii-v.
Butler, et al., "The Development of reduced size STR amplicons as tools for analysis of degraded DNA", J. Forensic Sci 48(5), 2003, 1054-64.
Caramazza, et al., "Chromosome 1 abnormalities in myeloid malignancies: a literature survey and karyotype-phenotype associations", European Journal of Haematology, vol. 84, 2010, 191-200.
Chan, et al., "DNA Mapping Using Micro fluidic Stretch-ing and Single-Molecule Detection of Fluorescent Site-Specific Tags", Genome Research, vol. 14, 2004, 1137-1146.
Chan, et al., "Size Distributions of maternal and fetal DNA in Maternal Plasma", Clin. Chem 50(1), Jan. 2004, 88-92.
Chang, et al., "Assessment of Plasma DNA Levels, Allelic Imbalance, and CA 125 as Diagnostic Tests for Cancer", Journal of the National Cancer Institute, vol. 94, No. 22, Nov. 22, 2002, 1697-1703.
Chen, et al., "Detection in Fecal DNA of Colon Cancer-Specific hylation of the Nonexpressed Vimentin Gene", Journal of the National Cancer Institute, vol. 97, No. 15, Aug. 2, 2005, 1124-1132.
Chen, et al., "Microsatellite alterations in plasma DNA of small cell lung cancer patients", Nat Med. 2(9), 1996, 1033-5.
Chiang, et al., "High-resolution mapping of copy-number alterations with massively parallel sequencing", Nature Methods, vol. 6, No. 1 (2009), published online: doi:10.1038/nmeth.1276, Jan. 2009, 99-103.
Chiu, et al., "Effects of Blood-Processing Protocols on Fetal and Total DNA Quantification in Maternal Plasma", Clinical Chemistry, vol. 47, No. 9, 2001, 1607-1613.
Chiu, et al., "Maternal Plasma DNA Analysis with Massively Parallel Sequencing by Ligation for Noninvasive Prenatal Diagnosis of Trisomy 21", Clinical Chemistry 56:3, 2010, 459-463.
Chiu, et al., "Non-invasive prenatal assessment of trisomy 21 by multiplexed maternal plasma DNA sequencing: large scale validity study", BMJ 342, Jan. 11, 2011, c7401.
Chiu, et al., "Noninvasive Prenatal Diagnosis by Analysis of Fetal DNA in Maternal Plasma", Methods in Molecular Biology, 336, Clinical Applications of PCR, Second Edition, Edited by Y.M. Dennis Lo et al., Humana Press Inc., 2006, 101-109.
Chiu, et al., "Non-invasive prenatal diagnosis by single molecule counting technologies", Trends Genet. 25 (7), Jul. 1, 2009, 324-331 pp.
Chiu, et al., "Noninvasive prenatal diagnosis of fetal chromosomal aneuploidy by massively parallel genomic sequencing of DNA in maternal plasma", PNAS, vol. 105, No. 51, Dec. 23, 2008, pp. 20458-20463.
Chu, et al., "Statistical model for whole genome sequencing and its application to minimally invasive of fetal genetic disease", Bioinformatics 25(10), May 15, 2009, 1244-1250.
Chuu et al., "U.S. Appl. No. 13/012,222", filed Jan. 24, 2010.
Clarke, et al., "Effects of chemotherapy and hormonal therapy for early breast cancer on recurrence and 15-year survival: an overview of randomised trials", Lancet vol. 365, 2005, 1687-1717.
Clarke, et al., "Effects of radiotherapy and of differences in the extent of surgery for early breast cancer on local recurrence and 15-year survival: an overview of the randomised trials", Lancet vol. 366, 2005, 2087-2106.
Coble, et al., "Characterization of New MiniSTR Loci to Aid Analysis of Degraded DNA", J Forensic Sci, 50(1), Jan. 2005, 43-53.

Deng, et al., "Enumeration and microfluidic chip separation of circulating fetal cells early in pregnancy from maternal blood", American Journal of Obstetrics & Gynecology, vol. 199, Issue 6, Dec. 2008, S134.
Dhallan, et al., "A non-invasive test for prenatal diagnosis based on fetal DNA present in maternal blood: a preliminary study", Lancet 369(9560), Feb. 10, 2007, 474-481.
Dhallan, et al., "Methods to Increase the Percentage of Free Fetal DNA Recovered From the Maternal Circulation", J. Am. Med. Soc., vol. 291, No. 9, Mar. 2004, 1114-1119.
Ding, et al., "MS analysis of single-nucleotide differences in circulating nucleic acids: Application to noninvasive prenatal diagnosis", Proceedings of National Academy of Sciences 101(29), 2004, 10762-10767 pp.
Dixon, et al., "Analysis of artificially degraded DNA using STRs and SNPs-results of a collaborative European (EDNAP) exercise", Forensic Sci Int 164(1), Dec. 1, 2006, 33-44.
Dressman, et al., "Transforming single DNA molecules into fluorescent magnetic particles for detection and enumeration of genetic variations", Proc. Natl. Acad. Sci. USA 100 (15), 2003, 8817-8822.
Ehrich, "Noninvasive detection of fetal trisomy 21 by sequencing of DNA in maternal blood: a study in a clinical setting", Am J Obstet Gynecol, 204(3), Mar. 2011, 205.el-11.
Eisenmann, et al., "5q-myelodysplastic syndromes: chromosome 5q genes direct a tumor-suppression network sensing actin dynamics", Oncogene, vol. 28, 2009, 3429-3441.
Fan, et al., "Analysis of the size distributions of fetal and maternal cell-free DNA by paired-end sequencing", Clin. Chem 56(8), Aug. 1, 2010, 1279-1286.
Fan, et al., "Detection of aneuploidy with digital polymerase chain reaction", Anal Chem. 79(19), Oct. 1, 2007, 7576-7579.
Fan, et al., "In principle method for noninvasive determination of the fetal genome", Nature Precedings: Nature Precedings 10.1038/npre, Dec. 8, 2010, 5373.1.
Fan, et al., "Microfluidic digital PCR enables rapid prenatal diagnosis of fetal aneuploidy", Am J Obstet Gynecol 200(5), May 2009, 543.el-7.
Fan, et al., "Microfluidic digital PCR enables rapid prenatal diagnosis of fetal aneuploidy", American Journal of Obstetrics & Gynecology, May 2009, 543e1-543.e7.
Fan, et al., "Noninvasive diagnosis of fetal aneuploidy by shotgun sequencing DNA from maternal blood", Proceedings of the National Academy of Sciences, vol. 105, No. 42, also available at: http://www.pnas.org/cgi/doi/10.1073/pnas.0808319105, Oct. 21, 2008, 16266-71.
Fan, et al., "Sensitivity of noninvasive prenatal detection of fetal aneuploidy from maternal plasma using shotgun sequencing is limited only by counting statistics", PLoS One 5(5), May 3, 2010, e10439.
Fan, et al., "U.S. Appl. No. 13/452,083", filed Apr. 20, 2012.
Fan, et al., "Whole-genome molecular haplotyping of single cells", Nature Biotechnology, Advanced Online Publication, Dec. 19, 2010, 9 pages.
Fonatsch, C., "The role of chromosome 21 in hematology and oncology", Genes, Chromosomes and Cancer, vol. 49, Issue 6, Jun. 2010, 497-508.
Frohling, et al., "Chromosomal Abnormalities in Cancer", New England Journal of Medicine, vol. 359, 2008, 722-734.
Fuscoe, et al., "An Efficient Method for Selecting Unique-Sequence Clones from DNA Libraries and Its Application to Fluorescent Staining of Human Chromosome 21 Using in Situ Hybridization", Genomics, vol. 5, 1989, 100-109.
Gardiner, et al., "Analysis of human chromosome 21: correlation of physical and cytogenetic maps; gene and CpG island distributions", The EMBOJ Journal, vol. 9, No. 1, 1990, 25-34.
Ghanta, et al., "Non-Invasive Prenatal Detection of Trisomy 21 Using Tandem Single Nucleotide Polymorphisms", PLos One, vol. 5, Issue 10, e13184, Oct. 2010, 10 pages.
Goossens, et al., "Simultaneous Mutation and Copy Number Variation (CNV) Detection by Multiplex PCR-Based GS-FLX Sequencing", Human Mutation, vol. 30, Issue 3, Dec. 2008, 472-476.

(56) References Cited

OTHER PUBLICATIONS

Grubweiser, et al., "A new "miniSTR-multiplex" displaying reduced amplicon lengths for the analysis of degrade DNA", Int J. Legal Med 120(2), 2006, 115-20.
Grundevik, et al., "Molecular Diagnostics of Aneuploidies", Chalmers University of Technology, Sweden, Department of Molecular Biotechnology, May 17, 2005, 1-12.
Hanson, et al., "Whole genome amplification strategy for forensic genetic analysis using single or few cell equivalents of genomic DNA", Anal Biochem. 346(2), Nov. 15, 2005, 246-57.
Harris, et al., "Single-Molecule DNA Sequencing of a Viral Genome", Science 320, Apr. 4, 2008, 106-109 and Suppl. Materials 1-25.
Harrison, et al., "Polymer-stimulated ligation: enhanced ligation of oligo-and polynucleotides by T4 RNA ligase in polymer solutions", Nucleic Acids Research vol. 12 No. 21 1984, 1984, 8235-51.
Hayashi, et al., "Regulation of inter-and intramolecular ligation with T4 DNA ligase in the presence of polyethylene glycol", Nucleic Acids Res. 14(19), Oct. 10, 1986, 7617-31.
Herzenberg, et al., "Fetal cells in the blood of pregnant women: Detection and enrichment by fluorescence-activated cell sorting", Proc. Natl. Acad. Sci. 76, 1979, 1453-1455.
Hesser, et al., "Down syndrome critical region protein 1 (DSCR1), a novel VEGF target gene that regulates expression of inflammatory markers on activated endothelial cells", Blood, vol. 104, No. 1, Jul. 1, 2004, 149-158.
Hill, et al., "Characterization of 26 new miniSTR Loci", Poster #44—17th International Symposium on Human Identification, Nashville, TN, Oct. 10-12, 2006, 1.
Hochstenbach, et al., "Array analysis and karyotyping: workflow consequences based on a retrospective study of 36,325 patients with idiopathic developmental delay in the Netherlands", Eur. J. Med. Genet., 52(4), Jul. 1, 2009, 161-169.
Hoffman, et al., "The genome-enabled electronic medical record", Journal of Biomedical Informatics 10 (2007) published online, Mar. 15, 2006, 44-46.
Howe, et al., "Retinoblastoma growth suppressor and a 300-kDa protein appear to regulate cellular DNA synthesis", Proc. Natl. Acad. Sci. USA, vol. 87, Aug. 1990, 5883-5887.
Hromadnikova, et al., "Quantitative analysis of DNA levels in maternal plasma in normal and Down syndrome pregnancies", Bio Med Central, May 2002, 1-5.
Huang, "Isolation of cell-free DNA from maternal plasma using manual and automated systems", Methods Mol Biol. 444, 2008, 203-8.
Huber, et al., "High-resolution liquid chromatography of DNA fragments on non-porous poly(styrene-divinylbenzene) particles", Nucleic Acids Res., vol. 21, No. 5, Mar. 11, 1993, 1061-1066.
Hung, "Detection of circulating fetal nucleic acids: a review of methods and applications", J Clin Pathol 62(4), 2009, 308-13.
Illanes, et al., "Early detection of cell-free fetal DNA in maternal plasma", Early Human Development, vol. 83, 2007, 563-566.
Illumina, "Preparing Samples for ChIP sequencing of DNA", E-pub at grcf.jhmi.edu/hts/protocols/11257047_ChIP_Sample_Prep.pdf, 2007, 15.
International, "The International HapMap Consortium Project", Nature 426:789-96, 2003.
Jama, et al., "Quantification of cell-free fetal DNA Levels on maternal plasma by STR analysis", 2010 ACMG Annual Clinical Genetics Meeting, 2010, 2 pages.
Jensen, et al., "Detection of Microdeletion 22q11.2 in a Fetus by Next-Generation Sequencing of Maternal Plasma", Clinical Chemistry 58:7; doi:10.1373/clinchem.2011.180794, May 4, 2012, 1148-1151.
Jiang, P. et al., "FetalQuant: deducing fractional fetal DNA concentration from massively parallel sequencing of DNA in maternal plasma", Bioinformatics, vol. 28, No. 22, 2012, 2883-2890.
Jongsma, et al., "Molecular evidence for putative tumour suppressor genes on chromosome 13q specific to BRCA1 related ovarian and fallopian tube cancer", J Clin Pathol: Mol Pathol., vol. 55(5), 2002, 305-309.

Jorgez, et al., "Improving Enrichment of circulating fetal DNA for genetic testing: size fractionation followed by whole gene amplification", Fetal Diagnosis and Therapy, Karger Basel, CH, vol. 25, No. 3, 2009, pp. 314-319.
Ju, et al., "Four-Color DNA Sequencing by Synthesis Using Cleavable Florescent Nucleotide Reversible Terminators", PNAS vol. 103, No. 52, 2006, 19635-19640.
Kaiser, J., "An Earlier Look at Baby's Genes", Science, vol. 309, Sep. 2, 2005, 1476.
Kato, et al., "A New Packing for Separation of DNA Restriction Fragments by High Performance Liquid Chromatography", J. Biochem., vol. 95, No. 1, 1984, 83-86.
Kidd, et al., "Developing a SNP panel for forensic identification of individuals", Forensic Science International 164 (2006), 20-32.
Kim, et al., "rSW-seq: algorithm for detection of copy number alterations in deep sequencing data", BMC Bioinformatics, vol. 11, Aug. 18, 2010, 432.
Koide, et al., "Fragmentation of cell-free fetal DNA in plasma and urine of pregnant women", Prenat Diagn. Jul. 2005;25(7), www.interscience.wiley.com, Mar. 14, 2005, 604-7.
Kozarewa, et al., "Amplification-free Illumina sequencing-library preparation facilitates improved mapping and assembly of GC-biased genomes", Nat. Methods, 6(4), Apr. 2009, 291-295.
Langmead, et al., "Ultrafast and memory-efficient alignment of short DNA sequences to the human genome", Genome Biology, vol. 10, 2009, R25.1-R25.10.
Lazinski, et al., "Modified Protocol for Illumina Paired-End Library Construction", http://genomics.med.tufts.edu/documents/htseq_protocol_for_illumina_paired.pdf, Feb. 27, 2009, 10.
Lee, et al., "Improving the efficiency of genomic loci capture using oligonucleotide arrays for high throughput resequencing", BMC Genomics, Biomed Central Ltd, London, UK, vol. 10, No. 646, Dec. 31, 2009, 1-12.
Leon, et al., "Free DNA in the Serum of Cancer Patients and the Effect of Therapy", Cancer Research 37, Mar. 1977, 646-650.
Levy, et al., "The Diploid Genome Sequence of an Individual Human", PLoS Biology, vol. 5, Issue 10, Oct. 2007, 2113-2144.
Li, et al., "Detection of paternally inherited fetal point mutations for beta-thalassemia using size-fractionated cell-free DNA in maternal plasma", J. Amer. Med. Assoc., vol. 293, Feb. 16, 2005, 843-849.
Li, et al., "Size Separation of Circulatory DNA in Maternal Plasma Permits Ready Detection of Fetal DNA Polymorphisms", Clin. Chem., vol. 50, No. 6, 2004, 1002-1011.
Li, et al., "SNP detection for massively parallel whole-genome resequencing", Genome Research, vol. 19, No. 6, Jun. 1, 2009, 1124-1132.
Liao, et al., "Targeted Massively parallel sequencing of maternal plasma DNA permits efficient and unbiased detection of fetal alleles", Clinical Chemistry 57:1, 2011, 92-101.
Liu, et al., "Feasibility study of using fetal DNA in maternal plasma for non-invasive prenatal diagnosis", Acta Obstet Gynecol Scand. 86(5), 2007, 535-41.
Lo, et al., "Digital PCR for the molecular detection of fetal chromosomal aneuploidy", Proc Natl Acad Sci USA. 104(32), Aug. 7, 2007, 13116-13121.
Lo, et al., "Fetal DNA in Maternal Plasma", Ann. NY Acad. Sci, vol. 906, Apr. 2000, 141-147.
Lo, et al., "Increased fetal DNA concentrations in the plasma of pregnant women carrying fetuses with trisomy 21", Clinical Chemistry 45:10, 1999, 1747-51.
Lo, et al., "Maternal Plasma DNA Sequencing Reveals The Genome-Wide Genetic And Mutational Profile of The Fetus", Sci Transl Med. 2(61) Dec. 8, 2010, 61ra91.
Lo, et al., "Noninvasive prenatal detection of fetal chromosomal aneuploidies by maternal plasma nucleic acid analysis: a review of the current state of the art", BJOG, vol. 116, 2009, 152-157.
Lo, et al., "Noninvasive prenatal diagnosis of fetal chromosomal aneuploidies by maternal plasma nucleic acid analysis", Clin Chem. 54(3), Jan. 2008, 461-466.
Lo, et al., "Prenatal diagnosis of fetal RhD Status by molecular analysis of maternal plasma", The New England Journal of Medicine, vol. 339, Dec. 10, 1998, 1734-1738.

(56) References Cited

OTHER PUBLICATIONS

Lo, et al., "Presence of fetal DNA in maternal plasma and serum", Lancet. 350(9076), Aug. 16, 1997, 485-487.
Lo, et al., "Quantitative analysis of fetal DNA in maternal plasma and serum: implications for noninvasive prenatal diagnosis", Am J Hum Genet 62(4), Apr. 1998, 768-775.
Lo, et al., "Rapid Clearance of fetal DNA from Maternal Plasma", Am J Hum Genet. 64(1), 1999, 218-24.
Lun, et al., "Microfluidics digital PCR Reveals a Higher than expected fraction of fetal DNA in maternal plasma", Clinical Chemistry, vol. 54, No. 10, Oct. 1, 2008, 1664-1672.
Lun, et al., "Noninvasive prenatal diagnosis of monogenic diseases by digital size selection and relative mutation dosage on DNA in maternal plasma", Proceedings of National Academy of Sciences 105(50), 2008, 19920-19925 pp.
Mann, et al., "Strategies for the rapid prenatal diagnosis of chromosome aneuploidy", European Journal of Human Genetics, vol. 12, 2004, pp. 907-915.
Margulies, et al., "Genome sequencing in microfabricated high-density picolitre reactors", Nature, vol. 437, 2005, 376-380 and Supplemental Materials.
McKernan, et al., "Sequence and structural variation in a human genome uncovered by short-read, massively parallel ligation sequencing using two-base encoding", Genome Res. 19(9), Sep. 2009, 1527-41.
Metzker, M.L., "Applications of Next-Generation Sequencing: Sequencing technologies-the next generation", Nature Reviews Genetics, Nature Publishing Group, GB, vol. 11(1), Jan. 1, 2010, 31-46.
Meyerson, et al., "Advances in understanding cancer genomes through second-generation sequencing", Nature Reviews Genetics, vol. 11, 2010, 685-696.
Mullighan, et al., "Genome-wide profiling of genetic alterations in acute lymphoblastic leukemia: recent insights and future directions.", Leukemia vol. 23, Feb. 26, 2009, 1209-1218.
Nakamoto, "Detection of Microsatellite alterations in Plasma DNA of Malignant Mucosal Melanoma Using Whole Genome Amplification", Bull Tokyo Dent Coll. May 2008; 49(2), May 2008, 77-87.
Narang, et al., "Improved phosphotriester method for the synthesis of gene fragments", Methods Enzmol., vol. 68, 1979, 90-98.
Ng, et al., "mRNA of placental origin is readily detectable in maternal plasma", Proc. Nat. Acad. Sci., vol. 100, No. 8, 2003, 4748-4753.
Ng, et al., "The Concentration of Circulating Corticotropin-releasing Hormone mRNA in Maternal Plasma is Increased in Preeclampsia", Clin. Chem., vol. 49:5, 2003, 727-731.
Nicklas, "A real-time multiplex SNP melting assay to discriminate individuals", J. Forensic Sci. 53(6):, Nov. 2008, 1316-24.
Norton, et al., "Non-invasive chromosomal evaluation (NICE) study: results of multicenter, prospective, cohort study for detection of fetal trisomy 21 and trisomy 18", American Journal of Obstetrics and Gynecology, doi: 10.1016/j.ajog.2012.05.021., May 21, 2012, 30 pages.
Oliphant, et al., "U.S. Appl. No. 61/371,605", [Utility Pub Already Cited (2012/0034603)—Delete?], Aug. 6, 2010.
Ottesen, et al., "Microfluidic Digital PCR Enables Multigene Analysis of Individual Environmental Bacteria", Science, vol. 314, Dec. 2006, 1464-1467.
Oudejans, et al., "Detection of Chromosome 21-encoded mRANA of Placental Origin in Maternal Plasma", Clinical Chemistry, vol. 49, 2003, 1445-1449.
Pakstis, et al., "Candidate SNPs for a universal individual identification panel", Hum Genet. 121(3-4), May 2007, 305-17.
Pakstis, et al., "SNPs for a universal individual identification panel", Hum Genet. 127(3), Mar. 2010, 315-24.
Pandey, et al., "Chapter 3 Applied Biosystems Solid Systems: Ligation-Based Sequencing", Next Generation Genome Sequencing: Towards Personalized Medicine 2008. Edited by Michael Janitz., 2008, 14.
Park, et al., "A single-tube protocol for next gen library construction increases complexity and simplifies parallel sample handling", Cancer Research 71(8): Suppl. 1, Abstract No. 4851, Apr. 15, 2011.
Park, et al., "Unraveling the Biologic and Clinical Complexities of HER2", Clinical Breast Cancer, vol. 8, Issue 5, Oct. 2008, 392-401.
Pathak, et al., "Circulating Cell-Free DNA in Plasma/Serum of Lung Cancer Patients as a Potential Screening and Prognostic Tool", Clin Chem. 52(10): Oct. 2006, 1833-42.
Pennisi, E., "Semiconductors Inspire New Sequencing Technologies", Science 327, Mar. 5, 2010, 1190.
Pertl, et al., "Detection of male and female fetal DNA in maternal plasma by multiplex fluorescent polymerase chain reaction amplification of short tandem repeats", Hum Genet. 106(1), Jan. 2000, 45-9.
Peters, D. et al., "Noninvasive Prenatal Diagnosis of a Fetal Microdeletion Syndrome", New England Journal of Medicine 365;19, Correspondence, Nov. 10, 2011, 1847-1848.
Pheiffer, et al., "Polymer-stimulated ligation: enhanced blunt- or cohesive-end ligation of DNA or deoxyribooligonucleotides by T4 DNA ligase in polymer solutions", Nucleic Acids Res. 11(22), Nov. 25, 1983, 7853-71.
Poon, et al., "Differential DNA Methylation between Fetus and Mother as a Strategy for Detecting Fetal DNA in Maternal Plasma", Clin. Chem., vol. 48, No. 1, 2002, 35-41.
Pui, et al., "Acute lymphoblastic leukaemia", Lancet vol. 371, 2008, 1030-1043.
Pushkarev, et al., "Single-molecule sequencing of an individual human genome", Nat Biotechnol. 27(9): Sep. 2009, 847-50.
Quail, et al., "A large genome center's improvements to the Illumina sequencing system", Nature Methods, 5, 2008, 1005-1010.
Quake, et al., "U.S. Appl. No. 12/958,356", filed Dec. 1, 2010.
Quake, et al., "U.S. Appl. No. 13/365,240", filed Feb. 2, 2012.
Rava, et al., "U.S. Appl. No. 12/958,347", filed Dec. 1, 2010.
Rava, et al., "U.S. Appl. No. 12/958,352", filed Dec. 1, 2010.
Rava, et al., "U.S. Appl. No. 12/958,353", filed Dec. 1, 2010.
Rava, et al., "U.S. Appl. No. 13/009,718", filed Jan. 19, 2010.
Rava, et al., "U.S. Appl. No. 13/087,842", filed Apr. 15, 2011.
Rava, et al., "U.S. Appl. No. 13/191,366", filed Jul. 26, 2011.
Rava, et al., "U.S. Appl. No. 13/333,832", filed Dec. 21, 2011.
Rava, et al., "U.S. Appl. No. 13/364,809", filed Feb. 2, 2012.
Rava, et al., "U.S. Appl. No. 13/365,134", filed Feb. 2, 2012.
Rava, et al., "U.S. Appl. No. 13/400,028", filed Feb. 17, 2012.
Rava, et al., "U.S. Appl. No. 13/461,582", filed May 1, 2012.
Redon, et al., "Global Variation in copy number in the human genome", Nature 444(7118), 2006, 444-54.
Rygaard, et al., "Abnormalities in Structure and Expression of the Retinoblastoma Gene in Small Cell Lung Cancer Cell Lines and Xenografts in Nude Mice", Cancer Res., vol. 50, 1990, 5312-5317.
Sambrook, et al., "Molecular Cloning: A Laboratory Manual", Chapter 10, 3rd Edition, Cold Spring Harbor Laboratory, New York, 2001.
Satiroglu Tufan, et al., "Analysis of cell-free fetal DNA from maternal plasma and serum using a conventional multiplex PCR: Factors influencing success", Turk J. Med Sci, No. 35, 2005, 85-92.
Sato, et al., "Allelotype of Breast Cancer: Cumulative Allele Losses Promote Tumor Progression in Primary Breast Cancer", Cancer Res., vol. 50,1990, 7184-7189.
Schwarzenbach, et al., "Cell-free Tumor DNA in Blood Plasma as a Marker for Circulating Tumor Cells in Prostate Cancer", Clin Cancer Res. 15(3):, Feb. 1, 2009, 1032-8.
Schwarzenbach, et al., "Comparative evaluation of cell-free tumor DNA in blood and disseminated tumor cells in bone marrow of patients with primary breast cancer", Breast Cancer Res. 11(5), 2009, R71.
Sehnert, et al., "Optimal Detection of Fetal Chromosomal Abnormalities by Massively Parallel DNA Sequencing of Cell-Free Fetal DNA from Maternal Blood", Clinical Chemistry, Jul. 2011, vol. 57 No. 7, E-pub on Apr. 25, 2011 as doi:10.1373/clinchem.2011.165910., Apr. 25, 2011, 1042-1049.
Shaikh, et al., "High-resolution mapping and analysis of copy number variations in the human genome: A data resource for clinical and research applications", Genome Res., vol. 19, 2009, 1682-1690.

(56) References Cited

OTHER PUBLICATIONS

Shendure, et al., "Accurate Multiplex Polony Sequencing of an Evolved Bacterial Genome", Science, 309(5741), Sep. 9, 2005, 1728-1732.
Shendure, et al., "Next-generation DNA sequencing", Nature Biotechnology 26(10), 2008, 1135-1145.
Soni, et al., "Progress toward Ultrafast DNA Sequencing Using Solid-State Nanopores", Clin Chem, 53(11), 2007, 1996-2001.
Sparks, et al., "Non-invasive prenatal detection and selective analysis of cell-free DNA obtained from maternal blood: evaluation for trisomy 21 and trisomy 18", American Journal of Obstetrics and Gynecology, doi: 10.1016/j.ajog.2012.01.030, Jan. 30, 2012, 33 pages.
SS139539, NCBI dbSNP rs131828, Jun. 8, 2000.
SS3206919, NCBI dbSNP rs560681, Sep. 5, 2001.
SS3470339, NCBI dbSNP rs807841, Sep. 24, 2001.
Storchova, et al., "The consequences of tetraploidy and aneuploidy", Journal of Cell Science 121 (23), 2008, 3859-3866.
Stoughton et al., "U.S. Appl. No. 13/433,232", filed Mar. 28, 2012.
Su, et al., "Human Urine Contains Small, 150 to 250 Nucleotide-Sized, Soluble DNA Derived from the Circulation and May be useful in the Detection of Colorectal Cancer", J Mol Diagn. 6(2), May 2004, 101-7.
Teixeira, et al., "Multiple numerical chromosome aberrations in cancer: what are their causes and what are their consequences?", Seminars in Cancer Biology, vol. 15, Issue 1, Feb. 3-12, 2005.
Thomas, et al., "Mechanisms of aneuploidy and its suppression by tumour suppressor proteins", Swiss Med Weekly, 141, 2011, w13170.
Thorstenson, et al., "An Automated Hydrodynamic Process for Controlled, Unbiased DNA Shearing", Genome Research 8, 1998, 848-855.
Tong, et al., "Noninvasive Prenatal Detection of Fetal Trisomy 18 by Epigenetic Allelic Ratio Analysis in Maternal Plasma: Theoretical and Empirical Considerations", Clinical Chemistry 52:12, 2006, 2194-2202.
Tong, et al., "Noninvasive prenatal detection of trisomy 21 by an epigenetic-genetic chromosome-dosage approach", Clin Chem. 56(1), Jan. 2010, 90-8.
Turner, et al., "Methods for Genomic Partitioning", Annual Review of Genomics and Human Genetics, vol. 10, No. 1, Sep. 1, 2009, 263-284.
Vallone, et al., "Demonstration of rapid multiplex PCR amplification involving 16 genetic loci", Forensic Sci Int Genet. 3(1), Dec. 2008, 42-5.
Varmus, H., "The Molecular Genetics of Cellular Oncogenes", Ann Rev Genetics, vol. 18, 1984, 553-612.
Voelkerding, et al., "Digital Fetal Aneuploidy Diagnosis by Next-Generation Sequencing", Clin Chem. 56(3), Mar. 2010, 336-8.
Voelkerding, et al., "Next-Generation Sequencing: From Basic Research to Diagnostics", Clinical Chemistry 55:4, 2009, 641-658.
Vogelstein, et al., "Digital PCR", PNAS USA, vol. 96, Aug. 3, 1999, 9236-9241.
Walsh, et al., "Rare Structural Variants Disrupt Multiple Genes in Neurodevelopmental Pathways in Schizophrenia", Science, vol. 320, 2008, 539-543.
Warren, et al., "Transcription factor profiling in individual hematopoietic progenitors by digital RT-PCR", PNAS, vol. 103 (47), 2006, 17807-17812.
Wheeler, et al., "The complete genome of an individual by massively parallel DNA sequencing", Nature. 452(7189), Apr. 17, 2008, 872-6.
Wong, et al., "Circulating placental RNA in maternal plasma is associated with a preponderance of 5" mRNA fragments: implications for noninvasive prenatal diagnosis and monitoring", Clinical Chemistry 51:10, 2005, 1786-1795.
Wright, et al., "The use of cell-free fetal nucleic acids in maternal blood for non-invasive prenatal diagnosis", Hum Reprod Update. 15(1), Jan. 1, 2009, 139-151.
Yamada, et al., "PrimerStation: a highly specific multiplex genomic PCR primer design server for the human genome", Nucleic Acids Res., vol. 34, Jul. 1, 2006, W665-W669.
Yamazawa, et al., "Monozygotic female twins for Silver-Russell syndrome and hypomethylation of H19-DMR", J. Human Genetics, vol. 53, 2008, 950-955.
Zhou, et al., "Counting alleles reveals a connection between chromosome 18q loss and vascular invasion", Nature Biotechnology, vol. 19, Jan. 2001, 78-81.
Zhou, et al., "Counting alleles to predict recurrence of early-stage colorectal cancers", The Lancet, vol. 359, Mechanisms of Disease, Jan. 19, 2002, 219-225.
Zhu, et al., "Single Molecule Profiling of Alternative Pre-mRNA Splicing", Science 301, 2003, 836-838.
Zimmerman, et al., "Macromolecular crowding allows blunt-end ligation by DNA ligases from rat liver or *Escherichia coli*", Proc Natl Acad Sci USA. 80(19), Oct. 1983, 5852-6.
Zimmerman, et al., "Novel real-time quantitative PCR test for trisomy 21", Clinical Chemistry 48, No. 2, 2002, pp. 362-363.

\* cited by examiner

| Amplified Loci: Locus Designation | Chromosome Location | Alleles Included in Identifiler Allelic Ladder | Dye Label | Control DNA 9947A |
|---|---|---|---|---|
| D8S1179 | 8 | 8, 9 10, 11, 12, 13, 14, 15, 16, 17, 18, 19 | 6-FAM | 13a |
| D21S11 | 21q11.2-q21 | 24, 24.2, 25, 26, 27, 28, 28.2, 29, 29.2, 30, 30.2, 31, 31.2, 32, 32.2, 33, 33.2, 34, 34.2, 35, 35.2, 36, 37, 38 | | 30b |
| D7S820 | 7q11.21-22 | 6, 7, 8, 9, 10, 11, 12, 13, 14, 15 | | 10, 11 |
| CSF1PO | 5q33.3-34 | 6, 7, 8, 9, 10, 11, 12, 13, 14, 15 | | 10, 12 |
| D3S1358 | 3p | 12, 13, 14, 15, 16, 17, 18, 19 | VIC | 14, 15 |
| TH01 | 11p15.5 | 4, 5, 6, 7, 8, 9, 9.3, 10, 11, 13.3 | | 8, 9.3 |
| D13S317 | 13q22-31 | 8, 9, 10, 11, 12, 13, 14, 15 | | 11c |
| D16S539 | 16q24-qter | 5, 8, 9, 10, 11, 12,13, 14, 15 | | 11, 12 |
| D2S1338 | 2q35-37.1 | 15, 16, 17, 18, 19, 20, 21, 22, 23, 24, 25, 26, 27, 28 | | 19, 23 |
| D19S433 | 19q12-13.1 | 9, 10, 11, 12, 12.2, 13, 13.2, 14, 14.2, 15, 15.2, 16, 16.2, 17, 17.2 | NED | 14, 15 |
| vWA | 12p12-pter | 11,12, 13, 14, 15, 16, 17, 18, 19, 20, 21, 22, 23, 24 | | 17, 18 |
| TPOX | 2p23-2per | 6, 7, 8, 9, 10, 11, 12, 13 | | 8d |
| D18S51 | 18q21.3 | 7, 9, 10, 10.2, 11, 12, 13, 13.2, 14, 14.2, 15, 16, 17, 18, 19, 20, 21, 22, 23, 24, 25, 26, 27 | | 15, 19 |
| Amelogenin | X: p22.1-22.3 Y: p11.2 | X, Y | PET | X |
| D5S818 | 5q21-31 | 7, 8, 9, 10, 11, 12, 13, 14, 15, 16 | | 11e |
| FGA | 4q28 | 17, 18, 19, 20, 21, 22, 23, 24, 25, 26, 26.2, 27, 28, 29, 30, 30.2, 31.2, 32.2, 33.2, 42.2, 43.2, 44.2, 45.2, 46.2, 47.2, 48.2, 50.2, 51.2 | | 23, 24 |

FIGURE 4

| Amplified Loci: Locus Designation | Chromosome Location | Alleles Included in Identifiler Allelic Ladder | Dye Label | Control DNA 9947A |
|---|---|---|---|---|
| D8S1179 | 8 | 8, 9 10, 11, 12, 13, 14, 15, 16, 17, 18, 19 | 6-FAM | 13a |
| D21S11 | 21q11.2-q21 | 24, 24.2, 25, 26, 27, 28, 28.2, 29, 29.2, 30, 30.2, 31, 31.2, 32, 32.2, 33, 33.2, 34, 34.2, 35, 35.2, 36, 37, 38 | | 30b |
| D7S820 | 7q11.21-22 | 6, 7, 8, 9, 10, 11, 12, 13, 14, 15 | | 10, 11 |
| CSF1PO | 5q33.3-34 | 6, 7, 8, 9, 10, 11, 12, 13, 14, 15 | | 10, 12 |
| D3S1358 | 3p | 12, 13, 14, 15, 16, 17, 18, 19 | VIC | 14, 15 |
| TH01 | 11p15.5 | 4, 5, 6, 7, 8, 9, 9.3, 10, 11, 13.3 | | 8, 9.3 |
| D13S317 | 13q22-31 | 8, 9, 10, 11, 12, 13, 14, 15 | | 11c |
| D16S539 | 16q24-qter | 5, 8, 9, 10, 11, 12,13, 14, 15 | | 11, 12 |
| D2S1338 | 2q35-37.1 | 15, 16, 17, 18, 19, 20, 21, 22, 23, 24, 25, 26, 27, 28 | | 19, 23 |
| D19S433 | 19q12-13.1 | 9, 10, 11, 12, 12.2, 13, 13.2, 14, 14.2, 15, 15.2, 16, 16.2, 17, 17.2 | NED | 14, 15 |
| vWA | 12p12-pter | 11,12, 13, 14, 15, 16, 17, 18, 19, 20, 21, 22, 23, 24 | | 17, 18 |
| TPOX | 2p23-2per | 6, 7, 8, 9, 10, 11, 12, 13 | | 8d |
| D18S51 | 18q21.3 | 7, 9, 10, 10.2, 11, 12, 13, 13.2, 14, 14.2, 15, 16, 17, 18, 19, 20, 21, 22, 23, 24, 25, 26, 27 | | 15, 19 |
| Amelogenin | X: p22.1-22.3 Y: p11.2 | X, Y | PET | X |
| D5S818 | 5q21-31 | 7, 8, 9, 10, 11, 12, 13, 14, 15, 16 | | 11e |
| FGA | 4q28 | 17, 18, 19, 20, 21, 22, 23, 24, 25, 26, 26.2, 27, 28, 29, 30, 30.2, 31.2, 32.2, 33.2, 42.2, 43.2, 44.2, 45.2, 46.2, 47.2, 48.2, 50.2, 51.2 | | 23, 24 |

FIGURE 5

SEQUENCE LISTING

<160> NUMBER OF SEQ ID NOS: 427

<210> SEQ ID NO 1
<211> LENGTH: 111
<212> TYPE: DNA
<213> ORGANISM: Homo sapiens

<400> SEQUENCE: 1
cacatgcaca gccagcaacc ctgtcagcag gagttcccac cagtttcttt ctgagaacat     60
ctgttcaggt ttctctccat ctctatttac tcaggtcaca ggaccttggg g             111

<210> SEQ ID NO 2
<211> LENGTH: 111
<212> TYPE: DNA
<213> ORGANISM: Homo sapiens

<400> SEQUENCE: 2
cacatgcaca gccagcaacc ctgtcagcag gagttcccac cagtttcttt ctgagaacat     60
ctgttcaggt ttctctccat ctctgtttac tcaggtcaca ggaccttggg g             111

<210> SEQ ID NO 3
<211> LENGTH: 126
<212> TYPE: DNA
<213> ORGANISM: Homo sapiens

<400> SEQUENCE: 3
tgaggaagtg aggctcagag ggtaagaaac tttgtcacag agctggtggt gagggtggag     60
attttacact ccctgcctcc cacaccagtt tctccagagt ggaaagactt tcatctcgca    120
ctggca                                                               126

<210> SEQ ID NO 4
<211> LENGTH: 126
<212> TYPE: DNA
<213> ORGANISM: Homo sapiens

<400> SEQUENCE: 4
tgaggaagtg aggctcagag ggtaagaaac tttgtcacag agctggtggt gagggtggag     60
attttacact ccctgcctcc cacaccagtt tctccggagt ggaaagactt tcatctcgca    120
ctggca                                                               126

<210> SEQ ID NO 5
<211> LENGTH: 121
<212> TYPE: DNA
<213> ORGANISM: Homo sapiens

<400> SEQUENCE: 5
gtgccttcag aacctttgag atctgattct attttttaaag cttcttagaa gagagattgc     60
aaagtgggtt gtttctctag ccagacaggg caggcaaata ggggtggctg gtgggatggg    120
a                                                                    121

<210> SEQ ID NO 6
<211> LENGTH: 121
<212> TYPE: DNA
<213> ORGANISM: Homo sapiens

<400> SEQUENCE: 6
gtgccttcag aacctttgag atctgattct attttttaaag cttcttagaa gagagattgc     60
aaagtgggtt gtttctctag ccagacaggg caggtaaata ggggtggctg gtgggatggg    120

|   |   |
|---|---|
| a | 121 |

<210> SEQ ID NO 7
<211> LENGTH: 111
<212> TYPE: DNA
<213> ORGANISM: Homo sapiens

<400> SEQUENCE: 7

| aggtgtgtct ctcttttgtg aggggagggg tcccttctgg cctagtagag ggcctggcct | 60 |
|---|---|
| gcagtgagca ttcaaatcct caaggaacag ggtggggagg tgggacaaag g | 111 |

<210> SEQ ID NO 8
<211> LENGTH: 111
<212> TYPE: DNA
<213> ORGANISM: Homo sapiens

<400> SEQUENCE: 8

| aggtgtgtct ctcttttgtg aggggagggg tcccttctgg cctagtagag ggcctggcct | 60 |
|---|---|
| gcagtgagca ttcaaatcct cgaggaacag ggtggggagg tgggacaaag g | 111 |

<210> SEQ ID NO 9
<211> LENGTH: 139
<212> TYPE: DNA
<213> ORGANISM: Homo sapiens

<400> SEQUENCE: 9

| cctcgcctac tgtgctgttt ctaaccatca tgcttttccc tgaatctctt gagtcttttt | 60 |
|---|---|
| ctgctgtgga ctgaaacttg atcctgagat tcacctctag tccctctgag cagcctcctg | 120 |
| gaatactcag ctgggatgg | 139 |

<210> SEQ ID NO 10
<211> LENGTH: 139
<212> TYPE: DNA
<213> ORGANISM: Homo sapiens

<400> SEQUENCE: 10

| cctcgcctac tgtgctgttt ctaaccatca tgcttttccc tgaatctctt gagtcttttt | 60 |
|---|---|
| ctgctgtgga ctgaaacttg atcctgagat tcacctctag tccctctggg cagcctcctg | 120 |
| gaatactcag ctgggatgg | 139 |

<210> SEQ ID NO 11
<211> LENGTH: 117
<212> TYPE: DNA
<213> ORGANISM: Homo sapiens

<400> SEQUENCE: 11

| aattgcaatg gtgagaggtt gatggtaaaa tcaaacggaa cttgttattt tgtcattctg | 60 |
|---|---|
| atggactgga actgaggatt ttcaatttcc tctccaaccc aagacacttc tcactgg | 117 |

<210> SEQ ID NO 12
<211> LENGTH: 117
<212> TYPE: DNA
<213> ORGANISM: Homo sapiens

<400> SEQUENCE: 12

| aattgcaatg gtgagaggtt gatggtaaaa tcaaacggaa cttgttattt tgtcattctg | 60 |
|---|---|
| atggactgga actgaggatt ttcaatttcc tttccaaccc aagacacttc tcactgg | 117 |

<210> SEQ ID NO 13
<211> LENGTH: 114
<212> TYPE: DNA
<213> ORGANISM: Homo sapiens

<400> SEQUENCE: 13
gaaatgcctt ctcaggtaat ggaaggttat ccaaatattt ttcgtaagta tttcaaatag      60
caatggctcg tctatggtta gtctcacagc cacattctca gaactgctca aacc           114

<210> SEQ ID NO 14
<211> LENGTH: 114
<212> TYPE: DNA
<213> ORGANISM: Homo sapiens

<400> SEQUENCE: 14
gaaatgcctt ctcaggtaat ggaaggttat ccaaatattt ttcgtaagta tttcaaatag      60
caatggctcg tctatggtta gtctcgcagc cacattctca gaactgctca aacc           114

<210> SEQ ID NO 15
<211> LENGTH: 128
<212> TYPE: DNA
<213> ORGANISM: Homo sapiens

<400> SEQUENCE: 15
acccaaaaca ctggagggc ctcttctcat tttcggtaga ctgcaagtgt tagccgtcgg       60
gaccagcttc tgtctggaag ttcgtcaaat tgcagttaag tccaagtatg ccacatagca     120
gataaggg                                                             128

<210> SEQ ID NO 16
<211> LENGTH: 128
<212> TYPE: DNA
<213> ORGANISM: Homo sapiens

<400> SEQUENCE: 16
acccaaaaca ctggagggc ctcttctcat tttcggtaga ctgcaagtgt tagccgtcgg       60
gaccagcttc tgtctggaag ttcgtcaaat tgcagttagg tccaagtatg ccacatagca     120
gataaggg                                                             128

<210> SEQ ID NO 17
<211> LENGTH: 110
<212> TYPE: DNA
<213> ORGANISM: Homo sapiens

<400> SEQUENCE: 17
gcaccagaat ttaaacaacg ctgacaataa atatgcagtc gatgatgact tcccagagct      60
ccagaagcaa ctccagcaca cagagaggcg ctgatgtgcc tgtcaggtgc                110

<210> SEQ ID NO 18
<211> LENGTH: 110
<212> TYPE: DNA
<213> ORGANISM: Homo sapiens

<400> SEQUENCE: 18
gcaccagaat ttaaacaacg ctgacaataa atatgcagtc gatgatgact tcccagagct      60
ccagaagcaa ctccagcaca cggagaggcg ctgatgtgcc tgtcaggtgc                110

<210> SEQ ID NO 19
<211> LENGTH: 116

```
<212> TYPE: DNA
<213> ORGANISM: Homo sapiens

<400> SEQUENCE: 19
tgactgtata ccccaggtgc acccttgggt catctctatc atagaactta tctcacagag      60
tataagagct gatttctgtg tctgcctctc acactagact tccacatcct tagtgc        116

<210> SEQ ID NO 20
<211> LENGTH: 116
<212> TYPE: DNA
<213> ORGANISM: Homo sapiens

<400> SEQUENCE: 20
tgactgtata ccccaggtgc acccttgggt catctctatc atagaactta tctcacagag      60
tataagagct gatttctgtg tctgcctgtc acactagact tccacatcct tagtgc        116

<210> SEQ ID NO 21
<211> LENGTH: 110
<212> TYPE: DNA
<213> ORGANISM: Homo sapiens

<400> SEQUENCE: 21
tgtacgtggt caccagggga cgcctggcgc tgcgagggag gccccgagcc tcgtgccccc      60
gtgaagcttc agctcccctc cccggctgtc cttgaggctc ttctcacact                110

<210> SEQ ID NO 22
<211> LENGTH: 110
<212> TYPE: DNA
<213> ORGANISM: Homo sapiens

<400> SEQUENCE: 22
tgtacgtggt caccagggga cgcctggcgc tgcgagggag gccccgagcc tcgtgccccc      60
gtgaagcttc agctcccctc cctggctgtc cttgaggctc ttctcacact                110

<210> SEQ ID NO 23
<211> LENGTH: 114
<212> TYPE: DNA
<213> ORGANISM: Homo sapiens

<400> SEQUENCE: 23
cagtggaccc tgctgcacct ttcctcccct cccatcaacc tcttttgtgc ctcccctcc       60 gtgtaccacc ttctctgtca ccaaccctgg cctcacaact ctctcctttg ccac          114

<210> SEQ ID NO 24
<211> LENGTH: 114
<212> TYPE: DNA
<213> ORGANISM: Homo sapiens

<400> SEQUENCE: 24
cagtggaccc tgctgcacct ttcctcccct cccatcaacc tcttttgtgc ctcccctcc       60 gtgtaccacc ttctctgtca ccaccctgg cctcacaact ctctcctttg ccac           114

<210> SEQ ID NO 25
<211> LENGTH: 110
<212> TYPE: DNA
<213> ORGANISM: Homo sapiens

<400> SEQUENCE: 25
cagtggcata gtagtccagg ggctcctcct cagcacctcc agcaccttcc aggaggcagc      60
```

```
agcgcaggca gagaacccgc tggaagaatc ggcggaagtt gtcggagagg            110

<210> SEQ ID NO 26
<211> LENGTH: 110
<212> TYPE: DNA
<213> ORGANISM: Homo sapiens

<400> SEQUENCE: 26
cagtggcata gtagtccagg ggctcctcct cagcacctcc agcaccttcc aggaggcagc   60
agcgcaggca gagaacccgc tggaaggatc ggcggaagtt gtcggagagg            110

<210> SEQ ID NO 27
<211> LENGTH: 129
<212> TYPE: DNA
<213> ORGANISM: Homo sapiens

<400> SEQUENCE: 27
aggtctgggg gccgctgaat gccaagctgg gaatcttaaa tgttaaggaa caaggtcata   60
caatgaatgg tgtgatgtaa aagcttggga ggtgatttct gagggtaggt gctgggttta  120
atgggagga                                                         129

<210> SEQ ID NO 28
<211> LENGTH: 129
<212> TYPE: DNA
<213> ORGANISM: Homo sapiens

<400> SEQUENCE: 28
aggtctgggg gccgctgaat gccaagctgg gaatcttaaa tgttaaggaa caaggtcata   60
caatgaatgg tgtgatgtaa aagcttggga ggtgattttt gagggtaggt gctgggttta  120
atgggagga                                                         129

<210> SEQ ID NO 29
<211> LENGTH: 107
<212> TYPE: DNA
<213> ORGANISM: Homo sapiens

<400> SEQUENCE: 29
acggttctgt cctgtagggg agaaaagtcc tcgttgttcc tctgggatgc aacatgagag   60
agcagcacac tgaggcttta tggattgccc tgccacaagt gaacagg              107

<210> SEQ ID NO 30
<211> LENGTH: 107
<212> TYPE: DNA
<213> ORGANISM: Homo sapiens

<400> SEQUENCE: 30
acggttctgt cctgtagggg agaaaagtcc tcgttgttcc tctgggatgc aacatgagag   60
agcagcacac tgaggcttta tgggttgccc tgccacaagt gaacagg              107

<210> SEQ ID NO 31
<211> LENGTH: 127
<212> TYPE: DNA
<213> ORGANISM: Homo sapiens

<400> SEQUENCE: 31
gcgcagtcag atgggcgtgc tggcgtctgt cttctctctc tcctgctctc tggcttcatt   60
tttctctcct tctgtctcac cttctttcgt gtgcctgtgc acacacgt ttgggacaag   120 ggctgga                                                          127
```

<210> SEQ ID NO 32
<211> LENGTH: 127
<212> TYPE: DNA
<213> ORGANISM: Homo sapiens

<400> SEQUENCE: 32
gcgcagtcag atgggcgtgc tggcgtctgt cttctctctc tcctgctctc tggcttcatt      60
tttctctcct tctgtctcac cttctttcgt gtgcctgtgc atacacacgt ttgggacaag     120
ggctgga                                                               127

<210> SEQ ID NO 33
<211> LENGTH: 130
<212> TYPE: DNA
<213> ORGANISM: Homo sapiens

<400> SEQUENCE: 33
gccggacctg cgaaatccca aaatgccaaa cattcccgcc tcacatgatc ccagagagag      60
gggacccagt gttcccagct tgcagctgag gagcccgagg ttgccgtcag atcagagccc     120
cagttgcccg                                                            130

<210> SEQ ID NO 34
<211> LENGTH: 130
<212> TYPE: DNA
<213> ORGANISM: Homo sapiens

<400> SEQUENCE: 34
gccggacctg cgaaatccca aaatgccaaa cattcccgcc tcacatgatc ccagagagag      60
gggacccagt gttcccagct tgcagctgag gagcccgagt ttgccgtcag atcagagccc     120
cagttgcccg                                                            130

<210> SEQ ID NO 35
<211> LENGTH: 121
<212> TYPE: DNA
<213> ORGANISM: Homo sapiens

<400> SEQUENCE: 35
agcagcctcc ctcgactagc tcacactacg ataaggaaaa ttcatgagct ggtgtccaag      60
gagggctggg tgactcgtgg ctcagtcagc atcaagattc ctttcgtctt tcccctctgc     120
c                                                                     121

<210> SEQ ID NO 36
<211> LENGTH: 121
<212> TYPE: DNA
<213> ORGANISM: Homo sapiens

<400> SEQUENCE: 36
agcagcctcc ctcgactagc tcacactacg ataaggaaaa ttcatgagct ggtgtccaag      60
gagggctggg tgactcgtgg ctcagtcagc gtcaagattc ctttcgtctt tcccctctgc     120
c                                                                     121

<210> SEQ ID NO 37
<211> LENGTH: 138
<212> TYPE: DNA
<213> ORGANISM: Homo sapiens

<400> SEQUENCE: 37
tggcattgcc tgtaatatac atagccatgg ttttttatag gcaatttaag atgaatagct      60
tctaaactat agataagttt cattacccca ggaagctgaa ctatagctac tttacccaaa     120
atcattagaa tggtgctt                                                   138

<210> SEQ ID NO 38
<211> LENGTH: 138
<212> TYPE: DNA
<213> ORGANISM: Homo sapiens

<400> SEQUENCE: 38
tggcattgcc tgtaatatac atagccatgg ttttttatag gcaatttaag atgaatagct      60
tctaaactat agataagttt cattacccca ggaagctgaa ctatagctac tttcccaaa     120 atcattagaa tggtgctt                                                   138

<210> SEQ ID NO 39
<211> LENGTH: 136
<212> TYPE: DNA
<213> ORGANISM: Homo sapiens

<400> SEQUENCE: 39
atgaagcctt ccaccaactg cctgtatgac tcatctgggg acttctgctc tatactcaaa      60
gtggcttagt cactgccaat gtatttccat atgagggacg atgattacta aggaaatata    120
gaaacaacaa ctgatc                                                     136

<210> SEQ ID NO 40
<211> LENGTH: 136
<212> TYPE: DNA
<213> ORGANISM: Homo sapiens

<400> SEQUENCE: 40
atgaagcctt ccaccaactg cctgtatgac tcatctgggg acttctgctc tatactcaaa      60
gtggcttagt cactgccaat gtatttccat atgagggacg gtgattacta aggaaatata    120
gaaacaacaa ctgatc                                                     136

<210> SEQ ID NO 41
<211> LENGTH: 118
<212> TYPE: DNA
<213> ORGANISM: Homo sapiens

<400> SEQUENCE: 41
acaacagaat caggtgattg gagaaaagat cacaggccta ggcacccaag gcttgaagga      60
tgaaagaatg aaagatggac ggaacaaaat taggacctta attctttgtt cagttcag     118

<210> SEQ ID NO 42
<211> LENGTH: 118
<212> TYPE: DNA
<213> ORGANISM: Homo sapiens

<400> SEQUENCE: 42
acaacagaat caggtgattg gagaaaagat cacaggccta ggcacccaag gcttgaagga      60
tgaaagaatg aaagatggac ggaagaaaat taggacctta attctttgtt cagttcag     118

<210> SEQ ID NO 43
<211> LENGTH: 150
<212> TYPE: DNA
<213> ORGANISM: Homo sapiens

<400> SEQUENCE: 43

```
ttggggtaaa ttttcattgt catatgtgga atttaaatat accatcatct acaaagaatt      60
ccacagagtt aaatatctta agttaaacac ttaaaataag tgtttgcgtg atattttgat     120
gacagataaa cagagtctaa ttcccacccc                                      150
```

<210> SEQ ID NO 44
<211> LENGTH: 150
<212> TYPE: DNA
<213> ORGANISM: Homo sapiens

<400> SEQUENCE: 44

```
ttggggtaaa ttttcattgt catatgtgga atttaaatat accatcatct acaaagaatt      60
ccacagagtt aaatatctta agttaaacac ttaaaataag tgtttgcgtg atattttgat     120
gatagataaa cagagtctaa ttcccacccc                                      150
```

<210> SEQ ID NO 45
<211> LENGTH: 145
<212> TYPE: DNA
<213> ORGANISM: Homo sapiens

<400> SEQUENCE: 45

```
tgcaattcaa atcaggaagt atgaccaaaa gacagagatc ttttttggat gatccctagc      60
ctagcaatgc ctggcagcca tgcaggtgca atgtcaacct taaataatgt attgcaaact     120
cagagctgac aaacctcgat gttgc                                            145
```

<210> SEQ ID NO 46
<211> LENGTH: 145
<212> TYPE: DNA
<213> ORGANISM: Homo sapiens

<400> SEQUENCE: 46

```
tgcaattcaa atcaggaagt atgaccaaaa gacagagatc ttttttggat gatccctagc      60
ctagcaatgc ctggcagcca tgcaggtgca atgtcaacct taaataatgt attgcaaatt     120
cagagctgac aaacctcgat gttgc                                            145
```

<210> SEQ ID NO 47
<211> LENGTH: 124
<212> TYPE: DNA
<213> ORGANISM: Homo sapiens

<400> SEQUENCE: 47

```
ctgtgctctg cgaatagctg cagaagtaac ttggggaccc aaaataaagc agaatgctaa      60
tgtcaagtcc tgagaaccaa gccctgggac tctggtgcca tttcggattc tccatgagca     120
tggt                                                                  124
```

<210> SEQ ID NO 48
<211> LENGTH: 124
<212> TYPE: DNA
<213> ORGANISM: Homo sapiens

<400> SEQUENCE: 48

```
ctgtgctctg cgaatagctg cagaagtaac ttggggaccc aaaataaagc agaatgctaa      60
tgtcaagtcc tgagaaccaa gccctgggac tctggtgcca ttttggattc tccatgagca     120
tggt                                                                  124
```

<210> SEQ ID NO 49

```
<211> LENGTH: 118
<212> TYPE: DNA
<213> ORGANISM: Homo sapiens

<400> SEQUENCE: 49
tttttccagc caactcaagg ccaaaaaaaa tttcttaata tagttattat gcgaggggag      60
gggaagcaaa ggagcacagg tagtccacag aataagacac aagaaacctc aagctgtg       118

<210> SEQ ID NO 50
<211> LENGTH: 118
<212> TYPE: DNA
<213> ORGANISM: Homo sapiens

<400> SEQUENCE: 50
tttttccagc caactcaagg ccaaaaaaaa tttcttaata tagttattat gcgaggggag      60
gggaagcaaa ggagcacagg tagtccacag aataggacac aagaaacctc aagctgtg       118

<210> SEQ ID NO 51
<211> LENGTH: 110
<212> TYPE: DNA
<213> ORGANISM: Homo sapiens

<400> SEQUENCE: 51
tcttctcgtc ccctaagcaa acaacatccg cttgcttctg tctgtgtaac cacagtgaat      60
gggtgtgcac gcttgatggg cctctgagcc cctgttgcac aaaccagaaa                110

<210> SEQ ID NO 52
<211> LENGTH: 110
<212> TYPE: DNA
<213> ORGANISM: Homo sapiens

<400> SEQUENCE: 52
tcttctcgtc ccctaagcaa acaacatccg cttgcttctg tctgtgtaac cacagtgaat      60
gggtgtgcac gcttggtggg cctctgagcc cctgttgcac aaaccagaaa                110

<210> SEQ ID NO 53
<211> LENGTH: 110
<212> TYPE: DNA
<213> ORGANISM: Homo sapiens

<400> SEQUENCE: 53
cacatggggg cattaagaat cgcccaggga ggaggaggga gaacgcgtgc ttttcacatt      60
tgcatttgaa tttcgagtt cccaggatgt gttttttgtgc tcatcgatgt                110

<210> SEQ ID NO 54
<211> LENGTH: 110
<212> TYPE: DNA
<213> ORGANISM: Homo sapiens

<400> SEQUENCE: 54
cacatggggg cattaagaat cgcccaggga ggaggaggga gaacgcgtgc ttttcacatt      60
tgcatttgaa tttttgagtt cccaggatgt gttttttgtgc tcatcgatgt               110

<210> SEQ ID NO 55
<211> LENGTH: 128
<212> TYPE: DNA
<213> ORGANISM: Homo sapiens

<400> SEQUENCE: 55
gggctctgag gtgtgtgaaa taaaaacaaa tgtccatgtc tgtccttta tggcattttg       60
```

-continued

```
ggactttaca tttcaaacat ttcagacatg tatcacaaca cgaaggaata acagttccag    120
ggatatct                                                             128

<210> SEQ ID NO 56
<211> LENGTH: 128
<212> TYPE: DNA
<213> ORGANISM: Homo sapiens

<400> SEQUENCE: 56
gggctctgag gtgtgtgaaa taaaaacaaa tgtccatgtc tgtcctttta tggcattttg    60
ggactttaca tttcaaacat ttcagacatg tatcacaaca cgagggaata acagttccag   120
ggatatct                                                             128

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cacatgcaca gccagcaacc c                                              21

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ccccaaggtc ctgtgacctg agt                                            23

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tgaggaagtg aggctcagag ggt                                            23

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tgccagtgcg agatgaaagt cttt                                           24

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 61
gtgccttcag aacctttgag atctgat                                        27

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tcccatccca ccagccaccc                                                20

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
aggtgtgtct ctcttttgtg agggg                                          25

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cctttgtccc acctcccac c                                               21

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cctcgcctac tgtgctgttt ctaacc                                         26

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ccatcccagc tgagtattcc aggag                                          25

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 67
aattgcaatg gtgagaggtt gatggt                                            26

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ccagtgagaa gtgtcttggg ttgg                                              24

<210> SEQ ID NO 69
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gaaatgcctt ctcaggtaat ggaaggt                                           27

<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ggtttgagca gttctgagaa tgtggct                                           27

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
acccaaaaca ctggaggggc ct                                                22

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cccttatctg ctatgtggca tacttgg                                           27

<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
```
gcaccagaat ttaaacaacg ctgacaa                                         27

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gcacctgaca ggcacatcag cg                                              22

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tgactgtata ccccaggtgc accc                                            24

<210> SEQ ID NO 76
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gcactaagga tgtggaagtc tagtgtg                                         27

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tgtacgtggt caccagggga cg                                              22

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
agtgtgagaa gagcctcaag gacagc                                          26

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cagtggaccc tgctgcacct t                                                 21

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gtggcaaagg agagagttgt gagg                                              24

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
cagtggcata gtagtccagg ggct                                              24

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cctctccgac aacttccgcc g                                                 21

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
aggtctgggg gccgctgaat                                                   20

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tcctcccatt aaacccagca cct                                               23

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
acggttctgt cctgtagggg aga                                               23

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cctgttcact tgtggcaggg ca                                              22

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gcgcagtcag atgggcgtgc                                                 20

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
tccagcccct gtcccaaacg tgt                                             23

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gccggacctg cgaaatccca a                                               21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
cgggcaactg gggctctgat c                                               21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
agcagcctcc ctcgactagc t                                               21

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 92
ggcagagggg aaagacgaaa gga                                              23

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 93
tggcattgcc tgtaatatac atag                                             24

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 94
aagcaccatt ctaatgattt tgg                                              23

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 95
atgaagcctt ccaccaactg                                                  20

<210> SEQ ID NO 96
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 96
gatcagttgt tgtttctata tttcctt                                          27

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 97
acaacagaat caggtgattg ga                                               22

```
<210> SEQ ID NO 98
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ctgaactgaa caaagaatta aggtc                                            25

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
ttggggtaaa ttttcattgt ca                                               22

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ggggtgggaa ttagactctg                                                  20

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tgcaattcaa atcaggaagt atg                                              23

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gcaacatcga ggtttgtcag                                                  20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ctgtgctctg cgaatagctg                                                  20

<210> SEQ ID NO 104
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
accatgctca tggagaatcc                                               20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
tttttccagc caactcaagg                                               20

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
cacagcttga ggtttcttgt g                                             21

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
tcttctcgtc ccctaagcaa                                               20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
tttctggttt gtgcaacagg                                               20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
cacatggggg cattaagaat                                               20

<210> SEQ ID NO 110
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
acatcgatga gcacaaaaac ac                                              22

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gggctctgag gtgtgtgaaa                                                 20

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
agatatccct ggaactgtta ttcc                                            24

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
acagtaactg ccttcataga tag                                             23

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gtgtcagacc ctgttctaag ta                                              22

<210> SEQ ID NO 115
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
aaataaaatt aggcatattt acaagc                                          26

<210> SEQ ID NO 116
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 116
gctgagtgat tgtctgtaa ttg                                           23

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
cctgttcctc ccttatttcc c                                            21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gggaacacag actccatggt g                                            21

<210> SEQ ID NO 119
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
cttagggaac cctcactgaa tg                                           22

<210> SEQ ID NO 120
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
gtccttgtca gcgtttattt gc                                           22

<210> SEQ ID NO 121
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
aataatcagt atgtgacttg gattga                                       26

<210> SEQ ID NO 122
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 122
ataggatgga tggatagatg ga                                              22

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
cagagcaaga ccctgtctca t                                               21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
tcaacagagg cttgcatgta t                                               21

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gggtgatttt cctctttggt                                                 20

<210> SEQ ID NO 126
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
aacatttgta tctttatctg tatccttatt tat                                  33

<210> SEQ ID NO 127
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gaacacttgt catagtttag aacgaac                                         27

<210> SEQ ID NO 128
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 128
tcattgacag aattgcacca                                              20

<210> SEQ ID NO 129
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
tttgtatttc atgtgtacat tcgtatc                                      27

<210> SEQ ID NO 130
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
acctatcctg tagattattt tcactgtg                                     28

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
tctgacccat ctaacgccta                                              20

<210> SEQ ID NO 132
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
cagacagaaa gatagataga tgattga                                      27

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
atacagacag acagacaggt g                                            21

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 134
gcatgtatct atcatccatc tct                                            23

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
tgagtgacaa attgagacct t                                              21

<210> SEQ ID NO 136
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
gtcttacaat aacagttgct actatt                                         26

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
attccccaag tgaattgc                                                  18

<210> SEQ ID NO 138
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
ggtagataga ctggatagat agacga                                         26

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
tggaaacaga aatggcttgg                                                20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gattgcagga gggaaggaag                                              20

<210> SEQ ID NO 141
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
gagcaagaca ccatctcaag aa                                           22

<210> SEQ ID NO 142
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
gaaattttac atttatgttt atgattctct                                   30

<210> SEQ ID NO 143
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
ggcgactgag caagactc                                                18

<210> SEQ ID NO 144
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
ggttattaat tgagaaaact ccttaca                                      27

<210> SEQ ID NO 145
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
attttccccg atgatagtag tct                                          23

<210> SEQ ID NO 146
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 146
gcgaatgtat gattggcaat attttt                                              26

<210> SEQ ID NO 147
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
acatgtatcc cagaacttaa agtaaac                                             27

<210> SEQ ID NO 148
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
gcagaaggga aaattgaagc tg                                                  22

<210> SEQ ID NO 149
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
cagagacacc gaaccaataa ga                                                  22

<210> SEQ ID NO 150
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
gccacatgaa tcaattccta taataaa                                             27

<210> SEQ ID NO 151
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
gcacatgtac cctaaaactt aaaat                                               25

<210> SEQ ID NO 152
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
```
gtcaaccaaa actcaacaag tagtaa                                              26

<210> SEQ ID NO 153
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
aagatgaaat tgccatgtaa aaata                                               25

<210> SEQ ID NO 154
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
gtgtgtataa caaaattcct atgatgg                                             27

<210> SEQ ID NO 155
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
gcacccaaaa ctgaatgtca ta                                                  22

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
ggtgagagtg agaccctgtc                                                     20

<210> SEQ ID NO 157
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
tgtaataact ctacgactgt ctgtctg                                             27

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
gaataggagg tggatggatg g                       21

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
gagcgagacc ctgtctcaag                          20

<210> SEQ ID NO 160
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
ggaaaagaca taggatagca attt                     24

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
tctggattga tctgtctgtc c                        21

<210> SEQ ID NO 162
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
gaattaaata ccatctgagc actgaa                   26

<210> SEQ ID NO 163
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
tgttataatg cattgagttt tattctg                  27

<210> SEQ ID NO 164
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
gcctgtctca aaaataaaga gatagaca                 28

<210> SEQ ID NO 165
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
ttaatgaatt gaacaaatga gtgag                                          25

<210> SEQ ID NO 166
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
gcaactctgg ttgtattgtc ttcat                                          25

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
caaagcgaga ctctgtctca a                                              21

<210> SEQ ID NO 168
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
gaaaatgcta tcctctttgg tataaat                                        27

<210> SEQ ID NO 169
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
gggtatttca agataactgt agatagg                                        27

<210> SEQ ID NO 170
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
gcttctgaaa gcttctagtt tacc                                           24

<210> SEQ ID NO 171
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
tccacatcct caccaacac                                                   19

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
gcctaggaag gctactgtca a                                                21

<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
ccacccgtcc atttaggc                                                    18

<210> SEQ ID NO 174
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
gtgaaaaagt agatataatg gttggtg                                          27

<210> SEQ ID NO 175
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
ggttttccaa gagatagacc aatta                                            25

<210> SEQ ID NO 176
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
gtcctctcat aaatccctac tcatatc                                          27

<210> SEQ ID NO 177
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 177
ctgttggtac ataataggta ggtaggt                     27

<210> SEQ ID NO 178
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 178
gtcgtgggcc ccataaatc                              19

<210> SEQ ID NO 179
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 179
aaggtacata acagttcaat agaaagc                     27

<210> SEQ ID NO 180
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 180
gtgaaatgac tgaaaatag taacca                       26

<210> SEQ ID NO 181
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 181
ctaggagatc atgtgggtat gatt                        24

<210> SEQ ID NO 182
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 182
gcagtgaata aatgaacgaa tgga                        24

<210> SEQ ID NO 183

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
cccaaaatta cttgagccaa t                                              21

<210> SEQ ID NO 184
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
gagacaaaat gaagaaacag acag                                           24

<210> SEQ ID NO 185
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
tctttgctct catgaataga tcagt                                          25

<210> SEQ ID NO 186
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
gtttgtgata atgaacccac tcag                                           24

<210> SEQ ID NO 187
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
tgaacacaga tgttaagtgt gtatatg                                        27

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
gtctgaggtg gacagttatg aaa                                            23

<210> SEQ ID NO 189
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
ctgtggctca tctatgaaaa ctt                                           23

<210> SEQ ID NO 190
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
gaagtggctg tggtgttatg at                                            22

<210> SEQ ID NO 191
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
ttctgttggt atagagcagt gttt                                          24

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
gtgacaggaa ggacggaatg                                               20

<210> SEQ ID NO 193
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
catgaggttt gcaaatacta tcttaac                                       27

<210> SEQ ID NO 194
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
gttttaattt tctccaaatc tcca                                          24

<210> SEQ ID NO 195
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 195
tcttagccta gatagatact tgcttcc                                             27

<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
gtcaaccttt gaggctatag gaa                                                 23

<210> SEQ ID NO 197
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
tcctggaaac aaaagtatt                                                      19

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
aaccttacaa caaagctaga a                                                   21

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
actaagcctt ggggatccag                                                     20

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
tgctgtggaa atactaaaag g                                                   21

<210> SEQ ID NO 201
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 201
ctccagaggt aatcctgtga                                                  20

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
tggtgtgaga tggtatctag g                                                21

<210> SEQ ID NO 203
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
gtataatcca tgaatcttgt tt                                               22

<210> SEQ ID NO 204
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
ttcaaattgt atataagaga gt                                               22

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
gcaggaaagt tattttttaat                                                 20

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
tgcttgagaa agctaacact t                                                21

<210> SEQ ID NO 207
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 207
cagtgtttgg aaattgtctg                                          20

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
ggcactggga gattattgta                                          20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
tcctgttgtt aagtacacat                                          20

<210> SEQ ID NO 210
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
gggccgtaat tacttttg                                            18

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
actcagtagg cactttgtgt c                                        21

<210> SEQ ID NO 212
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
tcttccacca caccaatc                                            18

<210> SEQ ID NO 213
<211> LENGTH: 19
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 213
tggcttttca aaggtaaaa                                                        19

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
gcaacgttaa catctgaatt t                                                     21

<210> SEQ ID NO 215

<400> SEQUENCE: 215

000

<210> SEQ ID NO 216
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
attttatatg tcatgatcta ag                                                    22

<210> SEQ ID NO 217
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
agagattaca ggtgtgagc                                                        19

<210> SEQ ID NO 218
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
atgatcctca actgcctct                                                        19

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
tgaaactcaa aagagaaaag                                                       20

```
<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
acagatttct acttaaaatt                                                    20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
tgaaactcaa aagagaaaag                                                    20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
acagatttct acttaaaatt                                                    20

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
gcaaaggggt actctatgta                                                    20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
tatcgggtca tcttgttaaa                                                    20

<210> SEQ ID NO 225
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
tctaacaaag ctctgtccaa aa                                                 22

<210> SEQ ID NO 226
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
ccacactgaa taactggaac a                                              21

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
gcaagcaagc tctctacctt c                                              21

<210> SEQ ID NO 228
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
tgttcttcca aaattcacat gc                                             22

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
atttcactat tccttcattt t                                              21

<210> SEQ ID NO 230
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
taattgttgc acactaaatt ac                                             22

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
aaaaagccac agaaatcagt c                                              21

<210> SEQ ID NO 232
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
ttcttatatc tcactgggca tt                                              22

<210> SEQ ID NO 233
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
ggatggtaga agagaagaaa gg                                              22

<210> SEQ ID NO 234
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
ggatggtaga agagaagaaa gg                                              22

<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
tgcaaagatg cagaaccaac                                                 20

<210> SEQ ID NO 236
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
ttttgttcct tgtcctggct ga                                              22

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
tgcaaagatg cagaaccaac                                                 20

<210> SEQ ID NO 238
<211> LENGTH: 21
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 238
gcctccagct ctatccaagt t    21

<210> SEQ ID NO 239
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 239
ccttaatatc ttcccatgtc ca    22

<210> SEQ ID NO 240
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 240
attgttagtg cctcttctgc tt    22

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 241
gagaagtgag gtcagcagct    20

<210> SEQ ID NO 242
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 242
tttctaaatt tccattgaac ag    22

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 243
gaaattggca atctgattct    20

<210> SEQ ID NO 244
<211> LENGTH: 21
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 244
caacttgtcc tttattgatg t                                              21

<210> SEQ ID NO 245
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
ctatgttgat aaaacattga aa                                             22

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
gcctgtctgg aatatagttt                                                20

<210> SEQ ID NO 247
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
cagggcatat aatctaagct gt                                             22

<210> SEQ ID NO 248
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
caatgactct gagttgagca c                                              21

<210> SEQ ID NO 249
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
actctctccc tccctct                                                   18

<210> SEQ ID NO 250
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 250
tatggcccca aaactattct                                               20

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
acaagtactg ggcagattga                                               20

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
gccaggttta gctttcaagt                                               20

<210> SEQ ID NO 253
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
ttttatatca ggagaaacac tg                                            22

<210> SEQ ID NO 254
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
ccagaatttt ggaggtttaa t                                             21

<210> SEQ ID NO 255
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
tgtcattcct cctttatctc ca                                            22

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 256
ttcttttgcc tctcccaaag                                           20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
accctggcac agtgttgact                                           20

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
tgggcctgag ttgagaagat                                           20

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
aatttgtaag tatgtgcaac g                                         21

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
tttttcccat ttccaactct                                           20

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
aaaagatgag acaggcaggt                                           20

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
acccctgtga atctcaaaat                                                     20

<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
gcacttgctt ctattgtttg t                                                   21

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
cccttcctct cttccattct                                                     20

<210> SEQ ID NO 265
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
agcactgcag gta                                                            13

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
acagatacca aagaactgca a                                                   21

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
tggacacctt tcaacttaga                                                     20

<210> SEQ ID NO 268
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 268
gaacagtaat gttgaacttt tt                                              22

<210> SEQ ID NO 269
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
tcttgcaaaa agcttagcac a                                               21

<210> SEQ ID NO 270
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
aaaaagatct caaagggtcc a                                               21

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
gcttttgctg aacatcaagt                                                 20

<210> SEQ ID NO 272
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
ccttccagca gcatagtct                                                  19

<210> SEQ ID NO 273
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
aaatccagga tgtgcagt                                                   18

<210> SEQ ID NO 274
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
```

```
atgatgaggt cagtggtgt                                              19
```

<210> SEQ ID NO 275
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275

```
catcacagat catagtaaat gg                                          22
```

<210> SEQ ID NO 276
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276

```
aattattatt ttgcaggcaa t                                           21
```

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277

```
catgaggcaa acacctttcc                                             20
```

<210> SEQ ID NO 278
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278

```
gctggactca ggataaagaa ca                                          22
```

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279

```
tggaagcctg agctgactaa                                             20
```

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
ccttcttttc ccccagaatc                                              20

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
taggagaaca gaagatcaga g                                            21

<210> SEQ ID NO 282
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
aaagactatt gctaaatgct tg                                           22

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
taagcgtagg gctgtgtgtg                                              20

<210> SEQ ID NO 284
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
ggacggatag actccagaag g                                            21

<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
gaatgacctt ggcactttta tca                                          23

<210> SEQ ID NO 286
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
aaggatagag atatacagat gaatgga                                      27

```
<210> SEQ ID NO 287
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
catgcaccgc gcaaatac                                                 18

<210> SEQ ID NO 288
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
atgcctcacc cacaaacac                                                19

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
tccaagccct tctcactcac                                               20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
ctgggacggt gacattttct                                               20

<210> SEQ ID NO 291
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
cccaggaaga gtggaaagat t                                             21

<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 292
ttagcttgca tgtacctgtg t                                             21
```

```
<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
agctagatgg ggtgaattتt                                                     20

<210> SEQ ID NO 294
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
tgggctgagg ggagattc                                                       18

<210> SEQ ID NO 295
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
atcaagctaa ttaatgttat ct                                                  22

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
aatgaataag gtcctcagag                                                     20

<210> SEQ ID NO 297
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
tttaatctga tcattgccct a                                                   21

<210> SEQ ID NO 298
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
agctgtgggt gaccttga                                                       18
```

```
<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
tgtcccacca ttgtgtatta                                              20

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
tcagacttga agtccaggat                                              20

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
gcttcagggg tgttagtttt                                              20

<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
ctttgtgaaa agtcgtccag                                              20

<210> SEQ ID NO 303
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
ccatcatgga aagcatgg                                                18

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
tcatctccat gactgcacta                                              20

<210> SEQ ID NO 305
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
gagatgacgg agtagctcat                                                  20

<210> SEQ ID NO 306
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
cccagctgca ctgtctac                                                    18

<210> SEQ ID NO 307
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
tcttgttcca atcacaggac                                                  20

<210> SEQ ID NO 308
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
atgctgttag ctgaagctct                                                  20

<210> SEQ ID NO 309
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
tgaaagctcc taaagcagag                                                  20

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
ttgaagagat gtgctatcat                                                  20

<210> SEQ ID NO 311
<211> LENGTH: 54
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
gccgcctgca gcccgcgccc ccgtgcccc cgccccgccg ccggcccggg cgcc            54

<210> SEQ ID NO 312
<211> LENGTH: 601
<212> TYPE: DNA
<213> ORGANISM: Homo sapiens

<400> SEQUENCE: 312
catagtgaca ggtatatgcc caactaactg tggaaaacag ttctttcttt caaccttact     60
catcaccctc acggtctgtt tatgaggctc tcctccacca gccagaaagg atgacgtgcc    120
atacctgcaa aacttataca gcatcaacag aatgaatctt tccaacaagc cgaaacattg    180
agtattgtgg cacagaatat gccccaccca ttactcaatc tagatatcct tttattccac    240
cgtctcatga ttttcttttt cctggaaaac aaaagtattt ctttcatagc ccagctagca    300
ygataaatca gcgagtcaga attctagctt tgttgtaagg ttttgcgaat atctgatcct    360
cttattttgt acttttctat ttcctaggca aatctgagta tttcacccag ttttccttaa    420
ctaggcattg aaaactcagt ttttttctta caaaccttca tgtcttcctg ctcatttgca    480
cagtcttatc ttgcacctcc tataaaatgg agaaacttga cattaaaacg taatttttat    540
tacattttga gggattccca gagaattttt ccccaatctc cttaggtagg gacttcttta    600
c                                                                   601

<210> SEQ ID NO 313
<211> LENGTH: 601
<212> TYPE: DNA
<213> ORGANISM: Homo sapiens

<400> SEQUENCE: 313
gtgggaacta tagtaaagaa gtccctacct aaggagattg gggaaaaatt ctctgggaat     60
ccctcaaaat gtaataaaaa ttacgtttta atgtcaagtt tctccatttt ataggaggtg    120
caagataaga ctgtgcaaat gagcaggaag acatgaaggt ttgtaagaaa aaaactgagt    180
tttcaatgcc tagttaagga aaactgggtg aaatactcag atttgcctag gaaatagaaa    240
agtacaaaat aagaggatca gatattcgca aaaccttaca acaaagctag aattctgact    300
ygctgattta tcgtgctagc tgggctatga agaaatact tttgttttcc aggaaaaaga    360
aaatcatgag acgtggaat aaaaggatat ctagattgag taatgggtgg ggcatattct    420
gtgccacaat actcaatgtt tcggcttgtt ggaaagattc attctgttga tgctgtataa    480
gttttgcagg tatggcacgt catcctttct ggctggtgga ggagagcctc ataaacagac    540
cgtgagggtg atgagtaagg ttgaaagaaa gaactgtttt ccacagttag ttgggcatat    600
a                                                                   601

<210> SEQ ID NO 314
<211> LENGTH: 650
<212> TYPE: DNA
<213> ORGANISM: Homo sapiens

<400> SEQUENCE: 314
tttattggtc ctgactggta caaatactga taaaaaggat tttaagatca tattcatact     60
```

```
tttgggaat gagagccaca attaattaac aatgtctgcc atgagattgg atgcaagagt    120
atggcactca tactattcct acttctgtct aattacacta tttgtttctg tgtgcaaaaa    180
tctttggtag gtggtggatg tgcccaagac acagggaaga aaagaagta aacagggaag    240 tacaacacag actctgaaat ggggcatcat ggaagacgga gctttgtcgt cttggtcttt    300
gctgtatatt cacttcctac aacagtgcta aataccttgt ggatgcttaa atatattaaa    360
tgaatgcata aatgaaaaga gtaaataaag agtgtatatg aaagtatgta gataaaattc    420
ttcactaagc cttggggatc cagctgcttm aggactaaga ccgtatctag ctcctttag    480 tatttccaca gcatgccatg gagatacatg tttctgatta tatatgatac atggaaatta    540
tatgttgttg aatgagtgat tgagtaaatg tgtactaggg cagctaatca taaatatttc    600
tactattgct aaaatgactg gatttatcca ttccttctga gagtttatac    650
```

<210> SEQ ID NO 315
<211> LENGTH: 626
<212> TYPE: DNA
<213> ORGANISM: Homo sapiens

<400> SEQUENCE: 315

```
ctgcttaagg actaagaccr tatctagctc cttttagtat ttccacagca tgccatggag    60
atacatgttt ctgattatat atgatacatg gaaattatat gttgttgaat gagtgattga    120
gtaaatgtgt actagggcag ctaatcataa atatttctac tattgctaaa atgactggat    180
ttatccattc cttctgagag tttatactga ttgcttatat tgtatcaaat accgtaactg    240
agggcaatgt ttactcaaac taatagcacc attcaaattt atgcaaacaa taacactata    300
tctttaaaat gttttcacta aaagctgcat aaagagtgta ttcaacaaca atagaataat    360
tttacaatct ttttttcttgc ttaatggcca tttgtgcctt ctgacatgct gctagccatt    420
caaaggtcac actaccttga agttgaagat caagacaaat gattagactc ataaagaca    480 aatcacgtct ttctggacag gtgattatta ataattaatt agcatttaaa catgtattat    540
ttaagttctt tttaagttat aaagtctttg atttgctaaa cagtttaaat aatgaataaa    600
acataaaata ataatagtta ccattt    626
```

<210> SEQ ID NO 316
<211> LENGTH: 1113
<212> TYPE: DNA
<213> ORGANISM: Homo sapiens

<400> SEQUENCE: 316

```
caagagctgc atctcactcc aattttctt ctccctataa ccttatctag attcccagtt    60
gagggaaccg atgacctaat tcctctcagt ttaaatgcaa cacaggagca aattccaaat    120
atctatgctg gtcttgctgg gattgcagaa ccccagggtg gttatcctcc tccagaggta    180
atcctgtgat cagcactaac rccacatacc agccctttca tcagcttgtt ggagaagcat    240
ctttacttcc caccaagcag tgacctagat accatctcac accagttaga atcaggatca    300
ttaaaaagtc aagaaaaaac agatgctgaa gaggatgtgg agaaatagga atgcttttac    360
actgttagtg ggaatgtaaa ttagttcaac cattgtcaaa gacagtgtgg cgatccctca    420
cagatctaga accagaaata ccatttgacc cagcaatccc attactgggt ctataccaa    480 aggattataa attactctac tataaagaca catgcacaca tatgtttatt gcagcaccat    540
tcacaatagc aaagaattgc aaccaacccct aatgcccatc aatgacagac tggataaaga    600
```

| | | | | | |
|---|---|---|---|---|---|
| aaatctggca | catatacacc | atggaatact | acgcagccat | aaaaaaggat | gagtttatgt | 660 |
| cctttacagg | gacatggatg | aagctggaaa | ccatcattct | cagcaaacta | acacaggaac | 720 |
| agaaaaccaa | acacatgttc | tcactcacaa | gtgggagttg | aacaatgaga | acacatggac | 780 |
| acagggaggg | gaacatcaca | caccactgct | tgtcaggggg | tggggggcta | ggggaaggat | 840 |
| agcattagga | gaaataccta | atgtagatga | agggttgatg | ggtgcagcaa | accaccatgg | 900 |
| catgtgtata | cctgtgtaac | aaacctccat | gttctgcacg | tgtatcccag | aacttaaagt | 960 |
| acaatacaaa | aaaaaaaaa | agtgtaatcc | agtttacatt | ttcaaggtca | aagtgggtac | 1020 |
| aatgctatct | atcttgggct | aagaagagaa | aaggaaaaat | tcttgcttta | aatcttagaa | 1080 |
| gtctggtttt | tttccctgtt | ttgtacccca | tcc | | | 1113 |

<210> SEQ ID NO 317
<211> LENGTH: 1113
<212> TYPE: DNA
<213> ORGANISM: Homo sapiens

<400> SEQUENCE: 317

| | | | | | |
|---|---|---|---|---|---|
| ttcccagttg | agggaaccga | tgacctaatt | cctctcagtt | taaatgcaac | acaggagcaa | 60 |
| attccaaata | tctatgctgg | tcttgctggg | attgcagaac | cccagggtgg | ttatcctcct | 120 |
| ccagaggtaa | tcctgtgatc | agcactaacg | ccacatacca | gcccttcat | cagcttgttg | 180 |
| gagaagcatc | tttacttccc | rccaagcagt | gacctagata | ccatctcaca | ccagttagaa | 240 |
| tcaggatcat | taaaaagtca | agaaaaaaca | gatgctgaag | aggatgtgga | gaaataggaa | 300 |
| tgctttttaca | ctgttagtgg | gaatgtaaat | tagttcaacc | attgtcaaag | acagtgtggc | 360 |
| gatccctcac | agatctagaa | ccagaaatac | catttgaccc | agcaatccca | ttactgggtc | 420 |
| tatcccaaa | ggattataaa | ttactctact | ataaagacac | atgcacacat | atgtttattg | 480 |
| cagcaccatt | cacaatagca | aagaattgca | accaaccta | atgcccatca | atgacagact | 540 |
| ggataaagaa | aatctggcac | atatacacca | tggaatacta | cgcagccata | aaaaaggatg | 600 |
| agtttatgtc | ctttacaggg | acatggatga | agctggaaac | catcattctc | agcaaactaa | 660 |
| cacaggaaca | gaaaaccaaa | cacatgttct | cactcacaag | tgggagttga | acaatgagaa | 720 |
| cacatggaca | cagggagggg | aacatcacac | accactgctt | gtcaggggt | gggggctag | 780 |
| gggaaggata | gcattaggag | aaatacctaa | tgtagatgaa | gggttgatgg | gtgcagcaaa | 840 |
| ccaccatggc | atgtgtatac | ctgtgtaaca | aacctccatg | ttctgcacgt | gtatcccaga | 900 |
| acttaaagta | caatacaaaa | aaaaaaaaa | gtgtaatcca | gtttacattt | tcaaggtcaa | 960 |
| agtgggtaca | atgctatcta | tcttgggcta | agaagagaaa | aggaaaaatt | cttgctttaa | 1020 |
| atcttagaag | tctggttttt | ttccctgttt | tgtacccat | cctcttggtc | tctctagata | 1080 |
| tatttaagac | tcacatagga | cttgtctttt | cta | | | 1113 |

<210> SEQ ID NO 318
<211> LENGTH: 1001
<212> TYPE: DNA
<213> ORGANISM: Homo sapiens

<400> SEQUENCE: 318

| | | | | | |
|---|---|---|---|---|---|
| tcatcaacta | aatagttgat | gaggggaaat | tgttctgtat | atgttcatac | ttcagctaat | 60 |
| caattaaaaa | tgatgaaata | ataagattac | cattttgcaa | accctaatg | caatgttgga | 120 |
| tccaggcaat | gatcatcaat | ggccactaaa | atcacacaaa | aggagataac | cagaatatgt | 180 |
| gctttgtgat | ggaagcatta | aatacaacta | atgagatatt | gtttataaga | agaaaggaa | 240 |

```
gcaagaaagc aatcacacca agctctgtat ctagctacca catttaagga aaaaaagaga      300
cagaagagca tgttaaatgt taccaagaag atacagtcag tcggaaaaaa tacagacaag      360
aaaatacaga gcaaaacaac ccagcttctt cagcaaatca atataaaaaa attttaagaa      420
agagttaaag tataaactga gagacttcag aaacatatta tccaagtata atccatgaat      480
cttgtttaaa tatagatcaa rtaaaccact ataccaaaaa catcaaaaga caactgggta      540
aattttttaa atgactagct atttgatgtt aaggaagtaa tgttactctc ttatatacaa      600
tttgaaataa tctagcgagg agcagcaaat gtgcggctat gaggaagaaa cacaattggc      660
cattcttgaa tcattagctg gatggtggct atatggggt agattttact actctctaat       720
tttacatata tttaaaatgt tccataataa attgttgagt tatcaaaaga aatatttcta      780
tataatagct aaaattattt ataaaagtta gtggtctcat aactttattt atttatttac      840
ttattttgag accgagtctc cctctgttat gcaggctgga gtgcagtggc tccatctcgg      900
ctcactgcaa acttcacctc ctggattgaa gcgattctcc tgcctcagcc ccccgagta       960 gctgggatta caggcttgca cccccacgcc cagctaattt t                         1001
```

```
<210> SEQ ID NO 319
<211> LENGTH: 601
<212> TYPE: DNA
<213> ORGANISM: Homo sapiens

<400> SEQUENCE: 319
agctaccaca tttaaggaaa aaagagaca gaagagcatg ttaaatgtta ccaagaagat       60
acagtcagtc ggaaaaaata cagacaagaa atacagagc aaaacaaccc agcttcttca      120
gcaaatcaat ataaaaaaat tttaagaaag agttaaagta taaactgaga gacttcagaa     180
acatattatc caagtataat ccatgaatct tgtttaaata tagatcaaat aaaccactat     240
accaaaaaca tcaaaagaca actgggtaaa ttttttaaat gactagctat ttgatgttaa     300
rgaagtaatg ttactctctt atatacaatt tgaaataatc tagcgaggag cagcaaatgt     360
gcggctatga ggaagaaaca caattggcca ttcttgaatc attagctgga tggtggctat     420 atggggggtag attttactac tctctaattt tacatatatt taaaatgttc cataataaat    480
tgttgagtta tcaaaagaaa tatttctata taatagctaa aattatttat aaaagttagt    540
ggtctcataa ctttatttat ttatttactt attttgagac cgagtctccc tctgttatgc    600
a                                                                     601
```

```
<210> SEQ ID NO 320
<211> LENGTH: 601
<212> TYPE: DNA
<213> ORGANISM: Homo sapiens

<400> SEQUENCE: 320
ccaactgatc taattagata aacttagtca atatatttga atcccacatt ccagcagcta     60
ttttctccat ttgcttttat tgctgtttgt ggtgagtttg atatataatt ttaaggtgtt     120
aacatcccta acttatgtat gggtacagct cataaatacg aacctgtgtc atgcaactca    180
tatatgactg tgttcaaaat aatgtgtatt agactgtaaa acgattttaa tattttaaat    240
aactttcctg catttgtcgg tttcagcagg aaagttattt ttaataactt ccctgtattt    300
sttggtttca gtattaatta atctcattaa tgctaaactt tgtgatccta ggttaaaaaa    360
catattcaag atagcttcag aatgtttggt atacaaatag gtctggctaa atataagtgt    420
```

```
tagctttctc aagcatctaa atgctggcgg gcttttaaaa aaccagggct ttaaggagaa    480
aacacctgct ctgtggtttt gtagcagata tgaagtattc aaatttctta ataaatagaa    540
aaagaaatat ataacagaaa caggttgcac ttgtctttct cattaagcag gtggttagta    600
c                                                                    601

<210> SEQ ID NO 321
<211> LENGTH: 501
<212> TYPE: DNA
<213> ORGANISM: Homo sapiens

<400> SEQUENCE: 321
agctcataaa tacgaacctg tgtcatgcaa ctcatatatg actgtgttca aaataatgtg     60
tattagactg taaaacgatt ttaatatttt aaataacttt cctgcatttg tcggtttcag    120
caggaaagtt attttaaata acttccctgt atttgttggt ttcagtatta attaatctca    180
ttaatgctaa actttgtgat cctaggttaa aaaacatatt caagatagct tcagaatgtt    240
tggtatacaa rtaggtctgg ctaaatataa gtgttagctt tctcaagcat ctaaatgctg    300
gcgggctttt aaaaaaccag ggctttaagg agaaaacacc tgctctgtgg ttttgtagca    360
gatatgaagt attcaaattt cttaataaat agaaaaagaa atatataaca gaaacaggtt    420
gcacttgtct ttctcattaa gcaggtggtt agtaccatta tttgcattct catagcctta    480
atatacattt tccttctcta g                                              501

<210> SEQ ID NO 322
<211> LENGTH: 601
<212> TYPE: DNA
<213> ORGANISM: Homo sapiens

<400> SEQUENCE: 322
ttttgagttt ctactttagt gtcttagtgc tttctcgata tgggagaatt catgtcctcc     60
attcagaagt atgcactaag taagaggtat catgtctggt tcttgattag gtactaatct    120
tgaaatatta tcctacaata ggttagagca cgtatatctc ctgataatat attgaatatg    180
atagatttaa ataattggtt aactaaatac taaagcaaat tgctgcacgt atcatttatt    240
attcattgtg tagaaagtgc ctgactcagt gtttggaaat tgtctgactt ttcctcatat    300
rtagtgtggt tcatgttat tgtatataag acctgacatg aactctgttt acaataatct    360
cccagtgcca taaagaccat aataaataat ataaccaatt ggtttcttta tgctgtcatt    420
tattagggca tatggcatta gtggaggatt accttgtatt acccatagtg cttagagtat    480
gaatcacaca tgcaccttga aggaaagag gtgcaatgta ataagaaacc agatattgaa    540
aatgcaagtt ttgttatgtt attctgggta tgttaacctt tattcctgcc ctccatatgc    600
a                                                                    601

<210> SEQ ID NO 323
<211> LENGTH: 501
<212> TYPE: DNA
<213> ORGANISM: Homo sapiens

<400> SEQUENCE: 323
aagaggtatc atgtctggtt cttgattagg tactaatctt gaaatactat cctacagtag     60
gttagagcac gtatatctcc tgataatata ttgaatatga tagatttaaa taattggtta    120
actaaatact aaagcaaatt gctgcacgta tcatttatta ttcattgtgt agaaagtgcc    180
tgactcagtg tttggaaatt gtctgacttt tcctcatata tagtgtggtt tcatgttatt    240
```

| | | |
|---|---|---|
| gtatataaga mctgacatga accctgttta caataatctc ccagtgccat aaagaccata | 300 | |
| ataaataata taaccaattg gtttctttat gctgtcattt attagggcat atggcattag | 360 | |
| tggaggatta ccttgtatta cccatagtgc ttagagtatg aatcacacat gcaccttgaa | 420 | |
| ggaaaagagg tgcaatgtaa taagaaacca gatattgaaa atgcaagttt tgttatgtta | 480 | |
| ttctgggtat gttaaccttt a | 501 | |

<210> SEQ ID NO 324
<211> LENGTH: 854
<212> TYPE: DNA
<213> ORGANISM: Homo sapiens

<400> SEQUENCE: 324

| | |
|---|---|
| tttcagcact gagagccaga gtggaattgt ctccttcatt gccactgcct tcacgttttg | 60 |
| tgtgtcgtat ctgttttgtg atcactgaga cccaagaacc cccgacttgc cgacatacta | 120 |
| tgtggccccg agagaggact tgagctctct gggtttcatc attaccatca attaaataaa | 180 |
| caggacagta gcttcttcct tggattgtta atttaaggct ctggataata catgtaaccg | 240 |
| ccttatgata gagcagaatt gtaagtaggc tcatggtaga atcgttcaat gacatttccc | 300 |
| tttcctttgg gagaaacaga aattcacagg tctaattctt ttcctattaa tagttcctgr | 360 |
| ccattattcc agaactgtcc taaggaatt ctttctcctt aaggacacca cctcccagga | 420 |
| gggtatttaa agatttgcac aggccgggca cggtggctca tgcttgtaat cccagcagtt | 480 |
| tgggaggcca aggcgggtgg atcacttgtg ctcaggggtt caagaccggc ctggccaaca | 540 |
| tggtgaaacc ctatctctac taaaaacaca aaagttagct gggcctggct atgcatgcct | 600 |
| gtaattccag ctactcggga ggctgaggct ggagaatagc ttgaaccagg aggtggaga | 660 |
| taacagtgag ctgagatgcc actatgacac tccagcctgg gtgacagagc aagactctct | 720 |
| ctcaaaaaaa aaaaaagatt tttatagtcc agtattcaac gttcatagta cacctttctt | 780 |
| atcctagtaa atcttctttt atcaaggtat atgatcccat atagtagtta actcttactc | 840 |
| ttactttatg acaa | 854 |

<210> SEQ ID NO 325
<211> LENGTH: 501
<212> TYPE: DNA
<213> ORGANISM: Homo sapiens

<400> SEQUENCE: 325

| | |
|---|---|
| aaatacttac tattaaatat gagaaactgt ggtgtttatc ggtaagatcc acgaaggaag | 60 |
| aagtttaaa gaaaatact ttaaccgtgg aaaaaaaaaa ctttaatgtc tattatcgaa | 120 |
| taggggccgt aattactttt gcaaataaaa aaacaaaca agactagcta tagtgtaaat | 180 |
| gtaatctgta tgcttttttaa tgaaacaatt aagtaggttg cccatttaca attagcctga | 240 |
| ttttctcctg ygtggtatta tgtgtactta acaacaggac ccagtggaaa ttcactcatt | 300 |
| taacaaagtc tgcctacatg gtttcaaata tgggcctaac ttgaaaattc agtcataatt | 360 |
| aaatctaagg actaaaacaa atctgtataa aaagattctg ctaaataagg gaaaattcaa | 420 |
| gtctagggct acattctgaa agatattgaa gtagaacctc tgcagcaaga ctaggcttgg | 480 |
| aaagtgcggg gaggagggaa a | 501 |

<210> SEQ ID NO 326
<211> LENGTH: 601
<212> TYPE: DNA

<213> ORGANISM: Homo sapiens

<400> SEQUENCE: 326

| | | | | | |
|---|---|---|---|---|---|
| ccacatcaga | aacatgagga | aattctacat | ggtaaaaaca | gcaacaacca | aaaatactt | 60 |
| aaagtcaaca | aaccaggaaa | agacatctct | gaatatagga | atgccaaacc | tttaacacaa | 120 |
| taaaacacag | attatatttc | agaaggctat | attatatgtg | tataccaaca | tcaatatgtc | 180 |
| cagagtagct | gcacagagtt | ccatatttta | gtctttataa | gttcccctcc | tcaccctact | 240 |
| cagtaggcac | tttgtgtcta | gaaacttctg | tgtcaacagt | tttccctctc | tctggaattc | 300 |
| mtcaggacag | aagtgattgg | tgtggtggaa | gagggttgtg | ctaagagtga | agttatatga | 360 |
| aagtaggatg | gaggttagca | agtagttaaa | gtccagaaag | gcaataaggt | gttaaggaag | 420 |
| aacttttcca | ttttacaggt | ctgagcaagc | aggaaatcaa | ctctacaaac | tttgaaactt | 480 |
| ggtaaatatg | aaaacattct | caataccatt | tgtcatttaa | taaatacaaa | ttatactatt | 540 |
| ttactgcttg | catctagaag | tttgtcaaag | atctcgtctt | aattattcat | tgtgtcggcg | 600 |
| a | | | | | | 601 |

<210> SEQ ID NO 327
<211> LENGTH: 601
<212> TYPE: DNA
<213> ORGANISM: Homo sapiens

<400> SEQUENCE: 327

| | | | | | |
|---|---|---|---|---|---|
| gacgagatct | ttgacaaact | tctagatgca | agcagtaaaa | tagtataatt | tgtatttatt | 60 |
| aaatgacaaa | tggtattgag | aatgttttca | tatttaccaa | gtttcaaagt | ttgtagagtt | 120 |
| gatttcctgc | ttgctcagac | ctgtaaaatg | gaaaagttct | tccttaacac | cttattgcct | 180 |
| ttctggactt | taactacttg | ctaacctcca | tcctactttc | atataacttc | actcttagca | 240 |
| caaccctctt | ccaccacacc | aatcacttct | gtcctgatga | attccagaga | gagggaaaac | 300 |
| ygttgacaca | gaagtttcta | gacacaaagt | gcctactgag | tagggtgagg | aggggaactt | 360 |
| ataaagacta | aaatatggaa | ctctgtgcag | ctactctgga | catattgatg | ttggtataca | 420 |
| catataatat | agccttctga | aatataatct | gtgttttatt | tgttaaagg | tttggcattc | 480 |
| ctatattcag | agatgtcttt | tcctggtttg | ttgactttaa | gtattttttg | gttgttgctg | 540 |
| tttttaccat | gtagaatttc | ctcatgtttc | tgatgtggaa | agtataagaa | tatcagccag | 600 |
| a | | | | | | 601 |

<210> SEQ ID NO 328
<211> LENGTH: 811
<212> TYPE: DNA
<213> ORGANISM: Homo sapiens

<400> SEQUENCE: 328

| | | | | | |
|---|---|---|---|---|---|
| taaataatct | ctaattagta | taatgggtgt | tcttagtgca | gtgggtactt | ttaaagtgct | 60 |
| ttgtggcttt | tgatgaaaat | tgtcttagta | tttaaaactt | ttcttaccc | aatttttgt | 120 |
| tcccatcgaa | ttagcaatgc | tgtaaagaaa | ggcatcttat | tccatttttt | gttgctataa | 180 |
| aggaatactt | gaggctgggt | aatttataaa | gatgaaaagt | ttatttggct | cgcaattctg | 240 |
| gatggctgga | aggttaagta | ctgggccaca | gcatctggtg | ggggcctcga | gctgcttcta | 300 |
| gtcataatgg | aaggtgaagg | gtgtaaagat | catgtgacaa | gggaggaaag | aagagaagga | 360 |
| aggaggtgct | ggttctttct | atcaaccaat | tcgcaagaga | actaatagag | aaagaactca | 420 |
| cttagccctg | tgggaacaca | ttaatctatt | cataagggat | ctggctgtat | gatacaaaca | 480 |

```
cctcccatta ggccccacct ccaaattgta tcccattggg gatcaaattt caaaaagaga    540
tttggaagga acaaacaaac catatctaag ccatagtaaa aggaatggct ttcaaaggt    600 aaaatttact ragtgtatta atattttacc aatttccagc caggagagta tgaatgttgc    660
attattacat tgctttgaaa caaagcatta gtcttaattc agaagtttaa attcagatgt    720
taacgttgca tatttaataa tgcacaacca gtactaaaat cctcattgaa atgacaaata    780
attttatttc gaatccctta tagaggttca c                                  811
```

<210> SEQ ID NO 329
<211> LENGTH: 811
<212> TYPE: DNA
<213> ORGANISM: Homo sapiens

<400> SEQUENCE: 329

```
tgtcttagta tttaaaactt tttcttaccc aatttttgt tcccatcgaa ttagcaatgc    60
tgtaaagaaa ggcatcttat tccattttt gttgctataa aggaatactt gaggctgggt    120
aatttataaa gatgaaaagt ttatttggct cgcaattctg gatggctgga aggttaagta    180
ctgggccaca gcatctggtg ggggcctcga gctgcttcta gtcataatgg aaggtgaagg    240
gtgtaaagat catgtgacaa gggaggaaag aagagaagga aggaggtgct ggttctttct    300
atcaaccaat tcgcaagaga actaatagag aaagaactca cttagccctg tgggaacaca    360
ttaatctatt cataagggat ctggctgtat gatacaaaca cctcccatta ggccccacct    420
ccaaattgta tcccattggg gatcaaattt caaaaagaga tttggaagga acaaacaaac    480
catatctaag ccatagtaaa aggaatggct ttcaaaggt aaaatttact aagtgtatta    540
atattttacc aatttccagc caggagagta tgaatgttgc attattacat tgctttgaaa    600
caaagcatta ktcttaattc agaagtttaa attcagatgt taacgttgca tatttaataa    660
tgcacaacca gtactaaaat cctcattgaa atgacaaata attttatttc gaatccctta    720
tagaggttca caatgtttta acaatgtagt tttgactaaa tagaagtagt caaaacctgt    780
cagattggaa atagtattta taaaacataa a                                  811
```

<210> SEQ ID NO 330
<211> LENGTH: 601
<212> TYPE: DNA
<213> ORGANISM: Homo sapiens

<400> SEQUENCE: 330

```
gctcatcaat tttgacttaa gaaaattcta gcaacattta tagattttgc caaaattcag    60
cttcttccca aatcaatcta taagaaggct cttccttaaa cataattttt atatctatga    120
actgcactag catttactat atatttttat cactctcacc attactggat aataaataaa    180
agctcattaa aagagttaac aaaacatatt tattttaggc atcctgaaaa aaagattcaa    240
ttttattatc atttctacaa taagtattga agaaaggaga atttaaatta cttcatatac    300
stgataaagg aaaacatatg caaggcaaat aaacatctta gatcatgaca tataaaataa    360
tagattatta ctaaagatta aaatactttc ttaagaatta aagcaattct aaaagcaata    420
gtaaataaca ttcttctag tgatcagaca ctggatacta tgtttgagat agacagtgaa    480
ttgggaatgt tgttttacag aagctcctac cttgcaagga caggcaagtt taaatgtcag    540
ctagaaaact atcttgagtt ttcagtaatg taagattttc ctattcaatt tcacacttta    600
a                                                                   601
```

<210> SEQ ID NO 331
<211> LENGTH: 601
<212> TYPE: DNA
<213> ORGANISM: Homo sapiens

<400> SEQUENCE: 331

| | | | | | |
|---|---|---|---|---|---|
| agaaaattct | agcaacattt | atagattttg | ccaaaattca | gcttcttccc | aaatcaatct | 60 |
| ataagaaggc | tcttccttaa | acataatttt | tatatctatg | aactgcacta | gcatttacta | 120 |
| tatattttta | tcactctcac | cattactgga | taataaataa | aagctcatta | aaagagttaa | 180 |
| caaaacatat | ttattttagg | catcctgaaa | aaaagattca | attttattat | catttctaca | 240 |
| ataagtattg | aagaaaggag | aatttaaatt | acttcatata | cctgataaag | gaaaacatat | 300 |
| rcaaggcaaa | taaacatctt | agatcatgac | atataaaata | atagattatt | actaaagatt | 360 |
| aaaatacttt | cttaagaatt | aaagcaattc | taaaagcaat | agtaaataac | attctttcta | 420 |
| gtgatcagac | actggatact | atgtttgaga | tagacagtga | attgggaatg | ttgttttaca | 480 |
| gaagctccta | ccttgcaagg | acaggcaagt | ttaaatgtca | gctagaaaac | tatcttgagt | 540 |
| tttcagtaat | gtaagatttt | cctattcaat | ttcacacttt | aaattttata | tatatataaa | 600 |
| a | | | | | | 601 |

<210> SEQ ID NO 332
<211> LENGTH: 1110
<212> TYPE: DNA
<213> ORGANISM: Homo sapiens

<400> SEQUENCE: 332

| | | | | | |
|---|---|---|---|---|---|
| tgtagaagtt | cttatcactt | cctggccttt | tggctaagat | caagtgtgaa | atgtagaagt | 60 |
| tcctctaagc | tttacttccc | tcaaaaacta | gttttatctt | gtcagcagga | ttcacttaaa | 120 |
| aagacaaatt | cagattatga | attttttttct | tttttacagg | gtctgctctg | ttgcccaggc | 180 |
| tggagtgcag | aggcacaatc | tcggctcact | gcagcctccg | cctcctgggt | tcaagcaatt | 240 |
| ctcttgcctc | agcctcccga | gtaactggga | ttacaggcat | gtgccaccac | ccagctaatt | 300 |
| tttgtattttt | tagtagagat | ggggtttcac | cacattggtc | aggctggtct | cgaactgctg | 360 |
| gcctcaagtg | atccacttgc | ctcggcctcc | caaagtgcag | agattacagg | tgtgagccac | 420 |
| cgtgcccagc | tcataaccg | tttcaactac | ttttcactt | gacaagcaga | tgtgaagtta | 480 |
| acaaagtcac | ccatatttga | aataaagata | gtatattcct | ggggyaggca | gaggcagttg | 540 |
| aggatcatga | ataactatg | ttggcatagt | tatttaggtg | ttgatactgt | tattatgcca | 600 |
| ttgaaagtta | aacagagaac | cctctgggta | catgttttat | accaatgcac | actatcttat | 660 |
| tagtccctct | cataatgtgc | agtcatcatt | actgttacgg | gttgaggtgt | ccccatcctc | 720 |
| tatgggacac | ctctatgttg | aagtctcaga | ttccctagaa | tctcagaatg | tgaccttgtt | 780 |
| tggaaacaga | tttgctacag | acgcaattag | ttgagatgcg | cttatatggg | taggtcctaa | 840 |
| ttcagtgact | ggtgtcctta | aaaaaatgga | aatgtacaca | cggtggtaga | catgcataga | 900 |
| gggaagagag | atggagaaaa | tggtcaccta | caagccaaag | acaggggtct | ggagcagatc | 960 |
| cttccctcac | agccctcaga | aggaaccaat | cttgccaata | ccttgatttt | ggacttccac | 1020 |
| ctccagaact | ataacacatt | tctgttcttc | aagcaatttg | tagccatttg | ttacagctaa | 1080 |
| tacaatcaca | catagaaatg | acttgtaaat | | | | 1110 |

<210> SEQ ID NO 333
<211> LENGTH: 691

<212> TYPE: DNA
<213> ORGANISM: Homo sapiens

<400> SEQUENCE: 333

```
taaaacatgt acccagaggg ttctctgttt aactttcaat ggcataataa cagtatcaac    60
acctaaataa ctatgccaac atagttattt catgatcctc aactgcctct gcctacccca   120
ggaatatact atctttattt caaatatggg tgactttgtt aacttcacat ctgcttgtca   180
agtgaaaaag tagttgaaac rgttatgagg ctgggcacgg tggctcacac ctgtaatctc   240
tgcactttgg gaggccgagg caagtggatc acttgaggcc agcagttcga gaccagcctg   300
accaatgtgg tgaaacccca tctctactaa aaatacaaaa attagctggg tggtggcaca   360
tgcctgtaat cccagttact cgggaggctg aggcaagaga attgcttgaa cccaggaggc   420
ggaggctgca gtgagccgag attgtgcctc tgcactccag cctgggcaac agagcagacc   480
ctgtaaaaaa gaaaaaaatt cataatctga atttgtcttt ttaagtgaat cctgctgaca   540
agataaaact agttttgag ggaagtaaag cttagaggaa cttctacatt tcacacttga   600
tcttagccaa aaggccagga agtgataaga acttctacat tttaagttat tcacaagata   660
actattaatg aacctgaaat agtttgtaaa g                                  691
```

<210> SEQ ID NO 334
<211> LENGTH: 640
<212> TYPE: DNA
<213> ORGANISM: Homo sapiens

<400> SEQUENCE: 334

```
aaacctttt cctgttttac tattactaaa ggtggcacaa cagcaacctc aacaactttg    60
caccatgcca acactgatgt ttacacccag cacagcattt tggtctctca tttttattct   120
cctctgaatg taatgaggat tcctagatgg ctagccaatt cgaatattta aggcaactga   180
aagttagaat gtttctgaaa catagtgttg ttgccagaga gtacgaaagt tttcaagaat   240
atcgggcaat tctgaaagta caaagaagcc agattaaatg aaataacact ggcgaagttt   300
tagcaaggtg actctcatat aatgatcatt atcattacca cagttaaaag aaaagagttg   360
tttatgaaag gccatgtgtc tgcaatgaaa ctcaaaagag aaaagttaac aggtgcaara   420
ggtagtttta ttataaaagg agggtaggca acaagaatat gtttaatttt tcttcctttt   480
catgagtaag acaagagtt tcatatatgt gaatatttt atttaatttt aagtagaaat    540
ctgtttttaa aatatgggta tatgcttatt tgtgtaagtg taagaaacag aagtaagtac   600
agcaaaccag aaataggcca aacactcctg agcataattt                        640
```

<210> SEQ ID NO 335
<211> LENGTH: 919
<212> TYPE: DNA
<213> ORGANISM: Homo sapiens

<400> SEQUENCE: 335

```
tacacccagc acagcatttt tggtctctat ttttattctc ctctgaatgt aatgaggatt    60
cctagatggc tagccaattc gaatatttaa ggcaactgaa agttagaatg tttctgaaac   120
atagtgttgt tgccagagag tacgaaagtt ttcaagaata tcgggcaatt ctgaaagtac   180
aaagaagcca gattaaatga ataacactg gcgaagtttt agcaaggtga ctctcatata    240
atgatcatta tcattaccac agttaaaaga aaagagttgt ttatgaaagg ccatgtgtct   300
gcaatgaaac tcaaaagaga aaagttaaca ggtgcaaaag gtagttttat tataaaagga   360
```

| | |
|---|---|
| gggtaggcaa caagaatatg tttaattttt cttcctttc atgagtaagg acaagagtkt | 420 |
| catatatgtg aatatttta tttaattta agtagaaatc tgttttaaa atatgggtat | 480 |
| atgcttattt gtgtaagtgt aagaaacaga agtaagtaca gcaaaccaga aataggccaa | 540 |
| acactcctga gcataatttt acttggtaga ttattcctga aacttaagga atcatctttg | 600 |
| aactctttc ctcacttgac ttccaggatt caccatgcac ttgtgatttt cctttcattt | 660 |
| cactctccgt tcctcctcag tctttttttc tcccccaggt cttttttgtt catcttaaac | 720 |
| tctaaattt agaatatccc aggggtctgc cttcggcctt tctttttata tctacactgg | 780 |
| cctcatacat aatcttaacc aagtcattat tttaaatacc tacaatatac tgaaaacttc | 840 |
| taaatttgta tttaattct tgacttcttc catacagtct agatttgtat gtccataggc | 900 |
| tgacatcatt ggctgatac | 919 |

<210> SEQ ID NO 336
<211> LENGTH: 1001
<212> TYPE: DNA
<213> ORGANISM: Homo sapiens

<400> SEQUENCE: 336

| | |
|---|---|
| ttactaaata ttctccaaca aatatatact tagtatatac tattagtgat gcatgctttc | 60 |
| aaatatttgg actatatcaa tgaatgaaac aaaaaattat tgcccttaa ggagcttaga | 120 |
| ttctaacaga tggattcaga tgattttat gccttatttc gtaggtttaa aagagcaatg | 180 |
| gggaaaaggg aagaagagag ggattgaaaa tattgagaag gttgggagac ttagcaattt | 240 |
| taagtaaggt agtgagggta ggttttattg gcaaagtgat ttttcagcag agactgggaa | 300 |
| agatgaacgt ggtatcctgg aggaaagcct cccaggcaga gttaagctgc taacaaaagt | 360 |
| gcccttaggc tggagtgggc ttgtttgatt aaggaacaaa gaggtcagca tggttgcact | 420 |
| agagagaaaa aatcagatgg cgtaaggaga tgaaatcaga agatacgag gctaggcaaa | 480 |
| ggggtactct atgtaatgaa yatgacctgg cagtactgac atctcctgag ggactgttag | 540 |
| aagtgcagac tcttgtatct tttctcaagt ctatgaaatc tagacttcat tttaacaaga | 600 |
| tgacccgata tttacataca cattaaagtt ccagaagcac tgatataaca cattgtaaga | 660 |
| tcgcacagga cttcaattct ttttctggtt tttagaggca gtcctttggg gtgttttgtg | 720 |
| tagagtataa tgacctgaaa tatctaggat cactctagct actatcttga ggaaagagtg | 780 |
| caataaggcg gaacagttca gaggcaatgg tggtcttcta aatgaaagac acacagcact | 840 |
| caaaccaggc agttgaggag ggatgggaag aagttgtcaa attctagaca tatttaaag | 900 |
| gtagtgtcca gagaatttcc ttagatgcgt aggaacatgg aggataggac atagggtgga | 960 |
| aataaacgaa ataagaaac tgaagctgat tctgacattt t | 1001 |

<210> SEQ ID NO 337
<211> LENGTH: 1576
<212> TYPE: DNA
<213> ORGANISM: Homo sapiens

<400> SEQUENCE: 337

| | |
|---|---|
| ataccttta agtgacatcc tagtgaatct ccatttgtca cgagacctca agctttccag | 60 |
| ttctggcaca aagtgattac tcataccatc acttcaaaat gatgattatc ttcatttatt | 120 |
| ttagttatat tgaacaaaat atacatttaa aaaatctaat tactaaatat tctccaacaa | 180 |
| atatatactt agtatatact attagtgatg catgctttca aatatttgga ctatatcaat | 240 |
| gaatgaaaca aaaaattatt tgcccttaag gagcttagat tctaacagat ggattcagat | 300 |

```
gattttatg ccttatttcg taggtttaaa agagcaatgg ggaaaaggga agaagagagg    360
gattgaaaat attgagaagg ttgggagact tagcaatttt aagtaaggta gtgagggtag    420
gttttattgg caaagtgatt tttcagcaga gactgggaaa gatgaacgtg gtatcctgga    480
ggaaagcctc ccaggcagag ttaagctgct aacaaaagtg cccttaggct ggagtgggct    540
tgtttgatta aggaacaaag aggtcagcat ggttgcacta gagagaaaaa atcagatggc    600
gtaaggagat gaaatcagaa agatacgagg ctaggcaaag gggtactcta tgtaatgaac    660
atgacctggc agtactgaca tctcctgagg gactgttaga agtgcagact cttgtatctt    720
ttctcaartc tatgaaatct agacttcatt ttaacaagat gacccgatat ttacatacac    780
attaaagttc cagaagcact gatataacac attgtaagat cgcacaggac ttcaattctt    840
tttctggttt ttagaggcag tcctttgggg tgttttgtgt agagtataat gacctgaaat    900
atctaggatc actctagcta ctatcttgag gaaagagtgc aataaggcgg aacagttcag    960
aggcaatggt ggtcttctaa atgaaagaca cacagcactc aaaccaggca gttgaggagg    1020
gatgggaaga agttgtcaaa ttctagacat attttaaagg tagtgtccag agaatttcct    1080
tagatgcgta ggaacatgga ggataggaca tagggtggaa ataaacgaaa taaagaaact    1140
gaagctgatt ctgacatttt agacctaaaa tctcaactaa aagttgccaa gatgggaaaa    1200
actaggtgca tcttgtttgg tgagtggaaa tcagccttgt gaattaagac ttaaactgat    1260
gtctttaatc ccgtagaaat accatgaagg cagtagaaga tggctaaaga gaggtctaga    1320
ctgtaggtac aaatttaaaa gtcacttgca tttggatgct taaagtcagg atattgtgaa    1380
gtcaacagag gaataaataa atgcagagag gggaaagaaa aggcccatag actgagccat    1440
tgtctggttt atttacatat tagtatatat tttcttaaag atgtttgcta tataataatg    1500
agttacctaa agtgtgactt ttctaaattt atggggaatt ttctacattg tgttatggca    1560
ctactaaaaa taataa                                                   1576
```

<210> SEQ ID NO 338
<211> LENGTH: 1275
<212> TYPE: DNA
<213> ORGANISM: Homo sapiens

<400> SEQUENCE: 338

```
gtaaaactaa ttataattaa aatcaaaata tttactgaac ctacttactc ctataatttg     60
cgttgctggt taaaacccag ctataaaaat tttgatcaaa aatttttatt ttgtaaatga    120
tctgacacag cataaatgtt aatcacattt ctttatttta tttgcagatt aatttgagta    180
atttgaaaaa ttattaatgt tacttaatta ctctcaacac cttacagtgt ctcctgtaag    240
cactattggt gatactgaat ttaagttaca tttaacaact atcagaaaat agtttttaaa    300
gtaaaaatta tgatttggag tttaccaact aaatcttgtt agctttcact gcctctattg    360
agaagagcag cagttcttat cttcctcctt tttcttcttt aattaacaag agattatttg    420
tatcatagcc ataaaatcag ttcaggtatt acatgaacga cacccctgac tgcaatggtg    480
tagtttattg tattagtcca ttttcatgct gctgataaag acatacataa gactgggtaa    540
tttataaaga aatagaagtt taacggactc acagttccat gtggctgggg aagcctcaca    600
atcatgatcg aaggcaaaag gcacatctta catggcaaca ggcaagagag aatgagagcc    660
aagtgaaagg agaaacccct tataaaacct tcagacctca tgagacttat tcactaccac    720
aagaacagta tgtgagaaac agtcccatga tccagttatc tcccactggg tccctcccac    780
```

```
cacacaaggg aattatggga actgcaattc aagatgaaat gtgggtggaa gcacaacgga    840
actatatcat gatcaaagca ttattgtttt ctctgataag ctgatctaga aagtgctgct    900
tgtgatcagc tttggtgacc atgatcagtg aaatggttaa ggaaatctac agattttgta    960
ggtttgtgcc ttgacagacg accggtatct gtttctcttt tcatgatgaa gtatctaaca   1020
aagctctgtc caaaattttg aatttctcgt taaawgcatc atgattatag aacagaggtt   1080
acaatcaatt attcagtcac acaatcactc tcatcagtca ttaaggtgca tacctggtgt   1140
tccagttatt cagtgtggta taacaaacta cctggaactt aatggcttga aatagtcacc   1200
attacattat gattgtccat tctctgcatc aataattagg atttggcaaa gagggaatgg   1260
tttgtttaca gacag                                                    1275
```

<210> SEQ ID NO 339
<211> LENGTH: 1275
<212> TYPE: DNA
<213> ORGANISM: Homo sapiens

<400> SEQUENCE: 339

```
gtaaaactaa ttataattaa aatcaaaata tttactgaac ctacttactc ctataatttg     60
cgttgctggt taaacccag ctataaaaat tttgatcaaa aatttttatt ttgtaaatga    120
tctgacacag cataaatgtt aatcacattt ctttatttta tttgcagatt aatttgagta    180
atttgaaaaa ttattaatgt tacttaatta ctctcaacac cttacagtgt ctcctgtaag    240
cactattggt gatactgaat ttaagttaca tttaacaact atcagaaaat agttttaaa    300 gtaaaaatta tgatttggag tttaccaact aaatcttgtt agctttcact gcctctattg    360
agaagagcag cagttcttat cttcctcctt tttcttcttt aattaacaag agattatttg    420
tatcatagcc ataaaatcag ttcaggtatt acatgaacga cacccctgac tgcaatggtg    480
tagtttattg tattagtcca ttttcatgct gctgataaag acatacataa gactgggtaa    540
tttataaaga aatagaagtt taacggactc acagttccat gtggctgggg aagcctcaca    600
atcatgatcg aaggcaaaag gcacatctta catggcaaca ggcaagagag aatgagagcc    660
aagtgaaagg agaaacccct tataaaacct tcagacctca tgagacttat tcactaccac    720
aagaacagta tgtgagaaac agtcccatga tccagttatc tcccactggg tccctcccac    780
cacacaaggg aattatggga actgcaattc aagatgaaat gtgggtggaa gcacaacgga    840
actatatcat gatcaaagca ttattgtttt ctctgataag ctgatctaga aagtgctgct    900
tgtgatcagc tttggtgacc atgatcagtg aaatggttaa ggaaatctac agattttgta    960
ggtttgtgcc ttgacagacg accggtatct gtttctcttt tcatgatgaa gtatctaaca   1020
aagctctgtc caaaattttg aatttctcgt taaatgcatc atgattatag aacagaggtt   1080
acaatcaatt attcagtcac acaatcactc tcatcagtca ttaaggtgcr tacctggtgt   1140
tccagttatt cagtgtggta taacaaacta cctggaactt aatggcttga aatagtcacc   1200
attacattat gattgtccat tctctgcatc aataattagg atttggcaaa gagggaatgg   1260
tttgtttaca gacag                                                   1275
```

<210> SEQ ID NO 340
<211> LENGTH: 1001
<212> TYPE: DNA
<213> ORGANISM: Homo sapiens

<400> SEQUENCE: 340

```
gaaacaaaaa attgcttttt atatattgat attttttgcac ggatttctta ggattttcta     60
```

```
tgtacatgac catgtcatct gcaaatgaaa tagttttatt tctttatcaa tccggatgaa      120
tttattaaaa ttatcttgcc taatttccca aatagggcct ccatgttgaa cataagtggt      180
ggcaagggtg atctgttgct aatctcagtg gatgatattc agtgttttac aatgatcttc      240
gacagctctg gctgttaaat tatcatagtc tgtatggcct aaacaaacaa aatacttatg      300
attatggggg aggctgggat atccaagatc aagttgctgg caggtctagc aacctgccac      360
tgggaagccc tgcttcccag ttttcagatg gccaccttct tatagtatct tcaccaaaga      420
tagggcagag agagcaagca agctctctac cttctcatat aagggcacta atcccaccat      480
gaaggcgcca ctgtcatgac stgattatgt cacaaagacc ccggggcaaa tattaccact      540
gtgaggagta cagttttagc atgtgaattt ggaagaaca caaacattta gtacagagtg       600
actattaagt atgttattaa ctatggagtt tttgtaggca ttttttaaca cattgagaaa      660
gtttcctcta ttcctacttt tgttgagaag ttttatgat gacaaggcat tacatttat       720 ccaatgactt ttctgtgtgt attgagatga ctgatttgtt ctgccaattt aaatccattg      780
ttgattctct ctaggatttt ttttatttca gttattaaat ttttcaacag gagaattact      840
gtcttgttct ttttttttgta atttctgtcc ccttactggt attccatatt taataaggca     900
tcataatagt actcttcttt agtttcttaa agatggtttt ctttagtttt taacatattt      960
atgtctattt agaagtcttt gttaagtctg acatctgagc t                         1001

<210> SEQ ID NO 341
<211> LENGTH: 1001
<212> TYPE: DNA
<213> ORGANISM: Homo sapiens

<400> SEQUENCE: 341
ggatttctta ggattttcta tgtacatgac catgtcatct gcaaatgaaa tagttttatt       60
tctttatcaa tccggatgaa tttattaaaa ttatcttgcc taatttccca aatagggcct      120
ccatgttgaa cataagtggt ggcaagggtg atctgttgct aatctcagtg gatgatattc      180
agtgttttac aatgatcttc gacagctctg gctgttaaat tatcatagtc tgtatggcct      240
aaacaaacaa aatacttatg attatggggg aggctgggat atccaagatc aagttgctgg      300
caggtctagc aacctgccac tgggaagccc tgcttcccag ttttcagatg gccaccttct      360
tatagtatct tcaccaaaga tagggcagag agagcaagca agctctctac cttctcatat      420
aagggcacta atcccaccat gaaggcgcca ctgtcatgac ctgattatgt cacaaagacc      480
ccggggcaaa tattaccact stgaggagta cagttttagc atgtgaattt ggaagaaca       540 caaacattta gtacagagtg actattaagt atgttattaa ctatggagtt tttgtaggca      600
ttttttaaca cattgagaaa gtttcctcta ttcctacttt tgttgagaag ttttatgat       660 gacaaggcat tacatttat ccaatgactt ttctgtgtgt attgagatga ctgatttgtt       720
ctgccaattt aaatccattg ttgattctct ctaggatttt ttttatttca gttattaaat      780
ttttcaacag gagaattact gtcttgttct ttttttttgta atttctgtcc ccttactggt     840
attccatatt taataaggca tcataatagt actcttcttt agtttcttaa agatggtttt     900
ctttagtttt taacatattt atgtctattt agaagtcttt gttaagtctg acatctgagc     960
tctctcaaag tttctgctga ttttttttttt cctatgtttg g                        1001

<210> SEQ ID NO 342
<211> LENGTH: 701
<212> TYPE: DNA
```

<213> ORGANISM: Homo sapiens

<400> SEQUENCE: 342

```
ggaaaccctg gcctcttgat cacactttcc tggagtttag tccctctgc aatatgtacc      60
tgggagtcat aagaaatgcc agttacaaaa acttcctgta cagatatcct agcactcaac    120
tggaaaccgg ggagagtcac aattctgtct ttccagccat atgtaactga atggagatc     180
ttttcaccct gagccagggg tgatgggaaa gggagctggt catggctcaa tgtttagcct    240
tttcttggtc ttcaagattt catagacatt cttaaataca tgtttctttc aatgaagttt    300
gcccttagga caattcacag ctacattagg tacttttaa ataatacttt tgaccatccg     360
tggttatttc attgaagaaa atctatagag cacctcagcc atcattccag aagtgactat    420
cctcctcagt aatggttctt attctaattt taaatatcat tgatgtagaa cattctattt    480
cactattcct tcattttatt rttatgggaa attatataca gttctccaga ttttaaagc    540
cttgctaaca tgttttaagt cacacaaata ttcttctgtg ggaaaatgac agtaatttag    600
tgtgcaacaa ttatatagaa ctattttca aacttataaa cgaagtgaaa ttctaaataa     660
aatcatttat caaacacaaa aatttgagcc agaataagga a                        701
```

<210> SEQ ID NO 343
<211> LENGTH: 701
<212> TYPE: DNA
<213> ORGANISM: Homo sapiens

<400> SEQUENCE: 343

```
aatgccagtt acaaaaactt cctgtacaga tatcctagca ctcaactgga accggggag     60
agtcacaatt ctgtctttcc agccatatgt aactgaaatg gagatctttt caccctgagc    120
caggggtgat gggaagggga gctggtcatg gctcaatgtt tagccttttc ttggtcttca    180
agatttcata gacattctta aatacatgtt tctttcaatg aagtttgccc ttaggacaat    240
tcacagctac attaggtact ttttaaataa tacttttgac catccgtggt tatttcattg    300
aagaaaatct atagagcacc tcagccatca ttccagaagt gactatcctc ctcagtaatg    360
gttcttattc taatttaaa tatcattgat gtagaacatt ctatttcact attccttcat     420
tttattatta tgggaaatta tatacagttc tccagatttt taaagccttg ctaacatgtt    480
ttaagtcaca caaatattct yctgtgggaa aatgacagta atttagtgtg caacaattat    540
atagaactat ttttcaaact tataaacgaa gtgaaattct aaataaaatc atttatcaaa    600
cacaaaaatt tgagccagaa taaggaatgt aaattacaat ttaaacacag attataaact    660
atcttacttt taaaatgtta aaattcctaa cttgtttgaa a                        701
```

<210> SEQ ID NO 344
<211> LENGTH: 768
<212> TYPE: DNA
<213> ORGANISM: Homo sapiens

<400> SEQUENCE: 344

```
ctaaaatcta ccattatatg atatccttcc caatacataa attaaaaaaa aaaacactgt     60
agaggaaaaa gcaatatttt gaatgatat gcttttcttt gtttgtcttc aaacaattac    120
atcttcatca taatggttgt attagtctgt ttttacactg ctataaagaa ttgcctgaga    180
ctgagtaaca tataaagaaa aaagttttaa ttgaccacag tttcacaggc ttaataggaa    240
gcatgactgg gaaacttaga atcatggcag aagaggaagg ggaagcaagg atcttcttca    300
catggtagca ggagagagag cacaaagggg gacacgctac acactttcaa acaacgagat    360
```

```
ctcctgagaa ctctatcggg agaacagcaa gagggaagtt cacccctatg attcaatcag      420
ctcccaccgg gcttctcccc tgacacatga ggaattacaa ttggatgaga gatttgggtg      480
gggacacaca gacaaaccat atcaactgtc atggacttaa acaattgtct ttgaattgtc      540 tttttcata cttttatttg catctttyca ctaaaaagat gacacaaagt aatcctagtt      600 tacattttt accatgtaat tccatattac ttttcctga aagttactta ttttaaatc       660 tcaaagctct tcatacttat ggtttgatct gcacttacaa ctggatctca gaaagattga      720
attctcccat cataccaagt tcatgtctct cactcttaat atttgttc                  768
```

<210> SEQ ID NO 345
<211> LENGTH: 701
<212> TYPE: DNA
<213> ORGANISM: Homo sapiens

<400> SEQUENCE: 345

```
aaatgatatg cttttctttg tttgtcttca acaattaca tcttcatcat aatggttgta      60
ttagtctgtt tttacactgc tataaagaat tgcctgagac tgagtaacat ataagaaaa      120 aagttttaat tgaccacagt ttcacaggct aataggaag catgactggg aaacttagaa      180
tcatggcaga agaggaaggg gaagcaagga tcttcttcac atggtagcag gagagagagc     240
acaagggggg acacgctaca cactttcaaa caacgagatc tcctgagaac tctatcggga      300
gaacagcaag agggaagttc acccctatga ttcaatcagc tcccaccggg cttctcccct     360
gacacatgag gaattacaat tggatgagag atttgggtgg ggacacacag acaaaccata     420
tcaactgtca tggacttaaa caattgtctt tgaattgtct ttttcatac ttttatttgc      480 atcttttcac taaaaagatg rcacaaagta atcctagttt actttttta ccatgtaatt     540 ccatattact tttcctgaa agttacttat ttaaatct caaagctctt catacttatg       600
gtttgatctg cacttacaac tggatctcag aaagattgaa ttctcccatc ataccaagtt      660
catgtctctc actcttaata tttgttccca agacaacaat t                        701
```

<210> SEQ ID NO 346
<211> LENGTH: 6758
<212> TYPE: DNA
<213> ORGANISM: Homo sapiens

<400> SEQUENCE: 346

```
agagtgggcc attgttctga ctagtctggg gctccccaaa gaactggtat ctgtctcacc      60
tgactcagaa caatgataag gctgtagatc ttttgaag tctatgaaaa caggcacaat      120
gaaggcagca tgttagagat ataattccac aggaagatgc caggtaaaac aaaagagaaa      180
aagcaggaac aagctgatta ggaaatttgt gatgactaaa agtatataca caagcccaaa      240
taagatactc caaagatgtt tgataggttc tagatctcta gatatactgc tcaatgaaag      300
tgtccccctg aacaaagcca gtctgcaaag actgggtgag atgatttttt ttaaatgtca      360
agtctcagca acaacaaaaa tgacaagaca tgcacagaag caagaaaata taacacaatc      420
aaagaaaaaa aagccacaga aatcagtcct agagaaaacy gatctatgag ctgcctgaca      480
ataattataa aataactatc ataaaaatgc ccagtgagat ataagaaaac acagacaact      540
aaatgaatca ggaaaatgat gcatgaacaa aatgggcata tcaacagaga tggaaatgac      600
aaagataaac aaacagaaat tttggagctt aaaaatacag taagtaaagt gaataattca      660
ctaaaaatat tcaatagcag actagatcag gcagaagaaa atatcaatga acttgaagac      720
```

```
agatcatcaa gtcagaggaa caacagcaac aaaaaagaat gaaaaagtg aagacagcct      780 aagggactta ggagtcagta ccaaggaaat caatatatac gttatagatg tatcagaaga      840
aaaagggaga aaaatgaaaa gaaagcatat ttgaaaaaat aatagctgaa gaattctcaa      900
tttcaaagag agaaattgat atacaaattc aagaagttca aaagactcta gccataataa      960
atctaaagag actcacacta agacatatta tcatcaaact gtcaaaatca aagacaaaga     1020
attgtgaaat ctgccaagga aaagtgactc atcacacata agagatataa cataagattg     1080
tcacaggatt tctgaacaga cactttgcag gtcagaggga agtagggtga catattccag     1140
gtgctgaaag aagaaaacac cctgccaacc aagaatatgg catccagaaa aactttccta     1200
gaagaatgaa ggagaaattt agactttccc aaataaacaa agctgaggg agttcattac      1260 taccagacct gctctgcaaa atgctaaaga gaaaccttca ggtgaaacaa aaagatgcta     1320
gacagtaaca caaaccact cataaataac ttcttcagta aaataatac atcgacaaat      1380 atggtaaccct gtattaatac tggtgcacaa attcactttc aaattttata aataagaatt     1440
taaaggatga aaacatctaa aactaactat aaatctatat aatgaatata caatatataa     1500
aaaaatttgt gatcacaata acataaaatg ggggaggtag agctgtatag gggtagagct     1560
tttgtatgca attgaaatta ccatcagttt aaactgaact gttataacat taagatgttt     1620
tatgtaattg caatggtaac tatattctat agaatatatt aaaagaaaa agaaaatagg      1680 aagggaatca aagcatgtcc ttgtaaaaaa gtcaatgaaa gcaaagaaa ggcagaaaga      1740 gtgaaaagga ggaataaaaa gttataagac ataaaaaaa tgaaaatagt aatagtcctg      1800
ccatatcagt aattacatta aatataaatg gattaaactc cctaatcaaa tcatagattg     1860
gtttgcaaga actaacttta caattaaaga cacacagctg acggtgaagg gagaaaaaaa     1920
acttccatgc agtgaccaaa atagaggagg gtggctgtat tactgtcaga caaaataaaa     1980
tttaagtcaa aaactgttac aagagtaaaa gaagggcatt atacagttaa aaaagtaaat     2040
tcgccaggca gacacaacaa ttataaatat caatacataa aaataagagc tcctaaatat     2100
atgcagcaaa cagacataat tgaagaaaga aataaatagc taaaatggta gaagacttta     2160 ataccccac ttacaataat gtataaaata acaagacaga atgtaaataa aaatgtagag     2220
aatttgagca acactgtaga ccaattggac ctaataaata tactcagaat aatccatcca     2280
accaaagcag aaacagaata tacattcttt tcaagtacac atttgacatt ctctgggatt     2340
aactacatgt tatgcaacaa acaagtctca acaatgttta aaagtctgat attacacaaa     2400
gtattgtttc tgatgacgat ggaaagaacc tagaagccaa tagcaaaaag aaaatagaaa     2460
atccacacat atgtggaaat taaactacat gcaattaagc aaagggccaa agaagaagaa     2520
gaaaaaagaa acaccgtga aacaaataaa aacaaaaata cagcatatga aaatgcatgg      2580
gatgcagcaa aagtgatggt aagagaaatg tttatagtta taaatgcaaa ccttaaaaaa     2640
gaagaaagaa aacaaaaata ctcaaattaa caactttaca agtcaagaag gtagagaaaa     2700
aagaacaaac tataccaaaa gctaacacag aaagaaaaga ataagatta aaacaaaaa      2760 caatttaaaa aatagcagaa ctaaagttg gttctttgaa aagatcaaca gaattgacaa      2820
tttcttagct acattaagaa aaatacaaga ctcaaataac acaatcagt ggtgaaaggg      2880 ggtattataa ctgatgccac agaaatacaa aaggatcata agggactact acaaattgta     2940
tgacaacaaa ttgagtaacc taggatacct tgataaattc caaaaaatgc acaatatact     3000
gaatcatgaa tacatgaccc ttataaatca agactaaatc ataagaaat agaaaatatc      3060 aacagaccaa taattagtaa ggagaataaa ctagtaatca gaaacctccc aacaaagaaa     3120
```

```
agcttaggac caaatggctt tactggagaa ttctaccaac cattaaaagg ataattaaga    3180
ccaatcttcc tcaaactttt aaaacaaatg ttaaagagga ggaaactctt tcaatctcat    3240
tcataaggtc agcattatcc ttataccaaa accagacaaa gacactatta aaaaaactta    3300
gaccaatatc cctgatgaat ttcgatgcaa gaatcctcag caaatactta tcaaacaatt    3360
caacagcata cttaaatgat tatatgctgt aatcaagatg catttattct ttgaatgcaa    3420
gtgtaattca acacataaaa ttcaatcaat gtaatacacc acattaacag aatgagagac    3480
aaaaaccaca taattatatc aactgatgca gaaaaaaatc tgacacagtt caacacccttt   3540 tgtgataaaa acactcaaca aactaggaaa agaaggaaac aactttaaca catcatatgc    3600
tcactgatga aaatctacaa gttctttata aaagatcagg aacaagacaa taatctgcat    3660
tgttaccact tctattatac gtagtattgg aagttctaat cagagcaaat taggcaagaa    3720
aaataaataa aaggcatcca agtggaaag gaagtaaaat aatctctttt tacagatgat     3780
ataaccttag aattagaaaa tcctaaaaat ttcacatacc aagaaaaagc gtgttaaaat    3840
taataagtaa attcagcaag ttgactgata caaaatcaac acagaaagct cagttgtgtg    3900
tctgtgtgtc tcatacacta acaatgaaca atctgaaaag gagattaaga aaacaatttc    3960
atttacaata gcatcaggaa aaaaaataaa tacttaggaa caaacttaac caaggggttg    4020
gaattcctgt atactgaaaa ctacaaatat tgccaaaaga aaataaagga gacacaaata    4080
agtgatatgt tttaatatg tccacccaaa gtgatcttca gattcaatga atccctatc      4140 aaagttataa tggcattttt ctgcaggaat gtaaaaattt atcctaaaat tcatatagaa    4200
tctctaggta ccctgagggc caaacaattt tgagaaaaaa aaagaacaa aattggagga     4260 ctcacacttc cagattacaa gaatatttac aaattacata tttacaaaaa aaattacaaa    4320
gccacaataa tcaaaacaac gtgggatttg cataaaggca gatatataga ccagtggaat    4380
agtattgaga gtccagaaat aaaccctag gtatatcatc aaatgacatt tgacaaagtg     4440
ctggtaccac tcaatgggaa tgggacaatt tgttcaacaa atagagcaaa gaaaactaaa    4500
catccatgtg caaagaata aatctggacc cttatattac actatagaca aaattaattc     4560
aaaatggatt aaagatctaa atgaaagatc taaaactata aaactcctag gagaaaacag    4620
aggaaaaatt tcatgctaat ttggcaacat tttgtgatgt gacaccaaaa gcagagtcaa    4680
taaaagcaaa aattagacag atggaaatcc atcatagttt ataacttttg gtcattaaag    4740
aacagtcaac agagtgaaaa ggcaatctat aaaatggggg aaaaacagaa aatatgtgca    4800
aatcacagat atctgatagg ggattcatat ccagaataaa taaagaactc ctatatctca    4860
acaacaaaaa atctaatcca atcaaaaaat gggccaaggg agtgaagata catttctcca   4920
aagatgttat acaatggcc aggaagcata tgaaagatg ttcaatgtca ctaatcatca     4980
gagaaatgca aatcaaaacc acagtgcaat atcacttcac attcattaga atggcttctg    5040
tcatgaacaa cagaaaataa caagtgttga tgagtgtgta gagaaattga gacctttata    5100
taattttggc agaaattcaa aatggtgcaa ccactataaa aaatgatatg gaggtcctca    5160
aaaaattaaa aatagaacta ccatatgatc cacaatccca cctctgggta catattcaaa    5220
agaattgaaa gcagggtgtt gaagatatat ttgcacactc tttatagcag cactgttcac    5280
aatagccaag agatgaaagt aacccaaagg ttcatgaagc aatgaataaa caaatatat    5340 tatgtacata gagtaaaata ctgtgcagct ttaaagagaa aggaaatctt atactatgct    5400
acaacatgaa tggaacttta gggcattata gtaagtaaaa taagccagtt ttttttaaag    5460
```

-continued

| | |
|---|---|
| gacaaataaa cactatacga ttctacttaa gtatttaatg ttgtcaaatt tataaatata | 5520 |
| gaatgtagaa tagtggttac cctgagctgg gggaaagggg caaaggggaa ttgttatttt | 5580 |
| aatgggtata gtttcagttc tgcaaaatga aaaggttctg gaaatctgtt tcacaatgtt | 5640 |
| gtaaatataa ttactctgaa attgtacact taaaaatggt taagatgaca aatagagttg | 5700 |
| tgatgtcttc ttttgttatt atatagaaaa acttttttcat atgataatag tctttgtttt | 5760 |
| taagctgact ttgctgatat taatataatc cttccatttt tctttaaaat gctatatgct | 5820 |
| ttcacataat tttgctttac gttgatgtat ttatacataa ggtgggtttc ttatagatac | 5880 |
| cacgttgtgt gtctttttta tctaagttga tagacttgcc ttttgttagg gtatttaaat | 5940 |
| aatttatatt taatgtaatt attgatatag ttgagtgtgt tgattttttgt tttctatttg | 6000 |
| ctccatctgt tgttggttct cattattcct ctgtttctac cttctttttgt actaattatt | 6060 |
| atattttatt attttttcatc tcaactgttg gcttattagc cacattgctt ttaaaatttt | 6120 |
| taatgattgc tctagggttt ataataaaca aaatgttagc attttctacc atcaaatatt | 6180 |
| tttacactat tcatgtatac ttcaatttct ttcttcccat cctttgaact atatcttcat | 6240 |
| acattttact ctacatttgt tataaactcag tgctttgaaa gtcaattatt tttgtctttg | 6300 |
| acagtcaatg attttttaaag agtttaacag tgaaaaaaaa tggctttcat cttttttccat | 6360 |
| tagatttcat actccttctg cctgaagaat ttcttttaat agaccttgta ctgcgggtct | 6420 |
| caggcaagaa attctctcag cctttgttgg tttgaaaaac tgcttattac accttttgttt | 6480 |
| ttgaaagata ttttcactag gtatagaagt ctgggttgac agttctcatt gtttgtcaca | 6540 |
| gcattttttaa gatgcccatt caattgtctt gtcttgtata attttggatt agtctggtgt | 6600 |
| atttcttacc tttgttcctc tctgtgcaat gcttcaacca tcccacttca ggctgccttt | 6660 |
| aagatgtttt cttttccctt aatctttagt ttttagctgg ttgacagtga cgcatctaag | 6720 |
| tgtagtgtat gaggttgctt ttattgtcac tgttgttg | 6758 |

<210> SEQ ID NO 347
<211> LENGTH: 6758
<212> TYPE: DNA
<213> ORGANISM: Homo sapiens

<400> SEQUENCE: 347

| | |
|---|---|
| agagtgggcc attgttctga ctagtctggg gctccccaaa gaactggtat ctgtctcacc | 60 |
| tgactcagaa caatgataag gctgtagatc ttttttggaag tctatgaaaa caggcacaat | 120 |
| gaaggcagca tgttagagat ataattccac aggaagatgc caggtaaaac aaaagagaaa | 180 |
| aagcaggaac aagctgatta ggaaatttgt gatgactaaa agtatataca caagcccaaa | 240 |
| taagatactc caaagatgtt tgataggttc tagatctcta gatatactgc tcaatgaaag | 300 |
| tgtcccctg aacaaagcca gtctgcaaag actgggtgag atgatttttt ttaaatgtca | 360 |
| agtctcagca acaacaaaaa tgacaagaca tgcacagaag caagaaaata taacacaatc | 420 |
| aaagaaaaaa aagccacaga atcagtcct agagaaaact gatctatgag ctgcctgama | 480 |
| ataattataa aataactatc ataaaaatgc ccagtgagat ataagaaaac acagacaact | 540 |
| aaatgaatca ggaaaatgat gcatgaacaa aatgggcata tcaacagaga tggaaatgac | 600 |
| aaagataaac aaacagaaat tttggagctt aaaaatacag taagtaaagt gaataattca | 660 |
| ctaaaaatat tcaatagcag actagatcag gcagaagaaa atatcaatga acttgaagac | 720 |
| agatcatcaa gtcagaggaa caacagcaac aaaaaagaat gaaaaaagtg aagacagcct | 780 |
| aagggactta ggagtcagta ccaaggaaat caatatatac gttatagatg tatcagaaga | 840 |

```
aaaagggaga  aaaatgaaaa  gaaagcatat  ttgaaaaaat  aatagctgaa  gaattctcaa    900
tttcaaagag  agaaattgat  atacaaattc  aagaagttca  aaagactcta  gccataataa    960
atctaaagag  actcacacta  agacatatta  tcatcaaact  gtcaaaatca  aagacaaaga   1020
attgtgaaat  ctgccaagga  aaagtgactc  atcacacata  agagatataa  cataagattg   1080
tcacaggatt  tctgaacaga  cactttgcag  gtcagaggga  agtagggtga  catattccag   1140
gtgctgaaag  aagaaaacac  cctgccaacc  aagaatatgg  catccagaaa  aacttttccta  1200 gaagaatgaa  ggagaaattt  agactttccc  aaataaacaa  agctgaggg   agttcattac   1260 taccagacct  gctctgcaaa  atgctaaaga  gaaaccttca  ggtgaaacaa  aaagatgcta   1320
gacagtaaca  caaaccact   cataaataac  ttcttcagta  aaaataatac  atcgacaaat   1380
atggtaacct  gtattaatac  tggtgcacaa  attcactttc  aaattttata  aataagaatt   1440
taaaggatga  aaacatctaa  aactaactat  aaatctatat  aatgaatata  caatatataa   1500
aaaaatttgt  gatcacaata  acataaaatg  ggggaggtag  agctgtatag  gggtagagct   1560
tttgtatgca  attgaaatta  ccatcagttt  aaactgaact  gttataacat  taagatgttt   1620
tatgtaattg  caatggtaac  tatattctat  agaatatatt  aaaagaaaa   agaaaatagg   1680 aagggaatca  aagcatgtcc  ttgtaaaaaa  gtcaatgaaa  gcaaagaaa   ggcagaaaga   1740 gtgaaaagga  ggaataaaaa  gttataagac  ataaaaaaaa  tgaaaatagt  aatagtcctg   1800
ccatatcagt  aattacatta  aatataaatg  gattaaactc  cctaatcaaa  tcatagattg   1860
gtttgcaaga  actaacttta  caattaaaga  cacacagctg  acggtgaagg  gagaaaaaaa   1920
acttccatgc  agtgaccaaa  atagaggagg  gtggctgtat  tactgtcaga  caaaataaaa   1980
tttaagtcaa  aaactgttac  aagagtaaaa  gaagggcatt  atacagttaa  aaagtaaat    2040 tcgccaggca  gacacaacaa  ttataaatat  caatacataa  aaataagagc  tcctaaatat   2100
atgcagcaaa  cagacataat  tgaagaaga   aataaatagc  taaaatggta  gaagacttta   2160 ataccccccac ttacaataat  gtataaaata  acaagacaga  atgtaaataa  aaatgtagag   2220
aatttgagca  acactgtaga  ccaattggac  ctaataaata  tactcagaat  aatccatcca   2280
accaaagcag  aaacagaata  tacattcttt  tcaagtacac  atttgacatt  ctctgggatt   2340
aactacatgt  tatgcaacaa  acaagtctca  acaatgttta  aaagtctgat  attacacaaa   2400
gtattgtttc  tgatgacgat  ggaaagaacc  tagaagccaa  tagcaaaaag  aaaatagaaa   2460
atccacacat  atgtggaaat  taaactacat  gcaattaagc  aaagggccaa  agaagaagaa   2520
gaaaaaagaa  aacaccgtga  aacaaataaa  aacaaaaata  cagcatatga  aaatgcatgg   2580
gatgcagcaa  aagtgatggt  aagagaaatg  tttatagtta  taaatgcaaa  ccttaaaaaa   2640
gaagaaagaa  aacaaaaata  ctcaaattaa  caactttaca  agtcaagaag  gtagagaaaa   2700
aagaacaaac  tataccaaaa  gctaacacag  aaagaaaaga  ataaagatta  aaaacaaaaa   2760
caatttaaaa  aatagcagaa  ctaaaagttg  gttctttgaa  aagatcaaca  gaattgacaa   2820
tttcttagct  acattaagaa  aaatacaaga  ctcaaataac  acaaatcagt  ggtgaaaggg   2880
ggtattataa  ctgatgccac  agaaatacaa  aaggatcata  agggactact  acaaattgta   2940
tgacaacaaa  ttgagtaacc  taggataccc  tgataaattc  caaaaaatgc  acaatatact   3000
gaatcatgaa  tacatgaccc  ttataaatca  agactaaatc  ataaagaaat  agaaaatatc   3060
aacagaccaa  taattagtaa  ggagaataaa  ctagtaatca  gaaacctccc  aacaaagaaa   3120
agcttaggac  caaatggctt  tactggagaa  ttctaccaac  cattaaaagg  ataattaaga   3180
```

```
ccaatcttcc tcaaactttt aaaacaaatg ttaaagagga ggaaactctt tcaatctcat    3240
tcataaggtc agcattatcc ttataccaaa accagacaaa gacactatta aaaaaactta    3300
gaccaatatc cctgatgaat ttcgatgcaa gaatcctcag caaaatacta tcaaacaatt    3360
caacagcata cttaaatgat tatatgctgt aatcaagatg catttattct ttgaatgcaa    3420
gtgtaattca acacataaaa ttcaatcaat gtaatacacc acattaacag aatgagagac    3480
aaaaaccaca taattatatc aactgatgca gaaaaaaatc tgacacagtt caacacccttt   3540 tgtgataaaa acactcaaca aactaggaaa agaaggaaac aactttaaca catcatatgc    3600
tcactgatga aaatctacaa gttctttata aagatcagg  aacaagacaa taatctgcat    3660
tgttaccact tctattatac gtagtattgg aagttctaat cagagcaaat taggcaagaa    3720
aaataaataa aaggcatcca aagtggaaag gaagtaaaat aatctctttt tacagatgat    3780
ataaccttag aattagaaaa tcctaaaaat ttcacatacc aagaaaaagc gtgttaaaat    3840
taataagtaa attcagcaag ttgactgata caaaatcaac acagaaagct cagttgtgtg    3900
tctgtgtgtc tcatacacta acaatgaaca atctgaaaag gagattaaga aaacaatttc    3960
atttacaata gcatcaggaa aaaaaataaa tacttaggaa caaacttaac caaggggttg    4020
gaattcctgt atactgaaaa ctacaaatat tgccaaaaga aaataaagga gacacaaata    4080
agtgatatgt ttttaatatg tccacccaaa gtgatcttca gattcaatga aatccctatc    4140
aaagttataa tggcattttt ctgcaggaat gtaaaaattt atcctaaaat tcatatagaa    4200
tctctaggta ccctgagggc caaacaattt tgagaaaaaa aaagaacaa  aattggagga    4260 ctcacacttc cagattacaa gaatatttac aaattacata tttacaaaaa aaattacaaa    4320
gccacaataa tcaaaacaac gtgggatttg cataaaggca gatatataga ccagtggaat    4380
agtattgaga gtccagaaat aaaccccttag gtatatcatc aaatgacatt tgacaaagtg    4440
ctggtaccac tcaatgggaa tgggacaatt tgttcaacaa atagagcaaa gaaaactaaa    4500
catccatgtg caaagaata  aatctggacc cttatattac actatagaca aaattaattc    4560
aaaatggatt aaagatctaa atgaaagatc taaaactata aaactcctag gagaaaacag    4620
aggaaaaatt tcatgctaat ttggcaacat tttgtgatgt gacaccaaaa gcagagtcaa    4680
taaaagcaaa aattagacag atggaaatcc atcatagttt ataacttttg gtcattaaag    4740
aacagtcaac agagtgaaaa ggcaatctat aaaatggggg aaaaacagaa aatatgtgca    4800
aatcacagat atctgatagg ggattcatat ccagaataaa taaagaactc ctatatctca    4860
acaacaaaaa atctaatcca atcaaaaaat gggccaaggg agtgaagata catttctcca    4920
aagatgttat acaaatggcc aggaagcata tgaaaagatg ttcaatgtca ctaatcatca    4980
gagaaatgca aatcaaaacc acagtgcaat atcacttcac attcattaga atggcttctg    5040
tcatgaacaa cagaaaataa caagtgttga tgagtgtgta gagaaattga gacctttata    5100
taattttggc agaaattcaa aatggtgcaa ccactataaa aaatgatatg gaggtcctca    5160
aaaaattaaa aatagaacta ccatatgatc cacaatccca cctctgggta catattcaaa    5220
agaattgaaa gcagggtgtt gaagatatat ttgcacactc tttatagcag cactgttcac    5280
aatagccaag agatgaaagt aacccaaagg ttcatgaagc aatgaataaa caaaatatat    5340
tatgtacata gagtaaaata ctgtgcagct ttaaagagaa aggaaatctt atactatgct    5400
acaacatgaa tggaacttta gggcattata gtaagtaaaa taagccagtt ttttttaaag    5460
gacaaataaa cactatacga ttctacttaa gtatttaatg ttgtcaaatt tataaatata    5520
gaatgtagaa tagtggttac cctgagctgg gggaaagggg caagggggaa ttgttatttt    5580
```

| | |
|---|---|
| aatgggtata gtttcagttc tgcaaaatga aaaggttctg gaaatctgtt tcacaatgtt | 5640 |
| gtaaatataa ttactctgaa attgtacact taaaaatggt taagatgaca aatagagttg | 5700 |
| tgatgtcttc ttttgttatt atatagaaaa acttttttcat atgataatag tctttgtttt | 5760 |
| taagctgact ttgctgatat taatataatc cttccatttt tctttaaaat gctatatgct | 5820 |
| ttcacataat tttgctttac gttgatgtat ttatacataa ggtgggtttc ttatagatac | 5880 |
| cacgttgtgt gtcttttttta tctaagttga tagacttgcc ttttgttagg gtatttaaat | 5940 |
| aatttatatt taatgtaatt attgatatag ttgagtgtgt tgattttttgt tttctatttg | 6000 |
| ctccatctgt tgttggttct cattattcct ctgtttctac cttcttttgt actaattatt | 6060 |
| atatttattt attttttcatc tcaactgttg gcttattagc cacattgctt ttaaaatttt | 6120 |
| taatgattgc tctagggttt ataataaaca aaatgttagc attttctacc atcaaatatt | 6180 |
| tttacactat tcatgtatac ttcaatttct ttcttcccat cctttgaact atatcttcat | 6240 |
| acattttact ctacatttgt tataactcag tgctttgaaa gtcaattatt tttgtctttg | 6300 |
| acagtcaatg attttttaaag agtttaacag tgaaaaaaaa tggctttcat cttttttccat | 6360 |
| tagatttcat actccttctg cctgaagaat ttcttttaat agaccttgta ctgcgggtct | 6420 |
| caggcaagaa attctctcag cctttgttgg tttgaaaaac tgcttattac acctttgttt | 6480 |
| ttgaaagata ttttcactag gtatagaagt ctgggttgac agttctcatt gtttgtcaca | 6540 |
| gcatttttaa gatgcccatt caattgtctt gtcttgtata attttggatt agtctggtgt | 6600 |
| atttcttacc tttgttcctc tctgtgcaat gcttcaacca tcccacttca ggctgccttt | 6660 |
| aagatgtttt cttttcccctt aatctttagt ttttagctgg ttgacagtga cgcatctaag | 6720 |
| tgtagtgtat gaggttgctt ttattgtcac tgttgttg | 6758 |

<210> SEQ ID NO 348
<211> LENGTH: 501
<212> TYPE: DNA
<213> ORGANISM: Homo sapiens

<400> SEQUENCE: 348

| | |
|---|---|
| gaccatgtta tgacatttta gtgcttgcta agcagtaaat actgacttac tttcctgcta | 60 |
| cactcttcag agcagaaaga gaaatctaca aaaagggcaa tgtagttggg atccaccaca | 120 |
| gccttgagac tgggccatgt ttctacagct tacccacatt ttaccccccac tttctctgag | 180 |
| aaacaatgca aactggagaa caaggtcaga gaagttatct tggatggtag aagagaagaa | 240 |
| aggagaagaa rggataagca gaaaatcaaa aagggcataa aaaaattact ggggaaaata | 300 |
| attcttagtc actcaccatt tcttatgttt gtgaaaacag aaacgaggag caagtgttgt | 360 |
| tgtaagaatt gttcttgccc ctccccctcc accacccaca tctgtcaagc tatccctgtt | 420 |
| tcactgtttc ctctgcactc tctattaact tcttttgtcct cctctttttct tttcctacag | 480 |
| caaagacttt ttgtcatgtt t | 501 |

<210> SEQ ID NO 349
<211> LENGTH: 501
<212> TYPE: DNA
<213> ORGANISM: Homo sapiens

<400> SEQUENCE: 349

| | |
|---|---|
| tgacttactt tcctgctaca ctcttcagag cagaaagaga aatctacaaa aagggcaatg | 60 |
| tagttgggat ccaccacagc cttgagactg ggccatgttt ctacagctta cccacatttt | 120 |

| accccccactt | tctctgagaa | acaatgcaaa | ctggagaaca | aggtcagaga | agttatcttg | 180 |
| gatggtagaa | gagaagaaag | gagaagaaag | gataagcaga | aaatcaaaaa | gggcataaaa | 240 |
| aaattactgg | rgaaaataat | tcttagtcac | tcaccatttc | ttatgtttgt | gaaaacagaa | 300 |
| acgaggagca | agtgttgttg | taagaattgt | tcttgcccct | cccctccac | cacccacatc | 360 |
| tgtcaagcta | tccctgtttc | actgtttcct | ctgcactctc | tattaacttc | tttgtcctcc | 420 |
| tcttttcttt | tcctacagca | aagacttttt | gtcatgtttt | gtttcttttt | ctattgtttc | 480 |
| tttcccttt  | ctaatccttg | a          |            |            |            | 501 |

<210> SEQ ID NO 350
<211> LENGTH: 1148
<212> TYPE: DNA
<213> ORGANISM: Homo sapiens

<400> SEQUENCE: 350

| tatgagattt | aatgttaaga | aataaaatgt | aggatctaaa | acgtaatcta | tagcataatc | 60 |
| tcaaaaatgg | tttagaaatg | acataataat | acagacattt | gtgggtggta | ggattatgca | 120 |
| tattttata | tattttaaa | tatattttc | aaaagcttcc | tataaagaat | gtaattcttt | 180 |
| cccaattcca | aatctagctt | aaacataatt | ttacaaaaat | tattctctca | gaatgtaaac | 240 |
| tagtaccacc | tctatggaaa | acattatgga | gatttcctaa | agagttaaaa | gtagatctac | 300 |
| catttgatcc | agcaatctta | atactgggta | tctacccgga | ggaaaagaag | tcattgtatg | 360 |
| aaaaagacac | ttgtacacat | atgtttacag | gaccacaatt | cacaaatgca | aagatgcaga | 420 |
| accaacctaa | gtggccastg | actaatgaga | ggataaagaa | gatgtggcat | atatatatca | 480 |
| gggactacta | ctcagccatt | acaaggaaca | aaataatgtc | ttttgcaaca | acttggatag | 540 |
| agctggaggc | cattattcta | agtaaagtaa | ttcaggaatt | ggaaaccaa | aaaccgtatg | 600 |
| ttctctctta | taagtgggaa | ctaagttagg | aataagcaaa | ggcacacaga | gggacatatt | 660 |
| ggactttaga | gactcacgag | gaggagggta | ataggggact | agggattaaa | agaaaaacta | 720 |
| gacattaggt | acaaggtacc | ctacttaagt | gcactaaaat | ctcagaattc | accactacgt | 780 |
| aattcaacta | agtaacaaga | aaccacttgt | accccaaaag | ctactgaaat | aaaaattatt | 840 |
| ctctcaaaaa | ttttaagccc | taaacttcag | ttcctattgt | ttatatttac | taagaaaaac | 900 |
| aacagaaaac | actgttttaa | aaatggtgga | ttttttaag | gttaaaggta | tataagacag | 960 |
| ctgcctaagg | aaacgcagat | acccctgtac | cttgttgttg | ttgttgtttt | tcactttttt | 1020 |
| aaaaaacata | gagatgggat | ctccttatgc | tgcccaggct | tgtctcaaac | tcctgagctc | 1080 |
| aagcaatcct | ctgacctcag | actctcaaag | ttttgggact | acaggcgaca | gtcaccatgc | 1140 |
| cagccaat   |            |            |            |            |            | 1148 |

<210> SEQ ID NO 351
<211> LENGTH: 1148
<212> TYPE: DNA
<213> ORGANISM: Homo sapiens

<400> SEQUENCE: 351

| tatgagattt | aatgttaaga | aataaaatgt | aggatctaaa | acgtaatcta | tagcataatc | 60 |
| tcaaaaatgg | tttagaaatg | acataataat | acagacattt | gtgggtggta | ggattatgca | 120 |
| tattttata | tattttaaa | tatattttc | aaaagcttcc | tataaagaat | gtaattcttt | 180 |
| cccaattcca | aatctagctt | aaacataatt | ttacaaaaat | tattctctca | gaatgtaaac | 240 |
| tagtaccacc | tctatggaaa | acattatgga | gatttcctaa | agagttaaaa | gtagatctac | 300 |

```
catttgatcc agcaatctta atactgggta tctacccgga ggaaaagaag tcattgtatg    360
aaaaagacac ttgtacacat atgtttacag gaccacaatt cacaaatgca aagatgcaga   420
accaacctaa gtggccactg actaatgaga ggataaagaa gatgtggcat atatayatca   480
gggactacta ctcagccatt acaaggaaca aaataatgtc ttttgcaaca acttggatag   540
agctggaggc cattattcta agtaaagtaa ttcaggaatt ggaaaaccaa aaaccgtatg   600
ttctctctta taagtgggaa ctaagttagg aataagcaaa ggcacacaga gggacatatt   660
ggactttaga gactcacgag gaggagggta atagggggact agggattaaa agaaaaacta  720
gacattaggt acaaggtacc ctacttaagt gcactaaaat ctcagaattc accactacgt   780
aattcaacta agtaacaaga aaccacttgt accccaaaag ctactgaaat aaaaattatt   840
ctctcaaaaa ttttaagccc taaacttcag ttcctattgt ttatatttac taagaaaaac   900
aacagaaaac actgttttaa aaatggtgga ttttttttaag gttaaaggta tataagacag  960
ctgcctaagg aaacgcagat acccctgtac cttgttgttg ttgttgtttt tcacttttt   1020 aaaaaacata gagatgggat ctccttatgc tgcccaggct tgtctcaaac tcctgagctc   1080
aagcaatcct ctgacctcag actctcaaag ttttgggact acaggcgaca gtcaccatgc   1140
cagccaat                                                           1148
```

<210> SEQ ID NO 352
<211> LENGTH: 1148
<212> TYPE: DNA
<213> ORGANISM: Homo sapiens

<400> SEQUENCE: 352

```
tatgagattt aatgttaaga aataaaatgt aggatctaaa acgtaatcta tagcataatc    60
tcaaaaatgg tttagaaatg acataataat acagacattt gtgggtggta ggattatgca   120 tattttttata tattttttaaa tatattttttc aaaagcttcc tataaagaat gtaattcttt  180
cccaattcca aatctagctt aaacataatt ttacaaaaat tattctctca gaatgtaaac  240
tagtaccacc tctatggaaa acattatgga gatttcctaa agagttaaaa gtagatctac   300
catttgatcc agcaatctta atactgggta tctacccgga ggaaaagaag tcattgtatg   360
aaaaagacac ttgtacacat atgtttacag gaccacaatt cacaaatgca aagatgcaga   420
accaacctaa gtggccactg actaatgaga ggataaagaa gatgtggcat atatayatca   480
gggactacta ctcagccatt acaaggaaca aaataatgtc ttttgcaaca acttggatag   540
agctggaggc cattattcta agtaaagtaa ttcaggaatt ggaaaaccaa aaaccgtatg   600
ttctctctta taagtgggaa ctaagttagg aataagcaaa ggcacacaga gggacatatt   660
ggactttaga gactcacgag gaggagggta atagggggact agggattaaa agaaaaacta  720
gacattaggt acaaggtacc ctacttaagt gcactaaaat ctcagaattc accactacgt   780
aattcaacta agtaacaaga aaccacttgt accccaaaag ctactgaaat aaaaattatt   840
ctctcaaaaa ttttaagccc taaacttcag ttcctattgt ttatatttac taagaaaaac   900
aacagaaaac actgttttaa aaatggtgga ttttttttaag gttaaaggta tataagacag  960
ctgcctaagg aaacgcagat acccctgtac cttgttgttg ttgttgtttt tcacttttt   1020 aaaaaacata gagatgggat ctccttatgc tgcccaggct tgtctcaaac tcctgagctc   1080
aagcaatcct ctgacctcag actctcaaag ttttgggact acaggcgaca gtcaccatgc   1140
cagccaat                                                           1148
```

<210> SEQ ID NO 353
<211> LENGTH: 1148
<212> TYPE: DNA
<213> ORGANISM: Homo sapiens

<400> SEQUENCE: 353

```
tatgagattt aatgttaaga aataaaatgt aggatctaaa acgtaatcta tagcataatc      60
tcaaaaatgg tttagaaatg acataataat acagacattt gtgggtggta ggattatgca     120
tatttttata tatttttaaa tatattttc aaaagcttcc tataaagaat gtaattcttt      180
cccaattcca aatctagctt aaacataatt ttacaaaaat tattctctca gaatgtaaac     240
tagtaccacc tctatggaaa acattatgga gatttcctaa agagttaaaa gtagatctac     300
catttgatcc agcaatctta atactgggta tctacccgga ggaaaagaag tcattgtatg     360
aaaaagacac ttgtacacat atgtttacag gaccacaatt cacaaatgca agatgcaga     420
accaacctaa gtggccactg actaatgaga ggataaagaa gatgtggcat atatatatca     480
gggactactr ctcagccatt acaaggaaca aaataatgtc ttttgcaaca acttggatag     540
agctggaggc cattattcta agtaaagtaa ttcaggaatt ggaaaaccaa aaaccgtatg     600
ttctctctta taagtgggaa ctaagttagg aataagcaaa ggcacacaga gggacatatt     660
ggactttaga gactcacgag gaggagggta atagggggact agggattaaa agaaaaacta    720
gacattaggt acaaggtacc ctacttaagt gcactaaaat ctcagaattc accactacgt     780
aattcaacta agtaacaaga aaccacttgt accccaaaag ctactgaaat aaaaattatt     840
ctctcaaaaa ttttaagccc taaacttcag ttcctattgt ttatatttac taagaaaaac     900
aacagaaaac actgttttaa aaatggtgga ttttttttaag gttaaaggta tataagacag     960
ctgcctaagg aaacgcagat acccctgtac cttgttgttg ttgttgtttt tcactttttt    1020
aaaaaacata gagatgggat ctccttatgc tgcccaggct tgtctcaaac tcctgagctc    1080
aagcaatcct ctgacctcag actctcaaag ttttgggact acaggcgaca gtcaccatgc    1140
cagccaat                                                            1148
```

<210> SEQ ID NO 354
<211> LENGTH: 611
<212> TYPE: DNA
<213> ORGANISM: Homo sapiens

<400> SEQUENCE: 354

```
caaaacctca accttccaga taagtctaag ggtgagaact tcacacaaga tgaataagaa      60
ccaatttctt ccagggcgat gttgaacctg gaaatgaaag ccaatctctc ttggaaggcc     120
tggtttgtag aaatgtcagt ctttgtttca agctgtggga gaatgagaag caagacttta     180
gggaaagagg aataaaatag atgtgcagaa ataacagagt gagaaagtct tcagggtgtc     240
gctagcccta attgcaggca tccctgaatc ctagaccttg gattgcaaga gactccttaa     300
tatcttccca tgtccacatt tgcttcacat agtttgaatg tggcttctat tatatacaga     360
tacaagattc aaatccaacc tctaygatga ctggtcttgt gaataagcag aagaggcact     420
aacaatatga cgtgagggat tcagggaaga gcactttctt gagcacatat cttccctggt     480
ctgccagctg tagtttatga aattccacaa tgaggatgaa atggaatcac catttacaga     540
gtactctcca gatgtctaac cctaagctag gtaccttcaa aatattatct agtttagata     600
atcaacccct t                                                         611
```

<210> SEQ ID NO 355
<211> LENGTH: 601
<212> TYPE: DNA
<213> ORGANISM: Homo sapiens

<400> SEQUENCE: 355

```
ttctctagtc caaagggttg attatctaaa ctagataata ttttgaaggt acctagctta      60
gggttagaca tctggagagt actctgtaaa tggtgattcc atttcatcct cattgtggaa     120
tttcataaac tacagctggc agaccaggga agatatgtgc tcaagaaagt gctcttccct     180
gaatccctca cgtcatattg ttagtgcctc ttctgcttat tcacaagacc agtcatcata     240
gaggttggat ttgaatcttg tatctgtata aatagaagc cacattcaaa ctatgtgaag      300
yaaatgtgga catgggaaga tattaaggag tctcttgcaa tccaaggtct aggattcagg     360
gatgcctgca attagggcta gcgacaccct gaagactttc tcactctgtt atttctgcac     420
atctatttta ttcctctttc cctaaagtct tgcttctcat tctcccacag cttgaaacaa     480
agactgacat ttctacaaac caggccttcc aagagagatt ggctttcatt tccaggttca     540
acatcgccct ggaagaaatt ggttcttatt catcttgtgt gaagttctca cccttagact     600
t                                                                    601
```

<210> SEQ ID NO 356
<211> LENGTH: 527
<212> TYPE: DNA
<213> ORGANISM: Homo sapiens

<400> SEQUENCE: 356

```
gctctagaat atggcattcc agaagtggga tgctacaaat agtctcattg agagtcaact      60
tgcacaatgt atcgtcctac ccttacatca atttctgaaa caacttctct ttgcacttcc     120
cctatagtta catgcataat aaattctgac aactcttatg aagtcatgga ataactttct     180
tcttatgttt cctatcaatg tcattagccc tttatcttgt ttgagtttcc atcagcaatg     240
ttttcaagtc ccaagatcat tcatgtatcc acaagcaatg atacgccaga tttggacaaa     300
taatactgaa tactatctta ttttcactgc catgatcaag gcagtgtgga ttgctgccaa     360
gtccaagaga agtgaggtca gcagctgcaa gccacctccg tcatttagaa aagcttcatg     420
atgtagtgtg tcgtttcgat gtgacactgt ctcacagagt taaaatgatg tgmaaggaac     480
tgttcaatgg aaatttagaa atttctcttt ttctcaattt tagtgta                   527
```

<210> SEQ ID NO 357
<211> LENGTH: 601
<212> TYPE: DNA
<213> ORGANISM: Homo sapiens

<400> SEQUENCE: 357

```
gaacaagatt ttcctgcttt taaaaatact acattaaagc tgaaaattta ggccaaaatt      60
ttcaagtggt aatagttaca ggcaattcat ctttctggtc agaaaagggt gttactgcag     120
ctatttctgc ctgaaactgg gtggcactac tacttttttt tttttttttt taactgagca     180
gacattttcc ttacactaaa attgagaaaa agagaaattt ctaaatttcc attgaacagt     240
tccttgcaca tcatttttaac tctgtgagac agtgtcacat cgaaacgaca cactacatca    300
ygaagctttt ctaaatgacg gaggtggctt gcagctgctg acctcacttc tcttggactt     360
ggcagcaatc cacactgcct tgatcatggc agtgaaaata agatagtatt cagtattatt     420
tgtccaaatc tggcgtatca ttgcttgtgg atacatgaat gatcttggga cttgaaaaca     480
```

| | |
|---|---|
| ttgctgatgg aaactcaaac aagataaagg gctaatgaca ttgataggaa acataagaag | 540 |
| aaagttattc catgacttca taagagttgt cagaatttat tatgcatgta actacagggg | 600 |
| a | 601 |

<210> SEQ ID NO 358
<211> LENGTH: 1001
<212> TYPE: DNA
<213> ORGANISM: Homo sapiens

<400> SEQUENCE: 358

| | |
|---|---|
| gcttaatacc tgagtgatgg aatattctgt tcaacaaacc cctctgacat aggtttgcct | 60 |
| atataataaa cctgttcatg tactcctgaa cctaaaagtt taaaaagat tatgtagaaa | 120 |
| acccaaagga atctataaaa agtctactag agctagagtg attttaacaa gatttcaata | 180 |
| cacaaattca aatgtctttc tatatattaa tgacaatcaa caataaaatt ttaaaacatt | 240 |
| attaaagtat aatgaaaata tcaactgttt agggagaaat gtaacaagaa tggtgaagga | 300 |
| cctatacact aaaaagcttc aatatgttgt tgagattaac tgaagaaggt ctaaatagat | 360 |
| ttttttttca tgtctcggaa gacttaatat gtgaagatac caattcttcc ccaaatgatc | 420 |
| aacaggtgaa atgcaatccc aatcaaaatc ccagcaatta ttttaagggg gaaattggca | 480 |
| atctgattct aaaattcata yggaaaaaaa caatggagtt agaataacta aaacaagtcc | 540 |
| gaaaagaaa aagaaatgga ggactaatgc tacctgattt caagtcttat cgtataaatc | 600 |
| tacatcaata aaggacaagt tggtattggg ttaaagatag ataaatacat cagtggaata | 660 |
| gaatattgaa tccagaataa atccacacat atatggataa aaataccaga caattcagtg | 720 |
| gagatggttt tgtttttaca acaaatgtta ctggaacaaa ttgatatatg tattagtcag | 780 |
| atatggctgc cataacaaag aaccacaaac aggtggttta ataatgaaa ataaatttcc | 840 |
| tcagaattct ggagtatgga agcccaagat caagttgctg ggaggattcg tttcttctga | 900 |
| gtgtctcttt ttttgatgac agatgactat ctttttaccaa tgtcttcact tggttttccc | 960 |
| tctgtgtgtg cctaggtcct attctccaat tcctataagg a | 1001 |

<210> SEQ ID NO 359
<211> LENGTH: 1001
<212> TYPE: DNA
<213> ORGANISM: Homo sapiens

<400> SEQUENCE: 359

| | |
|---|---|
| ctaaaagttt aaaaaagatt atgtagaaaa cccaaaggaa tctataaaaa gtctactaga | 60 |
| gctagagtga ttttaacaag atttcaatac acaaattcaa atgtctttct atatattaat | 120 |
| gacaatcaac aataaaattt taaaacatta ttaaagtata atgaaaatat caactgttta | 180 |
| gggagaaatg taacaagaat ggtgaaggac ctatacacta aaaagcttca atatgttgtt | 240 |
| gagattaact gaagaaggtc taaatagatt ttttttcat gtctcggaag acttaatatg | 300 |
| tgaagatacc aattcttccc caaatgatca acaggtgaaa tgcaatccca atcaaaatcc | 360 |
| cagcaattat tttaaggggg aaattggcaa tctgattcta aaattcatat ggaaaaaaac | 420 |
| aatggagtta gaataactaa aacaagtccg aaaagaaaa agaaatggag gactaatgct | 480 |
| acctgatttc aagtcttatc rtataaatct acatcaataa aggacaagtt ggtattgggt | 540 |
| taaagataga taaatacatc agtggaatag aatattgaat ccagaataaa tccacacata | 600 |
| tatggataaa aataccagac aattcagtgg agatggtttt gtttttacaa caaatgttac | 660 |
| tggaacaaat tgatatatgt attagtcaga tatggctgcc ataacaaaga accacaaaca | 720 |

| | |
|---|---|
| ggtggtttaa ataatggaaa taaatttcct cagaattctg gagtatggaa gcccaagatc | 780 |
| aagttgctgg gaggattcgt ttcttctgag tgtctctttt tttgatgaca gatgactatc | 840 |
| ttttaccaat gtcttcactt ggttttccct ctgtgtgtgc ctaggtccta ttctccaatt | 900 |
| cctataagga aaccagtcat attggattag ggcccactct aatggcccca ttttacttgc | 960 |
| attatctctt taaagacact atctccagat gtagccacac t | 1001 |

<210> SEQ ID NO 360
<211> LENGTH: 1058
<212> TYPE: DNA
<213> ORGANISM: Homo sapiens

<400> SEQUENCE: 360

| | |
|---|---|
| catgattagc tatgctactt tccactgctc ttagtatact gagaggcagc ataagtaaaa | 60 |
| ctaaaatatc tgaagatagc aatagactat ttaaagtaga agaagtatgc tattttttgtt | 120 |
| ttgttttcat ttcgaaggaa atatgcaaag gtttattgag tatttcagct tctcttacag | 180 |
| taggttttttt ttggattctt tctgtgtttg tctatgttga taaaacattg aaatgccata | 240 |
| tagctcaaag gtcattcact taagaaatct aagtactgat aacatcttag ccccgattct | 300 |
| tcataggcat tgttaagcct attataattt ggtwcagag agaaggtaaa ctatattcca | 360 |
| gacaggcata taaagcaatt tctcctataa ttggagttca cgaaaaattc acatatttct | 420 |
| ttttaatagt aactctcaca gcaagaacat atgtttgtaa ataatacatc acagaatctt | 480 |
| attggcagac aaggaaattc ctaaaatatt ttttactgcc acatcaatta agatatataa | 540 |
| aataccttat atagaagatg tttgcaccca ggccaaacaa atcaaacaag aatagaagca | 600 |
| ctgacagtct tatttcaaaa ttggtttaac ttgtatttac aggatattgt agtaccttat | 660 |
| aaagttgatt gctgattggc cgtctttttac agaattctgt cagattgtta ttatttcttg | 720 |
| taaagattga ttcaaacaaa taaaaattgt caggattgga tatgtcctat agtgaggtgt | 780 |
| agttatgtca catgagattt ttaattacaa agaaatggaa aataaaatga gatagaatt | 840 |
| gagactcccc tgtcacctca caaatatgtt gaaatacaat gaaatttcca aagatgttaa | 900 |
| agcatataaa gttgaataat tcttattatg tattaaactt acagaaattt aatttcttta | 960 |
| ctttataaga ggtagtgaaa atataaaatt aattatgaag acagagtagt cttagtcaga | 1020 |
| catggcccta taaagcatat tcccattcgt tacatcaa | 1058 |

<210> SEQ ID NO 361
<211> LENGTH: 1058
<212> TYPE: DNA
<213> ORGANISM: Homo sapiens

<400> SEQUENCE: 361

| | |
|---|---|
| catgattagc tatgctactt tccactgctc ttagtatact gagaggcagc ataagtaaaa | 60 |
| ctaaaatatc tgaagatagc aatagactat ttaaagtaga agaagtatgc tattttttgtt | 120 |
| ttgttttcat ttcgaaggaa atatgcaaag gtttattgag tatttcagct tctcttacag | 180 |
| taggttttttt ttggattctt tctgtgtttg tctatgttga taaaacattg aaatgccaya | 240 |
| tagctcaaag gtcattcact taagaaatct aagtactgat aacatcttag ccccgattct | 300 |
| tcataggcat tgttaagcct attataattt ggtacagag agaaggtaaa ctatattcca | 360 |
| gacaggcata taaagcaatt tctcctataa ttggagttca cgaaaaattc acatatttct | 420 |
| ttttaatagt aactctcaca gcaagaacat atgtttgtaa ataatacatc acagaatctt | 480 |

| | |
|---|---|
| attggcagac aaggaaattc ctaaaatatt ttttactgcc acatcaatta agatatataa | 540 |
| aataccttat atagaagatg tttgcaccca ggccaaacaa atcaaacaag aatagaagca | 600 |
| ctgacagtct tatttcaaaa ttggtttaac ttgtatttac aggatattgt agtaccttat | 660 |
| aaagttgatt gctgattggc cgtcttttac agaattctgt cagattgtta ttatttcttg | 720 |
| taaagattga ttcaaacaaa taaaaattgt caggattgga tatgtcctat agtgaggtgt | 780 |
| agttatgtca catgagattt ttaattacaa agaaatggaa aataaaatga aatagaattt | 840 |
| gagactcccc tgtcacctca caaatatgtt gaaatacaat gaaatttcca aagatgttaa | 900 |
| agcatataaa gttgaataat tcttattatg tattaaactt acagaaattt aatttcttta | 960 |
| ctttataaga ggtagtgaaa atataaaatt aattatgaag acagagtagt cttagtcaga | 1020 |
| catggcccta taaagcatat tcccattcgt tacatcaa | 1058 |

<210> SEQ ID NO 362
<211> LENGTH: 956
<212> TYPE: DNA
<213> ORGANISM: Homo sapiens

<400> SEQUENCE: 362

| | |
|---|---|
| aaaacaagga acaaacaaac aaaaatgtta caaccgaaca acagactttt gagtcatgtt | 60 |
| tcaggccaag aggtgatgag ttactgtagt tgcttgagct ggttggtgaa atattacctg | 120 |
| gcaacaaaac tgaaatagaa ggtggcttag taaaatgcag attcagaatg agtgccttaa | 180 |
| ggttaaggca tataagacca aactgatttt cttttttcacg aggtcttcag gtaaggccat | 240 |
| tgtagaagat accttgtttg cgaacttcag taaattactt cacttgtctc atattttcat | 300 |
| tttcaggatg gaggcttgag attgaattgt agtgcaatta ggtaaatttt tacccatttt | 360 |
| aaatataata ttaaaatatt aattataaat taccttattt gaatctggaa taatatttat | 420 |
| tgcagggcat ataatctaag ctgtaaacgt cctgtyagaa gacaacatat tcatcttgct | 480 |
| aaggtataag ctatatgact ggcactgtgc tcaactcaga gtcattgaat gaacagtatt | 540 |
| tatttaatct atgaatgaga gcacttcaag tatacagaaa gatatctcaa aagattcagc | 600 |
| cttacattgc tcataacttc aatgacttag atgaaaacct cctgaacatt tttatcagtt | 660 |
| gtataggtac cccaaatcat aagggaatgt ttatcaatta gatgatgaaa tggggatgca | 720 |
| actacatcat ggcaggctaa agcaatagaa tgactttgac aagaggaaat tacatagagg | 780 |
| caccctgagtc tcctaaaacca atttcaaagg tatgagaggg gggtgatata aataaatagt | 840 |
| tgatagatga aaaaactcag aagttatagt tgacagcaat tttaatataa tatgaaaaat | 900 |
| gtggttggac ttttagggaa aaaaacctaa taaaatctaa tggaaattag tggtcc | 956 |

<210> SEQ ID NO 363
<211> LENGTH: 956
<212> TYPE: DNA
<213> ORGANISM: Homo sapiens

<400> SEQUENCE: 363

| | |
|---|---|
| caaccgaaca acagactttt gagtcatgtt tcaggccaag aggtgatgag ttactgtagt | 60 |
| tgcttgagct ggttggtgaa atattacctg gcaacaaaac tgaaatagaa ggtggcttag | 120 |
| taaaatgcag attcagaatg agtgccttaa ggttaaggca tataagacca aactgatttt | 180 |
| cttttttcacg aggtcttcag gtaaggccat tgtagaagat accttgtttg cgaacttcag | 240 |
| taaattactt cacttgtctc atattttcat tttcaggatg gaggcttgag attgaattgt | 300 |
| agtgcaatta ggtaaatttt tacccatttt aaatataata ttaaaatatt aattataaat | 360 |

```
taccttattt gaatctggaa taatatttat tgcagggcat ataatctaag ctgtaaacgt    420
cctgtcagaa gacaacatat tcatcttgct aaggtrtaag ctatatgact ggcactgtgc    480
tcaactcaga gtcattgaat gaacagtatt tatttaatct atgaatgaga gcacttcaag    540
tatacagaaa gatatctcaa aagattcagc cttacattgc tcataacttc aatgacttag    600
atgaaaacct cctgaacatt tttatcagtt gtataggtac cccaaatcat aagggaatgt    660
ttatcaatta gatgatgaaa tggggatgca actacatcat ggcaggctaa agcaatagaa    720
tgactttgac aagaggaaat tacatagagg cacctgagtc tcctaaacca atttcaaagg    780
tatgagaggg gggtgatata aataaatagt tgatagatga aaaaactcag aagttatagt    840
tgacagcaat tttaatataa tatgaaaaat gtggttggac ttttagggaa aaaaacctaa    900
taaaatctaa tggaaattag tggtccactc atttctccac ctaggatgtt aaaaat        956

<210> SEQ ID NO 364
<211> LENGTH: 601
<212> TYPE: DNA
<213> ORGANISM: Homo sapiens

<400> SEQUENCE: 364
gtaaaacaca tagatcgctg tatccttgtt cagtaagcta caacatactc gtatctcctg     60
aaatcctggg cttaaatcga ggtctcaaag gctttgtttt gttttgttgt atggttgtat    120
ggtgagtgtg tgtgtgtgtg tgtgtgtgtg tgtttattct cctgaaattc tcctcctcac    180
ttgacttaag ctaaaagata aacgtcctct tcctttcagc cacagatggt gatggataaa    240
ttgaatgtca ttcacattat tcccttaaaa taaactctct ccctcccctc tccgtctca    300 wccttgtccc tttctttata taatgggtaa tgcgttaatg tcagcagaat agttttgggg    360
ccataatggc aagtatcacg tggatggttt agcattgttt ttagaatgct gtgaatttgg    420
gtatatgtga gttttgggga aagttttgca actatatgtt tgttaattaa atgaggacta    480
taaagtaata taaaattatg tttctggaac atattttgga agctataaag tcatctgtat    540
ttattatcca cagacataat gtcattgttc aggtcctgca accttcttat aatcaacata    600
c                                                                   601

<210> SEQ ID NO 365
<211> LENGTH: 601
<212> TYPE: DNA
<213> ORGANISM: Homo sapiens

<400> SEQUENCE: 365
agtaagctac aacatactcg tatctcctga aatcctgggc ttaaatcgag gtctcaaagg     60
ctttgttttg ttttgttgta tggttgtatg gtgagtgtgt gtgtgtgtgt gtgtgtgtgt    120
gtttattctc ctgaaattct cctcctcact tgacttaagc taaaagataa acgtcctctt    180
cctttcagcc acagatggtg atggataaat tgaatgtcat tcacattatt cccttaaaat    240
aaactctctc cctcccctct ccgtctcatc cttgtccctt tctttatat aatgggtaat    300 kcgttaatgt cagcagaata gttttggggc cataatggca agtatcacgt ggatggttta    360
gcattgtttt tagaatgctg tgaatttggg tatatgtgag ttttggggaa agttttgcaa    420
ctatatgttt gttaattaaa tgaggactat aaagtaatat aaaattatgt ttctggaaca    480
tattttggaa gctataaagt catctgtatt tattatccac agacataatg tcattgttca    540
ggtcctgcaa ccttcttata atcaacatac gtgggcccag ggattttatg tatcttcgcc    600
``` t                                                                    601

<210> SEQ ID NO 366
<211> LENGTH: 1079
<212> TYPE: DNA
<213> ORGANISM: Homo sapiens

<400> SEQUENCE: 366
gaatttatgg tctgatggag aagggaatca ttaaagttct atgtagtgag atatccccaa     60
ggggtgtatt aggcttacca ccactggaat ctggatagat gaagacagag tggcagggaa    120
gtcgtattaa ggttctgttt ctgctgggag ccacaggtcc tcaggaagca acaagtactg    180
ggcagattga tactgtagct rggctctagc tctatacctc tagaataaag gttacaaact    240
agcaacttga aagctaaacc tggcccacag atatgtttta tttggctctt acactgtttt    300
aaaaaatatt accaacattt aaaactggga agttttatga aaaaacccag acttctggat    360
tctgttgaaa aaaaaatca gaagatctgg caatactgag ctgacattcc tatatgacaa    420
caattggctg gatctatgca gcttctctcc aaaaagcaaa gaatgtgttc ttgcttaaca    480
cagtccccac cactccctca tattctccaa tcctggacct gagcgtcatt tgctatgtat    540
cgccatttgc catgaagttt tacactctac agaaatataa ttttttttgta gaagactatg    600
ctttaatcaa gatcaggata atataaagtg agatctgaaa gtggaaaaaa gataaatgtc    660
caacaatgat agactggatt aagaaaatgt ggcacatata caccgtggag tactatgcag    720
ccaaaaaaaa cgatgagttc atgtcctttg tagggacatg gatgaagctg aaaccacca    780
ttctcagcaa actatcgcaa ggacaaaaaa ccaaacgccg catgttctca ctcataggtg    840
ggaattgaac aatgagaaca cttgggcaca ggaagggaa catcacacac cgggccctgt    900
tgtggggtgg ggggaggagg gagggatagc atttggagat atacctaatg ttaaatgact    960
agtttctggg tgcagcacac catcatggca catgtataca tatgtaacta acctgcacat    1020
tgtgcacatg taccctaaaa cttaaagtat aattttttaa aaaagatatt ttcttatct    1079

<210> SEQ ID NO 367
<211> LENGTH: 501
<212> TYPE: DNA
<213> ORGANISM: Homo sapiens

<400> SEQUENCE: 367
ataaattttc tcttccctca agaatttatg gtctgatgga aagggaatc attaaagttc     60
tatgtagtga gatatcccca agggatgtat taggcttacc accactggaa tctggataga    120
tgaagacaga gtggcaggga gtcgtattaa ggttctgtt tctgctggga ccacaggtc    180
ctcaggaagc aacaagtact gggcagattg atactgtagc tgggctctag ctctatacct    240
ctagaataaa kgttacaaac tagcaacttg aaagctaaac ctggcccaca gatatgtttt    300
atttggctct tacactgttt taaaaaatat taccaacatt taaaactggg aagttttatg    360
aaaaaaccca gacttctgga ttctgttgaa aaaaaaatc agaagatctg gcaatactga    420
gctgacattc ctatatgaca acaattggct ggatctatgc agcttctctc caaaaagcaa    480
agaatgtgtt cttgcttaac a                                              501

<210> SEQ ID NO 368
<211> LENGTH: 1001
<212> TYPE: DNA
<213> ORGANISM: Homo sapiens

<400> SEQUENCE: 368

```
tgaagaagcc gcctggcttc ttgtttcttc tcatagcaaa atgcaatgag aaagagataa      60
tttgagaaaa gaaccgttta aacaaaaaga aaccaagaca taatgatttt ggaaattctc     120
agtttattca gactgcaaaa gatattaaaa taaagaaact cagtaacagg gatagataat     180
ctaaagaaaa agcctaggac acggctgtag taaccttctg tttttatacc tcagcaattt     240
gctaatgcct caaaaagatc aaaagtactc aaatataaag ggctctttga agagattaga     300
tttcctcaat caaaccaaag agcatcgagg aagcttaagg ttactgtccc tcacatatct     360
cagcagaagg caaaaataga agactgatta tctaagaaag atctctgaaa gagtctcata     420
ttatggagtg aacccctgtg gcatacatgg gagacccact tggttcttga aatttttata     480
tcaggagaaa cactgtcagt ytgtattgaa aggaacagag aaaatacgaa attaaagaag     540
actattaaac ctccaaaatt ctggcaggaa agaagcttac acagctactc agttgcaaag     600
atctgccact tttcatatac atgaaaggac tcagaggagg aagccacagg tttagaagga     660
aaagctaaaa gcaacatcgt attagtcttg gatctaggaa cctaatttct ctagcagaat     720
ctagaaatgg cttgggacaa gtgattgttt ttttacctag gattttctcc ctcttgaaaa     780
caggactgtc tgtaactatt atcctatgcc tgccctacca tcatatttca gaaacaggta     840
acttatgttt tcactttcaa agattcacaa taaagagaaa ttgtacctca gaatggatta     900
taccagagct ttcctcatgc ataaattaaa taatttaggt tatgtgattt gaagcttttg     960
agtgggtgag gtgacatttt ggatgctgag ttggtgccgt a                        1001

<210> SEQ ID NO 369
<211> LENGTH: 1001
<212> TYPE: DNA
<213> ORGANISM: Homo sapiens

<400> SEQUENCE: 369
tcttctcata gcaaaatgca atgagaaaga gataatttga gaaagaacc gtttaaacaa       60
aaagaaacca agacataatg attttggaaa ttctcagttt attcagactg caaagatat     120
taaaataaag aaactcagta acagggatag ataatctaaa gaaaaagcct aggacacggc     180
tgtagtaacc ttctgttttt atacctcagc aatttgctaa tgcctcaaaa agatcaaaag     240
tactcaaata taaagggctc tttgaagaga ttagatttcc tcaatcaaac caaagagcat     300
cgaggaagct taaggttact gtccctcaca tatctcagca gaaggcaaaa atagaagact     360
gattatctaa gaaagatctc tgaaagagtc tcatattatg gagtgaaccc ctgtggcata     420
catgggagac ccacttggtt cttgagaatt ttatatcagg agaaacactg tcagtctgta     480
ttgaaaggaa cagagaaaat rcgaaattaa agaagactat taaacctcca aaattctggc     540
aggaaagaag cttacacagc tactcagttg caaagatctg ccactttca tatacatgaa     600
aggactcaga ggaggaagcc acaggtttag aaggaaaagc taaaagcaac atcgtattag     660
tcttggatct aggaacctaa tttctctagc agaatctaga aatggcttgg gacaagtgat     720
tgttttttta cctaggattt tctccctctt gaaaacagga ctgtctgtaa ctattatcct     780
atgcctgccc taccatcata tttcagaaac aggtaactta tgttttcact ttcaaagatt     840
cacaataaag agaaattgta cctcagaatg gattatacca gagctttcct catgcataaa     900
ttaaataatt taggttatgt gatttgaagc ttttgagtgg gtgaggtgac attttggatg     960
ctgagttggt gccgtagtga gtccagaatt ctgcggaact t                        1001

<210> SEQ ID NO 370
```

<211> LENGTH: 601
<212> TYPE: DNA
<213> ORGANISM: Homo sapiens

<400> SEQUENCE: 370

```
ctctagactc ctcctgtatt ttaatttagc cacttttta gggcctacaa ttttagatct    60
ccacagggct cttgaaactt cttgaacctc atcagtaaca tgtccattag tggcatgacc   120
caagagttct agaacatcta ttcagcaagt gtgtatctgg taagtgaata ttccttctat   180
gtgttcccctt ttgcatcaaa ctacacactg tcattcctcc tttatctcca aaagcttgaa  240
aattcctcac ttgtatctca ttcttttctct cttagaaaac tgatcacctc tgatgaatta  300
raacggaatg accaagcttt gggagaggca aagaatctc ggtgttaaag actcagagtt   360
taagaagcaa caaaaagatt atacagatgt gaatatgtga ccttcctcca ccagggcatg  420
ttgccttgga gtaagataat ctaagcacac acttcatagc tgagaacaa ttttggaagt   480
ctttgcttta tggatattta cataaagcaa atatggatat ttacctaaag ctggaccaa   540
ggcctaattc ctctagagcc ccttgatcat gaacaccatt cctgtcatga ttcttaaggt  600
c                                                                 601
```

<210> SEQ ID NO 371
<211> LENGTH: 601
<212> TYPE: DNA
<213> ORGANISM: Homo sapiens

<400> SEQUENCE: 371

```
acaagctcca gccatggacg caattccttc tagaagcaaa atttatctct agactcctcc    60
tgtattttaa tttagccact tttttagggc ctacaatttt agatctccac agggctcttg   120
aaacttcttg aacctcatca gtaacatgtc cattagtggc atgacccaag agttctagaa  180
catctattca gcaagtgtgt atctggtaag tgaatattcc ttctatgtgt tcccttttgc   240
atcaaactac acactgtcat tcctccttta tctccaaaag cttgaaaatt cctcacttgt   300
rtctcattct ttctctctta gaaaactgat cacctctgat gaattagaac ggaatgacca   360
agctttggga gaggcaaaag aatctcggtg ttaaagactc agagtttaag aagcaacaaa   420
agattatac agatgtgaat atgtgacctt cctccaccag ggcatgttgc cttggagtaa   480
gataatctaa gcacacactt catagcctga gaacaatttt ggaagtcttt gctttatgga   540
tatttacata aagcaaatat ggatatttac ctaaaggctg gaccaaggcc taattcctct   600
a                                                                 601
```

<210> SEQ ID NO 372
<211> LENGTH: 701
<212> TYPE: DNA
<213> ORGANISM: Homo sapiens

<400> SEQUENCE: 372

```
gaagatgcac tctaatgttt tttcccagaa gctctgtagg tttagctttt acctttctgg    60
gtttgttttg ttttgttttt tgagatggag tcccactcgt gtcacccagg ctggagtaca   120
atggtgcaat ctcggttcac tgcaacctcc acctcccggg ttcaagcaat tcccctgtct   180
ccacctctcg agtagctggg atgggaggcg cctgccacca tacctggcta attttcatat   240
ttttagtaaa gatagggttt caccatgtta gccaggctgg tctcgaactc ctgacctcaa   300
gtgatccacc cgcctcagct tcccaaagtg ctgggattac aggcgtgagc cactgcgccc   360
agccctagct ttttggtcta tgattcctcc caaattaatt tctgtgaacc attaccttaa   420
```

```
gatgttgaga tttaatgtcc agaatctcat tgttcacct ttgaaaatta agaaaccctg      480
gcacagtgtt gactggagcc wcttaccta atagaaaata aagctcacat atatccataa      540
tgaaaagcag agaccagcac aaccatagtc acctgacagt tttaaaatcc aaggccagga      600
tcttctcaac tcaggcccac tcacttactc cacaacatac ttcttctttc ctcagcatct      660
actacttgtg ctgggacctt ggtcttccca ttgttcatgt c                         701
```

<210> SEQ ID NO 373
<211> LENGTH: 701
<212> TYPE: DNA
<213> ORGANISM: Homo sapiens

<400> SEQUENCE: 373

```
agatggagtc ccactcgtgt cacccaggct ggagtacaat ggtgcaatct cggttcactg       60
caacctccac ctcccgggtt caagcaattc ccctgtctcc acctctcgag tagctgggat      120
gggaggcgcc tgccaccata cctggctaat tttcatattt ttagtaaaga tagggtttca      180
ccatgttagc caggctggtc tcgaactcct gacctcaagt gatccacccg cctcagcttc      240
ccaaagtgct gggattacag gcgtgagcca ctgcgcccag ccctagcttt ttggtctatg      300
attcctccca aattaatttc tgtgaaccat taccttaaga tgttgagatt taatgtccag      360
aatctcattt gttcaccttt gaaaattaag aaaccctggc acagtgttga ctggagccac      420
ttaccttaat agaaaataaa gctcacatat atccataatg aaaagcagag accagcacaa      480
ccatagtcac ctgacagttt waaaatccaa ggccaggatc ttctcaactc aggcccactc      540
acttactcca acatacttct tctttcct cagcatctac tacttgtgct gggaccttgg      600
tcttcccatt gttcatgtca ttcttttcct cacagttccc attctttct ccctgaaata      660 agaaatttc aaaatatacc atgtttcatg aaaagacaa a                            701
```

<210> SEQ ID NO 374
<211> LENGTH: 701
<212> TYPE: DNA
<213> ORGANISM: Homo sapiens

<400> SEQUENCE: 374

```
gatttccacc ctcaggtgat ggggatggtt gaacatccaa cacctgaaac aggacagacg       60
atattgacag tacttgttag ttgcatataa tcacagacca gtggaaacag atgaaccaca      120
cagggccaca gcggggtttc actggggaac agagtgaaca atcaggaggt gtgggaggca      180
ggtttagtag tttaaagagg ttgaggtgtc cccctggatc ccatgggagg atcacattgg      240
ctcatttgaa ttatcatacg gactggcagg gaactgaaat cttctactca gggataagca      300
gaaactgtcc ctggtttcct tgataaaaag ggttgtttga taggggaccct tatccatggg      360 aggaaagtga ggagggaaat ttgtggctaa gccattcaag gccctccag ttttactaga      420 tgtcaaggca gcacacgtaa tattgggact taattttagc cacataacta ataaatttgt      480
aagtatgtgc aacggctcac rcttgcttcc agaatggcac ctaaaaaaca gatttacctc      540
tccccaaatt cagatatgga attaaatgta atgtcaggaa aattgtctaa gagttggaaa      600
tgggaaaaaa atgttctttt ggtggagtta tggactccag aggttatcag attctattga      660
ataacgtact tttgattgta tttgtaacaa ttaggctatt t                          701
```

<210> SEQ ID NO 375
<211> LENGTH: 1001
<212> TYPE: DNA

<213> ORGANISM: Homo sapiens

<400> SEQUENCE: 375

```
gcatataatc acagaccagt ggaaacagat gaaccacaca gggccacagc ggggtttcac    60
tggggaacag agtgaacaat caggaggtgt gggaggcagg tttagtagtt taaagaggtt   120
gaggtgtccc cctggatccc atgggaggat cacattggct catttgaatt atcatacgga   180
ctggcaggga actgaaatct tctactcagg gataagcaga aactgtccct ggtttccttg   240
ataaaaaggg ttgtttgata ggggaccttg tccatgggag gaaagtgagg agggaaattt   300
gtggctaagc cattcaaggc cctcccagtt ttactagatg tcaaggcagc acacgtaata   360
ttgggactta attttagcca cataactaat aaatttgtaa gtatgtgcaa cggctcacac   420
ttgcttccag aatggcacct aaaaaacaga tttacctctc cccaaattca gatatggaat   480
taaatgtaat gtcaggaaaa ytgtctaaga gttggaaatg ggaaaaaaat gttcttttgg   540
tggagttatg gactccagag gttatcagat tctattgaat aacgtacttt tgattgtatt   600
tgtaacaatt aggctatttg tgaactcggt aggggtagaa atcgagttgt agaaaatgga   660
tggtaatgca agtgattttt gaccatatca atgcaaatga attctgttgg tagaaatatt   720
catttccaca ctgtagatga ccctaaacat atgtcattac attatatttt attgccttat   780
agactattaa ccaattttga atcatacagt agcaaattta tttcagcatt cttgtgtgta   840
tgtgtttata tatacacgtg catatgtatt taagatatat aattgtatat tcttcaaatt   900
cttctttgaa caggtttgaa cctcttatta gtttcctcat taaggaattt aataagacct   960
ttaatgcatg tttgtatttt catgagagtc attatttac c                      1001
```

<210> SEQ ID NO 376
<211> LENGTH: 695
<212> TYPE: DNA
<213> ORGANISM: Homo sapiens

<400> SEQUENCE: 376

```
tgctccttca ttagtgcaat ggaacagcaa atcaggatac tttcacagtt ctcttaagtg    60
agcctagaag tggggagctg cttgttcaca aacttgaagc ctgaatatgt taatattctt   120
tcagtggccg gacgcggtgg ctcatgcctg taatcccaac actttgggag gccgaggtag   180
gcagatcaac ctgaagtcag gagttcgagg ccagcctggc caacatggtg aaaccccacc   240
tgttggtctg tactaaaaat agaaaaatta gctgggcatg gtggcgcatg cctgtaatcc   300
cagctactca ggaggctgtg gcagaagaat cgcctgcacc tgggaggcag aggttgcttt   360
gagttgatat cgtgtcactg cactccagcc tgggcaacag agtgagatcc tttcagaaac   420
ctgctgtctg tatttggata caattaaaaa aaaaaaaaag atgagacagg caggtgcgaa   480
agaaataaaa gtcamaactg atccagttgg gaaactcaga attgacagtt acgtgtcctt   540
tcatttattg atattttgag attcacaggg gtttaaactt tattttccca agactgaata   600
gttcccacct cccttccata tataaaattt gagtagctgg ggagatttaa aagaggctcc   660
ccataaactc agaagttaaa agagacaagg gtccc                             695
```

<210> SEQ ID NO 377
<211> LENGTH: 601
<212> TYPE: DNA
<213> ORGANISM: Homo sapiens

<400> SEQUENCE: 377

```
aaccccacct gttggtctgt actaaaaata gaaaaattag ctgggcatgg tggcgcatgc    60
```

```
ctgtaatccc agctactcag gaggctgtgg cagaagaatc gcctgcacct gggaggcaga    120
ggttgctttg agttgatatc gtgtcactgc actccagcct gggcaacaga gtgagatcct    180
ttcagaaacc tgctgtctgt atttggatac aattaaaaaa aaaaaaaaga tgagacaggc    240
aggtgcgaaa gaaataaaag tcacaactga tccagttggg aaactcagaa ttgacagtta    300
sgtgtccttt cattattga tattttgaga ttcacagggg tttaaacttt attcttccaa     360
gactgaatag ttcccacctc ccttccatat ataaaatttg agtagctggg gagatttaaa    420
agaggctccc cataaactca gaagttaaaa gagacaaggg tcccagtaaa tacaaaatga    480
ttggggttga ggaggcagat tttctgtcct cagtgaagtt tgttggttgg ttggttggtt    540
ggttggttaa ttggttggtt tttgagtcag ggtctcactt tgtcacccaa gctggagtgc    600
a                                                                  601
```

<210> SEQ ID NO 378
<211> LENGTH: 663
<212> TYPE: DNA
<213> ORGANISM: Homo sapiens

<400> SEQUENCE: 378

```
tgtagcaaca ggagggatga gacccaaagg tctgaaaagc cagtattta agaagtcttg     60 gaaaatgtgg aggttgaaaa atctaacagg agtgcttgct tcagcagcaa tttagagtag    120
attagcatgg cctctgcgcc aggatgacat gcacattcct aaaagtgttc cgtgttttaa    180 aaaaagaga gagacagaat ctaaggggat gtgtacattt gctagagcta ctataacaaa     240
gtaccagagg cagggtcact tcaacaacag aaatttattt ctcacagttc tggaggctag    300
acgtccaaga ttaaggtgtt gactgggttg aattcagccc ataacaggaa ataaggagtt    360
aaataaagca cttgcttcta ttgtttgtac ctaaacttaa cagaaycacag taagtaacaa    420 gtcattggga tgcagaaaag aaaaagaga gtgaaggaag gagagaaggt gaagggagaa     480
tggaagagag gaagggaggg aggaaagaaa agtttgatga atgattgcag tctaaactgg    540
ttcaaacaag agatcttgtt taattaagga attcatccca tctctgccta ttaggaggag    600
gaaaaagtct aaaatagaag atggtgaaag ttggatgacc ccaggcatta aggccattca    660
tct                                                                 663
```

<210> SEQ ID NO 379
<211> LENGTH: 662
<212> TYPE: DNA
<213> ORGANISM: Homo sapiens

<400> SEQUENCE: 379

```
ttaagaagtc ttgaaaatg tggaggttga aaaatctaac aggagtgctt gcttcagcag     60
caatttagag tagattagca tggcctctgc gccaggatga catgcacatt cctaaaagtg    120
ttccgtgttt taaaaaaaag agagacacag aatctaaggg gatgtgtaca tttgctagag    180
ctactataac aaagtaccag aggcagggtc acttcaacaa cagaaattta tttctcacag    240
ttctggaggc tagacgtcca agattaaggt gttgactggg ttgaattcag cccataacag    300
gaaataagga gttaaataaa gcacttgctt ctattgtttg tacctaaaact taacagaaca    360 cagtaagtaa caagtcattg ggatgcagaa aagaaaaaag agagtgaagg aaggagaraa    420
ggtgaaggga gaatggaaga gaggaaggga gggaaagaaa aagtttga tgaatgattg    480 cagtctaaac tggttcaaac aagagatctt gtttaattaa ggaattcatc ccatctctgc    540
```

```
ctattaggag gaggaaaaag tctaaaatag aagatggtga aagttggatg accccaggca     600
ttaaggccat tcatctttaa ctgttatgct tggatcatgc aaatgtgtct ggtagctaca     660
ag                                                                    662

<210> SEQ ID NO 380
<211> LENGTH: 615
<212> TYPE: DNA
<213> ORGANISM: Homo sapiens

<400> SEQUENCE: 380
ttccatacat tccttccaca ccattgccct taacctttca aattcctgct taaaactaat      60 cccatttttta tggctgacct caccctgtat caaaaactcc gacatccctt tacgacagag    120
agcacaaact agtggtccaa aatgtcatgg gggtcttctc agagttgttt tttcaatcag     180
gaaatttcac ataaaaatat ggattctgta tttctctttt aaaaacagaa aaacgagcca     240
ccagtgggag cactgcaggt atctgtgtga gaccygtact tcacaactcc tgctttccct     300
ccataaagta gcttgcattt tccacattga ctttgcagtt ctttggtatc tgtattggtt     360
ttaagataat ttctactata tcacatatct cctcacagta caaagatatc attttctttc     420 cctttttcttt ttaaaaaatt tgtatttta attttttgtgg gtacacagta gatatttatg    480
gggcatatga ggtattttat aggcatataa tatgtactag ggtaagtggg gtattcatca    540
cctcaagcat ttatccttttc tttgtgtaaa atatagcatt tctgaacac tatgaatact    600 taagtacaag gatca                                                      615

<210> SEQ ID NO 381
<211> LENGTH: 994
<212> TYPE: DNA
<213> ORGANISM: Homo sapiens

<400> SEQUENCE: 381
tcaaagtgta acaaatttcc tttcctcata aactagcaga cattctatcc cctcattatt      60
gtaacacatt tctaatatct ttctcaaatt gtcttcctgt attacaatgc actcaccttg    120
gcttagaatg tctgagacaa gaaaatctat tcaccattcc cacagatgac tccctcactc    180
tcctcccaag tcttccatac attccttcca caccattgcc cttaaccttt caaattcctg    240
cttaaaacta atcccatttt tatggctgac ctcaccctgt atcaaaaact ccgacatccc    300
tttacgacag agagcacaaa ctagtggtcc aaaatgtcat gggggtcttc tcagagttgt    360
tttttcaatc aggaaatttc acataaaaat atggatttct gatttctctt ttaaaaacag    420
aaaaacgagc caccagtggg agcactgcag gtatctgtgt gagacctgta cttcacaact    480
cctgctttcc ctccataaag yagcttgcat tttccacatt gactttgcag ttctttggta    540
tctgtattgg ttttaagata atttctacta tatcacatat ctcctcacag tacaaagata    600
tcattttctt tccctttttct ttttaaaaaa tttgtatttt taattttttgt gggtacacag    660 tagatattta tggggcatat gaggtatttt ataggcatat aatatgtact agggtaagtg    720 ggtattcat cacctcaagc atttatcctt tctttgtgta aaatatagca ttttctgaac    780
actatgaata cttaagtaca aggatcaagt cataggattt ggaattgatt tttaaaatat    840
gttgaccaaa gtgctcttat catcaaactt aacatcacta atgaaggatg aacatcccaa    900
atctgaaaat ccaaaatcca aaatgctcca taatctaaaa cttgttgagc accaacatga    960
tgcttaaagg aaatgctcct ggagcatttc agat                                 994
```

<210> SEQ ID NO 382
<211> LENGTH: 1001
<212> TYPE: DNA
<213> ORGANISM: Homo sapiens

<400> SEQUENCE: 382

```
ctatgagaaa tatttttaaa gtggttagga acaattcata gcactgacat gttatcagta      60
aaaatagaag aaaataaatt aatattatga aatattaatt atatttcatt aattatgtaa     120
tatgaattat gttttagctc aaatatttcc caagggacaa ttaagtaaat gaaaaataca     180
cacagattaa aataataaat agagaaggag atattaatga ggtacaaaaa gaaaaaatac     240
atgtaatcac atgaaatgct attatttgaa agattaacaa aacttgtaaa ctacctgcta     300
acttgatcaa agaaaaaaat cgagaaacca tatgcgcaat taatagtaag agggaaataa     360
acattgaaac agaagacatt tgaaatacca tataagactg ggtttcagag ctctatgtac     420
gtaaattgat aatgtcctgg agaagtgcag atgaccaaaa tggacacctt tcaacttaga     480
aatcataaac agattcattt ycttaaagtt aatgaaaaga attaacagac cctcctcaaa     540
aaagacatat atgcggccta caatcatatg aaaaaaagtt caacattact gttcattaga     600
gaaatgcaaa tcaaaaccac aatgagatac catctcacac cagtcagaat ggctattatt     660
aagaagtcaa aaaataaaag atgctggcga ggttgtggag aaaaaagaat gcttttatac     720
acttggtggg aatgtaaatt agttcagtca ttgtggaaga cttttgatgat tcctagaaga     780
cctaaataca gaactactat ttgacccaac aatcccatta ctgggtatat actcaaatga     840
ctataaatca ttctattata aagacacatg catggatatg ttcattacag cactatgcac     900
aatagcaaag acttggaatc aacatgaatg tccatcaatg atagactaga taagaaaat      960
gtggtacaca tataccatgg aatactatgc agccataaaa a                        1001
```

<210> SEQ ID NO 383
<211> LENGTH: 1001
<212> TYPE: DNA
<213> ORGANISM: Homo sapiens

<400> SEQUENCE: 383

```
tcagtaaaaa tagaagaaaa taaattaata ttatgaaata ttaattatat ttcattaatt      60
atgtaatatg aattatgttt tagctcaaat atttcccaag ggacaattaa gtaaatgaaa     120
aatacacaca gattaaaata ataaatagag aaggagatat taatgaggta caaaagaaa     180
aaatacatgt aatcacatga aatgctatta tttgaaagat taacaaaact tgtaaactac     240
ctgctaactt gatcaaagaa aaaatcgag aaaccatatg cgcaattaat agtaagaggg     300
aaataaacat tgaaacagaa gacatttgaa ataccatata agactgggtt tcagagctct     360
atgtacgtaa attgataatg tcctggagaa gtgcagatga ccaaaatgga cacctttcaa     420
cttagaaatc ataaacagat tcatttcctt aaagttaatg aaaagaatta acagaccctc     480
ctcaaaaaag acatatatgc rgcctacaat catatgaaaa aagttcaac attactgttc     540
attagagaaa tgcaaatcaa aaccacaatg agataccatc tcacaccagt cagaatggct     600
attattaaga agtcaaaaaa taaagatgc tggcgaggtt gtggagaaaa aagaatgctt     660
ttatacactt ggtgggaatg taaattagtt cagtcattgt ggaagacttt gatgattcct     720
agaagaccta atacagaac tactatttga cccaacaatc ccattactgg gtatatactc     780
aaatgactat aaatcattct attataaaga cacatgcatg gatatgttca ttacagcact     840
atgcacaata gcaaagactt ggaatcaaca tgaatgtcca tcaatgatag actagataaa     900
```

```
gaaaatgtgg tacacatata ccatggaata ctatgcagcc ataaaaatga aggagatcat    960
gccctttgca gggacacgaa tagaggtgga ggccattatc c                       1001
```

<210> SEQ ID NO 384
<211> LENGTH: 501
<212> TYPE: DNA
<213> ORGANISM: Homo sapiens

<400> SEQUENCE: 384

```
agttgcttga aagcaaagtt ctcgcagtag ctctctatct agaaggaggc atttttattta   60 tgtaaggaag tcacctaaaa gaaaattcat ttgttatggt gtggctttaa gagttactta   120
cttttaatgg aatccccag ataataataa attctgaaaa aaaaaaatca gaatcatggc   180
atgttaaaac tggatacatt cctagaaata gatggaaact gctcttgcaa aaagcttagc   240
acatgttaaa rcattttaga aacaatttgc caaagtttat ttagtctagt gatttcgaca   300
ggttaaatgg acccttttgag atctttttttc ctcaagtaca aaggctcact tgcttaatga   360
acacagtccc agaaaagcag ggggctgaac cttggctcta ccatcttacc taagattcta   420
gagttagcaa agggtttcca caagcccaaa ttattatgtt taatcttttc aattatctgt   480
gaagcattag gttggtgcaa a                                             501
```

<210> SEQ ID NO 385
<211> LENGTH: 501
<212> TYPE: DNA
<213> ORGANISM: Homo sapiens

<400> SEQUENCE: 385

```
gaggcatttt atttatgtaa ggaagtcacc taaagaaaa ttcatttgtt atggtgtggc    60
tttaagagtt acttactttt aatggaatcc cccagatat aataaattct gaaaaaaaaa   120
aatcagaatc atggcatgtt aaaactggat acattcctag aaatagatgg aaactgctct   180
tgcaaaaagc ttagcacatg ttaaagcatt ttagaaacaa tttgccaaag tttatttagt   240
ctagtgattt ygacaggtta aatggaccct tgagatctt ttttcctcaa gtacaaaggc   300
tcacttgctt aatgaacaca gtcccagaaa agcagggggc tgaaccttgg ctctaccatc   360
ttacctaaga ttctagagtt agcaaagggt ttccacaagc ccaaattatt atgtttaatc   420
ttttcaatta tctgtgaagc attaggttgg tgcaaaagta actgcaggtt ttgacattaa   480
aactggcaaa aactgcaata a                                             501
```

<210> SEQ ID NO 386
<211> LENGTH: 703
<212> TYPE: DNA
<213> ORGANISM: Homo sapiens

<400> SEQUENCE: 386

```
gacaccagtt agcatattgt cgcgggggag aggggtggga aaggcgagag aacagcatgt    60
ggtccagagg ccatacccag atggaggctg cagtcagctc cccagtcaaa ggcaaagccc   120
aagtcaaagc catgcttccc tcttgcccac ctgctccaat gccacccaca gagagtgcgc   180
cacagctcac aggatgcagg tctggttgaa tcttaacaat aactttgtaa gggaggtgtc   240
attagctcca ttctcctggc aggaggatga ggctcaaggc agctaaaggc ttttgctgaa   300
catcaagtgg tgagccagga ctcaawgcca gatcttcttg tttccctgtt aggtgtatgt   360
agcacaactg gtatctgcag actatgctgc tggaagggct agccgtcact gttatcacag   420
cgactgctgc ctgagatatg ccaggtactg ctgcaagaag tttacaaata taagctcact   480
```

```
tgatcttcat aacatactac ctaggtacaa tcattatatt tatttgacag atacagagac    540
agaggggaca cagaaaggat tagtaacttg ccccaaacca cacagccagc aaggtgtaag    600
tgagcacctg cagtctagat gagacaccac tcaaaacgtc attttctgg cagccccgtg    660 cagttaccac agtggtcacc ccagtggtca gctaaaggcc aag                      703
```

<210> SEQ ID NO 387
<211> LENGTH: 704
<212> TYPE: DNA
<213> ORGANISM: Homo sapiens

<400> SEQUENCE: 387

```
gcatattgtc gcgggggaga ggggtgggaa aggcgagaga acagcatgtg gtccagaggc     60
catacccaga tggaggctgc agtcagctcc ccagtcaaag gcaaagccca agtcaaagcc    120
atgcttccct cttgcccacc tgctccaatg ccacccacag agagtgcgcc acagctcaca    180
ggatgcaggt ctggttgaat cttaacaata actttgtaag ggaggtgtca ttagctccat    240
tctcctggca ggaggatgag gctcaaggca gctaaaggct tttgctgaac atcaagtggt    300
gagccaggac tcaatgccag atcttcttgt ttccctgtta ggtgtwtgta gcacaactgg    360
tatctgcaga ctatgctgct ggaagggcta gccgtcactg ttatcacagc gactgctgcc    420
tgagatatgc caggtactgc tgcaagaagt ttacaaatat aagctcactt gatcttcata    480
acatactacc taggtacaat cattatattt atttgacaga tacagagaca gaggggacac    540
agaaaggatt agtaacttgc cccaaaccac acagccagca aggtgtaagt gagcacctgc    600
agtctagatg agacaccact caaaacgtca ttttctggc agccccgtgc agttaccaca    660
gtggtcaccc cagtggtcag ctaaaggcca agcccaccgt ttct                     704
```

<210> SEQ ID NO 388
<211> LENGTH: 975
<212> TYPE: DNA
<213> ORGANISM: Homo sapiens

<400> SEQUENCE: 388

```
gacttaagac aagggggtct taatttgatt attttttct gttttatatg atttctatga     60
aaactacaac aaaataaagt taattctatt taagtgactt tttaatgaat tgcctttgtt    120
agaaaaaaaa ttaagtgttt ttgtctcact ctgtcaccca ggctggagca cagtggtgtg    180
atcatggctt actgcagcca tgacctcccg ggctcaggtg atcctcccac ctcagcttcc    240
caaatagatg ggactacagt tgtgtgccac aacgcctggc taattttgt attttttgt     300 agagacaggg tctcaccagg ttgcccaggc tgatcttgaa ctccttggct caagcgatcc    360
acccacctca gcctccctga gtgctgggat tacaggcatg agccagcgca cccagccaga    420
attacatttt tttaaatggt actgtcctag aaaatccagg atgtgcagtg atcaygtatg    480
aatgcatgga cctgcacaca caggagtgaa caaaagaccc accctgcca ggtcaccact    540 catatctcac cccagcccac gctagctcac actcctcccc acacaccact gacctcatca    600
ttgctaggta cccacttgac ttctcaacag gttcaagaca attggccttc ctcgtctctt    660
ctagaaacac cctctttct gggctttgtg taacacctgg tctttctccc ctctctggcc    720
acttctcagc ttttcttttt ctttctttct ttttttttt ttttttttg ccacttcctc    780 ttcctctaca tcaagcttgt ccaacccaca gcccaggaca gctttgaatg cagcctaaca    840
caaattcgta agctttctta aaacattatg agatgtgtgt gtgtgtgtgt gtgtgtgtgt    900
```

| | |
|---|---|
| gtgtgtgtgt gtgtgtgtgt gtttagctca tcagctatcg ttattgttag tgtattttat | 960 |
| gtgtggccca agaca | 975 |

<210> SEQ ID NO 389
<211> LENGTH: 976
<212> TYPE: DNA
<213> ORGANISM: Homo sapiens

<400> SEQUENCE: 389

| | |
|---|---|
| gacttttaa tgaattgcct ttgttagaaa aaaaattaag tgttttgtc tcactctgtc | 60 |
| acccaggctg gagcacagtg gtgtgatcat ggcttactgc agccatgacc tcccgggctc | 120 |
| aggtgatcct cccacctcag cttcccaaat agatgggact acagttgtgt gccacaacgc | 180 |
| ctggctaatt tttgtatttt tttgtagaga cagggtctca ccaggttgcc caggctgatc | 240 |
| ttgaactcct tggctcaagc gatccaccca cctcagcctc cctgagtgct gggattacag | 300 |
| gcatgagcca gcgcacccag ccagaattac attttttaa atggtactgt cctagaaaat | 360 |
| ccaggatgtg cagtgatcac gtatgaatgc atggacctgc acacacagga gtgaacaaaa | 420 |
| gacccacccc tgccaggtca ccactcatat ctcaccccag cccacgctag ctcacrctcc | 480 |
| tccccacaca ccactgacct catcattgct aggtaccac ttgacttctc aacaggttca | 540 |
| agacaattgg ccttcctcgt ctcttctaga aacaccctct tttctgggct ttgtgtaaca | 600 |
| cctggtcttt ctcccctctc tggccacttc tcagctttc tttttcttc tttcttttt | 660 |
| tttttttt ttttgccact tcctcttcct ctacatcaag cttgtccaac ccacagccca | 720 |
| ggacagcttt gaatgcagcc taacacaaat tcgtaagctt tcttaaaaca ttatgagatg | 780 |
| tgtgtgtgtg tgtgtgtgtg tgtgtgtgtg tgtgtgtgtg tgtgtgttta gctcatcagc | 840 |
| tatcgttatt gttagtgtat tttatgtgtg gcccaagaca tttcttcttc cagtgtggcc | 900 |
| cagggaagcc aaaagattgg acacccctgc tctacaacat ctcaatatag gccttttca | 960 |
| tgtttcattc tagatt | 976 |

<210> SEQ ID NO 390
<211> LENGTH: 801
<212> TYPE: DNA
<213> ORGANISM: Homo sapiens

<400> SEQUENCE: 390

| | |
|---|---|
| atccagacgg tgcccatact ccctgctctg tctagatggt gtccacattc cctgctccgt | 60 |
| ctagactgtg cccatattcg ctgctggctg caaatgcgag gagttgacag cagcctcccc | 120 |
| tttacaaggc aggaggtgcc actgttcgcc attgtctcca cctagggctt cacttgcttt | 180 |
| ctatctgcag acatcagagg gacccacatc tctctgttct gacacgctgt gtgttgatgg | 240 |
| cagagtttaa ttatccacat gcaatcttac tttccttatt cccaagtccg tggggctgcc | 300 |
| tcatcaaagc attgtaagaa ctgataacca tcttctagaa gtatcatagt gatattaaga | 360 |
| acacacatca cagatcatag taaatggctt taattttta rcgaaatctc actactgcaa | 420 |
| atgcattgtt gtcctagcta atgaatgcat agagtattgc ctgcaaaata ataattgaga | 480 |
| ttctatttt aagaagctta gaacagtaca tggtgcatag caaagactct gtgtatgtga | 540 |
| agccagattt taaaatatgg taacaagtgt ctgaaaatat gtggctcaat ttgtctcccg | 600 |
| gttacttttc cctctccccc tttaaaatgt agaggaagga gaagaagaga taagaggttt | 660 |
| gtgagtgaag acaggggccc tttaaggcct ggaagactaa cgccataggg atctcctc | 720 |
| tgccttaaaa ggcacaggaa tcttagtggg gaaaagaag tggtgataaa tagccagtcc | 780 |

```
gtgtgcctgg aatatcaaag t                                              801
```

<210> SEQ ID NO 391
<211> LENGTH: 801
<212> TYPE: DNA
<213> ORGANISM: Homo sapiens

<400> SEQUENCE: 391

```
ccctgctccg tctagactgt gcccatattc gctgctggct gcaaatgcga ggagttgaca     60
gcagcctccc ctttacaagg caggaggtgc cactgttcgc cattgtctcc acctagggct    120
tcacttgctt tctatctgca gacatcagag ggacccacat ctctctgttc tgacacgctg    180
tgtgttgatg gcagagttta attatccaca tgcaatctta ctttccttat tcccaagtcc    240
gtggggctgc ctcatcaaag cattgtaaga actgataacc atcttctaga agtatccatag    300
tgatattaag aacacacatc acagatcata gtaaatggct ttaattttt agcgaaatct     360
cactactgca aatgcattgt tgtcctagct aatgaatgca yagagtattg cctgcaaaat    420
aataattgag attctatttt taagaagctt agaacagtac atggtgcata gcaaagactc    480
tgtgtatgtg aagccagatt ttaaaatatg gtaacaagtg tctgaaaata tgtggctcaa    540
tttgtctccc ggttactttt ccctctcccc ctttaaaatg tagaggaagg agaagaagag    600
ataagaggtt tgtgagtgaa gacaagggcc ctttaaggcc tgggaagact aacgccatag    660
ggatctccct ctgccttaaa aggcacagga atcttagtgg ggaaaaagaa gtggtgataa    720
atagccagtc cgtgtgcctg gaatatcaaa gtcagtgcgt gccagggatc acactgcggg    780
tcacgtgcac tctgggtctc t                                              801
```

<210> SEQ ID NO 392
<211> LENGTH: 601
<212> TYPE: DNA
<213> ORGANISM: Homo sapiens

<400> SEQUENCE: 392

```
ttggcctggg gctgattcct ccaaagcaat gtgtctcttc gcagagtctc ttagagctgc     60
aaggcagtat gggatcatca gagaggatgc taggaagctt cagaaatgga ggtcctggta    120
gaaagggtcc tttggcgtgg cctctgaaga gtccaaatgt gggacaagac cctccgaaag    180
cggtggcctg gggagccaca ggtggggcag ccagcacgga agagggtggc tttgctacca    240
ttgggaaaac ttatcctcca catcctcatg aggcaaacac cttttcctacc ttaccgctcc    300
ycagtggcct ccctgttgcc ttcttattca agactaagac cctctagaat gttctttatc    360
ctgagtccag ctgattgtct atactaatat cagtacgggg tgtagatgag gacaaccagt    420
gtgcctggct gccaggcacc ccctccccaa accccaggag tttctggaac attccaactc    480
tgcttgaggg tatccatgca gcatctacta ctgtgagcag gtggtctgat ctgtggaaaa    540
cttctatgat tcacctgagg gtaactgccc tttgtgattt gaaagaatga tgctaacaga    600
a                                                                    601
```

<210> SEQ ID NO 393
<211> LENGTH: 601
<212> TYPE: DNA
<213> ORGANISM: Homo sapiens

<400> SEQUENCE: 393

```
gcagagtctc ttagagctgc aaggcagtat gggatcatca gagaggatgc taggaagctt     60
```

| | |
|---|---|
| cagaaatgga ggtcctggta gaaagggtcc tttggcgtgg cctctgaaga gtccaaatgt | 120 |
| gggacaagac cctccgaaag cggtggcctg gggagccaca ggtggggcag ccagcacgga | 180 |
| agagggtggc tttgctacca ttgggaaaac ttatcctcca catcctcatg aggcaaacac | 240 |
| ctttcctacc ttaccgctcc tcagtggcct ccctgttgcc ttcttattca agactaagac | 300 |
| yctctagaat gttctttatc ctgagtccag ctgattgtct atactaatat cagtacgggg | 360 |
| tgtagatgag gacaaccagt gtgcctggct gccaggcacc ccctcccaa acccaggag | 420 |
| tttctggaac attccaactc tgcttgaggg tatccatgca gcatctacta ctgtgagcag | 480 |
| gtggtctgat ctgtggaaaa cttctatgat tcacctgagg gtaactgccc tttgtgattt | 540 |
| gaaagaatga tgctaacaga aagtgttgtc atttctgaac ttttctgaac tctgcagcga | 600 |
| g | 601 |

<210> SEQ ID NO 394
<211> LENGTH: 1001
<212> TYPE: DNA
<213> ORGANISM: Homo sapiens

<400> SEQUENCE: 394

| | |
|---|---|
| agatttggat ggggacacaa aaccaaacca tatcataggt taaattgtgt ctcccacccc | 60 |
| aaaaatgtgt atgttgaagt cctaaccttc agtactcaga atgtgacatt atttggaaat | 120 |
| agggtcattg cagatggagt tagttaagat gaggtcatta ggatgagtcc ctaatccaat | 180 |
| atgactggtg ctcttacaaa aaggggaagt ttggacacag agccatgcac atgggtggga | 240 |
| agaatcccaa atgaacggat aggcagaggg ttggagagat gcatcaacaa ggaacaccaa | 300 |
| agattgccag caaccccag aagctggggg agaggcctgg aacagattct ccctcacagc | 360 |
| ctgagaggaa ccaagctggc tgacacccttg atctcaggtt accggccttg agaactgaga | 420 |
| gaccctgggt ttctgttgtt taagcctctc agggtgcagc actttattat ggaagcctga | 480 |
| gctgactaat acaggtgtct ytatatctca ctgagggaaa gtgacaggaa agtaagaacc | 540 |
| atttatgtcc aagagtccag aggagtcaac cagattctgg gggaaaagaa ggtacaatgc | 600 |
| tggcctctcc atgcagccta gtccccaaca cttgtagggc ccagggcaag atctaaagca | 660 |
| ctctctcacc tatgcatcta tatgctgtaa ctcagataaa caaactatta aataatatat | 720 |
| gtgtcttgcc tctcaatctg acaattacac ctttataata gcaacatagg aaaataacta | 780 |
| aaactatggt ttttaggcaa ccaaatacca gcaaaatgta ataattccta ttattagata | 840 |
| tgtttaagtg ttctgctggt gggtcagcat ctttggtaga gtcataaaat taaaatgtac | 900 |
| ataattaatt aaatattata tgtttattcc ctaacattta tttctgtcat tcttttttc | 960 |
| ttttttttcag acagtctcac tcttttgccc aggccggagt g | 1001 |

<210> SEQ ID NO 395
<211> LENGTH: 1001
<212> TYPE: DNA
<213> ORGANISM: Homo sapiens

<400> SEQUENCE: 395

| | |
|---|---|
| ttgtgtctcc caccccaaaa atgtgtatgt tgaagtccta accttcagta ctcagaatgt | 60 |
| gacattattt ggaaataggg tcattgcaga tggagttagt taagatgagg tcattaggat | 120 |
| gagtccctaa tccaatatga ctggtgctct tacaaaaagg ggaagtttgg acacagagcc | 180 |
| atgcacatgg gtgggaagaa tcccaaatga acggataggc agagggttgg agatgcat | 240 |
| caacaaggaa caccaaagat tgccagcaac ccccagaagc tgggggagag gcctggaaca | 300 |

```
gattctccct cacagcctga gaggaaccaa gctggctgac accttgatct caggttaccg    360
gccttgagaa ctgagagacc ctgggtttct gttgtttaag cctctcaggg tgcagcactt    420
tattatggaa gcctgagctg actaatacag gtgtctctat atctcactga gggaaagtga    480
caggaaagta agaaccattt rtgtccaaga gtccagagga gtcaaccaga ttctggggga    540
aaagaaggta caatgctggc ctctccatgc agcctagtcc ccaacacttg tagggcccag    600
ggcaagatct aaagcactct ctcacctatg catctatatg ctgtaactca gataaacaaa    660
ctattaaata atatatgtgt cttgcctctc aatctgacaa ttacacccttt ataatagcaa    720 cataggaaaa taactaaaac tatggttttt aggcaaccaa ataccagcaa aatgtaataa    780
ttcctattat tagatatgtt taagtgttct gctggtgggt cagcatcttt ggtagagtca    840
taaaattaaa atgtacataa ttaattaaat attatatgtt tattccctaa catttatttc    900
tgtcatttct tttttctttt tttcagacag tctcactctt ttgcccaggc cggagtgcag    960
tggcgtgatc tcagctcact gcaacctccg cctcccaggt t                       1001
```

<210> SEQ ID NO 396
<211> LENGTH: 1218
<212> TYPE: DNA
<213> ORGANISM: Homo sapiens

<400> SEQUENCE: 396

```
gataaagaaa ggtcatcctc aatttcaatt tactttatat attctttgag aggtaaccgt     60
gtcttatctc cccccaaaat tccttttaaa aggaaatttc caaagatgct ctattctgtg    120
aataaagcat tgtgccacag ccgagaggat ccagcaatga acatgagatt gcccttgatt    180
cataaggtct acaagctagt aaggatagag aacactttaa aataaaaaaa aatagttttt    240
ggtatattta tattgtgtat ttggtataat tgagttttct acattctcat atatgtattt    300
catattttga agaatatgca gaaaataatc aagcttccaa ataaacattt ttttttaaga    360
actgcacaag tgagaattta ggagaacaga agatcagagg gctgcacrgg ctaaactaga    420
caatgagccc atgcaagtaa gttaagagga gaagcgggta agtatgcacc tgctttgtct    480
aggtgaccag caagcattta gcaatagtct tttcaaaaca acagctcctt atattgtcaa    540
atctcaagaa gtaatattta tggttaaaaa aatctcagac ccaacagaaa atccatgagg    600
gagatggttt tggaaacgca gaattttcag ctatgatatc ctttttataaa caagcagata    660 ctttccccaa atataattca atgcctcagt ctacctcctg ctgaaaccac taacaccacc    720
actaaagctc gactatatgg gaaaatttag gtgtcacttt caaatatgt cctagcataa    780 aggcaattaa aaaatgtaaa gcaccaaaga tgcaagagag acataaatga ataaaatatc    840
tggcacgaaa gttttcaaaa gcttgggaat ctgattcaaa aaaaaataaa atcagccaag    900
cagtgttagt aagttagcca atcaggtttc aagaaggcag aaagacaaaa tcaacatcac    960
cagcatttga caccgctact gggggaaaaa aggggggatgg agttcgttta tggcctttt    1020 aaaaatgcca ttacttggac aagagtcata acagagaagc actgcttatt tcagttctgt    1080
taactgtaaa tatcagagcc aacacccaga aaaagttcac cattagccaa ttggttttgc    1140
ctggccaatt ggagatggta ataggcctgc tatggatgac attctttctg atataagttg    1200
tttcttgctt tttctcccc                                                  1218
```

<210> SEQ ID NO 397
<211> LENGTH: 1218
<212> TYPE: DNA

<213> ORGANISM: Homo sapiens

<400> SEQUENCE: 397

| | |
|---|---|
| gataaagaaa ggtcatcctc aatttcaatt tactttatat attctttgag aggtaaccgt | 60 |
| gtcttatctc cccccaaaat tccttttaaa aggaaatttc caaagatgct ctattctgtg | 120 |
| aataaagcat tgtgccacag ccgagaggat ccagcaatga acatgagatt gcccttgatt | 180 |
| cataaggtct acaagctagt aaggatagag aacactttaa aataaaaaaa aatagttttt | 240 |
| ggtatattta tattgtgtat ttggtataat tgagttttct acattctcat atatgtattt | 300 |
| catattttga agaatatgca gaaaataatc aagcttccaa ataaacattt tttttaaga | 360 |
| actgcacaag tgagaattta ggagaacaga agatcagagg gctgcacggg ctaaactaga | 420 |
| caatgagccc atgcaagtaa gttaagagga gaagcgggta agtatgcacc tgctttgtct | 480 |
| aggwgaccag caagcattta gcaatagtct tttcaaaaca acagctcctt atattgtcaa | 540 |
| atctcaagaa gtaatattta tggttaaaaa aatctcagac ccaacagaaa atccatgagg | 600 |
| gagatggttt tggaaacgca gaattttcag ctatgatatc cttttataaa caagcagata | 660 |
| cttttccccaa atataattca atgcctcagt ctacctcctg ctgaaaccac taacaccacc | 720 |
| actaaagctc gactatatgg gaaaatttag gtgtcacttt caaaatatgt cctagcataa | 780 |
| aggcaattaa aaaatgtaaa gcaccaaaga tgcaagagag acataaatga ataaaatatc | 840 |
| tggcacgaaa gttttcaaaa gcttgggaat ctgattcaaa aaaaaataaa atcagccaag | 900 |
| cagtgttagt aagttagcca atcaggtttc aagaaggcag aaagacaaaa tcaacatcac | 960 |
| cagcatttga caccgctact gggggaaaaa aggggatgg agttcgttta tggccttttt | 1020 |
| aaaaatgcca ttacttggac aagagtcata acagagaagc actgcttatt tcagttctgt | 1080 |
| taactgtaaa tatcagagcc aacacccaga aaaagttcac cattagccaa ttggttttgc | 1140 |
| ctggccaatt ggagatggta ataggcctgc tatggatgac attctttctg atataagttg | 1200 |
| tttcttgctt tttctccc | 1218 |

<210> SEQ ID NO 398
<211> LENGTH: 1072
<212> TYPE: DNA
<213> ORGANISM: Homo sapiens

<400> SEQUENCE: 398

| | |
|---|---|
| cacttaaaag ctctggaaac ctacgagatt atctttaaaa tcgtggggac caaatggctg | 60 |
| gccaaggact tgtttctgta caggtgcgat tgcttctctg ctgtgttcct ttttattacc | 120 |
| caagtaaccg gtatttcagc tcacaagatg agaaaatgac aaacaggcaa aataagcgta | 180 |
| gggctgtgtg tgcaacagtt watcataaag ccatcaccag gagacgtcac tgggcgcctt | 240 |
| ctggagtcta tccgtcctaa cttttgctttc tttctttttt tttttaaatt taagttctag | 300 |
| ggtacatatg cacaacgtgc aggtttgtca cacatgtata catgtgccat gttggtgtgc | 360 |
| tgcacccatt aactcgtcat ttacattagg tgtatctcct agtgctatcc ctccccactc | 420 |
| ccccgacccc atgacaggcc ccagtgtgtg atgttcccct tcctgtgtcc aagtgttctc | 480 |
| attgttcaat ccccacctat gagtgagaac atgccatgtt tggttttttg tccttgcgat | 540 |
| agtttgctga gaatgatggt ttccagcttc atccatgtcc ctacaaagga catgaactca | 600 |
| tcctttttta tggctacata gtattccatg gtgtatatgt gccacatttt cttaatccag | 660 |
| tctatcatcg atggacattt gggttggttc caagtctttg ctattgtgac tagtgttgca | 720 |
| ataaatatac gtgtggatgt gtctttatag cagtttgatt tataatcctt tgggtatata | 780 |

```
cccagtaacg ggatggctgg gtcaaatggt atttctagtt ctagatcctt gaggaatcgc      840
cacactgact tccacaatgg ttgaactagt taacagtccc accaacagtg tgaaagtgtt      900
cctatttctc cacatcctct ccagcacccc attttgactt tgctataagg gaactttagc      960
atctgaacgt gcggacagct tcattgctgg cttgttacgt aacagtgttt tgtgaccatc     1020
tcatgtcata cccacacatc gaaaccagca gtttaaatgg ccagctgttt gc             1072
```

<210> SEQ ID NO 399
<211> LENGTH: 1072
<212> TYPE: DNA
<213> ORGANISM: Homo sapiens

<400> SEQUENCE: 399

```
agattatctt taaaatcgtg gggaccaaat ggctggccaa ggacttgttt ctgtacaggt       60
gcgattgctt ctctgctgtg ttccttttta ttacccaagt aaccggtatt tcagctcaca      120
agatgagaaa atgacaaaca ggcaaaataa gcgtagggct gtgtgtgcaa cagtttatca      180
taaagccatc accaggagac rtcactgggc gccttctgga gtctatccgt cctaactttg      240 cttttttct tttttttttt aaatttaagt tctagggtac atatgcacaa cgtgcaggtt      300
tgtcacacat gtatacatgt gccatgttgg tgtgctgcac ccattaactc gtcatttaca      360
ttaggtgtat ctcctagtgc tatccctccc cactcccccg acccatgac aggcccagt       420 gtgtgatgtt cccttcctg tgtccaagtg ttctcattgt tcaatcccca cctatgagtg       480
agaacatgcc atgtttggtt ttttgtcctt gcgatagttt gctgagaatg atggtttcca      540
gcttcatcca tgtccctaca aaggacatga actcatcctt ttttatggct acatagtatt      600
ccatggtgta tatgtgccac atttttcttaa tccagtctat catcgatgga catttgggtt      660
ggttccaagt ctttgctatt gtgactagtg ttgcaataaa tatacgtgtg gatgtgtctt      720
tatagcagtt tgatttataa tccttgggt ataccccag taacgggatg gctgggtcaa      780
atggtatttc tagttctaga tccttgagga atcgccacac tgacttccac aatggttgaa      840
ctagttaaca gtcccaccaa cagtgtgaaa gtgttcctat ttctccacat cctctccagc      900
acccattttg actttgcta agggaact ttagcatctg aacgtgcgga cagcttcatt        960
gctggcttgt tacgtaacag tgttttgtga ccatctcatg tcatacccac acatcgaaac     1020
cagcagttta aatggccagc tgtttgcttg tgaaaactcc cctcggctgg ct             1072
```

<210> SEQ ID NO 400
<211> LENGTH: 948
<212> TYPE: DNA
<213> ORGANISM: Homo sapiens

<400> SEQUENCE: 400

```
aaattttctt tgctgaagtg tcttttcaaa tttttgcctt ttaaaaaaat tgagttgtct       60
taatattgag tcgtaaggtt ctttatatat tctggctata tgtcctttgt cagatatatg      120
tcttgcaaat attttctccc agtctgtggc ttacctttc cattttaaa ctgtgtttta      180 taaaaaaag aagttttttt agatcaaagt ccattttaat catttttct tttatagttc      240 atgcttttg tgtctcattt aagaaatctt tccctactcc aatgtcacaa atatattctc      300
tgagaagctt aacagttttt gcaactaaat ttaggtctat gatccgtttt gacttaattt      360
ttccatatgg tgtcatgtaa cagttgagat ttttttccta tgcaggcaga tattcaatgg      420
ttcaagtacc atttattgaa atggctatct tttctccact gaatgacctt ggcacttta      480
```

| | |
|---|---|
| tcaaacatca actggccaca yacaggtgag tctacttctg gacacttacc ctgttccatt | 540 |
| catctgtata tctctatcct tacaccaaca cgcatagtct tgaatactag ggcaagttaa | 600 |
| ttttaagatg tctcctggat atgtaaaaat tatatctgag ttgaactaca gtttatttat | 660 |
| atatccaggc agcaaataaa tgtgagaatc tggaggtgag ggaagagatc agagatacca | 720 |
| ccttggaaac catcaattta gagatgattc ttaaggcagg ggactaaggg acactctgta | 780 |
| ggacacagac atagagaagg gaaggggctg cggcctgaac accccacctg catgctcact | 840 |
| cacatacttt cgtcggcctg tgttaacgaa gtgctgggtc tccccagcct ctctcatctg | 900 |
| taagcagtgc caacaacgtc caacacagtt ccatccaatt tggatctg | 948 |

<210> SEQ ID NO 401
<211> LENGTH: 920
<212> TYPE: DNA
<213> ORGANISM: Homo sapiens

<400> SEQUENCE: 401

| | |
|---|---|
| aattttttgcc ttttaaaaaa attgagttgt cttaatattg agtcgtaagg ttctttatat | 60 |
| attctggcta tatgtccttt gtcagatata tgtcttgcaa atattttctc ccagtctgtg | 120 |
| gcttaccttt tccattttta aactgtgttt tataaaaaaa agaagttttt ttagatcaaa | 180 |
| gtccatttta atcattttt cttttatagt tcatgctttt tgtgtctcat ttaagaaatc | 240 |
| tttccctact ccaatgtcac aaatatattc tctgagaagc ttaacagttt ttgcaactaa | 300 |
| atttaggtct atgatccgtt ttgacttaat ttttccatat ggtgtcatgt aacagttgag | 360 |
| attttttttcc tatgcaggca gatattcaat ggttcaagta ccatttattg aaatggctat | 420 |
| cttttctcca ctgaatgacc ttggcacttt tatcaaacat caactggcca cacacaggtg | 480 |
| agtctacttc tggacactta ycctgttcca ttcatctgta tatctctatc cttacaccaa | 540 |
| cacgcatagt cttgaatact agggcaagtt aattttaaga tgtctcctgg atatgtaaaa | 600 |
| attatatctg agttgaacta cagtttattt atatatccag gcagcaaata atgtgagaa | 660 |
| tctggaggtg agggaagaga tcagagatac caccttggaa accatcaatt tagagatgat | 720 |
| tcttaaggca ggggactaag ggacactctg taggacacag acatagagaa gggaaggggc | 780 |
| tgcggcctga acaccccacc tgcatgctca ctcacatact ttcgtcggcc tgtgttaacg | 840 |
| aagtgctggg tctccccagc ctctctcatc tgtaagcagt gccaacaacg tccaacacag | 900 |
| ttccatccaa tttggatctg | 920 |

<210> SEQ ID NO 402
<211> LENGTH: 701
<212> TYPE: DNA
<213> ORGANISM: Homo sapiens

<400> SEQUENCE: 402

| | |
|---|---|
| tgtgctgctt ccattccata ggcacctgat cctaagtgtt aaccaatccc agaactctcc | 60 |
| ccttatttct tgctgcatgt tttgaattga tgtgataaac aatgtgattc gagcgtctta | 120 |
| actcagccta tgagcctctc tattctgtga ctgctggaat aggctgcttg gccatgttct | 180 |
| tggaagctac caccatatca rggtaatttc ccacacaaca ttccagcccc tgctttcccc | 240 |
| tctggcctta tctagggcca ttccccaact caggtgaatg cagactccaa atgtactgag | 300 |
| ctgtgtgcag gggccaggtg caaatgcttt ctgtgcatct gcacatgctg ttctacctgg | 360 |
| gaagtccttt cctcctttca cctatttta ccttaaacct cagacatcat ctaccctgga | 420 |
| aagtccttcc tgacctcacg catctaagta ggtccccccc ataatcccta tccatgcctt | 480 |

```
ctatagtact taacatggtg acctttaatt gttcatttac ttagctctct gctctcccac    540
actgtgaact ccttacaaac agggaatgtc atctctgaat gaatctttca tctccatgta    600
acacatgcct ccaaccctac ctagcacaca atctggcata taacaggcac tcaataaacc    660
ttcaatgaat gccttgatca agtacaagga acataagcaa a                        701
```

<210> SEQ ID NO 403
<211> LENGTH: 701
<212> TYPE: DNA
<213> ORGANISM: Homo sapiens

<400> SEQUENCE: 403

```
ttaaccaatc ccagaactct ccccttattt cttgctgcat gttttgaatt gatgtgataa     60
acaatgtgat tcgagcgtct taactcagcc tatgagcctc tctattctgt gactgctgga    120
ataggctgct tggccatgtt cttggaagct accaccatat cagggtaatt cccacacaa    180 cattccagcc cctgctttcc yctctggcct tatctagggc cattcccaa ctcaggtgaa     240 tgcagactcc aaatgtactg agctgtgtgc aggggccagg tgcaaatgct ttctgtgcat    300
ctgcacatgc tgttctacct gggaagtcct ttcctccttt cacctatttt taccttaaac    360
ctcagacatc atctaccctg gaaagtcctt cctgacctca cgcatctaag taggtccccc    420
ccataatccc tatccatgcc ttctatagta cttaacatgg tgacctttaa ttgttcattt    480
acttagctct ctgctctccc acactgtgaa ctccttacaa acagggaatg tcatctctga    540
atgaatcttt catctccatg taacacatgc ctccaaccct acctagcaca caatctggca    600
tataacaggc actcaataaa ccttcaatga atgccttgat caagtacaag gaacataagc    660
aaatttcctg tggaaaaaaa gaattgtatt aagttctttg g                        701
```

<210> SEQ ID NO 404
<211> LENGTH: 601
<212> TYPE: DNA
<213> ORGANISM: Homo sapiens

<400> SEQUENCE: 404

```
atgttcactt acacatcttt ctttcactta attgaatcct ttattttgt cttagaatct      60 tctgaatatt gaaacagag aactatactg gaagaacata gtgtattaag actcatggag    120
agggagatgt gatactgtgt cactgaggtc gttccagtca taggagaaat gttaccactg    180
gattgaggtc tggtacattt taaagatga tttaattcta tgatatgtgt tcaacttgca     240
ctaggatagt ttttactttc acctttgttc catgcaccgc gcaaatacct gggaacccctt    300 rttgcccaac tcaagagcca gagtcctctg tcatcatttt gcctctctcc taagtgacag    360
gactgagtgc agacttggtg tttgtgggtg aggcatgtgg actgacaggc aggcttcagt    420
ttatttagcg agtgtgagcc ctggcaggaa gattctcttt ctctgcttgc caggttgagg    480
aggcctcatt aagcagtttg aacttgtggt tttggcgtgt ctagtcctgg tgcaggtggc    540
ttggtatcct cacaggcatt tctttggcct cacccttggg gtgactgttc acttgtgttt    600
g                                                                     601
```

<210> SEQ ID NO 405
<211> LENGTH: 601
<212> TYPE: DNA
<213> ORGANISM: Homo sapiens

<400> SEQUENCE: 405

```
tcttctgaat attgaaaaca gagaactata ctggaagaac atagtgtatt aagactcatg      60
gagagggaga tgtgatactg tgtcactgag gtcgttccag tcataggaga aatgttacca     120
ctggattgag gtctggtaca ttttaaaaga tgatttaatt ctatgatatg tgttcaactt     180
gcactaggat agttttttact ttcacctttg ttccatgcac cgcgcaaata cctgggaacc    240
cttgttgccc aactcaagag ccagagtcct ctgtcatcat tttgcctctc tcctaagtga     300
saggactgag tgcagacttg gtgtttgtgg gtgaggcatg tggactgaca ggcaggcttc     360
agtttattta gcgagtgtga gccctggcag gaagattctc tttctctgct tgccaggttg     420
aggaggcctc attaagcagt ttgaacttgt ggttttggcg tgtctagtcc tggtgcaggt     480
ggcttggtat cctcacaggc atttctttgg cctcacccctt ggggtgactg ttcacttgtg    540
tttgagcggc tgggactcag taggttcact ggagtaggta tttctttaga gccactggcg     600
g                                                                    601

<210> SEQ ID NO 406
<211> LENGTH: 701
<212> TYPE: DNA
<213> ORGANISM: Homo sapiens

<400> SEQUENCE: 406
cagctccttg gcaagcctgc tccttcccca gcaaatggaa acaccattct gaacacctgg      60
gcattgtctc tgatgtccct tttcatctcc ctactctcac acaatccagc tgcctctctg     120
ccttccacgg atattaagaa cgtccaccat ctcctgagtc aagcccttc tcactcacct      180 cttttcttgaa ctaatttctt yctgtttttt tccagtcctc ccttctgttc atgtctctcc    240
tctgcacact tccatttct ggttcagaaa atgtcaccgt cccagtcaca cttgccttat      300
ggctgttgtg tcataaatac agttgacact gaacaacat gggtttgaac tgcatggatt      360
cacttataca catatttttt caatacaaat atatttaaaa attttggaga tttgcaacaa     420
tttgaaaaaa cttgcagatg aacagcatag catagaaata ttgaaaaatt aagaaaaagg     480
tatgtcatga atgcataaaa catatgcaga tactagtcta ttttaacctt tactgccata     540
aaatatacac aaatctatta taaaaggtta aagtttatca aagcttatgc acacaaacac     600
ttatagacca tagggagc cattcagtag agagaaatgt aagcgaacgt aaaggtgtgc       660
tatttaatca caactgcata cacactgtac cactgcacta a                         701

<210> SEQ ID NO 407
<211> LENGTH: 701
<212> TYPE: DNA
<213> ORGANISM: Homo sapiens

<400> SEQUENCE: 407
gggcattgtc tctgatgtcc cttttcatct ccctactctc acacaatcca gctgcctctc      60
tgccttccac ggatattaag aacgtccacc atctcctgag tccaagccct tctcactcac     120 ctcttttcttg aactaatttc tttctgtttt tttccagtcc tcccttctgt tcatgtctct    180
cctctgcaca cttccatttt stggttcaga aaatgtcacc gtcccagtca cacttgcctt    240
atggctgttg tgtcataaat acagttgaca cttgaacaac atgggtttga actgcatgga    300
ttcacttata cacatatttt ttcaatacaa atatatttaa aaattttgga gatttgcaac    360
aatttgaaaa aacttgcaga tgaacagcat agcatagaaa tattgaaaaa ttaagaaaaa    420
ggtatgtcat gaatgcataa acatatgcag atactagtc tatttaacc tttactgcca     480 taaaatatac acaaatctat tataaaaggt taagtttat caaagcttat gcacacaaac     540
```

```
acttatagac catataggga gccattcagt agagagaaat gtaagcgaac gtaaaggtgt      600
gctatttaat cacaactgca tacacactgt accactgcac taatttcaga gccacctcct      660
gttgtgattg tggtgagccc aagtgttgtg aggatctgct t                          701
```

<210> SEQ ID NO 408
<211> LENGTH: 501
<212> TYPE: DNA
<213> ORGANISM: Homo sapiens

<400> SEQUENCE: 408

```
caggtagggt aagcaaatga acacaaattc aaactcggaa ttcaaaacca gcctctgtgt       60
attcctgagg accatactgt ctgctaagtg tagagaaagg cacatcctgg ttcaacagca      120
gagaaagcaa acaggaggca ctttctgtga gtcatctcca ccacagggcc ctctcttttg      180
tgatccagcg atacttgttc acagtcaaag cccaggaaga gtggaaagat taacctttgt      240
gagccaaacc rtgtgacact tgattacttg acagaactaa tccttctgtc ctgatgacag      300
aaattcaact acacaggtac atgcaagcta atatctgttg taatgcctcc cagtttctct      360
ggagaattcc ttagtttcct ggacatctct gaaatgcaaa gttttggcaa cgagtctctg      420
aattaacctc tgaaaatctc acccagccaa gatggccttc ttgagaagac tgaagaacat      480
ggttggtttc aggctgagct g                                                501
```

<210> SEQ ID NO 409
<211> LENGTH: 604
<212> TYPE: DNA
<213> ORGANISM: Homo sapiens

<400> SEQUENCE: 409

```
cactttctgt gagtcatctc caccacaggg ccctctcttt tgtgatccag cgatacttgt       60
tcacagtcaa agcccaggaa gagtggaaag attaaccttt gtgagccaaa ccgtgtgaca      120
cttgattact tgacagaact aatccttctg tcctgatgac agaamttcaa ctacacaggt      180
acatgcaagc taatatctgt tgtaatgcct cccagtttct ctggagaatt ccttagtttc      240
ctggacatct ctgaaatgca aagttttggc aacgagtctc tgaattaacc tctgaaaatc      300
tcacccagcc aagatggcct tcttgagaag actgaagaac atggttggtt tcaggctgag      360
ctggaagtgg tttacctccc aggagaggtt ccccacagtg gtgtttaagg catggggtgg      420
accaacacca ggaagactca gacatcacac cacccacctt caactcagtc acatccacct      480
acattttctg aaaacaaaag gcagtctccc caaaaagcac tgagactctt gtgtaggtaa      540
tctgagcaga caccaacttc ccagggcttc cttttatcca ggagagcttg gctgttcttt      600
ttaa                                                                   604
```

<210> SEQ ID NO 410
<211> LENGTH: 701
<212> TYPE: DNA
<213> ORGANISM: Homo sapiens

<400> SEQUENCE: 410

```
ctccttccgc catggttgta agtttcctga cgcctcccag tcatgcttcc cgtacagcct       60
gcagaactgc gagtcaatga aatccctttt ctccacaaat tacccagtct caggtagttc      120
cttacagcag cgtgggaaca gactcaagag ctgaagcaag caaggccgtt agcaaggagc      180
gggctgggga gagcactcca ggcagaggga acagccaggg ccagggcctt gagacagacg      240
```

| | |
|---|---:|
| tgagccagga tatctgagga acagcagaga agccagtgtg gccgcagcta aatgaggaac | 300 |
| aatgtgtgag ttccctgggg cggccaaaac aaacaccacg gacggggcc ttcaaccaca | 360 |
| gacaccgatt tcctcacagc tctggaggcg aaaagtccaa gaaaactgca cggagtatct | 420 |
| atgaggccct gatggagacc tgacctggtc cacacccatg gcctggcaag ctagatgggg | 480 |
| tgaattttca cctgccacag ycgcaagtca agccaccgg cttctctctt ctccctccca | 540 |
| ttgctcctga cagccagggt taatattttg cctcatgtaa acaggaggc atccacccga | 600 |
| gaatctcccc tcagcccaca taagctctgc agagagggct gtgttgctcc agttcccacc | 660 |
| tggacatgag cactttgaag ggcagcttcc ctcccggggt c | 701 |

<210> SEQ ID NO 411
<211> LENGTH: 612
<212> TYPE: DNA
<213> ORGANISM: Homo sapiens

<400> SEQUENCE: 411

| | |
|---|---:|
| gggctgggga gagcactcca ggcagaggga acagccaggg ccagggcctt gagacagacg | 60 |
| tgagccagga tatctgagga acagcagaga agccagtgtg gccgcagcta aatgaggaac | 120 |
| aatgtgtgag ttccctgggg cggccaaaac aaacaccacg gacggggcc ttcaaccaca | 180 |
| gacaccgatt tcctcacagc tctggaggcg aaaagtccaa gaaaactgca cggagtatct | 240 |
| atgaggccct gatggagacc tgacctggtc cacacccatg gcctggcaag ctagatgggg | 300 |
| tgaattttca cctgccacag tcgcaagtca agccaccgg cttctctctt ctccctccca | 360 |
| ttgctcctga cagccagggt taatattttg cctcatgtaa acaggaggc ayccacccga | 420 |
| gaatctcccc tcagcccaca taagctctgc agagagggct gtgttgctcc agttcccacc | 480 |
| tggacatgag cactttgaag ggcagcttcc ctcccggggt ctggctgagc tcagggtagg | 540 |
| cgtcagtctg catggattgg atggaggaag gctgtgcgtg gcaggagatg acactgccct | 600 |
| tgggctgtgt gg | 612 |

<210> SEQ ID NO 412
<211> LENGTH: 1001
<212> TYPE: DNA
<213> ORGANISM: Homo sapiens

<400> SEQUENCE: 412

| | |
|---|---:|
| ttggggaagg aagcactggg gggaaggaag cactgggctt gggacagggc tgggcgctgc | 60 |
| ctcttcactg gaccatgaca aggttgttac ctcaccaagg agaggtgcaa aaagcttagg | 120 |
| ggcttggatt tctagatttc agtgccaact atgccactta ctggctttat ccttggggaa | 180 |
| tttatctact ctgtgaccct cagtttttt atcttaatta ttaatacata cctcataatg | 240 |
| tgactgtgag gattcactta ataatatatg gaaaaccata gaatagtgcc cagcatctag | 300 |
| gaagtgccac agccccttc agaagctagt gaaacctgca gaccacttt cagagtgata | 360 |
| ttattatttt tttctaggtt tactgagtta aattgaaaa ataaaaatg gaatatagat | 420 |
| gtacaacatg aagctctgat gcatatatcc attgtgaaat gatgaccaca atcaagctaa | 480 |
| ttaatgttat ctatcacttc wcatagttca accttttttt gtggtgagag tactgaagat | 540 |
| ctactctctt agcaattttc aaatctaaaa tacattatta ttaacacagt cactgtgccg | 600 |
| tacgttagct ctgaggacct tattcatttt atacctaaaa gtctgtatcc tttaaccaac | 660 |
| ctctcctaat ttcccactgt catccctact gccacctctg gtaaccagcc ttctgctctg | 720 |
| tttctgagtc caaccttctt agattccaca tatgagtgag atcatgctgt gcagtgtttg | 780 |

```
tttttctgtg tctggcttgc tttcacttag cataatgtcc tccaggtcca cccatgttgt      840
tgcaaatggc agaatcttct tcttgttaaa gactgaataa tatccctgtg tgtgcgtgca      900
tgtgtgtgtg tgtttgtgtg tgtgtgtgta tcacattttc ttcatccatt catccatcaa      960
tggacactaa gcactaaggt tgattccgta tcttggctat t                         1001

<210> SEQ ID NO 413
<211> LENGTH: 2480
<212> TYPE: DNA
<213> ORGANISM: Homo sapiens

<400> SEQUENCE: 413
aacattactt ggggaaggaa gcactggggg gaaggaagca ctgggcttgg acagggctg       60 ggcgctgcct cttcactgga ccatgacaag gttgttacct caccaaggag aggtgcaaaa     120
agcttagggg cttggatttc tagatttcag tgccaactat gccacttact ggctttatcc     180
ttggggaatt tatctactct gtgaccctca gttttttttat cttaattatt aatacatacc    240
tcataatgtg actgtgagga ttcacttaat aatatatgga aaaccataga atagtgccca     300
gcatctagga agtgccacag ccccccttcag aagctagtga aacctgcaga ccacttttca    360
gagtgatatt attatttttt tctaggttta ctgagttata attgaaaaaa taaaaatgga     420
atatagatgt acaacatgaa gctctgatgc atatatccat tgtgaaatga tgaccacaat    480
caagctaatt aatgttatct atcacttcac atagttcaac ctttttttgt ggtgagagta    540
ctgaagatct actctcttag caattttcaa atctaaaata cattattatt aacacagtca    600
ctgtgccrta cgttagctct gaggacctta ttcattttat acctaaaagt ctgtatcctt    660
taaccaacct ctcctaattt cccactgtca tccctactgc cacctctggt aaccagcctt    720
ctgctctgtt tctgagtcca accttcttag attccacata tgagtgagat catgctgtgc    780
agtgtttgtt tttctgtgtc tggcttgctt tcacttagca taatgtcctc caggtccacc    840
catgttgttg caaatggcag aatcttcttc ttgttaaaga ctgaataata tccctgtgtg    900
tgcgtgcatg tgtgtgtgtg tttgtgtgtg tgtgtgtatc acattttctt catccattca    960
tccatcaatg gacactaagc actaaggttg attccgtatc ttggctattg tgaataatgc   1020
tgcaataaac atatgagtcc agatacctct tcaagatact gatttcattt cctttaaata   1080
tatgcccaga agtgggattg ctggatcata tggtagttct atatttagta tcttgaggaa   1140
tttccatact gtttttcata atgattgtag caatctatat tcccatcaac agtgtacaag   1200
ggttccattt tctacatggc cttaccaacg tttgttatca cttatctttt tgataataga   1260
tattctagca ggtgtgaggt ggtatctcat tgtggtttta atttgcattt cctgatgat    1320 tagtggtgta gagcatcttt tcatattccc attggtaatt cgtatatctt cctttgagaa   1380
atatttattc agatcttttg cccattgtta gctgagttat atgtgagttg gttttggttt   1440
gttgttgttt tttgttttg ctattgagct gagttccttg tatattttgg atattaaatc    1500
cttctcagct gtatggttga cagatacatt cttgcattct gtaagttgca tctgtaggtt   1560
gcaacagagt ctctttactc tgttgattgc ttgcttact gtgtgaaagc ttttttagct     1620
tgatgtaatt gtgtttgtct attttgctt ttgttgcttg acttttagt gtcatatcca      1680 aaaagttatt gcccagacca gtgtcatccc ctatgttttc ttctagtaat tttaaagttt   1740
caggtcttat gtctatgtct ttaatccatt ttgagttaat ttttgtgtag ggtttaagat    1800
aagaatccaa tttatttttt atttttttgta tatggatatc caatttcccc aacaccattt   1860
```

```
attgaaaatt ctatccttc tttgttgtgt attaacatca gaataatatt tttaaataca    1920
taaaattcag aagatgacaa aggaaaccaa ttacattgaa atgcatacag agttataatt    1980
ctgaaagagc aatatatgtg cctctttgta aacacatcat atatcaaact gcagtgaccg    2040
ttctaacaac tattgcaatt tcaaagtcat gttgagtagg aggagtactt tgagattctg    2100
aaacaacgtt cttgtgctat gaaatatcca tgattttgat tggtgatggt atcccaggtc    2160
ttgttaatgc tgctgtaatc tgttgcttcc attccatagt tgaataaaat gcttgatatc    2220
tgttggaaat tagtaaaaat aaaaacgtat tttttccat ccaagttcat tctcagaccc     2280
tgaagagtca cttctctgga ttctgcagca aagttcccag ctggggcagc aagatttagg    2340
caattgaaaa gaacatacac cttgttctca gtggcaaacc acatggaaag ctttaaatgt    2400
cagagaagaa ttctgccatt ttgctgactt ttttgtagtt ctcctaataa acaagtgtta    2460
agtgacaagc ttttcagagg                                                2480

<210> SEQ ID NO 414
<211> LENGTH: 601
<212> TYPE: DNA
<213> ORGANISM: Homo sapiens

<400> SEQUENCE: 414
cccccccccc ccccgcagat ctcaggtggg cattttgaa cttaactaga taacaaaaca      60
cagctaagac aagtcctttt ctccagcaaa gatggcaatg ctctaataac tctgagcata    120
ttaaagattc tccaagactc tagcctctgc tgcaaaaaca catacaaata cctactacta    180
ctgctgctgt gatgatgatg atgacagcaa tagtgagaat atttaaata tgccaggcac     240
ggtggcaact gctttccaaa tattatcata tttaatctga tcattgccct atgaggtagg    300
ragtattctg attcccattt tataaataag gaacccgagg cttagagagc atcggtgact    360
tgttcaaggt cacccacagc tgtcaagtga cagaacttcg ataaaaatcc agactccttt    420
aatggagtat ggagggaggt cagaaaacat aggaagtaag ggattgtgat tgacaatgtg    480
tccttgcaaa gggacaggtt aagagacaca agggcagctg tctgaggtgt gccattcacc    540
agcttcagga gagaagtggc aggctacctc cagctatcca gccctatcca gccaaggaag    600
c                                                                   601

<210> SEQ ID NO 415
<211> LENGTH: 601
<212> TYPE: DNA
<213> ORGANISM: Homo sapiens

<400> SEQUENCE: 415
caaaacacag ctaagacaag tccttttctc cagcaaagat ggcaatgctc taataactct     60
gagcatatta aagattctcc aagactctag cctctgctgc aaaaacacat acaaatacct    120
actactactg ctgctgtgat gatgatgatg acagcaatag tgagaatatt ttaaatatgc    180
caggcacggt ggcaactgct ttccaaatat tatcatattt aatctgatca ttgccctatg    240
aggtagggag tattctgatt cccatttttat aaataaggaa cccgaggctt agagagcatc    300
rgtgacttgt tcaaggtcac ccacagctgt caagtgacaa acttcgata aaaatccaga     360
ctccttaat ggagtatgga gggaggtcag aaaacatagg aagtaaggga ttgtgattga     420
caatgtgtcc ttgcaaaggg acaggttaag agacacaagg gcagctgtct gaggtgtgcc    480
attcaccagc ttcaggagag aagtggcagg ctacctccag ctatccagcc ctatccagcc    540
aaggaagctt gggagacatg ttagttcccg ccttcatttc catcagcaac ctcaaagcca    600
``` c                                                                             601

<210> SEQ ID NO 416
<211> LENGTH: 5823
<212> TYPE: DNA
<213> ORGANISM: Homo sapiens

<400> SEQUENCE: 416

| | | | | | |
|---|---|---|---|---|---|
| tatttcaggc | tttcttcttt | ctatggataa | gaaagctcct | caggtggcaa | caaaggccat | 60 |
| ttctttggaa | gcaggcatgg | catgtgacga | aaaaaagaca | tctcagaaaa | gagccaagaa | 120 |
| taagactgga | gagccactgt | cagagaacag | aaactgggct | taatcaagga | acatctcttg | 180 |
| ttcccagagt | aggaggctgg | caatattttc | tcactgaaat | ttcagaattg | ttatggacca | 240 |
| gtgactgctc | tatgtgttca | atttgttccc | ttttcaaatg | gaagcattta | ttgcagacga | 300 |
| cctgcctctg | tcccaccatt | gtgtattagg | tttgtagagy | gtagacaact | tgcctttta | 360 |
| gtttgtaggt | ttctgtatca | agagaagatg | tgtgtgggcc | taacctagat | tacaggatcc | 420 |
| tggacttcaa | gtctgatata | atgactggat | gagactttga | ctgtcctaga | attgggatga | 480 |
| acatattttg | ccggtgggag | ggcgtgagta | attgcggtta | gagggcagac | tgtccctcac | 540 |
| acctattcct | tttcatggtg | ccttcccaaa | ctgcctctgg | aggtggccac | acaaatggct | 600 |
| ttggccattg | tgaccatggg | aaacttgatg | cagaggctgg | aaaaagcact | tgcatgtttc | 660 |
| tgtctcctct | cttgttcctc | tacaatcaca | agaaatgtct | aggcaggtct | gagcaggccc | 720 |
| aggctcatct | gccatggaag | aagaatggca | catggaagag | ggtcacattg | tcccaaccaa | 780 |
| gacgatccta | gaccagccag | gccccagttc | atggttcaag | acacatgaac | atagttgcac | 840 |
| gaaccaagat | tagttgtgta | tggcccagac | tagcagcagc | acccatccaa | cctacagact | 900 |
| ctgagaaata | aatactagtt | gtcttaagct | tccaagtttc | agtgtgagca | ttaggtagta | 960 |
| acagttaatg | aataagacag | ataatcattt | tatctgtctg | gatacttata | caatgatttc | 1020 |
| tattttttat | tgatacataa | tattttacat | attgctgggg | tacatgtgac | attttgctac | 1080 |
| atacatagaa | tgtgtaatga | tccagtcagg | atatctgagg | tgtccatcac | tttgagaatt | 1140 |
| tctcacttct | gtgtgttggg | aacaattcaa | gtcgtctctt | ctagttattt | taaaatatac | 1200 |
| aatacattgt | taactgtagt | ctttttttatt | gaatgacagg | acttgtacct | tttatctaac | 1260 |
| tgtatgtttg | tatctattaa | gctagttctc | tttatccctg | cccctccta | cccactcact | 1320 |
| cttcccaacc | tctaacatgt | atcatcctat | tctatatctc | catgagatca | acttctttag | 1380 |
| ctcccacata | tgagcaaaaa | catatgatgt | ttgtctttct | gtgcccggtt | tatttcactt | 1440 |
| atgacctcca | tttccatcca | tgttactata | aatgacagga | tttcattctt | tttgtggcca | 1500 |
| aacagtattt | cattgtgtat | atatactaca | ttttctttat | ccattcatcc | attgatgaac | 1560 |
| acttacgttg | attccatatc | tttgctattg | tgaatggtgc | tgcaataaac | atgcacgtgc | 1620 |
| agttatccct | ttgatacact | gatttatttt | cctttggata | aatacccagt | agtgagattg | 1680 |
| ctggatcata | cggtagttct | acttttagtt | tttgagacat | ttccatactt | ttccagtgtt | 1740 |
| tgtattaatt | tacattccca | tcaacaatgt | ataagatttc | cctttcctcc | acatcctcac | 1800 |
| cagcatctgc | tattttttgt | cttttaata | atagtcattc | taactggggt | gagaggtatat | 1860 |
| ctcgctatgg | ttttgatttg | catttccctg | atatttaatg | atattgagca | tttcttcata | 1920 |
| taacctattg | gccatttgtg | tgtctttttt | ttttttttt | tttttttga | gaattgtcta | 1980 |
| ctcattttg | gcttttaaa | agatttatttt | tttgttgttg | ttgagtttag | tgcatatcct | 2040 |

```
ggatattagt ctcttatctg atgaagagtt tgccaatatt ttctcccatt caacaggttg   2100
tctcttcatt ctgttgactg tttcctttgc tgtgcagaag cactttatat acagtcccat   2160
ttgtctattt tttagtagtc tatgcattta aggtctcagc cacaaaatct ttgcctagac   2220
cagtcctaaa gtgttttccc tatattttct tctagtagtt ttattgtttc atgtcttata   2280
tttaagtcta taatccattg tgagttgatt tttgtatatg gtgagatagg ggccttgttt   2340
cattcctctg catatagata tttaattttc tcagcaccat ttattgaagg tgtccttccc   2400
tattgtatgt tcttggtgcc tttgtcaaaa ttcagttggc tataaatatg tgaatttatt   2460
tctgggttct ctatgtggtt ccattagtct atgtgtctat ttttatacca atatcatgct   2520
gttttgatta ccatagcctt gtaatatatt ttgaagtcag gtagtgtgat gcctccagct   2580
ttgttctttt tgctcaggat tgctgtgcat actctggctt tttggttaca tacaaatttc   2640
aggattttg tatttctgtg aaaaatggca ttagtatttt gataggaatt gcactggatc   2700
tgtatattgt cctggacaac atggtcattt taacaatatt aattcttcta atctatgagt   2760
atgagacgtc ttcccacttg tttgtgtcct cttcaatttc tttcattggt gtttcataat   2820
ctcccttcta caggcctttc acctccttgg ttaaattaat tcctaggtat ttttttgtag   2880
ctactgtaaa tgggactgcc ttcttttctca gctagttcat ttttggtgca tagaaaccct   2940
atttttgtat gttcattttc tatcctgcaa cattaccaaa tttgcttatc agctttaagt   3000
gtgtattttg ctttgcttgt agagtcttct ggtttctcta aatgtaagac gatgtcatct   3060
gcaaacgggg acaatttgac ttcctcttaa aaatctgtat gccttttatt cctttctctt   3120
gcctgattgc tctggctcta cctccagtac tatactgaat aaaagtggta aaagtgagca   3180
tccttccttg tcttgctcta gttcttagag gaaatacttt cagttttttcc ccactcagta   3240
tgatgttagc tgtgggtcat atatagcctt tattatgtta agatatgttt cttctgtacc   3300
tggtttgttg acagcttttt atcataaaag gatgtagaat tttatcaaat gttttttctg   3360
catctgttga gataatcata tggttttttgt cattccttct actgttgtga tgtatcatgt   3420
ttattgattt gtgtatgtta aaccatcctt gtgtccttgg tataaattat acttggtcat   3480
ggtgtattat cttttttggca tcctgtcgaa ttgtttgcta gcttttttgtt ttgttcttt   3540
tgagaatttt tatgtctagg ttccttagaa acactggcct gtagttctct ttttgtgtgt   3600
gtgtccttgt ctagtttggt gtcagggaaa tggtggtctt gtagaatgag ttgtttttttc   3660
tttgattttt ttgcaagagt ttgaggagaa tgggtattag ttcttcttta tgtggttggt   3720
caaattggca gtgaattcat tcagtcatga gcttttcttt ttttgggagg ttctcatta   3780
ctgagttaat cacactgctc attactgatc tgttcagatt ttctatttct tctggaatct   3840
cagtagttgt atgtttccag caatttatcc atttcctcta ggttttctag tttggtagta   3900
tatagctatt cataatagtc tctgatgatc ttttgtattt ctgtgatatc agttgtaatg   3960
tcttttttcat ttcctatttt atttgggtct tttcttgttt agtctagcaa ggggtttatc   4020
tattttatct ttttgaagaa ccaactttttt gtttcattga ccctttctac gtctttagtc   4080
tttatttcat ttagatttgc tctgaacttt actatgtctt tccttctaat tttgggtttg   4140
gtttgttctt ttctagttcc ttgaggtgca tcattgaatt gtttctttga tatctatcta   4200
ctcatttgat gtaggtgttt attgctatac actctcccct cctagagctc cttttgttgt   4260
gtcccatagg tcttggtatg ttgtttctat tttcatttgt ttcaaacatt ttatttccat   4320
attaatttttt atcattcagg aggagcatat tatttaattc ccatgtattt gtatagtttc   4380
caaagttcct cttatttcta ttttttactcc attgtggtct gagaagatac ttcatatgat   4440
```

-continued

```
ttcaattttt aaaaatttgt caagacttgt ttttgtcct aacatatggt ctatcctgga    4500
gaatgttcca tgtgctgatg agaaaaatgt gtactcagca gttgttgagt aacatgttct    4560
acaaatatct gttagatcca tttggtctaa agtctagttt aaatccaatg agttttgtt     4620
aattttgtct agatgatcat gatctgagac tgaggtgaag tccccaacaa ttatcgtgtt    4680
ggagtctacc tctcttttta aatctagaaa tatttgcttt ataaatccgg gtggtctagt    4740
gttgggtgca tatatttagt tgttatttcc tcattagatt gatctcttta ctattatata    4800
ataactgttt actgcttctg gcataaagtc tgttttatgt aagtacagcc attcctgctt    4860
gagtttagta ccatgttgac aaagggatgc atagagagtt ggtaaagcat gatttctggg    4920
tgtctgtgtg aaggtgtttt gagaagagtt tagcatgagt ctgtggagtg agtgggaaga    4980
ttctccctca atgtcagcag gaaccatcca tccactgggg gcccaggtag aaaaagatga    5040
agaaatggtg aattctctct ctctcctgga gctgggtcac ccttcttctg cccttgaaca    5100
ggacatcaca actccaggct ctccagcctt tggactccaa gactgacacc agtgcccctc    5160
cccaattacc ccaggccctc aggcctttgg cctaggattg agacttacac catcagcttc    5220
cctggttctg aggcttctgg acttgcactg ggccatacta ccagcatccc agggtctcca    5280
gcttgcagag agcctgttgt gggacttttc agcctccata atcaagtaag ccaatttccc    5340
tggtatctat atagatatac aatcatgttt tgcttaccag cctgaaaaat gtatcgctag    5400
atgagtctgt cattgcataa acatcatagt gtacttacac aaacctagat tctatagcct    5460
actacacacc tagtctataa acatgtcacag catgttactg tactgaatat tgtaggcaac    5520
tgtaacacaa tggtgaatat ttgcatattt aaacatatct tatcattaaa aagatacagt    5580
aaacataagg tataaaagac aaaaaccggc acacctatat agggcactta ccataaatgc    5640
agcttgcagg actagaagtc actcagggtg agtcagtgag cgaacgtgaa ggcctaggtt    5700
attactgtcc actacggtag actttatcaa cactgtacac aggctacact aaatttattt    5760
tttaaaaatt tgctctccaa taataaatta atcttcgcat ccttttttg ttgttcactg    5820
tgg                                                                  5823
```

<210> SEQ ID NO 417
<211> LENGTH: 5823
<212> TYPE: DNA
<213> ORGANISM: Homo sapiens

<400> SEQUENCE: 417

```
tatttcaggc tttcttcttt ctatggataa gaaagctcct caggtggcaa caaaggccat      60
ttctttggaa gcaggcatgg catgtgacga aaaaaagaca tctcagaaaa gagccaagaa     120
taagactgga gagccactgt cagagaacag aaactgggct taatcaagga acatctcttg     180
ttcccagagt aggaggctgg caatattttc tcactgaaat ttcagaattg ttatggacca    240
gtgactgctc tatgtgttca atttgttccc ttttcaaatg gaagcattta ttgcagacga    300
cctgcctctg tcccaccatt gtgtattagg tttgtagagt gtagacaact tgcctttta    360
gtttgtaggt ttctgtatca agagaagatg tgtgtrggcc taacctagat tacaggatcc    420
tggacttcaa gtctgatata atgactggat gagactttga ctgtcctaga attgggatga    480
acatattttg ccggtgggag ggcgtgagta attgcggtta gagggcagac tgtccctcac    540
acctattcct tttcatggtg ccttcccaaa ctgcctctgg aggtggccac acaaatggct    600
ttggccattg tgaccatggg aaacttgatg cagaggctgg aaaaagcact tgcatgtttc    660
```

```
tgtctcctct cttgttcctc tacaatcaca agaaatgtct aggcaggtct gagcaggccc   720
aggctcatct gccatggaag aagaatggca catggaagag ggtcacattg tcccaaccaa   780
gacgatccta gaccagccag gccccagttc atggttcaag acacatgaac atagttgcac   840
gaaccaagat tagttgtgta tggcccagac tagcagcagc acccatccaa cctacagact   900
ctgagaaata aatactagtt gtcttaagct tccaagtttc agtgtgagca ttaggtagta   960
acagttaatg aataagacag ataatcattt tatctgtctg gatacttata caatgatttc  1020
tatttttttat tgatacataa tattttacat attgctgggg tacatgtgac attttgctac  1080
atacatagaa tgtgtaatga tccagtcagg atatctgagg tgtccatcac tttgagaatt  1140
tctcacttct gtgtgttggg aacaattcaa gtcgtctctt ctagttattt taaaatatac  1200
aatacattgt taactgtagt cttttttatt gaatgacagg acttgtacct tttatctaac  1260
tgtatgtttg tatctattaa gctagttctc tttatccctg cccctccta cccactcact  1320
cttcccaacc tctaacatgt atcatcctat tctatatctc catgagatca acttcttttag  1380
ctcccacata tgagcaaaaa catatgatgt tgtctttct gtgcccggtt tatttcactt  1440
atgacctcca tttccatcca tgttactata aatgacagga tttcattctt tttgtggcca  1500
aacagtattt cattgtgtat atatactaca ttttctttat ccattcatcc attgatgaac  1560
acttacgttg attccatatc tttgctattg tgaatggtgc tgcaataaac atgcacgtgc  1620
agttatccct ttgatacact gatttatttt cctttggata aatacccagt agtgagattg  1680
ctggatcata cggtagttct acttttagtt tttgagacat ttccatactt ttccagtgtt  1740
tgtattaatt tacattccca tcaacaatgt ataagatttc cctttcctcc acatcctcac  1800
cagcatctgc tattttttgt cttttttaata atagtcattc taactggggt gagaggatat  1860
ctcgctatgg ttttgatttg catttccctg atatttaatg atattgagca tttcttcata  1920
taacctattg gccatttgtg tgtctttttt tttttttttt ttttttttga gaattgtcta  1980
ctcatttttg gcttttaaa agatttattt tttgttgttg ttgagtttag tgcatatcct  2040
ggatattagt ctcttatctg atgaagagtt tgccaatatt ttctcccatt caacaggttg  2100
tctcttcatt ctgttgactg tttccttgc tgtgcagaag cactttatat acagtcccat  2160
ttgtctattt tttagtagtc tatgcattta aggtctcagc cacaaaatct ttgcctagac  2220
cagtcctaaa gtgtttcccc tatattttct tctagtagtt ttattgtttc atgtcttata  2280
tttaagtcta taatccattg tgagttgatt tttgtatatg gtgagatagg ggccttgttt  2340
cattcctctg catatagata tttaattttc tcagcaccat ttattgaagg tgtccttccc  2400
tattgtatgt tcttggtgcc tttgtcaaaa ttcagttggc tataaatatg tgaatttatt  2460
tctgggttct ctatgtggtt ccattagtct atgtgtctat ttttataccca atatcatgct  2520
gttttgatta ccatagcctt gtaatatatt ttgaagtcag gtagtgtgat gcctccagct  2580
ttgttctttt tgctcaggat tgctgtgcat actctggctt tttggttaca tacaaatttc  2640
aggatttttg tatttctgtg aaaaatggca ttagtatttt gataggaatt gcactggatc  2700
tgtatattgt cctggacaac atggtcattt taacaatatt aattcttcta atctatgagt  2760
atgagacgtc ttcccacttg tttgtgtcct cttcaatttc tttcattggt gtttcataat  2820
ctcccttcta caggccttc acctccttgg ttaaattaat tcctaggtat ttttttgtag  2880
ctactgtaaa tgggactgcc ttcttttctca gctagttcat ttttggtgca tagaaaccct  2940
attttttgtat gttcatttc tatcctgcaa cattaccaaa tttgcttatc agctttaagt  3000
gtgtattttg ctttgcttgt agagtcttct ggtttctcta aatgtaagac gatgtcatct  3060
```

```
gcaaacgggg acaatttgac ttcctcttaa aaatctgtat gccttttatt cctttctctt    3120
gcctgattgc tctggctcta cctccagtac tatactgaat aaaagtggta aaagtgagca    3180
tccttccttg tcttgctcta gttcttagag gaaatacttt cagttttcc ccactcagta    3240
tgatgttagc tgtgggtcat atatagcctt tattatgtta agatatgttt cttctgtacc   3300
tggtttgttg acagcttttt atcataaaag gatgtagaat tttatcaaat gttttttctg   3360
catctgttga gataatcata tggttttgt cattccttct actgttgtga tgtatcatgt    3420
ttattgattt gtgtatgtta aaccatcctt gtgtccttgg tataaattat acttggtcat   3480
ggtgtattat cttttggca tcctgtcgaa ttgtttgcta gcttttgtt ttgttctttt     3540
tgagaatttt tatgtctagg ttccttagaa acactggcct gtagttctct ttttgtgtgt   3600
gtgtccttgt ctagtttggt gtcagggaaa tggtggtctt gtagaatgag ttgttttttc   3660
tttgattttt ttgcaagagt ttgaggagaa tgggtattag ttcttcttta tgtggttggt   3720
caaattggca gtgaattcat tcagtcatga gcttttcttt ttttgggagg gttctcatta   3780
ctgagttaat cacactgctc attactgatc tgttcagatt ttctatttct tctggaatct   3840
cagtagttgt atgtttccag caatttatcc atttcctcta ggttttctag tttggtagta   3900
tatagctatt cataatagtc tctgatgatc ttttgtattt ctgtgatatc agttgtaatg   3960
tcttttcat ttcctattt atttgggtct tttcttgttt agtctagcaa ggggtttatc    4020
tattttatct ttttgaagaa ccaactttt gtttcattga cccttctac gtctttagtc    4080
tttatttcat ttagatttgc tctgaacttt actatgtctt tccttctaat tttgggtttg   4140
gtttgttctt ttctagttcc ttgaggtgca tcattgaatt gtttctttga tatctatcta   4200
ctcatttgat gtaggtgttt attgctatac actctcccct cctagagctc cttttgttgt   4260
gtcccatagg tcttggtatg ttgtttctat tttcatttgt ttcaaacatt ttatttccat   4320
attaattttt atcattcagg aggagcatat tatttaattc ccatgtattt gtatagtttc   4380
caaagttcct cttatttcta tttttactcc attgtggtct gagaagatac ttcatatgat   4440
ttcaattttt aaaaatttgt caagacttgt ttttgtcct aacatatggt ctatcctgga   4500
gaatgttcca tgtgctgatg agaaaaatgt gtactcagca gttgttgagt aacatgttct   4560
acaaatatct gttagatcca tttggtctaa agtctagttt aaatccaatg agttttttgtt   4620
aattttgtct agatgatcat gatctgagac tgaggtgaag tccccaacaa ttatcgtgtt   4680
ggagtctacc tctctttta aatctagaaa tatttgcttt ataaatccgg gtggtctagt   4740
gttgggtgca tatatttagt tgttatttcc tcattagatt gatctcttta ctattatata   4800
ataactgttt actgcttctg gcataaagtc tgttttatgt aagtacagcc attcctgctt   4860
gagtttagta ccatgttgac aaagggatgc atagagagtg ggtaaagcat gatttctggg   4920
tgtctgtgtg aaggtgtttt gagaagagtt tagcatgagt ctgtggagtg agtgggaaga   4980
ttctccctca atgtcagcag gaaccatcca tccactgggg gcccaggtag aaaaagatga   5040
agaaatggtg aattctctct ctctcctgga gctgggtcac ccttcttctg cccttgaaca   5100
ggacatcaca actccaggct ctccagcctt tggactccaa gactgacacc agtgcccctc   5160
cccaattacc ccaggccctc aggcctttgg cctaggattg agacttacac catcagcttc   5220
cctggttctg aggcttctgg acttgcactg ggccatacta ccagcatccc agggtctcca   5280
gcttgcagag agcctgttgt gggacttttc agcctccata atcaagtaag ccaatttccc   5340
tggtatctat atagatatac aatcatgttt tgcttaccag cctgaaaaat gtatcgctag   5400
```

| | |
|---|---|
| atgagtctgt cattgcataa acatcatagt gtacttacac aaacctagat tctatagcct | 5460 |
| actacacacc tagtctataa acatgtacag catgttactg tactgaatat tgtaggcaac | 5520 |
| tgtaacacaa tggtgaatat tgcatattt aaacatatct tatcattaaa aagatacagt | 5580 |
| aaacataagg tataaaagac aaaaaccggc acacctatat agggcactta ccataaatgc | 5640 |
| agcttgcagg actagaagtc actcagggtg agtcagtgag cgaacgtgaa ggcctaggtt | 5700 |
| attactgtcc actacggtag actttatcaa cactgtacac aggctacact aaatttattt | 5760 |
| tttaaaaatt tgctctccaa taataaatta atcttcgcat ccttttttg ttgttcactg | 5820 |
| tgg | 5823 |

<210> SEQ ID NO 418
<211> LENGTH: 707
<212> TYPE: DNA
<213> ORGANISM: Homo sapiens

<400> SEQUENCE: 418

| | |
|---|---|
| aacggtgtca gctggagtga actcctgtgt gtgcaaggcc tgggtctcct ggtcagacta | 60 |
| ctttctatgg gaaaggcata gtgtatagtc tatatactat acataggggt gctgggagga | 120 |
| actggggttt tcacagccag cttggttttt cattaggttt gtttagtttc cattgcttca | 180 |
| ggggtgttag ttttgtgttc mcaactagat tataaactcc tcttgcattc ctgatggcag | 240 |
| tgacttgaag gcatttattt gaagaataat agacatacag aaaggggcgc atgtcataaa | 300 |
| ggtacagctg gacgactttt cacaaagtga gcacatttgt atgatcgatg ttgagaccaa | 360 |
| gagcattcag tggacaactc ctttccagtt actccacccc actcccagtg accatcattc | 420 |
| tgacttctaa ctgtgtagac atgttttgct tgttttgtac tttacaaaca tatctactct | 480 |
| atttaggtg gctagacaat gtgttttaca atgctggcca tgacagtgtt tgaaagaata | 540 |
| aaatggaatc aaatagaatg ggcagtatca gagtgtgttg cctgcctaag aaatgttttg | 600 |
| tgacattttg gctttgggtc tatttacaca ttaaatctaa gagcaccaga atgtggtgtc | 660 |
| aaaatgtgtt tggggatgaa gatattctaa agtcctgtag taagcaa | 707 |

<210> SEQ ID NO 419
<211> LENGTH: 712
<212> TYPE: DNA
<213> ORGANISM: Homo sapiens

<400> SEQUENCE: 419

| | |
|---|---|
| cagactactt tctatgggaa aggcatagtg tatagtctat atactataca tagggtgct | 60 |
| gggaggaact ggggttttca gccagcttt ggttttcat taggtttgtt tagtttccat | 120 |
| tgcttcaggg gtgttagttt tgtgttccca actagattat aaactcctct tgcattcctg | 180 |
| atggcagtga cttgaaggca tttatttgaa gaataataga catacagaaa ggggcrcatg | 240 |
| tcataaaggt acagctggac gacttttcac aaagtgagca catttgtatg atcgatgttg | 300 |
| agaccaagag cattcagtgg acaactcctt tccagttact caccccact cccagtgacc | 360 |
| atcattctga cttctaactg tgtagacatg ttttgcttgt tttgtacttt acaaacatat | 420 |
| ctactctatt taggtggct agacaatgtg ttttacaatg ctggccatga cagtgttga | 480 |
| aagaataaaa tggaatcaaa tagaatgggc agtatcagag tgtgttgcct gcctaagaaa | 540 |
| tgttttgtga cattttggct ttgggtctat ttacacatta aatctaagag caccagaatg | 600 |
| tggtgtcaaa atgtgtttgg ggatgaagat attctaaagt cctgtagtaa gcaatgcaaa | 660 |
| acgttctgga ggtgtttatt aaacatttgt ttgtagaatg gagaggaaga ca | 712 |

<210> SEQ ID NO 420
<211> LENGTH: 1210
<212> TYPE: DNA
<213> ORGANISM: Homo sapiens

<400> SEQUENCE: 420

| | | | | | |
|---|---|---|---|---|---|
| aaagcagcac | tgctctgcat | tcagccttgc | tacgtctcct | tcagatgggc gcactagata | 60 |
| ctgagtgatg | atcatgcctt | gtctaggatc | tcaccaagac | agttcatgaa agagacagtg | 120 |
| cagctcatgg | aggagatggt | gcagctcaca | gagaggatgg | tgccatcatg aaagcatgg | 180 |
| ggcagtcatg | gagatgacgg | rgtagctcat | ggagaatata | atgccatcat ggaaggcata | 240 |
| gtgcagtcat | ggagatgatg | gtgcagctca | tggagaagat | ggtgccatca tggaaggcat | 300 |
| ggtgcaatca | tggagtagac | agtgcagctg | ggccaagatt | ctccctgact aagctcttct | 360 |
| caggcacctc | tgagccgtcg | tcttaactag | gcctccagct | tggcttgtga aaactgcaga | 420 |
| ctctcagcac | aaatgatttg | cctcctacat | taagagactt | aaataaacac ttgcatggct | 480 |
| gtgtttattt | aaacagctca | aggctgtgtc | cctgggatga | caatgactcc agcccctaaa | 540 |
| attcctgctt | gtgaaagctc | attgctgaca | gaaggatcta | ccatttgttc cagccaacac | 600 |
| ctggtggcag | gcagataggc | cctgagcccc | atttaagagc | agttccttta gaaagcttgc | 660 |
| aattgtaaat | cttttctctg | cccatttgag | atgtaaatct | tctaccacct agaactgtct | 720 |
| tctcaaggac | ctgtgagctg | actcactgaa | atgcaaacat | tcagggagat aactccactc | 780 |
| ctgtccccat | gcgacggcga | ggccctgact | ttggtgggca | ccttgctctt atttgcacca | 840 |
| ccacctcctg | tcctaaagac | atgagacgtt | tgtctctcct | ctggataagt gcctattaac | 900 |
| caacccaggt | gtcctggtca | catgaaccag | tccagcctag | cacctggcac tgcctttccc | 960 |
| tcagcacact | ccagtctgta | aaagtctcct | tatggttgtt | ttggcaaagt tgagcttagt | 1020 |
| taatgctaga | ccccttctct | actgcaatag | ttactgctga | ataaagtcta tccttaccac | 1080 |
| tttaactagt | gttgggcttt | gtttctcttt | cataagctca | tggagaagac aatgcagttc | 1140 |
| catcaagttt | ctggctctta | cactgctaac | agtcagctct | ggggtccctg agagggacag | 1200 |
| actcacacca | | | | | 1210 |

<210> SEQ ID NO 421
<211> LENGTH: 1194
<212> TYPE: DNA
<213> ORGANISM: Homo sapiens

<400> SEQUENCE: 421

| | | | | | |
|---|---|---|---|---|---|
| gcattcagcc | ttgctacgtc | tccttcagat | gggcgcacta | gatactgagt gatgatcatg | 60 |
| ccttgtctag | gatctcacca | agacagttca | tgaaagagac | agtgcagctc atggaggaga | 120 |
| tggtgcagct | cacagagagg | atggtgccat | catggaaagc | atggggcagt catggagatg | 180 |
| acggagtagc | tcatggagaa | kataatgcca | tcatggaagg | catagtgcag tcatggagat | 240 |
| gatggtgcag | ctcatggaga | agatggtgcc | atcatggaag | gcatggtgca atcatggagt | 300 |
| agacagtgca | gctgggccaa | gattctccct | gactaagctc | ttctcaggca cctctgagcc | 360 |
| gtcgtcttaa | ctaggcctcc | agcttggctt | gtgaaaactg | cagactctca gcacaaatga | 420 |
| tttgcctcct | acattaagag | acttaaataa | acacttgcat | ggctgtgttt atttaaacag | 480 |
| ctcaaggctg | tgtccctggg | atgacaatga | ctccagcccc | taaaattcct gcttgtgaaa | 540 |
| gctcattgct | gacagaagga | tctaccattt | gttccagcca | acacctggtg gcaggcagat | 600 |

| | |
|---|---:|
| aggccctgag ccccatttaa gagcagttcc tttagaaagc ttgcaattgt aaatctttc | 660 |
| tctgcccatt tgagatgtaa atcttctacc acctagaact gtcttctcaa ggacctgtga | 720 |
| gctgactcac tgaaatgcaa acattcaggg agataactcc actcctgtcc ccatgcgacg | 780 |
| gcgaggccct gactttggtg ggcaccttgc tcttatttgc accaccacct cctgtcctaa | 840 |
| agacatgaga cgtttgtctc tcctctggat aagtgcctat taaccaaccc aggtgtcctg | 900 |
| gtcacatgaa ccagtccagc ctagcacctg gcactgcctt tccctcagca cactccagtc | 960 |
| tgtaaaagtc tccttatggt tgttttggca aagttgagct tagttaatgc tagacccctt | 1020 |
| ctctactgca atagttactg ctgaataaag tctatcctta ccactttaac tagtgttggg | 1080 |
| cttttgtttct ctttcataag ctcatggaga agacaatgca gttccatcaa gtttctggct | 1140 |
| cttacactgc taacagtcag ctctggggtc cctgagaggg acagactcac acca | 1194 |

<210> SEQ ID NO 422
<211> LENGTH: 1194
<212> TYPE: DNA
<213> ORGANISM: Homo sapiens

<400> SEQUENCE: 422

| | |
|---|---:|
| gcattcagcc ttgctacgtc tccttcagat gggcgcacta gatactgagt gatgatcatg | 60 |
| ccttgtctag gatctcacca agacagttca tgaaagagac agtgcagctc atggaggaga | 120 |
| tggtgcagct cacagagagg atggtgccat catggaaagc atgggcagt catggagatg | 180 |
| acggagtagc tcatggagaa kataatgcca tcatggaagg catagtgcag tcatggagat | 240 |
| gatggtgcag ctcatggaga agatggtgcc atcatggaag gcatggtgca atcatggagt | 300 |
| agacagtgca gctgggccaa gattctccct gactaagctc ttctcaggca cctctgagcc | 360 |
| gtcgtcttaa ctaggcctcc agcttggctt gtgaaaactg cagactctca gcacaaatga | 420 |
| tttgcctcct acattaagag acttaaataa acacttgcat ggctgtgttt atttaaacag | 480 |
| ctcaaggctg tgtccctggg atgacaatga ctccagcccc taaaattcct gcttgtgaaa | 540 |
| gctcattgct gacagaagga tctaccattt gttccagcca acacctggtg gcaggcagat | 600 |
| aggccctgag ccccatttaa gagcagttcc tttagaaagc ttgcaattgt aaatcttttc | 660 |
| tctgcccatt tgagatgtaa atcttctacc acctagaact gtcttctcaa ggacctgtga | 720 |
| gctgactcac tgaaatgcaa acattcaggg agataactcc actcctgtcc ccatgcgacg | 780 |
| gcgaggccct gactttggtg ggcaccttgc tcttatttgc accaccacct cctgtcctaa | 840 |
| agacatgaga cgtttgtctc tcctctggat aagtgcctat taaccaaccc aggtgtcctg | 900 |
| gtcacatgaa ccagtccagc ctagcacctg gcactgcctt tccctcagca cactccagtc | 960 |
| tgtaaaagtc tccttatggt tgttttggca aagttgagct tagttaatgc tagacccctt | 1020 |
| ctctactgca atagttactg ctgaataaag tctatcctta ccactttaac tagtgttggg | 1080 |
| cttttgtttct ctttcataag ctcatggaga agacaatgca gttccatcaa gtttctggct | 1140 |
| cttacactgc taacagtcag ctctggggtc cctgagaggg acagactcac acca | 1194 |

<210> SEQ ID NO 423
<211> LENGTH: 1118
<212> TYPE: DNA
<213> ORGANISM: Homo sapiens

<400> SEQUENCE: 423

| | |
|---|---:|
| accaagacag ttcatgaaag agacagtgca gctcatggag gagatggtgc agctcacaga | 60 |
| gaggatggtg ccatcatgga aagcatgggg cagtcatgga gatgacggag tagctcatgg | 120 |

```
agaagataat gccatcatgg aaggcatagt gcagtcatgg agatgatggt gcagctcatg    180
gagaagatgg tgccatcatg raaggcatgg tgcaatcatg gagtagacag tgcagctggg    240
ccaagattct ccctgactaa gctcttctca ggcacctctg agccgtcgtc ttaactaggc    300
ctccagcttg gcttgtgaaa actgcagact ctcagcacaa atgatttgcc tcctacatta    360
agagacttaa ataaacactt gcatggctgt gtttatttaa acagctcaag gctgtgtccc    420
tgggatgaca atgactccag cccctaaaat tcctgcttgt gaaagctcat tgctgacaga    480
aggatctacc atttgttcca gccaacacct ggtggcaggc agataggccc tgagccccat    540
ttaagagcag ttcctttaga aagcttgcaa ttgtaaatct tttctctgcc catttgagat    600
gtaaatcttc taccacctag aactgtcttc tcaaggacct gtgagctgac tcactgaaat    660
gcaaacattc agggagataa ctccactcct gtccccatgc gacggcgagg ccctgacttt    720
ggtgggcacc ttgctcttat ttgcaccacc acctcctgtc ctaaagacat gagacgtttg    780
tctctcctct ggataagtgc ctattaacca acccaggtgt cctggtcaca tgaaccagtc    840
cagcctagca cctggcactg cctttccctc agcacactcc agtctgtaaa agtctcctta    900
tggttgtttt ggcaaagttg agcttagtta atgctagacc ccttctctac tgcaatagtt    960
actgctgaat aaagtctatc cttaccactt taactagtgt tgggctttgt ttctctttca   1020
taagctcatg gagaagacaa tgcagttcca tcaagtttct ggctcttaca ctgctaacag   1080
tcagctctgg ggtccctgag agggacagac tcacacca                           1118

<210> SEQ ID NO 424
<211> LENGTH: 601
<212> TYPE: DNA
<213> ORGANISM: Homo sapiens

<400> SEQUENCE: 424 gtagggcac tgtctatact ggctgcactc tggccagtgc tgtcccaacg ctgacccctc      60
tggaagctaa tctggcttat aatgaggatg cttctcttag aggggactct ccatgcacag    120
cagaaaatcc caatggagtg gttcttccct atgtccccaa gggactggga atattctttc    180
agtaacaatg gcccattggg ggaagaagga tgaaagtggg gtgagagacg tgaaatttgg    240
agaggtccct caaagattgt gatgtgcctc tcttgttcca atcacaggac aggggtataa    300
yggctttcct ttgaaacacg gggatgaatt taactattca cttcccaggt agattcatca    360
gggtctagag cttcagctaa cagcatgagg aagattccaa atgtgccccc atcagcatag    420
gaactgggta tgttgagtct atggtctcat aaaaccagaa gaaggacaag ggattgtggc    480
tccaggcttg ggagcacctt ttccttacca tgggctacag tatttattta gggtaaagga    540
aggaaactcc tgaggtgcta tggggtgcca gcaatttgga gcatcagtaa ttcaatgtcc    600
c                                                                    601

<210> SEQ ID NO 425
<211> LENGTH: 601
<212> TYPE: DNA
<213> ORGANISM: Homo sapiens

<400> SEQUENCE: 425
acgctgaccc ctctggaagc taatctggct tataatgagg atgctttctt tagaggggac     60
tctccatgca cagcagaaaa tcccaatgga gtggttcttc cctatgtccc caagggactg    120
ggaatattct ttcagtaaca atggcccatt gggggaagaa ggatgaaagt ggggtgagag    180
```

| | |
|---|---|
| acgtgaaatt tggagaggtc cctcaaagat tgtgatgtgc ctctcttgtt ccaatcacag | 240 |
| gacaggggta taacggcttt cctttgaaac acgggatga atttaactat tcacttccca | 300 |
| rgtagattca tcagggtcta gagcttcagc taacagcatg aggaagattc caaatgtgcc | 360 |
| cccatcagca taggaactgg gtatgttgag tctatggtct cataaaacca gaagaaggac | 420 |
| aagggattgt ggctccaggc ttgggagcac ctttcctta ccatgggcta cagtatttat | 480 |
| ttagggtaaa ggaaggaaac tcctgaggtg ctatggggtg ccagcaattt ggagcatcag | 540 |
| taattcaatg tcccttcagc catgtgtatt caactcctgc tgtgggtgtg gacttggtgc | 600 |
| a | 601 |

<210> SEQ ID NO 426
<211> LENGTH: 701
<212> TYPE: DNA
<213> ORGANISM: Homo sapiens

<400> SEQUENCE: 426

| | |
|---|---|
| ttcctgggca tcgtcatatt ctgtaaaaca aggaagctca gcccagtgtg ttctaacatg | 60 |
| acctcctttc tacatcctta ggtgttgtta tgcgtgaatc acgtcccccc aaaagacatg | 120 |
| ttcatgtcct aaccccagg acctcagaat gtgtgatctg gtttggaaat aaggtcatca | 180 |
| cagatgaaat tagctaagac aaggtcatat tggaataggg ttggcccta atccactgtg | 240 |
| actggtgtcc ttttaagaag aggacacaga cacaggaggg gagagggcca tgggatgatg | 300 |
| caggtggaga ctggagtgct acagctgcaa gcaaatacat ttctgtgctg tgaagccacc | 360 |
| catttggtgg tactacgtta aaacagctct aggaaattaa tacagatgtt gcctgtatt | 420 |
| ttgtttctca tattactact cattgtttta atgatgactg ttttattcat taagttgaaa | 480 |
| gctcctaaag cagagggacc rtattttat gtcccaactc tccttaaggc cttgcctatg | 540 |
| atagcacatc tcttcaatag aattgtccta actttaacag agacaacttg ggttattaa | 600 |
| tatggagaac aaagggttaa gctggtgcca gatgggtttc atttctcta aatctggaac | 660 |
| caaaggcagc aagtctatgg ggtggacgga gttcttagct c | 701 |

<210> SEQ ID NO 427
<211> LENGTH: 701
<212> TYPE: DNA
<213> ORGANISM: Homo sapiens

<400> SEQUENCE: 427

| | |
|---|---|
| caaggaagct cagcccagtg tgttctaaca tgacctcctt tctacatcct taggtgttgt | 60 |
| tatgcgtgaa tcacgtcccc ccaaaagaca tgttcatgtc ctaaccccca ggacctcaga | 120 |
| atgtgtgatc tggtttggaa ataaggtcat cacagatgaa attagctaag acaaggtcat | 180 |
| attggaatag ggttggccct aatccactg tgactggtgt ccttttaaga agaggacaca | 240 |
| gacacaggag gggagagggc catgggatga tgcaggtgga gactggagtg ctacagctgc | 300 |
| aagcaaatac atttctgtgc tgtgaagcca cccatttggt ggtactacgt taaaacagct | 360 |
| ctaggaaatt aatacagatg ttgcctgtat ttttgtttct catattacta ctcattgttt | 420 |
| taatgatgac tgttttattc attaagttga aagctcctaa agcagaggga ccatattttt | 480 |
| atgtcccaac tctccttaag scccttgccta tgatagcaca tctcttcaat agaattgtcc | 540 |

-continued

```
taactttaac agagacaact tgggttattt aatatggaga acaaagggtt aagctggtgc      600
cagatgggtt tcattttctc taaatctgga accaaaggca gcaagtctat ggggtggacg      660
gagttcttag ctcaaccctt tggtgaggta agaagaagga t                         701
```

METHODS FOR DETERMINING FRACTION OF FETAL NUCLEIC ACIDS IN MATERNAL SAMPLES

CROSS-REFERENCE

This application is a Continuation of Ser. No. 15/299,335, filed on Oct. 20, 2016, which is a Continuation of U.S. application Ser. No. 13/461,582, filed on May 1, 2012, which is a Continuation of U.S. application Ser. No. 12/958,347, filed on Dec. 1, 2010, which claims priority to U.S. Provisional Application Ser. No. 61/296,358 entitled "Methods for Determining Fraction of Fetal Nucleic Acids in Maternal Samples", filed on Jan. 19, 2010; U.S. Provisional Application Ser. No. 61/360,837 entitled "Methods for Determining Fraction of Fetal Nucleic Acids in Maternal Samples", filed on Jul. 1, 2010; U.S. Provisional Application Ser. No. 61/407,017 entitled "Method for Determining Copy Number Variations", filed on Oct. 26, 2010; and U.S. Provisional Application Ser. No. 61/455,849 entitled "Simultaneous determination of Aneuploidy and Fetal Fraction", filed on Oct. 26, 2010; each of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Apr. 30, 2012, is named Seq_List_0117_301US.txt and is 238,613 bytes in size.

FIELD OF THE INVENTION

The present invention relates to methods and compositions for detecting fetal nucleic acids in a maternal sample and determining the fraction of cell-free fetal nucleic acid circulating in a maternal sample.

BACKGROUND OF THE INVENTION

Invasive prenatal tests are potentially harmful to the mother and to the fetus. Therefore, there is a need for the development of noninvasive prenatal tests. Maternal blood can contain fetal cells (see e.g., U.S. Patent Application Publication No. 20080070792) and cell-free fetal DNA (see e.g., Huang et al. (2008), *Methods in Molecular Biology*, 444:203-208). While circulating fetal cells present an attractive target for non invasive prenatal diagnostics, particularly for the diagnosis of fetal sex and chromosomal abnormalities by simple karyotyping, the scarcity of intact fetal cells in the maternal circulation (around one cell per ml of maternal blood), low efficiency of enrichment (Bianchi et al., Am J Hum Genet 61:822-829 [1997]) and difficulties with chromosomal analysis associated with abnormally dense nuclei in some cells (Babochkina et al., Haematologica 90:740-745 [2005]), have favored research on cell-free DNA.

The establishment of the concentrations of cell-free fetal DNA (cfDNA) in maternal plasma in healthy pregnant women has formed the platform on which fetal DNA abnormalities in pregnancy-associated disorders can be studied. The finding of a gradual increase in fetal DNA concentration in maternal serum as gestation progresses has been shown to precede complications associated with pre-term labor. A five-fold increase in fetal DNA concentration has also been found in the serum obtained from women affected by preeclampsia. Other pregnancy-related disorders that have been linked to an elevated concentration of cfDNA include hyperemesis gravidarum (severe morning sickness), invasive placentation (in which the placenta contacts the maternal bloodstream), intrauterine growth restriction, feto-maternal haemorrhage and polyhydramnios. (Wright C. F. and Burton H., Human Reproduction Update 15(1):139-151 [2009]).

Quantitative analysis of cell free DNA by real-time PCR strategies has also indicated that the concentrations of circulatory fetal DNA are increased in pregnancies with fetal aneuploidies, most notably trisomy 21 (Lo et al., Clin Chem 45:1747-1751 [1999]). However, the fraction of fetal DNA in maternal cell-free plasma DNA is usually determined by comparing the amount of fetal-specific locus (such as the SRY locus on chromosome Y in male pregnancies) to that of a locus on any autosome that is common to both the mother and the fetus by using quantitative real-time PCR (Dahllan et al., Lancet 369:474-481 [2007]; Li et al., Clin Chem 1002-1011 [2004]; Fan et al., Proc Natl Acad Sci 105:16266-16271 [2008]).

Thus, there is a need for additional methods that would enable the determination of the fraction of fetal nucleic acid in both male and female pregnancies.

The method of the invention fulfills the need in providing the means to determine fetal fraction that is independent of the gender of the fetus. The method can be applied for determining simultaneously the presence or absence of a chromosomal aneuploidy or other copy number variation, and may be used in conjunction with nay known methods that are used to determine aneuploidies in maternal sample.

SUMMARY OF THE INVENTION

The invention provides compositions and methods for determining the fraction of fetal nucleic acids in a maternal sample comprising a mixture of fetal and maternal nucleic acids. The fraction of fetal nucleic acids can be used in determining the presence or absence of fetal aneuploidy.

In one embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction. The plurality of polymorphic nucleic acids are located on a plurality of different chromosomes. In one embodiment, the plurality of polymorphic nucleic acids can be located on chromosomes 1-22. In another embodiment, the plurality of polymorphic nucleic acids can be located on different autosomes other than chromosomes 13, 18 and 21. The maternal sample is selected from blood, plasma, serum, urine and saliva. Preferably, the maternal sample is a plasma sample.

In one embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22 For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In one embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In one embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In one embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In one embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In one embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In one embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). The massively parallel sequencing is sequencing-by-synthesis with reversible dye terminators. Alternatively, the massively parallel sequencing is sequencing-by-ligation or single molecule sequencing. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 &

34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363);

rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In one embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 &

56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375);

rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In one embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The maternal sample is selected from blood, plasma, serum, urine and saliva. Preferably, the maternal sample is a plasma sample.

In one embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction, wherein determining the fraction comprises determining the number of fetal and maternal sequence tags mapped to a reference genome comprising of at least one polymorphic nucleic acid. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367);

rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In another embodiment, the invention provides a method for determining the fraction of fetal nucleic acids in a maternal plasma sample comprising a mixture of fetal and maternal genomic DNA, wherein the method comprises the steps of: (a) amplifying a plurality of polymorphic nucleic acids in said mixture of fetal and maternal nucleic acids, wherein each of said at least one polymorphic nucleic acid comprises an STR; (b) determining the amount of fetal and maternal STR alleles at least one polymorphic nucleic acid; and (c) determining said fraction using said amount of fetal and maternal STR alleles. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The method is a fetal gender-independent method.

In another embodiment, the invention provides a method for determining the fraction of fetal nucleic acids in a maternal plasma sample comprising a mixture of fetal and maternal genomic DNA, wherein the method comprises the steps of: (a) amplifying a plurality of polymorphic nucleic acids in said mixture of fetal and maternal nucleic acids, wherein each of said at least one polymorphic nucleic acid comprises an STR; (b) determining the amount of fetal and maternal STR alleles at least one polymorphic nucleic acid; and (c) determining said fraction using said amount of fetal and maternal STR alleles. The plurality of polymorphic nucleic acids are located on a plurality of different chromosomes. In one embodiment, the plurality of polymorphic nucleic acids can be located on chromosomes 1-22. For example, the plurality of polymorphic nucleic acids are located on a plurality of different chromosomes other than chromosomes 13, 18, 21, X or Y. The method further comprises preamplifying the mixture of fetal and maternal nucleic acids. The method is a fetal gender-independent method.

In another embodiment, the invention provides a method for determining the fraction of fetal nucleic acids in a maternal plasma sample comprising a mixture of fetal and maternal genomic DNA, wherein the method comprises the steps of: (a) amplifying a plurality of polymorphic nucleic acids in said mixture of fetal and maternal nucleic acids, wherein each of said at least one polymorphic nucleic acid comprises an STR; (b) determining the amount of fetal and maternal STR alleles at least one polymorphic nucleic acid; and (c) determining said fraction using said amount of fetal and maternal STR alleles. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The method further comprises resolving the size of the STRs using capillary electrophoresis. The method is a fetal gender-independent method.

In another embodiment, the invention provides a method for determining the fraction of fetal nucleic acids in a maternal plasma sample comprising a mixture of fetal and maternal genomic DNA, wherein the method comprises the steps of: (a) amplifying a plurality of polymorphic nucleic acids in said mixture of fetal and maternal nucleic acids, wherein each of said at least one polymorphic nucleic acid comprises an STR; (b) determining the amount of fetal and maternal STR alleles at least one polymorphic nucleic acid; and (c) determining said fraction using said amount of fetal and maternal STR alleles. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The method further comprises preamplifying the mixture of fetal and maternal nucleic acids, and resolving the size of the STRs using capillary electrophoresis. The method is a fetal gender-independent method.

In another embodiment, the invention provides a method for determining the fraction of fetal nucleic acids in a maternal plasma sample comprising a mixture of fetal and maternal genomic DNA, wherein the method comprises the steps of: (a) amplifying a plurality of polymorphic nucleic acids in said mixture of fetal and maternal nucleic acids, wherein each of said at least one polymorphic nucleic acid comprises an STR; (b) determining the amount of fetal and maternal STR alleles at least one polymorphic nucleic acid; and (c) determining said fraction using said amount of fetal and maternal STR alleles. The plurality of polymorphic nucleic acids can be located on a plurality of different chromosomes. For example, the plurality of polymorphic nucleic acids are located on a plurality of different chromosomes other than chromosomes 13, 18, 21, X or Y. The at least one STR is selected from CSF1PO, FGA, TH01, vWA, D3S1358, D5S818, D7S820, D8S1179, D13S317, D16S539, D18S51, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. Optionally, the at least one STR can be the panel of STRs comprising CSF1PO, D13S317, D16S539, D18S51, D21S11, D2S1338, D7S820 and FGA. The method is a fetal gender-independent method.

In another embodiment, the invention provides a method for determining the fraction of fetal nucleic acids in a maternal plasma sample comprising a mixture of fetal and maternal genomic DNA, wherein the method comprises the steps of: (a) amplifying a plurality of polymorphic nucleic acids in said mixture of fetal and maternal nucleic acids, wherein each of said at least one polymorphic nucleic acid comprises an STR; (b) determining the amount of fetal and maternal STR alleles at least one polymorphic nucleic acid; and (c) determining said fraction using said amount of fetal and maternal STR alleles. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The method further comprises preamplifying the mixture of fetal and maternal nucleic acids. The at least one STR is selected from CSF1PO, FGA, TH01, vWA, D3S1358, D5S818, D7S820, D8S1179, D13S317, D16S539, D18S51, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. Optionally, the at least one STR can be the panel of STRs comprising CSF1PO, D13S317, D16S539, D18S51, D21S11, D2S1338, D7S820 and FGA. The method is a fetal gender-independent method.

In another embodiment, the invention provides a method for determining the fraction of fetal nucleic acids in a maternal plasma sample comprising a mixture of fetal and maternal genomic DNA, wherein the method comprises the steps of: (a) amplifying a plurality of polymorphic nucleic acids in said mixture of fetal and maternal nucleic acids, wherein each of said at least one polymorphic nucleic acid comprises an STR; (b) determining the amount of fetal and maternal STR alleles at least one polymorphic nucleic acid; and (c) determining said fraction using said amount of fetal and maternal STR alleles. The plurality of polymorphic nucleic acids are located on a plurality of different chromosomes. In one embodiment, the plurality of polymorphic nucleic acids can be located on chromosomes 1-22. For example, the plurality of polymorphic nucleic acids are located on a plurality of different chromosomes other than chromosomes 13, 18, 21, X or Y. The method further comprises resolving the size of the STRs using capillary electrophoresis. The at least one STR is selected from CSF1PO, FGA, TH01, vWA, D3S1358, D5S818, D7S820, D8S1179, D13S317, D16S539, D18S51, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. Optionally, the at least one STR can be the panel of STRs comprising CSF1PO, D13S317, D16S539, D18S51, D21S11, D2S1338, D7S820 and FGA.

In another embodiment, the invention provides a method for determining the fraction of fetal nucleic acids in a maternal plasma sample comprising a mixture of fetal and maternal genomic DNA, wherein the method comprises the steps of: (a) amplifying a plurality of polymorphic nucleic acids in said mixture of fetal and maternal nucleic acids, wherein each of said at least one polymorphic nucleic acid comprises an STR; (b) determining the amount of fetal and maternal STR alleles at least one polymorphic nucleic acid; and (c) determining said fraction using said amount of fetal and maternal STR alleles. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The method further comprises preamplifying the mixture of fetal and maternal nucleic acids, and resolving the size of the STRs using capillary electrophoresis. The at least one STR is selected from CSF1PO, FGA, TH01, vWA, D3S1358, D5S818, D7S820, D8S1179, D13S317, D16S539, D18S51, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. Optionally, the at least one STR can be the panel of STRs comprising CSF1PO, D13S317, D16S539, D18S51, D21S11, D2S1338, D7S820 and FGA.

In another embodiment, the invention provides a composition for determining the fraction of fetal cfDNA in a maternal sample, e.g. a plasma sample, wherein the composition comprises at least one set of primers for amplifying at least one polymorphic nucleic acid in said mixture. The set of primers does not amplify a sequence on the Y chromosome.

In another embodiment, the invention provides a composition for determining the fraction of fetal cfDNA in a maternal sample, e.g. a plasma sample, wherein the composition comprises at least one set of primers for amplifying at least one polymorphic nucleic acid in said mixture. The polymorphic nucleic acid comprises an STR, a SNP and/or a tandem SNP.

In another embodiment, the invention provides a composition for determining the fraction of fetal cfDNA in a maternal sample, e.g. a plasma sample, wherein the composition comprises at least one set of primers for amplifying at least one polymorphic nucleic acid in said mixture. The polymorphic nucleic acid comprises an STR selected from CSF1PO, FGA, TH01, vWA, D3S1358, D5S818, D7S820, D8S1179, D13S317, D16S539, D18S51, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113; and/or a SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), rs530022 (SEQ ID NOS 55 & 56); and/or a tandem SNP rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427).

In another embodiment, the invention provides a composition for determining the fraction of fetal cfDNA in a maternal sample by massively parallel sequencing the fetal and maternal cfDNA in the maternal sample, e.g. a plasma sample, wherein the composition comprises at least one set of primers for amplifying at least one polymorphic nucleic acid in said mixture.

In another embodiment, the invention provides a composition for determining the fraction of fetal cfDNA in a maternal sample, e.g. a plasma sample, wherein the composition comprises at least one set of primers for amplifying at least one polymorphic nucleic acid in said mixture. The polymorphic nucleic acid comprises an STR, a SNP and/or a tandem SNP.

In another embodiment, the invention provides a composition for determining the fraction of fetal cfDNA in a maternal sample by massively parallel sequencing the fetal and maternal cfDNA in the maternal sample, e.g. a plasma sample, wherein the composition comprises at least one set of primers for amplifying at least one polymorphic nucleic acid in said mixture. The polymorphic nucleic acid comprises an STR selected from CSF1PO, FGA, TH01, vWA, D3S1358, D5S818, D7S820, D8S1179, D13S317, D16S539, D18S51, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113; a SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56); and/or a tandem SNP rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427).

In another embodiment, the invention provides a composition for determining the fraction of fetal cfDNA in a maternal sample, e.g. a plasma sample, wherein the composition comprises at least one set of primers for amplifying at least one polymorphic nucleic acid in said mixture. The set of primers does not amplify a sequence on the Y chromosome.

In another embodiment, the invention provides a composition for determining the fraction of fetal cfDNA in a maternal sample, e.g. a plasma sample, wherein the composition comprises at least one set of primers for amplifying at least one polymorphic nucleic acid in the mixture. The set of primers does not amplify a sequence on the Y chromosome. The polymorphic nucleic acid comprises an STR, a SNP and/or a tandem SNP.

In another embodiment, the invention provides a composition for determining the fraction of fetal cfDNA in a maternal sample, e.g. a plasma sample, wherein the composition comprises at least one set of primers for amplifying at least one polymorphic nucleic acid in said mixture. The polymorphic nucleic acid comprises an STR selected from CSF1PO, FGA, TH01, vWA, D3S1358, D5S818, D7S820, D8S1179, D13S317, D16S539, D18S51, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113; a SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56); and/or a tandem SNP rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981

(SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427).

In another embodiment, the invention provides a composition for determining the fraction of fetal cfDNA in a maternal sample by massively parallel sequencing the fetal and maternal cfDNA in the maternal sample, e.g. a plasma sample, wherein the composition comprises at least one set of primers for amplifying at least one polymorphic nucleic acid in said mixture.

In another embodiment, the invention provides a composition for determining the fraction of fetal cfDNA in a maternal sample, e.g. a plasma sample, wherein the composition comprises at least one set of primers for amplifying at least one polymorphic nucleic acid in said mixture. The set of primers does not amplify a sequence on the Y chromosome. The polymorphic nucleic acid comprises an STR, a SNP and/or a tandem SNP.

In another embodiment, the invention provides a composition for determining the fraction of fetal cfDNA in a maternal sample by massively parallel sequencing the fetal and maternal cfDNA in the maternal sample, e.g. a plasma sample, wherein the composition comprises at least one set of primers for amplifying at least one polymorphic nucleic acid in said mixture. The polymorphic nucleic acid comprises an STR selected from CSF1PO, FGA, TH01, vWA, D3S1358, D5S818, D7S820, D8S1179, D13S317, D16S539, D18S51, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113; a SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56); and/or a tandem SNP rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397);

rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427).

In another embodiment, the invention provides a kit that comprises the composition of the invention as described above and in the following.

INCORPORATION BY REFERENCE

All patents, patent applications, and other publications, including all sequences disclosed within these references, referred to herein are expressly incorporated by reference, to the same extent as if each individual publication, patent or patent application was specifically and individually indicated to be incorporated by reference. All documents cited are, in relevant part, incorporated herein by reference. However, the citation of any document is not to be construed as an admission that it is prior art with respect to the present invention.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4 illustrates STR markers used in the AmpFlSTR® Identifiler® PCR Amplification Kit.

FIG. 5 illustrates STR markers used in the AmpFlSTR® MiniFiler® PCR Amplification Kit.

DETAILED DESCRIPTION OF THE INVENTION

Figure 1:
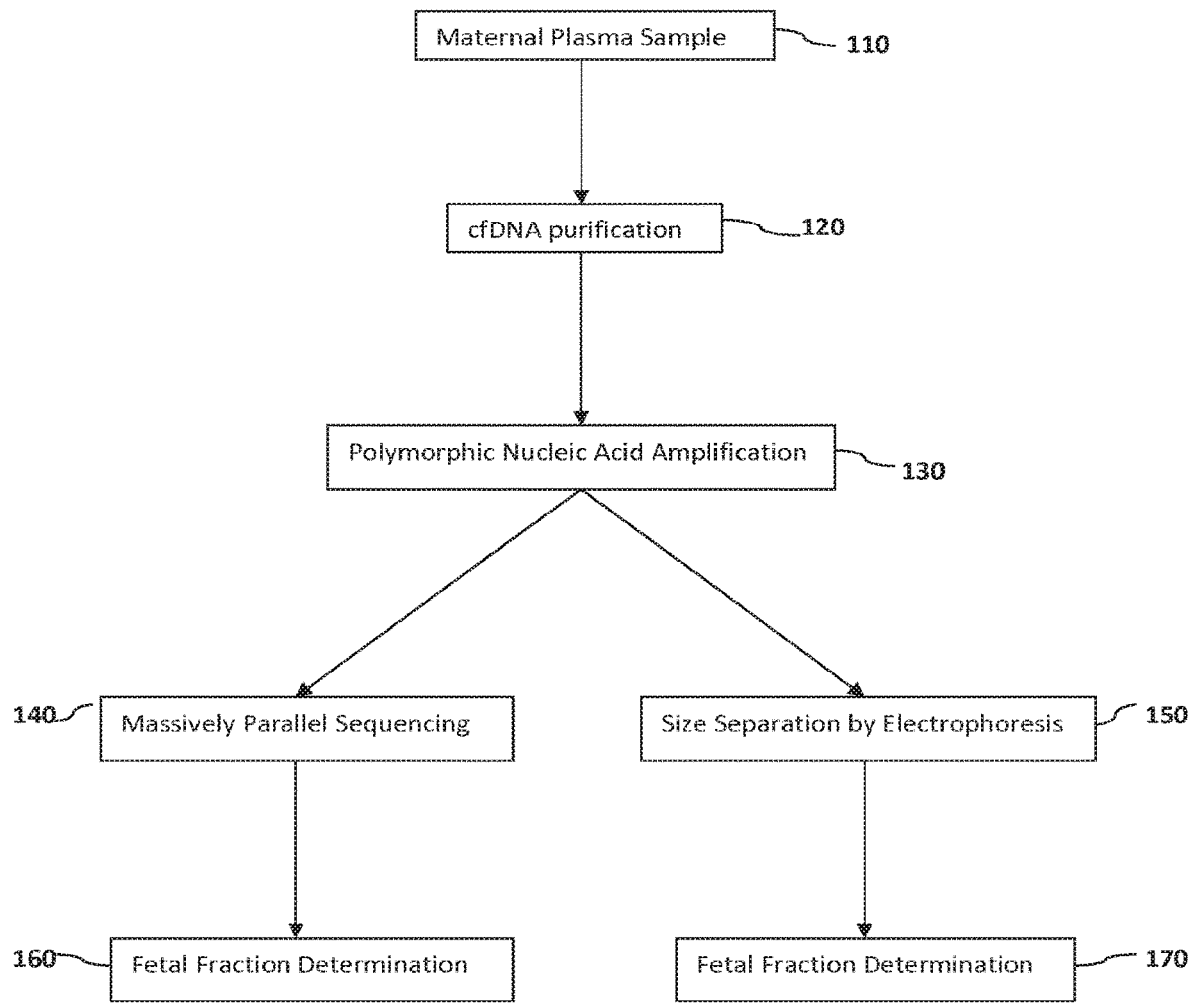
FIG. 1 is a flowchart of a method 100 for determining the fetal fraction in a maternal test sample comprising a mixture of fetal and maternal nucleic acids using massively parallel sequencing methods or size separation of polymorphic nucleic acid sequences.

The invention provides compositions and methods for determining the fraction of fetal nucleic acids in a maternal sample comprising a mixture of fetal and maternal nucleic acids. The fraction of fetal nucleic acids can be used in determining the presence or absence of fetal aneuploidy.

Unless otherwise indicated, the practice of the present invention involves conventional techniques commonly used in molecular biology, microbiology, protein purification, protein engineering, protein and DNA sequencing, and recombinant DNA fields, which are within the skill of the art. Such techniques are known to those of skill in the art and are described in numerous standard texts and reference works. All patents, patent applications, articles and publications mentioned herein are hereby expressly incorporated herein by reference in their entirety.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not limitations of the various aspects or embodiments of the invention which can be had by reference to the Specification as a whole. Accordingly, as indicated above, the terms defined immediately below are more fully defined by reference to the specification as a whole.

Unless defined otherwise herein, all technical and scientific terms used herein have the same meaning as commonly understood by one of ordinary skill in the art to which this invention belongs. Various scientific dictionaries that include the terms included herein are well known and available to those in the art. Although any methods and materials similar or equivalent to those described herein find use in the practice or testing of the present invention, some preferred methods and materials are described. Accordingly, the terms defined immediately below are more fully described by reference to the Specification as a whole. It is to be understood that this invention is not limited to the particular methodology, protocols, and reagents described, as these may vary, depending upon the context they are used by those of skill in the art.

Definitions

As used herein, the singular terms "a", "an," and "the" include the plural reference unless the context clearly indicates otherwise. Unless otherwise indicated, nucleic acids are written left to right in 5' to 3' orientation and amino acid sequences are written left to right in amino to carboxy orientation, respectively.

As used herein, the singular terms "a", "an," and "the" include the plural reference unless the context clearly indicates otherwise. Unless otherwise indicated, nucleic acids are written left to right in 5' to 3' orientation and amino acid sequences are written left to right in amino to carboxy orientation, respectively.

The term "portion" when used in reference to the amount of sequence information of fetal and maternal nucleic acid molecules in a biological sample herein refers to the amount of sequence information of fetal and maternal nucleic acid molecules in a biological sample that in sum amount to less than the sequence information of <1 human genome.

The terms "polynucleotide", "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next, include sequences of any form of nucleic acid, including, but not limited to RNA, DNA and cfDNA molecules. The term "polynucleotide" includes, without limitation, single- and double-stranded polynucleotide.

The term "copy number variation" herein refers to variation in the number of copies of a nucleic acid sequence that is 1 kb or larger present in a test sample in comparison with the copy number of the nucleic acid sequence present in a qualified sample. A "copy number variant" refers to the 1 kb or larger sequence of nucleic acid in which copy-number differences are found by comparison of a sequence of interest in test sample with that present in a qualified sample. Copy number variants/variations include deletions, including microdeletions, insertions, including microinsertions, duplications, multiplications, inversions, translocations and complex multi-site variants. CNV encompass chromosomal aneuploidies and partial aneuplodies.

As used herein, the term "fetal fraction" is used interchangeably with "fraction of fetal nucleic acid", which refers to the fraction of fetal nucleic acid in a sample comprising fetal and maternal nucleic acid. Similarly, the term "minor fraction" or "minor component" herein refers to the lesser fraction of the total genetic material that is present in a sample containing genetic material derived from separate sources e.g. individuals.

As used herein the term "allele" refers to one specific form of a genetic sequence (such as a gene) within a cell, a sample, an individual or within a population, the specific form differing from other forms of the same gene in the sequence of at least one, and frequently more than one, variant sites within the sequence of the gene. The sequences at these variant sites that differ between different alleles are termed "variants", "polymorphisms", or "mutations". In general, polymorphism is used to refer to variants that have a frequency of at least 1% in a population, while the term mutation is generally used for variants that occur at a frequency of less than 1% in a population. In diploid organisms such as humans, at each autosomal specific chromosomal location or "locus" an individual possesses two alleles, a first inherited from one parent and a second inherited from the other parent, for example one from the mother and one from the father. An individual is "heterozygous" at a locus if it has two different alleles at the locus. An individual is "homozygous" at a locus if it has two identical alleles at that locus.

The term "enrich" herein refers to the process of amplifying polymorphic target nucleic acids contained in a portion of a maternal sample, and combining the amplified product with the remainder of the maternal sample from which the portion was removed.

As used herein, the term "genotyping" refers to the determination of the genetic information an individual carries at one or more positions in the genome. For example, genotyping may comprise the determination of which allele or alleles an individual carries for a single SNP or the determination of which allele or alleles an individual carries for a plurality of SNPs. For example, a particular nucleotide in a genome may be a T in some individuals and a C in other individuals. Those individuals who have a T at the position have the T allele and those who have a C have the C allele.

In a diploid organism the individual will have two copies of the sequence containing the polymorphic position so the individual may have a T allele and a C allele or alternatively two copies of the T allele or two copies of the C allele. Those individuals who have two copies of the C allele are homozygous for the C allele, those individuals who have two copies of the T allele are homozygous for the T allele, and those individuals who have one copy of each allele are heterozygous. The alleles are often referred to as the A allele, often the major allele, and the B allele, often the minor allele. The genotypes may be AA (homozygous A), BB (homozygous B) or AB (heterozygous). Genotyping methods generally provide for identification of the sample as AA, BB or AB.

As used herein the term "chromosome" refers to the heredity-bearing gene carrier of a living cell which is derived from chromatin and which comprises DNA and protein components (especially histones). The conventional internationally recognized individual human genome chromosome numbering system is employed herein. The size of an individual chromosome can vary from one type to another with a given multi-chromosomal genome and from one genome to another. In the case of the human genome, the entire DNA mass of a given chromosome is usually greater than about 100,000,000 bp. For example, the size of the entire human genome is about $3.\text{times}.10.\text{sup}.9$ bp. The largest chromosome, chromosome no. 1, contains about $2.4.\text{times}.10.\text{sup}.8$ by while the smallest chromosome, chromosome no. 22, contains about $5.3.\text{times}.10.\text{sup}.7$ bp.

The term "aneuploidy" herein refers to the occurrence of one or more extra or missing chromosomes.

As used herein the term "chromosomal region" is a portion of a chromosome. The actual physical size or extent of any individual chromosomal region can vary greatly. The term "region" is not necessarily definitive of a particular one or more genes because a region need not take into specific account the particular coding segments (exons) of an individual gene.

As used herein the term "genetic marker" refers to a sequence of DNA that has a specific location on a chromosome that can be measured in a laboratory. The term "genetic marker" can also be used to refer to, e.g., a cDNA and/or an mRNA encoded by a genomic sequence, as well as to that genomic sequence. To be useful, a marker needs to have two or more alleles or variants. Markers can be either direct, that is, located within the gene or locus of interest (i.e., candidate gene), or indirect, that is closely linked with the gene or locus of interest (presumably due to a location which is proximate to, but not inside the gene or locus of interest). Moreover, markers can also include sequences which either do or do not modify the amino acid sequence of a gene.

As used herein, the term "maternal sample" refers to a biological sample obtained from a pregnant subject, and comprises a mixture of fetal and maternal nucleic acids. A "pregnant subject" is not limited to a human being, but may also include other organisms including but not limited to mammals, plants, bacteria or cells derived from any of the above.

The term "whole genome amplification" or "WGA" as used herein generally refers to a method for amplification of a limited DNA sample in a non-specific manner, in order to generate a new sample that is indistinguishable from the original but with a higher DNA concentration. The ideal whole genome amplification technique would amplify a sample up to a microgram level while maintaining the original sequence representation. The DNA of the sample may include an entire genome or a portion thereof. Degenerate oligonucleotide-primed PCR (DOP), primer extension PCR technique (PEP) including modified improved primer extension preamplification (mIPEP), and multiple displacement amplification (MDA), are examples of whole genome amplification methods.

The term "short tandem repeat" or "STR" as used herein refers to a class of polymorphisms that occurs when a pattern of two or more nucleotides are repeated and the repeated sequences are directly adjacent to each other. The pattern can range in length from 2 to 10 base pairs (bp) (for example (CATG)n in a genomic region) and is typically in the non-coding intron region. By examining several STR loci and counting how many repeats of a specific STR sequence there are at a given locus, it is possible to create a unique genetic profile of an individual.

The term "primer," as used herein refers to an isolated oligonucleotide which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, use of the method, and the parameters used for primer design, as disclosed herein.

The term "primer pair" or "primer set" refers to a set of primers including a 5' "upstream primer" or "forward primer" that hybridizes with the complement of the 5' end of the DNA sequence to be amplified and a 3' "downstream primer" or "reverse primer" that hybridizes with the 3' end of the sequence to be amplified. As will be recognized by those of skill in the art, the terms "upstream" and "downstream" or "forward" and "reverse" are not intended to be limiting, but rather provide illustrative orientation in particular embodiments. A primer pair is said to be "unique" if it can be employed to specifically amplify a particular target nucleotide sequence in a given amplification mixture.

A "polymorphic marker" or "polymorphic site" is a locus at which nucleotide sequence divergence occurs. The locus may be as small as one base pair. Illustrative markers have at least two alleles, each occurring at frequency of greater than 1%, and more typically greater than 10% or 20% of a selected population. A polymorphic site may be as small as one base pair. Polymorphic markers include restriction fragment length polymorphism (RFLPs), variable number of tandem repeats (VNTR's), hypervariable regions, minisatellites, dinucleotide repeats, trinucleotide repeats, tetranucleotide repeats, simple sequence repeats, deletions, and insertion elements such as Alu. The first identified allelic form is arbitrarily designated as the reference form and other allelic forms are designated as alternative or variant alleles. The allelic form occurring most frequently in a selected population is sometimes referred to as the wild type form. Diploid organisms may be homozygous or heterozygous for allelic forms. A diallelic polymorphism has two forms. A triallelic polymorphism has three forms. A polymorphism between two nucleic acids can occur naturally, or be caused by exposure to or contact with chemicals, enzymes, or other agents, or exposure to agents that cause damage to nucleic acids, for example, ultraviolet radiation, mutagens or carcinogens. The terms "polymorphic locus" and "polymorphic site" are herein used interchangeably.

The terms "polymorphic target nucleic acid", "polymorphic sequence", "polymorphic target nucleic acid sequence" and "polymorphic nucleic acid" are used interchangeably herein to refer to a nucleic acid sequence e.g. a DNA sequence, that comprises one or more polymorphic sites e.g one SNP or a tandem SNP. Polymorphic sequences according to the present technology can be used to specifically differentiate between maternal and non-maternal alleles in the maternal sample comprising a mixture of fetal and maternal nucleic acids.

A "single nucleotide polymorphism" (SNP) occurs at a polymorphic site occupied by a single nucleotide, which is the site of variation between allelic sequences. The site is usually preceded by and followed by highly conserved sequences of the allele (e.g., sequences that vary in less than $1/100$ or $1/1000$ members of the populations). A SNP usually arises due to substitution of one nucleotide for another at the polymorphic site. A transition is the replacement of one purine by another purine or one pyrimidine by another pyrimidine. A transversion is the replacement of a purine by a pyrimidine or vice versa. SNPs can also arise from a deletion of a nucleotide or an insertion of a nucleotide relative to a reference allele. Single nucleotide polymorphisms (SNPs) are positions at which two alternative bases occur at appreciable frequency (>1%) in the human population, and are the most common type of human genetic variation.

As used herein, the term "short tandem repeat" or "STR" as used herein refers to a class of polymorphisms that occurs when a pattern of two or more nucleotides are repeated and the repeated sequences are directly adjacent to each other. The pattern can range in length from 2 to 10 base pairs (bp) (for example (CATG)n in a genomic region) and is typically in the non-coding intron region. By examining several STR loci and counting how many repeats of a specific STR sequence there are at a given locus, it is possible to create a unique genetic profile of an individual.

As used herein, the term "miniSTR" herein refers to tandem repeat of four or more base pairs that spans less than about 300 base pairs, less than about 250 base airs, less than about 200 base pairs, less than about 150 base pairs, less than about 100 base pairs, less than about 50 base pairs, or less than about 25 base pairs. "miniSTRs" are STRs that are amplifiable from cfDNA templates.

The term "tandem SNPs" herein refers to two or more SNPs that are present within a polymorphic target nucleic acid sequence.

The terms "plurality of polymorphic target nucleic acids", "polymorphic nucleic acids" and "polymorphic sequences" are used interchangeably herein and refer to a number of nucleic acid sequences each comprising at least one polymorphic site e.g. one SNP, such that at least 1, 2, 3, 4, 5, 6, 7, 8, 9, 10, 15, 20, 25, 30, or 40 or more different polymorphic sites are amplified from the polymorphic target nucleic acids to identify and/or quantify fetal alleles present in maternal samples comprising fetal and maternal nucleic acids.

As used herein, the term "substantially cell free" encompasses preparations of the desired sample from which components that are normally associated with it are removed. For example, a plasma sample is rendered essentially cell free by removing blood cells e.g. red cells, that are normally associated with it. In some embodiments, substantially free samples are processed to remove cells that would otherwise contribute to the desired genetic material that is to be tested for an abnormality As used herein the term "chromosome" refers to the heredity-bearing gene carrier of a living cell which is derived from chromatin and which comprises DNA and protein components (especially histones). The conventional internationally recognized individual human genome chromosome numbering system is employed herein. The size of an individual chromosome can vary from one type to another with a given multi-chromosomal genome and from one genome to another. In the case of the human genome, the entire DNA mass of a given chromosome is usually greater than about 100,000,000 bp. For example, the size of the entire human genome is about 3.times.10.sup.9 bp. The largest chromosome, chromosome no. 1, contains about 2.4.times.10.sup.8 by while the smallest chromosome, chromosome no. 22, contains about 5.3.times.10.sup.7 bp.

The term "oligonucleotide" is used to refer to a nucleic acid that is relatively short, generally shorter than 200 nucleotides, more particularly, shorter than 100 nucleotides, most particularly, shorter than 50 nucleotides. Typically, oligonucleotides are single-stranded DNA molecules.

The term "primer" refers to an oligonucleotide that is capable of hybridizing (also termed "annealing") with a nucleic acid and serving as an initiation site for nucleotide (RNA or DNA) polymerization under appropriate conditions (i.e., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but primers are typically at least 7 nucleotides long and, more typically range from 10 to 30 nucleotides, or even more typically from 15 to 30 nucleotides, in length. Other primers can be somewhat longer, e.g., 30 to 50 nucleotides long.

The term "allele call" as used herein, refers to successful characterization of an allele by a given analysis method. If the analysis provides successful characterization of both alleles of a gene locus of a DNA sample, it is said that two allele calls are made. If one allele is characterized while the other allele is not characterized, it is said that one allele call is made. If neither of the two alleles is successfully characterized, no allele calls are made.

The term "allele" as used herein, is any one of a number of viable DNA codings occupying a given locus (position) on a chromosome. Usually alleles are DNA (deoxyribonucleic acid) sequences that code for a gene, but sometimes the term is used to refer to a non-gene sequence. An individual's genotype for that gene is the set of alleles it happens to possess. In a diploid organism, one that has two copies of each chromosome, two alleles make up the individual's genotype.

The term "reaction mixture" as used herein refers to a mixture containing sufficient components to carry out an amplification reaction.

The term "sequence tag density" herein refers to the number of sequence reads that are mapped to a reference genome sequence e.g. the sequence tag density for chromosome 21 is the number of sequence reads generated by the sequencing method that are mapped to chromosome 21 of the reference genome. The term "sequence tag density ratio" herein refers to the ratio of the number of sequence tags that are mapped to a chromosome of the reference genome e.g. chromosome 21, to the length of the reference genome chromosome 21.

The terms "threshold value" and "qualified threshold value" herein refer to any number that is calculated using a qualifying data set and serves as a limit of diagnosis of a copy number variation e.g. an aneuploidy, in an organism. If a threshold is exceeded by results obtained from practicing the invention, a subject can be diagnosed with a copy number variation e.g. trisomy 21.

The term "read" refers to a DNA sequence of sufficient length (e.g., at least about 30 bp) that can be used to identify a larger sequence or region, e.g. that can be aligned and specifically assigned to a chromosome or genomic region or gene.

The term "sequence tag" is herein used interchangeably with the term "mapped sequence tag" to refer to a sequence read that has been specifically assigned i.e. mapped, to a larger sequence e.g. a reference genome, by alignment. Mapped sequence tags are uniquely mapped to a reference genome i.e. they are assigned to a single location to the reference genome. Tags that can be mapped to more than one location on a reference genome i.e. tags that do not map uniquely, are not included in the analysis.

The terms "aligned", "alignment", or "aligning" refer to one or more sequences that are identified as a match in terms of the order of their nucleic acid molecules to a known sequence from a reference genome. Such alignment can be done manually or by a computer algorithm, examples including the Efficient Local Alignment of Nucleotide Data (ELAND) computer program distributed as part of the Illumina Genomics Analysis pipeline. The matching of a sequence read in aligning can be a 100% sequence match or less than 100% (non-perfect match).

The term "reference genome" refers to any particular known genome sequence, whether partial or complete, of any organism or virus which may be used to reference identified sequences from a subject. For example, a reference genome used for human subjects as well as many other organisms is found at the National Center for Biotechnology Information via the World Wide Web at ncbi.nlm.nih.gov. A "genome" refers to the complete genetic information of an organism or virus, expressed in nucleic acid sequences.

The term "artificial target sequences genome" herein refers to a grouping of known sequences that encompass alleles of known polymorphic sites. For example, a "SNP reference genome" is an artificial target sequences genome comprising a grouping of sequences that encompass alleles of known SNPs.

The term "clinically-relevant sequence" herein refers to a nucleic acid sequence that is known or is suspected to be associated or implicated with a genetic or disease condition. Determining the absence or presence of a clinically-relevant sequence can be useful in determining a diagnosis or confirming a diagnosis of a medical condition, or providing a prognosis for the development of a disease.

The term "mixed sample" herein refers to a sample containing a mixture of nucleic acids, which are derived from different genomes.

The term "original maternal sample" herein refers to a biological sample obtained from a pregnant subject e.g. a woman, who serves as the source from which a portion is removed to amplify polymorphic target nucleic acids. The "original sample" can be any sample obtained from a pregnant subject, and the processed fractions thereof e.g. a purified cfDNA sample extracted from a maternal plasma sample. The term "original maternal sample" herein refers to a biological sample obtained from a pregnant subject e.g. a woman, who serves as the source from which a portion is removed to amplify polymorphic target nucleic acids. The "original sample" can be any sample obtained from a pregnant subject, and the processed fractions thereof e.g. a purified cfDNA sample extracted from a maternal plasma sample.

The term "biological fluid" herein refers to a liquid taken from a biological source and includes, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

The terms "maternal nucleic acids" and "fetal nucleic acids" herein refer to the nucleic acids of a pregnant female subject and the nucleic acids of the fetus being carried by the pregnant female, respectively.

The term "corresponding to" herein refers to a nucleic acid sequence e.g. a gene or a chromosome, that is present in the genome of different subjects, and which does not necessarily have the same sequence in all genomes, but serves to provide the identity rather than the genetic information of a sequence of interest e.g. a gene or chromosome.

The term "group of chromosomes" herein refers to two or more chromosomes.

The term "subject" herein refers to a human subject as well as a non-human subject such as a mammal, an invertebrate, a vertebrate, a fungus, a yeast, a bacteria, and a virus. Although the examples herein concern human cells and the language is primarily directed to human concerns, the concept of this invention is applicable to genomes from any plant or animal, and is useful in the fields of veterinary medicine, animal sciences, research laboratories and such.

Description

The methods described herein enable the determination of the fraction of the minor fetal nucleic acid component in a sample comprising a mixture of fetal and maternal nucleic acids. In particular, the method enables the determination of the fraction of cfDNA contributed by a fetus to the mixture of fetal and maternal cfDNA in a maternal sample e.g. a plasma sample. The difference between the maternal and fetal fraction is determined by the relative contribution of a polymorphic allele derived from the fetal genome to the contribution of the corresponding polymorphic allele derived from the maternal genome. Polymorphic sequences can be used in conjunction with clinically-relevant diagnostic tests as a positive control for the presence of cfDNA in order to highlight false-negative or false-positive results stemming from low levels of cfDNA below the identification limit. The methods described are independent of the gender of the fetus, and are useful across a range of gestational ages.

FIG. 1 provides a flow diagram of an embodiment of method of the invention 100 for determining the fraction of fetal nucleic acids in a maternal biological sample by massively parallel sequencing of PCR-amplified polymorphic target nucleic acids. In step 110 a maternal sample comprising a mixture of fetal and maternal nucleic acids is obtained from a subject. The sample is a maternal sample that is obtained from a pregnant female, for example a pregnant woman. Other maternal samples can be from mammals, for example, cow, horse, dog, or cat. If the subject is a human, the sample can be taken in the first or second trimester of pregnancy. Any maternal biological sample can be used a source of fetal and maternal nucleic acids which are contained in cells or that are "cell-free". In some embodiments, it is advantageous to obtain a maternal sample that comprises cell-free nucleic acids e.g. cfDNA. Preferably, the maternal biological sample is a biological fluid sample. A biological fluid includes, as non-limiting examples, blood, plasma, serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples. In some embodiments, the biological fluid sample is a sample that is easily obtainable by non-invasive procedures e.g. blood, plasma, serum, sweat, tears, sputum, urine, sputum, ear flow, and saliva. In some embodiments, the biological sample is a peripheral blood sample, or the plasma and/or the serum fractions thereof. In another embodiment, the sample is a mixture of two or more biological samples e.g. a biological sample can comprise two or more of a biological fluid samples. As used herein, the terms "blood," "plasma" and "serum" expressly encompass fractions or processed portions thereof. In some embodiments, the biological sample is processed to obtain a sample fraction e.g. plasma, that contains the mixture of fetal and maternal nucleic acids. A sample that can be used to determine the genotype of one or more fetal alleles can be any sample that contains fetal cells or fetal nucleic acid. For example, maternal serum or plasma sample comprising fetal and maternal cell-free nucleic acids (e.g., DNA or RNA) can be used to determine the genotypes of fetal alleles. In one embodiment, the sample can comprise a fetal cell, e.g., a fetal nucleated red blood cell or a trophoblast.

In step 120, the mixture of fetal and maternal nucleic acids is further processed from the sample fraction e.g. plasma, to obtain a sample comprising a purified mixture of fetal and maternal nucleic acids e.g. cfDNA. Cell-free nucleic acids, including cell-free DNA, can be obtained by various methods known in the art from biological samples including but not limited to plasma, serum and urine (Fan et al., Proc Natl Acad Sci 105:16266-16271 [2008]; Koide et al., Prenatal Diagnosis 25:604-607 [2005]; Chen et al., Nature Med. 2: 1033-1035 [1996]; Lo et al., Lancet 350: 485-487 [1997]. To separate cfDNA from cells, fractionation, centrifugation (e.g., density gradient centrifugation), DNA-specific precipitation, or high-throughput cell sorting and/or separation methods can be used. Examples of methods for processing fluid samples have been previously disclosed, e.g., U.S. Patent Application Nos. 20050282293, 20050224351, and 20050065735, which are herein incorporated by reference in their entireties. Commercially available kits for manual and automated separation of cfDNA are available (Roche Diagnostics, Indianapolis, IN, Qiagen, Valencia, CA, Macherey-Nagel, Duren, DE). In some instances, it can be advantageous to fragment the nucleic acid molecules in the nucleic acid sample. Fragmentation can be random, or it can be specific, as achieved, for example, using restriction endonuclease digestion. Methods for random fragmentation are well known in the art, and include, for example, limited DNAse digestion, alkali treatment and physical shearing. In one embodiment, sample nucleic acids are obtained as cfDNA, which is not subjected to fragmentation. In other embodiments, the sample nucleic acids are obtained as genomic DNA, which is subjected to fragmentation into fragments of approximately 500 or more base pairs, and to which NGS methods can be readily applied.

In step 130, a portion of the purified mixture of fetal and maternal cfDNA is used for amplifying a plurality of polymorphic target nucleic acids each comprising a polymorphic site. In some embodiments, the target nucleic acids each comprise a SNP. In other embodiments, each of the target nucleic acids comprises a pair of tandem SNPs. In yet other embodiments, each the target nucleic acids comprises an STR. Polymorphic sites that are contained in the target nucleic acids include without limitation single nucleotide polymorphisms (SNPs), tandem SNPs, small-scale multi-base deletions or insertions, called IN-DELS (also called deletion insertion polymorphisms or DIPs), Multi-Nucleotide Polymorphisms (MNPs) Short Tandem Repeats (STRs), restriction fragment length polymorphism (RFLP), or a polymorphism comprising any other change of sequence in a chromosome. In some embodiments, the polymorphic sites that are encompassed by the method of the invention are located on autosomal chromosomes, thereby enabling the determination of fetal fraction independently of sex of the fetus. Polymorphisms associated with chromosomes other than chromosome 13, 18, 21 and Y can also be used in the methods described herein.

Polymorphisms can be indicative, informative, or both. Indicative polymorphisms indicate the presence of fetal cell-free DNA in a maternal sample. For example, the more there is of a particular genetic sequence, e.g. a SNP, the more a method will translate its presence into a particular color intensity, density of color, or some other property which is detectable and measurable and indicative of the presence, absence, and quantity of a particular fragment of DNA and/or particular polymorphism e.g. SNP of the embryo. Informative polymorphisms yield information about the fetus—for example, the presence or absence of a disease, genetic abnormality, or any other biological information such as the stage of gestation or gender. With regard to the present invention, the methods are not conducted using all possible SNPs in a genome, but use those which are said to be "informative". "Informative SNPs" in this instance are those which identify differences in the sequence of the mother and the fetus. Any polymorphic site that can be encompassed by the reads generated by the sequencing methods described herein can be used to determine the fetal fraction.

In one embodiment, a portion of the mixture of fetal and maternal nucleic acids in the sample e.g. cfDNA, is used as template for amplifying target nucleic acids that comprise at least one SNP. In some embodiments, each target nucleic acid comprises a single i.e. one SNP. Target nucleic acid sequences comprising SNPs are available from publicly accessible databases including, but not limited to Human SNP Database at world wide web address wi.mit.edu, NCBI dbSNP Home Page at world wide web address ncbi.nlm.nih.gov, world wide web address lifesciences.perkinelmer.com, Applied Biosystems by Life Technologies™ (Carlsbad, CA) at world wide web address appliedbiosystems.com, Celera Human SNP database at world wide web address celera.com, the SNP Database of the Genome Analysis Group (GAN) at world wide web address gan.iarc.fr. In one embodiment, the SNPs chosen for enriching the fetal and maternal cfDNA are selected from the group of 92 individual identification SNPs (IISNPs) described by Pakstis el al. (Pakstis et el. Hum Genet 127:315-324 [2010]), which have been shown to have a very small variation in frequency across populations ($F_{st}$<0.06), and to be highly informative around the world having an average heterozygosity ≥0.4. SNPs that are encompassed by the method of the invention include linked and unlinked SNPs. Other useful SNPs applicable or useful for the methods described herein are disclosed in U.S. Pat. Application Nos. 20080070792, 20090280492, 20080113358, 20080026390, 20080050739, 20080220422, and 20080138809, which are herein incorporated by reference in their entireties. Each target nucleic acid comprises at least one polymorphic site e.g. a single SNP, that differs from that present on another target nucleic acid to generate a panel of polymorphic sites e.g. SNPs, that contain a sufficient number of polymorphic sites of which at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40 or more are informative. For example, a panel of SNPs can be configured to comprise at least one informative SNP. In one embodiment, the SNPs that are targeted for amplification are selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In one embodiment, the panel of SNPs comprises at least 3, at least 5, at least 10, at least 13, at least 15, at least 20, at least 25, at least 30 or more SNPs. In one embodiment, the panel of SNPs comprises rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), and rs2567608 (SEQ ID NOS 25 & 26). The polymorphic nucleic acids comprising the SNPs can be amplified using exemplary primer pairs provided in Example 3, and disclosed as SEQ ID NOs:57-112.

In other embodiments, each target nucleic acid comprises two or more SNPs i.e. each target nucleic acid comprises tandem SNPs. Preferably, each target nucleic acid comprises two tandem SNPs. The tandem SNPs are analyzed as a single unit as short haplotypes, and are provided herein as sets of two SNPs. To identify suitable tandem SNP sequences, the International HapMap Consortium database can be searched (The International HapMap Project, Nature 426:789-796 [2003]). The database is available on the world wide web at hapmap.org. In one embodiment, tandem SNPs that are targeted for amplification are selected from the following sets of tandem pairs of SNPS rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The polymorphic nucleic acids comprising the tandem SNPs can be amplified using primer pairs that amplify polymorphic sequences comprising the tandem SNPs. Examples of primer pairs that can be used to amplify the tandem SNPs disclosed herein are SEQ ID NOs:197-310 as provided in Example 8.

In one embodiment, a portion of the mixture of fetal and maternal nucleic acids in the sample e.g. cfDNA, is used as template for amplifying target nucleic acids that comprise at least one STR. In some embodiments, each target nucleic acid comprises a single i.e. one STR. STR loci are found on almost every chromosome in the genome and may be amplified using a variety of polymerase chain reaction (PCR) primers. Tetranucleotide repeats have been preferred among forensic scientists due to their fidelity in PCR amplification, although some tri- and pentanucleotide repeats are also in use. A comprehensive listing of references, facts and sequence information on STRs, published PCR primers, common multiplex systems, and related population data are compiled in STRBase, which may be accessed via the World Wide Web at ibm4.carb.nist.gov: 8800/dna/home.htm. Sequence information from GenBank® via the World Wide Web at ncbi.nlm.nih.gov/cgi-bin/genbank for commonly used STR loci is also accessible through STRBase. Commercial kits available for the analysis of STR loci generally provide all of the necessary reaction components and controls required for amplification. STR multiplex systems allow the simultaneous amplification of multiple nonoverlapping loci in a single reaction, substantially increasing throughput. With multicolor fluorescent detection, even overlapping loci can be multiplexed. The polymorphic nature of tandem repeated DNA sequences that are widespread throughout the human genome have made them important genetic markers for gene mapping studies, linkage analysis, and human identity testing. Because of the high polymorphism of STRs, most individuals will be heterozygous i.e. most people will possess two alleles (versions) of each—one inherited from each parent—with a different number of repeats. The PCR products comprising the STRs can be separated and detected using manual, semi-automated or automated methods. Semi-automated systems are gel-based and combine electrophoresis, detection and analysis into one unit. On a semiautomated system, gel assembly and sample loading are still manual processes; however, once samples are loaded onto the gel, electrophoresis, detection and analysis proceed automatically. Data collection occurs in "real time" as fluorescently labeled fragments migrate past the detector at a fixed point and can be viewed as they are collected. As the name implies, capillary electrophoresis is carried out in a microcapillary tube rather than between glass plates. Once samples, gel polymer and buffer are loaded onto the instrument, the capillary is filled with gel polymer and the sample is loaded automatically. Therefore, the non-maternally inherited fetal STR sequence will differ in the number of repeats from the maternal sequence. Amplification of these STR sequences can result in one or two major amplification products corresponding to the maternal alleles (and the maternally inherited fetal allele) and one minor product corresponding to the non-maternally inherited fetal allele. This technique was first reported in 2000 (Pertl et al., Human Genetics 106:45-49 [2002]) and has subsequently been developed using simultaneous identification of multiple different STR regions using real-time PCR (Liu et al., Acta Obset Gyn Scand 86:535-541 [2007]). Various sized PCR amplicons have been used to discern the respective size distributions of circulating fetal and maternal DNA species, and have shown that the fetal DNA molecules in the plasma of pregnant women are generally shorter than maternal DNA molecules (Chan et al., Clin Chem 50:8892 [2004]). Size fractionation of circulating fetal DNA has confirmed that the average length of circulating fetal DNA fragments is <300 bp, while maternal DNA has been estimated to be between about 0.5 and 1 Kb (Li et al., Clin Chem, 50:1002-1011 [2004]). The invention provides a method for determining the fraction of fetal nucleic acid in a maternal sample comprising determining the amount of copies of at least one fetal and one maternal allele at a polymorphic miniSTR site, which can be amplified to generate amplicons that are of lengths about the size of the circulating fetal DNA fragments e.g. less than about 250 base pairs. In one embodiment, the fetal fraction can be determined by a method that comprises sequencing at least a portion of amplified polymorphic target nucleic acids each comprising a miniSTR. Fetal and maternal alleles at an informative STR site are discerned by their different lengths i.e. number of repeats, and the fetal fraction can be calculated as a percent ratio of the amount of fetal maternal alleles at that site. The method can use one or a combination of any number of informative miniSTRs to determine the fraction of fetal nucleic acid. For example, any one or a combination of any number of miniSTRs, for example the miniSTRs disclosed in Table 7 and FIGS. 4 and 5, can be used. In one embodiment, the fraction of fetal nucleic acid in a maternal sample is performed using a method that includes determining the number of copies of the maternal and fetal nucleic acid present in the maternal sample by amplifying at least one autosomal miniSTR chosen from CSF1PO, FGA, TH01, TPOX, vWA, D3S1358,D5S818, D7S820, D8S1179, D13S317, D16S539, D18S51, D21S11, Penta D, Penta E, D2S1338, D1S1677, D2S441, D4S2364, D10S1248, D14S1434, D22S1045, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D5S2500, D4S2408, D4S2364, D3S4529, D3S3053, D2S1776, D2S441, D1S1677, D1S1627, and D1GATA113. In another embodiment, the at least one autosomal miniSTR is the group of miniSTRs CSF1PO, FGA, D13S317, D16S539, D18S51, D2S1338, D21S11, D2S1338 and D7S820. In one embodiment, the method comprises determining the number of copies of at least one fetal and at least one maternal allele at least at one polymorphic miniSTR that is amplified to generate amplicons that are less than about 300 bp, less than about 250 bp, less than about 200 bp, less than about 150 bp, less than about 100 bp, or less than about 50 bp. In another embodiment, the amplicons that are generated by amplifying the miniSTRs are less than about 300 bp. In another embodiment, the amplicons that are generated by amplifying the miniSTRs are less than about 250 bp. In another embodiment, the amplicons that are generated by amplifying the miniSTRs are less than about 200 bp. Amplification of the informative allele includes using miniSTR primers, which allow for the amplification of reduced-size amplicons to detect STR alleles that are less than about 500 bp, less than about 450 bp, less than about 400 bp, less than about 350 bp, less than about 300 base pairs (bp), less than about 250 bp, less than about 200 bp, less than about 150 bp, less than about 100 bp, or less than about 50 bp. The reduced-size amplicons generated using the miniSTR primers are known as miniSTRs that are identified according to the marker name corresponding to the locus to which they have been mapped. In one embodiment, the miniSTR primers include mini STR primers that have permitted the maximum size reduction in amplicon size for all 13 CODIS STR loci in addition to the D2S1338, Penta D, and pentaE found in commercially available STR kits (Butler et al., J Forensic Sci 48:1054-1064 [2003]), miniSTR loci that are unlinked to the CODIS markers as described by Coble and Butler (Coble and Butler, J Forensic Sci 50:43-53 [2005]), and other minSTRs that have been characterized at NIST. Information regarding the miniSTRs characterized at NIST is accessible via the world wide web at cstl.nist.gov/biotech/strbase/newSTRs.htm. Any one pair or a combination of two or more pairs of miniSTR primers can be used to amplify at least one miniSTR.

In one embodiment, exemplary primer sets that can be used to amplify STRs in maternal cfDNA samples include the primer sets provided in Example 9 and disclosed as SEQ ID NOs:113-196.

Gender identification (sex-typing) in commonly performed in conjunction with STR typing using PCR products generated from the Amelogenin gene that occurs on both the X- and Y-chromosome. Amelogenin is not an STR locus, but it produces X and Y chromosome specific PCR products. A commonly used PCR primer set first published by Sullivan et al. (1993) (Sullivan et al., BioTechniques 15:637-641 [1993]) targets a 6 bp deletion that occurs on the X-chromosome, which enables amplicons generated from the X- and Y-chromosome to be distinguished from one another when electrophoretic separation is performed to separate STR alleles. Most commercial STR kits utilize the Sullivan et al. (1993) primers or minor modifications. Since females are X,X, only a single peak is observed when testing female DNA whereas males, which possess both X and Y chromosomes, exhibit two peaks with a standard Amelogenin test. In one embodiment, the method to determine the fraction of fetal nucleic acid in a maternal sample comprises coamplifying Ameleogenin with at least one miniSTR. In another embodiment, the method does not comprise coamplifying Amelogenin with miniSTR loci.

Amplification of the target nucleic acids in the mixture of fetal and maternal nucleic acid e.g. cfDNA, is accomplished any method that uses PCR or variations of the method including but not limited to digital PCR, real time PCR (RT-PCR), TaqMan PCR System (Applied Biosystems), SNPlex or GenPlex methods, asymmetric PCR, helicase-dependent amplification, hot-start PCR, qPCR, solid phase PCR, and touchdown PCR. Alternatively, replication of target nucleic acid sequences can be obtained by enzyme-independent methods e.g. chemical solid-phase synthesis using the phosphoramidites. Amplification of the target sequences is accomplished using primer pairs each capable of amplifying a target nucleic acid sequence comprising the polymorphic site e.g. SNP, in a multiplex PCR reaction. Multiplex PCR reactions include combining at least 2, at least three, at least 3, at least 5, at least 10, at least 15, at least 20, at least 25, at least 30, at least 40 or more sets of primers in the same reaction to quantify the amplified target nucleic acids comprising at least two, at least three, at least 5, at least 10, at least 15, at least 20, at least 25, at least 30, at least 40 or more polymorphic sites in the same sequencing reaction. Any panel of primer sets can be configured to amplify at least one informative polymorphic sequence.

In step 140 of method 100 (FIG. 1), a portion or all of the amplified polymorphic sequences are used to prepare a sequencing library for sequencing in a parallel fashion as described. In one embodiment, the library is prepared for sequencing-by-synthesis using Illumina's reversible terminator-based sequencing chemistry.

In step 140, sequence information that is needed for determining fetal fraction is obtained using any of the known DNA sequencing methods. In one embodiment, the method described herein employs next generation sequencing technology (NGS) in which clonally amplified DNA templates or single DNA molecules are sequenced in a massively parallel fashion within a flow cell (e.g. as described in Volkerding et al. Clin Chem 55:641-658 [2009]; Metzker M Nature Rev 11:31-46 [2010]). In addition to high-throughput sequence information, NGS provides digital quantitative information, in that each sequence read is a countable "sequence tag" representing an individual clonal DNA template or a single DNA molecule. This quantification allows NGS to expand the digital PCR concept of counting cell-free DNA molecules (Fan et al., Proc Natl Acad Sci USA 105:16266-16271 [2008]; Chiu et al., Proc Natl Acad Sci USA 2008; 105:20458-20463 [2008]). The sequencing technologies of NGS include pyrosequencing, sequencing-by-synthesis with reversible dye terminators, sequencing by oligonucleotide probe ligation and real time sequencing.

Some of the sequencing technologies are available commercially, such as the sequencing-by-hybridization platform from Affymetrix Inc. (Sunnyvale, CA) and the sequencing-by-synthesis platforms from 454 Life Sciences (Bradford, CT), Illumina/Solexa (Hayward, CA) and Helicos Biosciences (Cambridge, MA), and the sequencing-by-ligation platform from Applied Biosystems (Foster City, CA), as described below. In addition to the single molecule sequencing performed using sequencing-by-synthesis of Helicos Biosciences, other single molecule sequencing technologies are encompassed by the method of the invention and include the SMRT™ technology of Pacific Biosciences, the Ion Torrent™ technology, and nanopore sequencing being developed for example, by Oxford Nanopore Technologies.

While the automated Sanger method is considered as a 'first generation' technology, Sanger sequencing including the automated Sanger sequencing, can also be employed by the method of the invention. Additional sequencing methods that comprise the use of developing nucleic acid imaging technologies e.g. atomic force microscopy (AFM) or transmission electron microspcopy (TEM), are also encompassed by the method of the invention. Exemplary sequencing technologies are described below.

In one embodiment, the DNA sequencing technology that is used in the method of the invention is the Helicos True Single Molecule Sequencing (tSMS) (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step.

In one embodiment, the DNA sequencing technology that is used in the method of the invention is the 454 sequencing (Roche) (e.g. as described in Margulies, M. et al. Nature 437:376-380 [2005]). 454 sequencing involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is discerned and analyzed.

In one embodiment, the DNA sequencing technology that is used in the method of the invention is the SOLiD technology (Applied Biosystems). In SOLiD sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In one embodiment, the DNA sequencing technology that is used in the method of the invention is the single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength identifiers (ZMW identifiers) that obtain sequence information while phospolinked nucleotides are being incorporated into the growing primer strand. A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Identification of the corresponding fluorescence of the dye indicates which base was incorporated. The process is repeated.

In one embodiment, the DNA sequencing technology that is used in the method of the invention is nanopore sequencing (e.g. as described in Soni GV and Meller A. Clin Chem 53: 1996-2001 [2007]). Nanopore sequencing DNA analysis techniques are being industrially developed by a number of companies, including Oxford Nanopore Technologies (Oxford, United Kingdom). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence.

In one embodiment, the DNA sequencing technology that is used in the method of the invention is the chemical-sensitive field effect transistor (chemFET) array (e.g., as described in U.S. Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In one embodiment, the DNA sequencing technology that is used in the method of the invention is the Halcyon Molecular's method that uses transmission electron microscopy (TEM). The method, termed Individual Molecule Placement Rapid Nano Transfer (IMPRNT), comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445. The method allows for sequencing complete human genomes in less than ten minutes.

In one embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be identified by Ion Torrent's ion sensor. The sequencer—essentially the worlds smallest solid-state pH meter—calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct identification allows recordation of nucleotide incorporation in seconds.

Other sequencing methods include digital PCR and sequencing by hybridization. Digital polymerase chain reaction (digital PCR or dPCR) can be used to directly identify and quantify nucleic acids in a sample. Digital PCR can be performed in an emulsion. Individual nucleic acids are separated, e.g., in a microfluidic chamber device, and each nucleic can is individually amplified by PCR. Nucleic acids can be separated such there is an average of approximately 0.5 nucleic acids/well, or not more than one nucleic acid/well. Different probes can be used to distinguish fetal alleles and maternal alleles. Alleles can be enumerated to determine copy number. In sequencing by hybridization, the hybridization comprises contacting the plurality of polynucleotide sequences with a plurality of polynucleotide probes, wherein each of the plurality of polynucleotide probes can be optionally tethered to a substrate. The substrate might be flat surface comprising an array of known nucleotide sequences. The pattern of hybridization to the array can be used to determine the polynucleotide sequences present in the sample. In other embodiments, each probe is tethered to a bead, e.g., a magnetic bead or the like. Hybridization to the beads can be identified and used to identify the plurality of polynucleotide sequences within the sample.

In one embodiment, the method employs massively parallel sequencing of millions of DNA fragments using Illumina's sequencing-by-synthesis and reversible terminator-based sequencing chemistry (e.g. as described in Bentley et al., Nature 6:53-59 [2009]). Template DNA can be genomic DNA e.g. cfDNA. In some embodiments, genomic DNA from isolated cells is used as the template, and it is fragmented into lengths of several hundred base pairs. In other embodiments, cfDNA is used as the template, and fragmentation is not required as cfDNA exists as short fragments. For example fetal cfDNA circulates in the bloodstream as fragments of <300 bp, and maternal cfDNA has been estimated to circulate as fragments of between about 0.5 and 1 Kb (Li et al., Clin Chem, 50: 1002-1011 [2004]). Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchors. Under limiting-dilution conditions, adapter-modified, single-stranded template DNA is added to the flow cell and immobilized by hybridization to the anchors. Attached DNA fragments are extended and bridge amplified to create an ultra-high density sequencing flow cell with hundreds of millions of clusters, each containing ~1,000 copies of the same template. The cluster amplified DNA molecules are sequenced using a robust four-color DNA sequencing-by-synthesis technology that employs reversible terminators with removable fluorescent dyes. High-sensitivity fluorescence identification is achieved using laser excitation and total internal reflection optics. Short sequence reads of about 20-40 bp e.g. 36 bp, are aligned against a repeat-masked reference genome and genetic differences are called using specially developed data analysis pipeline software. After completion of the first read, the templates can be regenerated in situ to enable a second read from the opposite end of the fragments. Thus, either single-end or paired end sequencing of the DNA fragments is used according to the method. Partial sequencing of DNA fragments present in the sample is performed, and sequence tags comprising reads of predetermined length e.g. 36 bp, that are mapped to a known reference genome are counted.

The length of the sequence read is associated with the particular sequencing technology. NGS methods provide sequence reads that vary in size from tens to hundreds of base pairs. In some embodiments of the method described herein, the sequence reads are about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, about 500 bp, about 550 bp or about 600 bp. It is expected that technological advances will enable single-end reads of greater than 500 bp enabling for reads of greater than about 1000 bp when paired end reads are generated. In one embodiment, the sequence reads are 36 bp. Other sequencing methods that can be employed by the method of the invention include the single molecule sequencing methods that can sequence nucleic acids molecules >5000 bp. The massive quantity of sequence output is transferred by an analysis pipeline that transforms primary imaging output from the sequencer into strings of bases. A package of integrated algorithms performs the core primary data transformation steps: image analysis, intensity scoring, base calling, and alignment.

In one embodiment, partial sequencing of amplified target polymorphic nucleic acids is performed, and sequence tags comprising reads of predetermined length e.g. 36 bp, that map to a known reference genome are counted. Only sequence reads that uniquely align to a reference genome are counted as sequence tags. In one embodiment, the reference genome is an artificial target sequences genome that comprises the sequences of the polymorphic target nucleic acids e.g. SNPs. In one embodiment, the reference genome is an artificial SNP reference genome. In another r embodiment, the reference genome is an artificial STR reference genome. In yet another embodiment, the reference genome is an artificial tandem-STR reference genome. Artificial reference genomes can be compiled using the sequences of the target polymorphic nucleic acids. Artificial reference genomes can comprise polymorphic target sequence each comprising one or more different types of polymorphic sequences. For example, an artificial reference genome can comprise polymorphic sequences comprising SNP alleles and/or STRs. In one embodiment, the reference genome is the human reference genome NCBI36/hg18 sequence, which is available on the world wide web at genome.ucsc.edu/cgi-bin/hgGateway?org-Human&db=hg18&hgsid=166260105). Other sources of public sequence information include GenBank, dbEST, dbSTS, EMBL (the European Molecular Biology Laboratory), and the DDBJ (the DNA Databank of Japan). In another embodiment, the reference genome comprises the human reference genome NCBI36/hg18 sequence and an artificial target sequences genome, which includes the target polymorphic sequences e.g. a SNP genome. Mapping of the sequence tags is achieved by comparing the sequence of the mapped tag with the sequence of the reference genome to determine the chromosomal origin of the sequenced nucleic acid (e.g. cfDNA) molecule, and specific genetic sequence information is not needed. A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al., Genome Biology 10: R25.1-R25.10 [2009]), or ELAND (Illumina, Inc., San Diego, CA, USA). In one embodiment, one end of the clonally expanded copies of the plasma cfDNA molecules is sequenced and processed by bioinformatic alignment analysis for the Illumina Genome Analyzer, which uses the Efficient Large-Scale Alignment of Nucleotide Databases (ELAND) software. In embodiments of the method that comprise determining the presence or absence of an aneuploidy and fetal fraction using NGS sequencing methods, analysis of sequencing information for the determination of aneuploidy may allow for a small degree of mismatch (0-2 mismatches per sequence tag) to account for minor polymorphisms that may exist between the reference genome and the genomes in the mixed sample. Analysis of sequencing information for the determination of fetal fraction may allow for a small degree of mismatch depending on the polymorphic sequence. For example, a small degree of mismatch may be allowed if the polymorphic sequence is an STR. In cases when the polymorphic sequence is a SNP, all sequence that match exactly to either of the two alleles at the SNP site are counted first and filtered from the remaining reads, for which a small degree of mismatch may be allowed. Quantification of the number of sequence reads aligning to each chromosome for determining chromosomal aneuploidies can be determined as described herein, or using alternative analyses that employ normalizing the median number of sequence tags for a chromosome of interest to the median number of tags for each of the other autosomes (Fan et al., Proc Natl Acad Sci 105:16266-16271 [2008]), or that compare the number of unique reads aligning to each chromosome to the total number of reads aligning to all chromosomes to derive a percent genomic representation for each chromosome. A "z score" is generated to represent the difference between the percent genomic representation of the chromosome of interest and the mean percent representation for the same chromosome between a euploid control group, divided by the standard deviation (Chiu et al., Clin Chem 56:459-463 [2010]). In another embodiment, the sequencing information can be determined as described in U.S. Provisional Patent Application No. 61/296,464, titled "Normalizing Biological Assays," filed Jan. 19, 2010, which is herein incorporated by reference in its entirety.

Analysis of sequencing information for the determination of fetal fraction may allow for a small degree of mismatch depending on the polymorphic sequence. For example, a small degree of mismatch may be allowed if the polymorphic sequence is an STR. In cases when the polymorphic sequence is a SNP, all sequences that match exactly to either of the two alleles at the SNP site are counted first and filtered from the remaining reads, for which a small degree of mismatch may be allowed. The present method for determining fetal fraction by sequencing of nucleic acids can be used in combination with other methods.

In step 160, fetal fraction is determined based on the total number of tags that map to the first allele and the total number of tags that map to second allele at an informative polymorphic site e.g. a SNP, contained in a reference genome. For example, the reference genome is an artificial target sequence genome that encompasses the polymorphic sequences that comprise SNPs rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In one embodiment, the artificial reference genome includes the polymorphic target sequences of SEQ ID NOs:1-56 (see Example-3).

In another embodiment, the artificial genome is an artificial target sequence genome that encompasses polymorphic sequences that comprise tandem SNPs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427).

In another embodiment, the artificial target genome encompasses polymorphic sequences that comprise STRs selected from CSF1PO, FGA, TH01, TPOX, vWA, D3S1358, D5S818, D7S820, D8S1179, D13S317, D16S539, D18S51, D21S11, Penta D, Penta E, D2S1338, D1S1677, D2S441, D4S2364, D10S1248, D14S1434, D22S1045, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D5S2500, D4S2408, D4S2364, D3S4529, D3S3053, D2S1776, D2S441, D1S1677, D1S1627, and D1GATA113. The composition of the artificial target sequences genome will vary depending on the polymorphic sequences that are used for determining the fetal fraction. Accordingly, an artificial target sequences genome is not limited to the SNP, tandem SNP or STR sequences exemplified herein.

Figure 2:
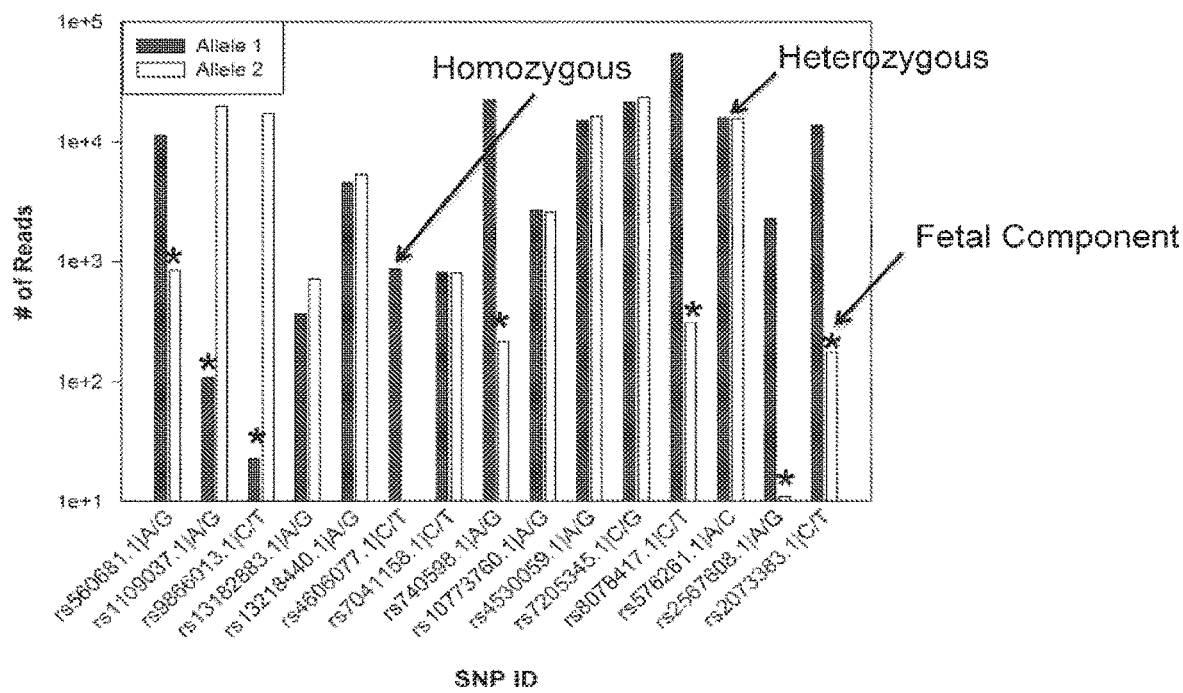
FIG. 2 is a bar diagram showing the identification of fetal and maternal polymorphic sequences (SNPs) used to determine fetal fraction in a test sample. The total number of sequence reads (Y-axis) mapped to the SNP sequences identified by rs numbers (X-axis), and the relative level of fetal nucleic acids (*) are shown.

The informative polymorphic site e.g. SNP, is identified by the difference in the allelic sequences and the amount of each of the possible alleles. Fetal cfDNA is present at a concentration that is <10% of the maternal cfDNA. Thus, the presence of a minor contribution of an allele to the mixture of fetal and maternal nucleic acids relative to the major contribution of the maternal allele can be assigned to the fetus. Alleles that are derived from the maternal genome are herein referred to as major alleles, and alleles that are derived from the fetal genome are herein referred to as minor alleles. Alleles that are represented by similar levels of mapped sequence tags represent maternal alleles. The results of an exemplary multiplex amplification of target nucleic acids comprising SNPs and derived from a maternal plasma sample is shown in FIG. 2. Informative SNPs are discerned from the single nucleotide change at a polymorphic site, and fetal alleles are discerned by their relative minor contribution to the mixture of fetal and maternal nucleic acids in the sample when compared to the major contribution to the mixture by the maternal nucleic acids. Accordingly, the relative abundance of fetal cfDNA in the maternal sample is determined as a parameter of the total number of unique sequence tags mapped to the target nucleic acid sequence on a reference genome for each of the two alleles of the predetermined polymorphic site. In one embodiment, the fraction of fetal nucleic acids in the mixture of fetal and maternal nucleic acids is calculated for each of the informative allele (allele$_x$) as follows:

$$\% \text{ fetal fraction allele}_x = ((\Sigma \text{Fetal sequence tags for allele}_x)/(\Sigma \text{Maternal sequence tags for allele}_x)) \times 100$$

and fetal fraction for the sample is calculated as the average of the fetal fraction of all of the informative alleles. Optionally, the fraction of fetal nucleic acids in the mixture of fetal and maternal nucleic acids is calculated for each of the informative allele (allele$_x$) as follows:

$$\% \text{ fetal fraction allele}_x = ((2 \times \Sigma \text{Fetal sequence tags for allele}_x)/(\Sigma \text{Maternal sequence tags for allele}_x)) \times 100,$$

to compensate for the presence of 2 fetal alleles, one being masked by the maternal background.

The percent fetal fraction is calculated for at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40 or more informative alleles. In one embodiment, the fetal fraction is the average fetal fraction determined for at least 3 informative alleles.

Figure 3:
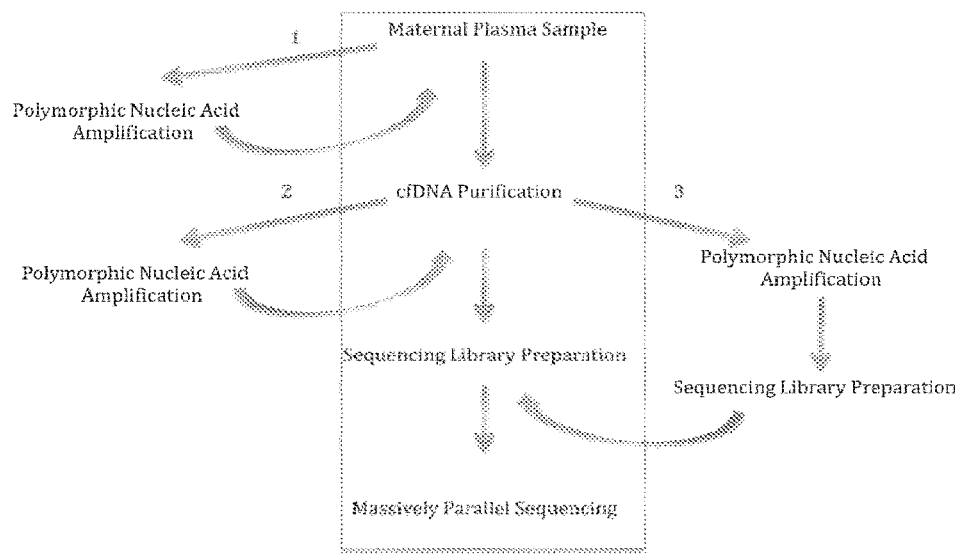
FIG. 3 is a flowchart outlining alternative embodiments of the method for determining fetal fraction by massively parallel sequencing shown in FIG. 1.

FIG. 3, shows a flowchart of alternate methods whereby fetal fraction can be determined from amplified target nucleic acids that have been combined with unamplified fetal and maternal cfDNA sample to allow for the simultaneous determination of fetal fraction and the presence or absence of fetal aneuploidy by enriching the maternal sample comprising fetal and maternal nucleic acids for polymorphic target nucleic acids. In one embodiment, the sample that is enriched is the plasma fraction of a blood sample (a). For example, a portion of an original maternal plasma sample is used for amplifying target nucleic acid sequences. Subsequently, some or all of the amplified product is combined with the remaining unamplified original plasma sample thereby enriching it (see Example 7). In another embodiment, the sample that is enriched is the sample of purified cfDNA that is extracted from plasma (b). For example, enrichment comprises amplifying the target nucleic acids that are contained in a portion of an original sample of purified mixture of fetal and maternal nucleic acids e.g. cfDNA that has been purified from a maternal plasma sample, and subsequently combining some or all of the amplified product with the remaining unamplified original purified sample (see Example 6). In yet another embodiment, the sample that is enriched is a sequencing library sample prepared from a purified mixture of fetal and maternal nucleic acids (c). For example, enrichment comprises amplifying the target nucleic acids that are contained in a portion of an original sample of purified mixture of fetal and maternal nucleic acids e.g. cfDNA that has been purified from a maternal plasma sample, preparing a first sequencing library of unamplified nucleic acid sequences, preparing a second sequencing library of amplified polymorphic target nucleic acids, and subsequently combining some or all of the second sequencing library with some or all of the first sequencing library (see Example 5). The amount of amplified product that is used to enrich the original sample is selected to obtain sufficient sequencing information for determining both the presence or absence of aneuploidy and the fetal fraction from the same sequencing run. At least about 3%, at least about 5%, at least about 7%, at least about 10%, at least about 15%, at least about 20%, at least about 25%, at least about 30% or more of the total number of sequence tags obtained from sequencing are mapped to determine the fetal fraction. Sequencing of the library generated following any one of the methods depicted in FIG. 3, provides sequence tags derived from the amplified target nucleic acids and tags derived from the original unamplified maternal sample. Fetal fraction is calculated from the number of tags mapped to an artificial reference genome, and the presence or absence of aneuploidy is determined from the number of tags that map to the subject genome e.g. human genome.

An alternative method for determining fetal fraction from amplified polymorphic target nucleic acids at step 130 of FIG. 1, uses size separation of amplified polymorphic target nucleic acids comprising STRs (step 150 of FIG. 1). As described above, the polymorphic character of a STR locus is due to variation in the number of tandemly repeated units between alleles. Because of the high polymorphism of the STRs most individuals will be heterozygous for STRs. Amplification of an STR will result in one or two PCR products in most samples. In samples obtained from pregnant women e.g. plasma samples, amplification of an STR will result in one or two major PCR products, which correspond to the one or two maternal alleles including one fetal maternally-inherited allele, and a third paternally-inherited fetal allele that is detected at an informative STR.

The STRs that are targeted for amplification are miniSTRs as described herein that are less than about 300 base pairs and that are amplified in a multiplex PCR reaction, which allows the simultaneous amplification of multiple loci in a single reaction. The primers are labeled with different fluorescent dyes each emitting fluorescence at a different wavelength e.g. 6FAM™, VIC™, NED™, and PET™, and the number of repeat units for each fluorescently tagged STR in the resulting PCR products is detected following their separation and accurate sizing that is achieved by slab or capillary electrophoresis. In one embodiment, capillary electrophoresis is used, and it can be performed in microfabricated channels or capillary arrays. Alternatively, methods utilizing mass spectrometry and microarray technology are used. Multiplex STR analysis can be performed to determine fetal fraction using commercially-available kits e.g. AmpFlSTR® Identifiler® PCR Amplification Kit (FIG. 4) and AmpFlSTR® MiniFiler® PCR Amplification Kit (FIG. 5) (Applied Biosystems, Foster City, CA). The AmpFlSTR® MiniFiler® PCR Amplification Kit was designed to amplify as miniSTRs eight of the largest sized loci in the AmpFlSTR® Identifiler® PCR Amplification Kit. Together with the gender-identification locus Amelogenin, the nine-locus multiplex enables simultaneous amplification of loci of cfDNA samples (see Example 10).

In one embodiment, multiplex STR analysis for determining fetal fraction is performed by amplifying polymorphic target nucleic acids present in a maternal plasma sample that each comprise a miniSTR selected from CSF1PO, FGA, TH01, vWA, D3S1358, D5S818, D7S820, D8S1179, D13S317, D16S539, D18S51, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. In another embodiment, multiplex STR analysis for determining fetal fraction is performed by amplifying polymorphic target nucleic acids present in a maternal plasma sample for the panel of miniSTRs: CSF1PO, D13S317, D16S539, D18S51, D21S11, D2S1338, D7S820 and FGA. The miniSTRs can be located on the same or on different chromosomes. The method is a fetal gender-independent method. Therefore, in some embodiments, the miniSTRs are located on chromosomes other than the Y chromosome. In other embodiments, the miniSTRs are located on chromosomes other than chromosomes 13, 18, 21 or X i.e. chromosomes that might be involved in an aneuploidy.

Samples of maternal plasma often contain less than 100 pg of cfDNA. The low copy number DNA samples can fall below the sensitivity limitations of STR analysis methods. The intractable samples can be made amenable by increasing the number of starting cfDNA available for subsequent STR analysis by a whole genome amplification strategy. In one embodiment, the mixture of fetal and maternal nucleic acids can be preamplified before alleles are detected or quantified. For example, template cell-free DNA can be amplified by PCR. The nucleic acid can be amplified for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 cycles. Nucleic acid can be amplified for about 1-10 cycles, about 1-20 cycles, about 1-30 cycles, about 1-40 cycles, about 5-15 cycles, about 5-20 cycles, about 5-30 cycles, about 5-40 cycles, about 10-15 cycles, about 10-20 cycles, about 10-30 cycles, about 10-40 cycles, about 20-30 cycles, about 20-40 cycles, or about 30-40 cycles. The amount of template nucleic acid that can be amplified can about 10-1000 pg, 25-1000 pg, 50-1000 pg, 100-1000, pg, 200-1000 pg, 300-1000 pg, 400-1000 pg, 500-1000 pg, 600-1000, 700-1000 pg, or 800-1000 pg. Following preamplification, the nucleic acids can be diluted before alleles are detected or quantified. Preamplification can be used to increase the detection sensitivity of alleles in a sample, for example, a maternal sample (Example 11). In another embodiment, genotyping a polymorphism need not require a pre-amplification step. Any PCR-based amplification method can be used to pre-amplify the cfDNA. Amplification methods include but are not limited to whole genome amplification strategies including methods such as primer extension preamplification, degenerate oligonucleotide-primed PCR (DOP-PCR), low fragments from low quantities of DOP-PCR, improved primer extension preamplification PCR (IPEP PCR), and modified improved primer extension preamplification (mI-PEP). Thus, in one embodiment, the method that is used for determining the fetal fraction in a maternal sample e.g. plasma sample, comprises preamplifying the mixture of fetal and maternal nucleic acids present in the plasma cfDNA sample using a whole genome amplification method, amplifying a plurality of polymorphic nucleic acids in said mixture of fetal and maternal nucleic acids, wherein each of said at least one polymorphic nucleic acid comprises an STR; determining the amount of fetal and maternal STR alleles at least one polymorphic nucleic acid; and calculating the fetal fraction from the amount of fetal and maternal STR alleles. Following preamplification, multiplex STR analysis for determining fetal fraction is performed by amplifying polymorphic target nucleic acids present in a maternal plasma sample that each comprise a miniSTR selected from CSF1PO, FGA, TH01, vWA, D3S1358, D5S818, D7S820, D8S1179, D13S317, D16S539, D18S51, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. Alternatively, multiplex STR analysis for determining fetal fraction is performed by amplifying polymorphic target nucleic acids for the panel of miniSTRs: CSF1PO, D13S317, D16S539, D18S51, D21S11, D2S1338, D7S820 and FGA.

Applications

Methods described herein are applicable to diagnosis or prognosis of various disease conditions including, but not limited to, cancer, genetic disorders and infection. The fetal fraction of nucleic acid in a maternal sample can be used for determining a chromosomal abnormality. Examples of chromosomal abnormalities include, for example, aneuploidy, monosomy, trisomy, duplication, inversion, deletion, polyploidy, deletion of a part of a chromosome, addition, addition of a part of chromosome, insertion, a fragment of a chromosome, a region of a chromosome, chromosomal rearrangement, and translocation. For example, aneuploidy can refer to the occurrence of one or more extra or missing chromosomes in a sample.

Examples of fetal conditions that can be determined using the methods of the provided invention include, for example, Angleman syndrome (15q11.2-q13), cri-du-chat syndrome (5p−), DiGeorge syndrome and Velo-cardiofacial syndrome (22q11.2), Miller-Dieker syndrome (17 p13.3), Prader-Willi syndrome (15q11.2-q13), retinoblastoma (13q14), Smith-Magenis syndrome (17 p11.2), trisomy 13, trisomy 16, trisomy 18, trisomy 21 (Down's syndrome), triploidy, Williams syndrome (7q 11.23), and Wolf-Hirschhom syndrome (4p−). Examples of sex chromosome abnormalities that can be detected by methods described herein include, but are not limited to, Kallman syndrome (Xp22.3), steroid sulfate deficiency (STS) (Xp22.3), X-linked ichthyosis (Xp22.3), Klinefelter syndrome (XXY), fragile X syndrome, Turner syndrome metafemales or trisomy X, and monosomy X.

In one embodiment, fetal fraction information can be used to set thresholds and estimate minimum sample size in aneuploidy detection. Such use is described in Example 7 below. Fetal fraction information can be used in conjunction with sequencing information. For example, nucleic acids from a cell-free sample, for example a maternal plasma or serum sample, can be used to enumerate sequences in a sample. Sequences can be enumerated using any of the sequencing techniques described above. Knowledge of fetal fraction can be used to set "cutoff" thresholds to call "aneuploidy," "normal," or "marginal/no call" (uncertain) states. Then, calculations can be performed to estimate the minimum number of sequences required to achieve adequate sensitivity (i.e. probability of correctly identifying an aneuploidy state).

The determination of fetal fraction according to the method of the invention can be practiced in combination with any method used to determine the presence of absence of fetal aneuploidy in a maternal plasma sample. In addition to the method described herein for the determination of aneuploidy, the determination of fetal fraction by massively parallel sequencing can be used in conjunction with other methods for determining fetal aneuploidy, for example, according to the methods described in U.S. U.S. Patent Application Publication Nos. US 2007/0202525A1; US2010/0112575A1, US 2009/0087847A1; US2009/0029377A1; US 2008/0220422A1; US2008/0138809A1, US2008/0153090A1, and U.S. Pat. No. 7,645,576. The methods can also be combined with assays for determining other prenatal conditions associated with the mother and/or the fetus. For example, the method can be used in conjunction with prenatal analyses, for example, as described in U.S. Patent Application Publication Nos. US2010/0112590A1, US2009/0162842A1, US2007/0207466A1, and US2001/0051341A1, all of which are incorporated by reference in their entirety.

The methods described can be applied to determine the fraction of any one population of nucleic acids in a mixture of nucleic acids contributed by different genomes. In addition to determining the fraction contributed to a sample by two individuals e.g. the different genomes are contributed by the fetus and the mother carrying the fetus, the methods can be used to determine the fraction of a genome in a mixture derived from two different cells of from one individual e.g. the genomes are contributed to the sample by aneuploid cancerous cells and normal euploid cells from the same subject.

Compositions and Kits

The present invention is also directed to compositions and kits or reagent systems useful for practicing the methods described herein.

The compositions of the invention can be included in kits for massively parallel sequencing mixtures of fetal and maternal nucleic acid molecules e.g. cfDNA, present in a maternal sample e.g. a plasma sample. The kits comprise a composition comprising at least one set of primers for amplifying at least one polymorphic target nucleic acid in said fetal and maternal nucleic acid molecules. Polymorphic target nucleic acids can comprise without limitation single nucleotide polymorphisms (SNPs), tandem SNPs, small-scale multi-base deletions or insertions, called IN-DELS (also called deletion insertion polymorphisms or DIPs), Multi-Nucleotide Polymorphisms (MNPs) Short Tandem Repeats (STRs), restriction fragment length polymorphism (RFLP), or a polymorphism comprising any other change of sequence in a chromosome. Sequencing methods utilizing the compositions of the invention are NGS methods of single nucleic acid molecules or clonally amplified nucleic acid molecules as described herein. The massively parallel sequencing methods of NGS include pyrosequencing, sequencing by synthesis with reversible dye terminators, real-time sequencing, or sequencing by oligonucleotide probe ligation.

In one embodiment, the compositions includes primers for amplifying polymorphic target nucleic acids that each comprise at least one SNP. In one embodiment, the at least one SNP is selected from SNPs rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). Exemplary corresponding sets of primers for amplifying the SNPs are provided as SEQ ID NOs:57-112.

In another embodiment, the composition includes primers for amplifying polymorphic target nucleic acids that each comprise at least one tandem SNP. In one embodiment, the composition includes primers for amplifying tandem SNPs. In one embodiment, the composition includes primers for amplifying the tandem SNPs disclosed herein, and the composition comprises the corresponding exemplary primers of SEQ ID NOS:197-310.

In another embodiment, the composition includes primers for amplifying polymorphic target nucleic acids that each comprise at least one STR. Exemplary STRs include CSF1PO, FGA, TH01, TPOX, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627 and D1GATA113, which can be amplified by the corresponding sets of primers of SEQ ID NOs:113-196.

Kits can contain a reagent combination including the elements required to conduct an assay according to the methods disclosed herein. The reagent system is presented in a commercially packaged form, as a composition or admixture where the compatibility of the reagents will allow, in a test device configuration, or more typically as a test kit, i.e., a packaged combination of one or more containers, devices, or the like holding the necessary reagents, and preferably including written instructions for the performance of assays. The kit of the present invention may be adapted for any configuration of assay and may include compositions for performing any of the various assay formats described herein. Kits for determining fetal fraction comprise compositions including primer sets for amplifying polymorphic nucleic acids present in a maternal sample as described and, where applicable, reagents for purifying cfDNA, are within the scope of the invention. In one embodiment, a kit designed to allow quantification of fetal and maternal polymorphic sequences e.g. STRs and/or SNPs and/or tandem SNPs, in a cfDNA plasma sample, includes at least one set of allele specific oligonucleotides specific for a selected SNP and/or region of tandem repeats. Preferably, the kit includes a plurality of primer sets to amplify a panel of polymorphic sequences. A kit can comprise other reagents and/or information for genotyping or quantifying alleles in a sample (e.g., buffers, nucleotides, instructions). The kits also include a plurality of containers of appropriate buffers and reagents.

The present invention is described in further detail in the following Examples which are not in any way intended to limit the scope of the invention as claimed. The attached Figures are meant to be considered as integral parts of the specification and description of the invention. The following examples are offered to illustrate, but not to limit the claimed invention.

EXPERIMENTAL

Example 1

Determination of Fetal Fraction Using Massively Parallel Sequencing: Sample Processing and cfDNA Extraction Peripheral blood samples were collected from pregnant women in their first or second trimester of pregnancy and who were deemed at risk for fetal aneuploidy. Informed consent was obtained from each participant prior to the blood draw. Blood was collected before amniocentesis or chorionic villus sampling. Karyotype analysis was performed using the chorionic villus or amniocentesis samples to confirm fetal karyotype.

Peripheral blood drawn from each subject was collected in ACD tubes. One tube of blood sample (approximately 6-9 mL/tube) was transferred into one 15-mL low speed centrifuge tube. Blood was centrifuged at 2640 rpm, 4° C. for 10 min using Beckman Allegra 6 R centrifuge and rotor model GA 3.8.

For cell-free plasma extraction, the upper plasma layer was transferred to a 15-ml high speed centrifuge tube and centrifuged at 16000×g, 4° C. for 10 min using Beckman Coulter Avanti J-E centrifuge, and JA-14 rotor. The two centrifugation steps were performed within 72 h after blood collection. Cell-free plasma comprising cfDNA was stored at −80° C. and thawed only once before amplification of plasma cfDNA or for purification of cfDNA.

Purified cell-free DNA (cfDNA) was extracted from cell-free plasma using the QIAamp Blood DNA Mini kit (Qiagen) essentially according to the manufacturer's instruction. One milliliter of buffer AL and 100 μl of Protease solution were added to 1 ml of plasma. The mixture was incubated for 15 minutes at 56° C. One milliliter of 100% ethanol was added to the plasma digest. The resulting mixture was transferred to QIAamp mini columns that were assembled with VacValves and VacConnectors provided in the QIAvac 24 Plus column assembly (Qiagen). Vacuum was applied to the samples, and the cfDNA retained on the column filters was washed under vacuum with 750 µl of buffer AW1, followed by a second wash with 750 µl of buffer AW24. The column was centrifuged at 14,000 RPM for 5 minutes to remove any residual buffer from the filter. The cfDNA was eluted with buffer AE by centrifugation at 14,000 RPM, and the concentration determined using Qubit™ Quantitation Platform (Invitrogen).

Example 2

Determination of Fetal Fraction Using Massively Parallel Sequencing: Preparation of Sequencing Libraries, Sequencing, and Analysis of Sequencing Data
a. Preparation of Sequencing Libraries All sequencing libraries i.e. target, primary and enriched libraries, were prepared from approximately 2 ng of purified cfDNA that was extracted from maternal plasma. Library preparation was performed using reagents of the NEBNext™ DNA Sample Prep DNA Reagent Set 1 (Part No. E6000L; New England Biolabs, Ipswich, MA) for Illumina® as follows. Because cell-free plasma DNA is fragmented in nature, no further fragmentation by nebulization or sonication was done on the plasma DNA samples. The overhangs of approximately 2 ng purified cfDNA fragments contained in 40 µl were converted into phosphorylated blunt ends according to the NEBNext® End Repair Module by incubating in a 1.5 ml microfuge tube the cfDNA with 5 µl 10X phosphorylation buffer, 2 µl deoxynucleotide solution mix (10 mM each dNTP), 1 µl of a 1:5 dilution of DNA Polymerase I, 1 µl T4 DNA Polymerase and 1 µl T4 Polynucleotide Kinase provided in the NEBNext™ DNA Sample Prep DNA Reagent Set 1 for 15 minutes at 20° C. The enzymes were then heat inactivated by incubating the reaction mixture at 75° C. for 5 minutes. The mixture was cooled to 4° C., and dA tailing of the blunt-ended DNA was accomplished using 10 µl of the dA-tailing master mix containing the Klenow fragment (3' to 5' exo minus) (NEBNext™ DNA Sample Prep DNA Reagent Set 1), and incubating for 15 minutes at 37° C. Subsequently, the Klenow fragment was heat inactivated by incubating the reaction mixture at 75° C. for 5 minutes. Following the inactivation of the Klenow fragment, 1 µl of a 1:5 dilution of Illumina Genomic Adaptor Oligo Mix (Part No. 1000521; Illumina Inc., Hayward, CA) was used to ligate the Illumina adaptors (Non-Index Y-Adaptors) to the dA-tailed DNA using 4 µl of the T4 DNA ligase provided in the NEBNext™ DNA Sample Prep DNA Reagent Set 1, by incubating the reaction mixture for 15 minutes at 25° C. The mixture was cooled to 4° C., and the adaptor-ligated cfDNA was purified from unligated adaptors, adaptor dimers, and other reagents using magnetic beads provided in the Agencourt AMPure XP PCR purification system (Part No. A63881; Beckman Coulter Genomics, Danvers, MA). Eighteen cycles of PCR were performed to selectively enrich adaptor-ligated cfDNA using Phusion® High-Fidelity Master Mix (Finnzymes, Woburn, MA) and Illumina's PCR primers complementary to the adaptors (Part No. 1000537 and 1000537). The adaptor-ligated DNA was subjected to PCR (98° C. for 30 seconds; 18 cycles of 98° C. for 10 seconds, 65° C. for 30 seconds, and 72° C. for 30 seconds; final extension at 72° C. for 5 minutes, and hold at 4° C.) using Illumina Genomic PCR Primers (Part Nos. 100537 and 1000538) and the Phusion HF PCR Master Mix provided in the NEBNext™ DNA Sample Prep DNA Reagent Set 1, according to the manufacturer's instructions. The amplified product was purified using the Agencourt AMPure XP PCR purification system (Agencourt Bioscience Corporation, Beverly, MA) according to the manufacturer's instructions available via the World Wide Web at beckmangenomics.com/products/AMPureXPProtocol_000387v001.pdf. The purified amplified product was eluted in 40 µl of Qiagen EB Buffer, and the concentration and size distribution of the amplified libraries was analyzed using the Agilent DNA 1000 Kit for the 2100 Bioanalyzer (Agilent technologies Inc., Santa Clara, CA).
b. Sequencing Sequencing of library DNA was performed using the Genome Analyzer II (Illumina Inc., San Diego, CA, USA) according to standard manufacturer protocols. Copies of the protocol for whole genome sequencing using Illumina/Solexa technology may be found at BioTechniques® Protocol Guide 2007 Published December 2006: p 29, and on the world wide web at biotechniques.com/default.asp?page=protocol&subsection=article_display&id=112378.
The DNA library was diluted to 1 nM and denatured. Library DNA (5 pM) was subjected to cluster amplification according to the procedure described in Illumina's Cluster Station User Guide and Cluster Station Operations Guide, available on the world wide web at illumina.com/systems/genomeanalyzer/cluster_station.ilmn. The amplified DNA was sequenced using Illumina's Genome Analyzer II to obtain single-end reads of 36 bp. Only about 30 bp of random sequence information are needed to identify a sequence as belonging to a specific human chromosome. Longer sequences can uniquely identify more particular targets. In the present case, a large number of 36 bp reads were obtained, covering approximately 10% of the genome.
c. Analysis of Sequencing Data for the Determination of Fetal Fraction Upon completion of sequencing of the sample, the Illumina "Sequencer Control Software" transferred image and base call files to a Unix server running the Illumina "Genome Analyzer Pipeline" software version 1.51. the 36 bp reads were aligned to an artificial reference genome e.g. a SNP genome, using the BOWTIE program. The artificial reference genome was identified as the grouping of the polymorphic DNA sequences that encompass the alleles comprised in the polymorphic target sequences. For example, the artificial reference genome is a SNP genome comprising SEQ ID NOs: 1-56. Only reads that mapped uniquely to the artificial genome were used for the analysis of fetal fraction. Reads that matched perfectly to the SNP genome were counted as tags and filtered. Of the remaining reads, only reads having one or two mismatches were counted as tags and included in the analysis. Tags mapped to each of the polymorphic alleles were counted, and the fetal fraction was determined as a percent of the ratio of the number of tags mapped to the major allele i.e. maternal allele, and the number of tags mapped to the minor allele i.e. fetal allele.

Example 3

Selection of Autosomal SNPs for the Determination of Fetal Fraction

A set of 28 autosomal SNPs were selected from a list of 92 SNPs (Pakstis et al., Hum Genet 127:315-324 [2010]) and from Applied Biosystems by Life Technologies™ (Carlsbad, CA) at world wide web address appliedbiosystems.com, and validated for use in multiplexed PCR amplification. Primers were designed to hybridize to a sequence close to the SNPs site on the cfDNA to ensure that it be included in the 36 bp read generated from the massively parallel sequencing on the Illumina Analyzer GII, and to generate amplicons of sufficient length to undergo bridge-amplification during cluster formation. Thus, primers were designed to generate amplicons that were at least 110 bp, which when combined with the universal adaptors (Illumina Inc., San Diego, CA) used for cluster amplification, resulted in DNA molecules of at least 200 bp. Primer sequences were identified, and primer sets i.e. forward and reverse primers, were synthesized by Integrated DNA Technologies (San Diego, CA), and stored as a 1 µM solution to be used for amplifying polymorphic target sequences as described in Examples 4-7. Table 1 provides the RefSNP (rs) accession ID numbers, the primers used for amplifying the target cfDNA sequence, and the sequences of the amplicons comprising the possible SNP alleles that would be generated using the primers. The SNPs given in Table 1 were used for the simultaneous amplification of 13 target sequences in a multiplexed assay. The panel provided in Table 1 is an exemplary SNP panel. Fewer or more SNPs can be employed to enrich the fetal and maternal DNA for polymorphic target nucleic acids. Additional SNPs that can be used include the SNPs given in Table 2. The SNP alleles are shown in bold and are underlined. Other additional SNPs that can be used to determine fetal fraction according to the present method include rs315791, rs3780962, rs1410059, rs279844, rs38882, rs9951171 (SEQ ID NOS 29 & 30), rs214955, rs6444724, rs2503107, rs1019029, rs1413212, rs1031825, rs891700, rs1005533, rs2831700, rs354439, rs1979255, rs1454361, rs8037429, and rs1490413, which have been analyzed for determining fetal fraction by TaqMan PCR, and are disclosed in U.S. Provisional applications 61/296,358 and 61/360,837.

TABLE 1

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
| --- | --- | --- | --- | --- | --- |
| rs560681 | 1 | CACATGCACAGCCAGCAACCCTGTCAGCAGGAGTTCCCACCAGTTTCTTTCTGAGAACATCTGTTCAGGTTTCTCTCCATCTCTATTTACTCAGGTCACAGGACCTTGGGG (SEQ ID NO: 1) | CACATGCACAGCCAGCAACCCTGTCAGCAGGAGTTCCCACCAGTTTCTTTCTGAGAACATCTGTTCAGGTTTCTCTCCATCTCTGTTTACTCAGGTCACAGGACCTTGGGG (SEQ ID NO: 2) | CACATGCACAGCCAGCAACCC (rs560681_C1_1_F; SEQ ID NO: 57) | CCCCAAGGTCCTGTGACCTGAGT (rs560681_C1_1_R; SEQ ID NO: 58) |
| rs1109037 | 2 | TGAGGAAGTGAGGCTCAGAGGGTAAGAAACTTTGTCACAGAGCTGGTGGTGAGGGTGGAGATTTTACACTCCCTGCCTCCCACACCAGTTTCTCCAGAGTGGAAAGACTTTTCATCTCGCACTGGCA (SEQ ID NO: 3) | TGAGGAAGTGAGGCTCAGAGGGTAAGAAACTTTGTCACAGAGCTGGTGGTGAGGGTGGAGATTTTACACTCCCTGCCTCCCACACCAGTTTCTCCGGAGTGGAAAGACTTTTCATCTCGCACTGGCA (SEQ ID NO: 4) | TGAGGAAGTGAGGCTCAGAGGGT (rs110937_C2_1_F; SEQ ID NO: 59) | TGCCAGTGCGAGATGAAAGTCTTT (rs110937_C2_1_R; SEQ ID NO: 60) |
| rs9866013 | 3 | GTGCCTTCAGAACCTTTGAGATCTGATTCTATTTTTAAAGCTTCTTAGAAGAGAGATTGCAAAGTGGGTTGTTTCTCTAGCCAGACAGGGCAGGCAAATAGGGGTGGCTGGTGGGATGGGA (SEQ ID NO: 5) | GTGCCTTCAGAACCTTTGAGATCTGATTCTATTTTTAAAGCTTCTTAGAAGAGAGATTGCAAAGTGGGTTGTTTCTCTAGCCAGACAGGGCAGGTAAATAGGGGTGGCTGGTGGGATGGGA (SEQ ID NO: 6) | GTGCCTTCAGAACCTTTGAGATCTGAT (rs9866013_C3_1_F; SEQ ID NO: 61) | TCCCATCCCACCAGCCACCC (rs9866013_C3_1_R; SEQ ID NO: 62) |
| rs13182883 | 5 | AGGTGTGTCTCTCTTTTGTGAGGGGAGGGGTCCCTTCTGGCCTAGTAGAGGGCCTGGCCTGCAGTGAGCATTCAAATCCTCAAGGAACAGGGTGGGGAGGTGGGACAAAGG (SEQ ID NO: 7) | AGGTGTGTCTCTCTTTTGTGAGGGGAGGGGTCCCTTCTGGCCTAGTAGAGGGCCTGGCCTGCAGTGAGCATTCAAATCCTCGAGGAACAGGGTGGGGAGGTGGGACAAAGG (SEQ ID NO: 8) | AGGTGTGTCTCTCTTTTGTGAGGGG (rs13182883_C5_1_F; SEQ ID NO:63) | CCTTTGTCCCACCTCCCCACC (rs13182883_C5_1_R; SEQ ID NO: 64) |
| rs13218440 | 6 | CCTCGCCTACTGTGCTGTTTCTAACCATCATGCTTTTCCCTGAATCTCTTGAGTCTTTTTCTGCTGTGGACTGAAACTTGATCCTGAGATTCACCTCTAGTCCCTCTGAGCAGCCTCCTGGATACTCAGCTGGGATGG (SEQ ID NO: 9) | CCTCGCCTACTGTGCTGTTTCTAACCATCATGCTTTTCCCTGAATCTCTTGAGTCTTTTTCTGCTGTGGACTGAAACTTGATCCTGAGATTCACCTCTAGTCCCTCTGGGCAGCCTCCTGGATACTCAGCTGGGATGG (SEQ ID NO: 10) | CCTCGCCTACTGTGCTGTTTCTAACC (rs13218440_C6_1_F; SEQ ID NO: 65) | CCATCCCAGCTGAGTATTCCAGGAG (rs13218440_C6_1_R; SEQ ID NO: 66) |

TABLE 1-continued

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| rs7041158 | 9 | AATTGCAATGGTGAGAGGTTGATGGTAAAATCAAACGGAACTTGTTATTTTGTCATTCTGATGGACTGGAACTGAGGATTTTCAATTTCCTCTCCAACCCAAGACACTTCTCACTGG (SEQ ID NO: 11) | AATTGCAATGGTGAGAGGTTGATGGTAAAATCAAACGGAACTTGTTATTTTGTCATTCTGATGGACTGGAACTGAGGATTTTCAATTTCCTTTCCAACCCAAGACACTTCTCACTGG (SEQ ID NO: 12) | AATTGCAATGGTGAGAGGTTGATGGT (SEQ ID NO: 67) | CCAGTGAGAAGTGTCTTGGGTTGG (SEQ ID NO: 68) |
| rs740598 | 10 | GAAATGCCTTCTCAGGTAATGAAGGTTATCCAAATATTTTTCGTAAGTATTTCAAATAGCAATGGCTCGTCTATGGTTAGTCTCACAGCCACATTCTCAGAACTGCTCAAACC (SEQ ID NO: 13) | GAAATGCCTTCTCAGGTAATGAAGGTTATCCAAATATTTTTCGTAAGTATTTCAAATAGCAATGGCTCGTCTATGGTTAGTCTCGCAGCCACATTCTCAGAACTGCTCAAACC (SEQ ID NO: 14) | GAAATGCCTTCTCAGGTAATGAAGGT (SEQ ID NO: 69) | GGTTTGAGCAGTTCTGAGAATGTGGCT (SEQ ID NO: 70) |
| rs10773760 | 12 | ACCCAAAACACTGGAGGGGCCTCTTCTCATTTTCGGTAGACTGCAAGTGTTAGCCGTCGGGACCAGCTTCTGTCTGGAAGTTCGTCAAATTGCAGTTAAGTCCAAGTATGCCACATAGCAGATAAGGG (SEQ ID NO: 15) | ACCCAAAACACTGGAGGGGCCTCTTCTCATTTTCGGTAGACTGCAAGTGTTAGCCGTCGGGACCAGCTTCTGTCTGGAAGTTCGTCAAATTGCAGTTAGGTCCAAGTATGCCACATAGCAGATAAGGG (SEQ ID NO: 16) | ACCCAAAACACTGGAGGGGCCT (SEQ ID NO: 71) | CCCTTATCTGCTATGTGGCATACTTGG (SEQ ID NO: 72) |
| rs4530059 | 14 | GCACCAGAATTTAAACAACGCTGACAATAAATATGCAGTCGATGATGACTTCCCAGAGCTCCAGAAGCAACTCCAGCACACAGAGAGGCGCTGATGTGCCTGTCAGGTGC (SEQ ID NO: 17) | GCACCAGAATTTAAACAACGCTGACAATAAATATGCAGTCGATGATGACTTCCCAGAGCTCCAGAAGCAACTCCAGCACACCGAGAGGCGCTGATGTGCCTGTCAGGTGC (SEQ ID NO: 18) | GCACCAGAATTTAAACAACGCTGACAA (SEQ ID NO: 73) | GCACCTGACAGGCACATCAGCG (SEQ ID NO: 74) |
| rs7205345 | 16 | TGACTGTATACCCCAGGTGCACCCTTGGGTCATCTCTATCATAGAACTTATCTCACAGAGTATAAGAGCTGATTTCTGTGTCTGCCTCTCACACTAGACTTCCACATCCTTAGTGC (SEQ ID NO: 19) | TGACTGTATACCCCAGGTGCACCCTTGGGTCATCTCTATCATAGAACTTATCTCACAGAGTATAAGAGCTGATTTCTGTGTCTGCCTGTCACACTAGACTTCCACATCCTTAGTGC (SEQ ID NO: 20) | TGACTGTATACCCCAGGTGCACCC (SEQ ID NO: 75) | GCACTAAGGATGTGGAAGTCTAGTGTG (SEQ ID NO: 76) |
| rs8078417 | 17 | TGTACGTGGTCACCAGGGGACGCCTGGCGCTGCGAGGGAGGCCCCGAGCCTCGTGCCCCCGTGAAGCTTCAGCTCCCCTCCCCGGCTGTCCTTGAGGCTCTTCTCACACT (SEQ ID NO: 21) | TGTACGTGGTCACCAGGGGACGCCTGGCGCTGCGAGGGAGGCCCCGAGCCTCGTGCCCCCGTGAAGCTTCAGCTCCCCTCCCTGGCTGTCCTTGAGGCTCTTCTCACACT (SEQ ID NO: 22) | TGTACGTGGTCACCAGGGGACG (SEQ ID NO: 77) | AGTGTGAGAAGAGCCTCAAGGACAGC (SEQ ID NO: 78) |
| rs576261 | 19 | CAGTGGACCCTGCTGCACCTTTCCTCCCCTCCCATCAACCTCTTTTGTGCCTCCCCCTCCGTGTACCACCTTCTCTGTCACCAACCCTGGCCTCACAACTCTCTCCTTTGCCAC (SEQ ID NO: 23) | CAGTGGACCCTGCTGCACCTTTCCTCCCCTCCCATCAACCTCTTTTGTGCCTCCCCCTCCGTGTACCACCTTCTCTGTCACCACCCTGGCCTCACAACTCTCTCCTTTGCCAC (SEQ ID NO: 24) | CAGTGGACCCTGCTGCACCTT (SEQ ID NO: 79) | GTGGCAAAGGAGAGAGTTGTGAGG (SEQ ID NO: 80) |

TABLE 1-continued

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| rs2567608 | 20 | CAGTGGCATAGTAGTCCAGGGGCTCCTCCTCAGCACCTCCAGCACCTTCCAGGAGGCAGCAGCGCAGGCAGAGAACCCGCTGGAAGAATCGGCGGAAGTTGTCGGAGAGG (SEQ ID NO: 25) | CAGTGGCATAGTAGTCCAGGGGCTCCTCCTCAGCACCTCCAGCACCTTCCAGGAGGCAGCAGCGCAGGCAGAGAACCCGCTGGAAGGATCGGCGGAAGTTGTCGGAGAGG (SEQ ID NO: 26) | CAGTGGCATAGTAGTCCAGGGGCT (SEQ ID NO: 81) | CCTCTCCGACAACTTCCGCCG (SEQ ID NO: 82) |

TABLE 2

Additional SNPs for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| rs430046 | 16 | AGGTCTGGGGGCCGCTGAATGCCAAGCTGGGAATCTTAAATGTTAAGGAACAAGGTCATACAATGAATGGTGTGATGTAAAAGCTTGGGAGGTGATTTCTGAGGGTAGGTGCTGGGTTTAATGGGAGGA (SEQ ID NO: 27) | AGGTCTGGGGGCCGCTGAATGCCAAGCTGGGAATCTTAAATGTTAAGGAACAAGGTCATACAATGAATGGTGTGATGTAAAAGCTTGGGAGGTGATTTTTGAGGGTAGGTGCTGGGTTTAATGGGAGGA (SEQ ID NO: 28) | AGGTCTGGGGCCGCTGAAT (rs430046_C1_1_F; SEQ ID NO: 83) | TCCTCCCATTAAACCCAGCACCT (rs430046_C1_1_R; SEQ ID NO: 84) |
| rs9951171 | 18 | ACGGTTCTGTCCTGTAGGGGAGAAAAGTCCTCGTTGTTCCTCTGGGATGCAACATGAGAGAGCAGCACACTGAGGCTTTATGGATTGCCCTGCCACAAGTGAACAGG (SEQ ID NO: 29) | ACGGTTCTGTCCTGTAGGGGAGAAAAGTCCTCGTTGTTCCTCTGGGATGCAACATGAGAGAGCAGCACACTGAGGCTTTATGGGTTGCCCTGCCACAAGTGAACAGG (SEQ ID NO: 30) | ACGGTTCTGTCCTGTAGGGGAGA (rs9951171_C1_1_F; SEQ ID NO: 85) | CCTGTTCACTTGTGGCAGGGCA (rs9951171_C1_1_R; SEQ ID NO: 86) |
| rs338882 | 5 | GCGCAGTCAGATGGGCGTGCTGGCGTCTGTCTTCTCTCTCTCCTGCTCTCTGGCTTCATTTTTCTCTCCTTCTGTCTCACCTTCTTTCGTGTGCCTGTGCACACACACGTTTGGGACAAGGGCTGGA (SEQ ID NO: 31) | GCGCAGTCAGATGGGCGTGCTGGCGTCTGTCTTCTCTCTCCTGCTCTCTGGCTTCATTTTTCTCTCCTTCTGTCTCACCTTCTTTCGTGTGCCTGTGCATACACACGTTTGGGACAAGGGCTGGA (SEQ ID NO: 32) | GCGCAGTCAGATGGGCGTGC (rs338882_C1_1_F; SEQ ID NO: 87) | TCCAGCCCTTGTCCCAAACGTGT (rs338882_C1_1_R; SEQ ID NO: 88) |
| rs10776839 | 9 | GCCGGACCTGCGAAATCCCAAATGCCAAACATTCCCGCCTCACATGATCCCAGAGAGAGGGGACCCAGTGTTCCCAGCTTGCAGCTGAGGAGCCCGAGGTTGCCGTCAGATCAGAGCCCCAGTTGCCCG (SEQ ID NO: 33) | GCCGGACCTGCGAAATCCCAAAATGCCAAACATTCCCGCCTCACATGATCCCAGAGAGAGGGGACCCAGTGTTCCCAGCTTGCAGCTGAGGAGCCCGAGTTTGCCGTCAGATCAGAGCCCCAGTTGCCCG (SEQ ID NO: 34) | GCCGGACCTGCGAAAT CCCAA (rs10776839C1_1_F; SEQ ID NO: 89) | CGGGCAACTGGGGCTCTGATC (rs10776839_C1_1_R; SEQ ID NO: 90) |

TABLE 2-continued

Additional SNPs for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| rs9905977 | 17 | AGCAGCCTCCCTCGACTAGCTCACACTACGATAAGGAAAATTCATGAGCTGGTGTCCAAGGAGGGCTGGGTGACTCGTGGCTCAGTCAGCATCAAGATTCCTTTCGTCTTTCCCCTCTGCC (SEQ ID NO: 35) | AGCAGCCTCCCTCGACTAGCTCACACTACGATAAGGAAAATTCATGAGCTGGTGTCCAAGGAGGGCTGGGTGACTCGTGGCTCAGTCAGCGTCAAGATTCCTTTCGTCTTTCCCCTCTGCC (SEQ ID NO: 36) | AGCAGCCTCCCTCGACTAGCT (rs9905977_C1_1_F; SEQ ID NO: 91) | GGCAGAGGGGAAAGACGAAAGGA (rs9905977_C1_1_R; SEQ ID NO: 92) |
| rs1277284 | 4 | TGGCATTGCCTGTAATATACATAGCCATGGTTTTTTATAGGCAATTTAAGATGAATAGCTTCTAAACTATAGATAAGTTTCATTACCCCAGGAAGCTGAACTATAGCTACTTTACCCAAAATCATTAGAATGGTGCTT (SEQ ID NO: 37) | TGGCATTGCCTGTAATATACATAGCCATGGTTTTTTATAGGCAATTTAAGATGAATAGCTTCTAAACTATAGATAAGTTTCATTACCCCAGGAAGCTGAACTATAGCTACTTTCCCCAAAATCATTAGAATGGTGCTT (SEQ ID NO: 38) | TGGCATTGCCTGTAATATACATAG (rs1277284_C4_1_F; SEQ ID NO: 93) | AAGCACCATTCTAATGATTTG (rs1277284_C4_1_R; SEQ ID NO: 94) |
| rs258684 | 7 | ATGAAGCCTTCCACCAACTGCCTGTATGACTCATCTGGGGACTTCTGCTCTATACTCAAAGTGGCTTAGTCACTGCCAATGTATTTCCATATGAGGGACGATGATTACTAAGGAAATATAGAAACAACAACTGATC (SEQ ID NO: 39) | ATGAAGCCTTCCACCAACTGCCTGTATGACTCATCTGGGGACTTCTGCTCTATACTCAAAGTGGCTTAGTCACTGCCAATGTATTTCCATATGAGGGACGGTGATTACTAAGGAAATATAGAAACAACAACTGATC (SEQ ID NO: 40) | ATGAAGCCTTCCACCAACTG (rs258684_C7_1_F; SEQ ID NO: 95) | GATCAGTTGTTGTTTCTATATTCCTT (rs258684_C7_1_R; SEQ ID NO: 96) |
| rs1347696 | 8 | ACAACAGAATCAGGTGATTGGAGAAAAGATCACAGGCCTAGGCACCCAAGGCTTGAAGGATGAAAGAATGAAAGATGGACGGAACAAAATTAGGACCTTAATTCTTTGTTCAGTTCAG (SEQ ID NO: 41) | ACAACAGAATCAGGTGATTGGAGAAAAGATCACAGGCCTAGGCACCCAAGGCTTGAAGGATGAAAGAATGAAAGATGGACGGAAGAAAATTAGGACCTTAATTCTTTGTTCAGTTCAG (SEQ ID NO: 42) | ACAACAGAATCAGGTGATTGGA (rs1347696_C8_4_F; SEQ ID NO: 97) | CTGAACTGAACAAAGAATTAAGGTC (rs1347696_C8_4_F; SEQ ID NO: 98) |
| rs508485 | 11 | TTGGGGTAAATTTTCATTGTCATATGTGGAATTTAAATATACCATCATCTACAAAGAATTCCACAGAGTTAAATATCTTAAGTTAAACACTTAAAATAAGTGTTTAGTGTTTGCGTGATATTTTGATGACAGATAAACAGAGTCTAATTCCCACCCC (SEQ ID NO: 43) | TTGGGGTAAATTTTCATTGTCATATGTGGAATTTAAATATACCATCATCTACAAAGAATTCCACAGAGTTAAATATCTTAAGTTAAACACTTAAAATAAGTGTTTAGTGTTTGCGTGATATTTTGATGATAGATAAACAGAGTCTAATTCCCACCCC (SEQ ID NO: 44) | TTGGGGTAAATTTTCATTGTCA (rs508485_C1_1_F; SEQ ID NO: 99) | GGGGTGGGAATTAGACTCTG (rs508485_C11_1_R; SEQ ID NO 100) |
| rs9788670 | 15 | TGCAATTCAAATCAGGAAGTATGACCAAAAGACAGAGATCTTTTTTGGATGATCCCTAGCCTAGCAATGCCTGGCAGCCATGCAGGTGCAATGTCAACCTTAAATAATGTATTGCAAACTCAGAGCTGACAAACCTCGATGTTGC (SEQ ID NO: 45) | TGCAATTCAAATCAGGAAGTATGACCAAAAGACAGAGATCTTTTTGGATGATCCCTAGCCTAGCAATGCCTGGCAGCCATGCAGGTGCAATGTCAACCTTAAATAATGTATTGCAAATTCAGAGCTGACAAACCTCGATGTTGC (SEQ ID NO: 46) | TGCAATTCAAATCAGGAAGTATG (rs9788670_c15_2_F; SEQ ID NO: 101) | GCAACATCGAGGTTTGTCAG (rs9788670_c15_2_R; SEQ ID NO: 102) |

TABLE 2-continued

Additional SNPs for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| rs8137254 | 22 | CTGTGCTCTGCGAATAGCTGCAGAAGTAACTTGGGGACCCAAATAAAGCAGAATGCTAATGTCAAGTCCTGAGAACCAAGCCCTGGGACTCTGGTGCCATTTCGGATTCCATGAGCATGGT (SEQ ID NO: 47) | CTGTGCTCTGCGAATAGCTGCAGAAGTAACTTGGGGACCCAAAATAAAGCAGAATGCTAATGTCAAGTCCTGAGAACCAAGCCCTGGGACTCTGGTGCCATTTTGGATTCTCCATGAGCATGGT (SEQ ID NO: 48) | CTGTGCTCTGCGAATAGCTG (rs8137254_c22_2_F: SEQ ID NO: 103) | ACCATGCTCATGGAGAATCC (rs8137254_c22_2_R; SEQ ID NO: 104) |
| rs3143 | 19 | TTTTTCCAGCCAACTCAAGGCCAAAAAAAATTTCTTAATATAGTTATTATGCGAGGGGAGGGAAGCAAAGGAGCACAGGTAGTCCACAGAATAAGACACAAGAAACCTCAAGCTGTG (SEQ ID NO: 49) | TTTTTCCAGCCAACTCAAGGCCAAAAAAAATTTCTTAATATAGTTATTATGCGAGGGGAGGGAAGCAAAGGAGCACAGGTAGTCCACAGAATAGGACACAAGAAACCTTCAAGCTGTG (SEQ ID NO: 50) | TTTTTCCAGCCAACTCAAGG (rs3143_c19_2_F: SEQ ID NO: 105) | CACAGCTTGAGGTTTCTTGTG (rs3143_c19_2_R; SEQ ID NO: 106) |
| rs2182957 | 13 | TCTTCTCGTCCCCTAAGCAAACAACATCCGCTTGCTTCTGTCTGTGTAACCACAGTGAATGGGTGTGCACGCTTGATGGGCCTCTGAGCCCCTGTTGCACAAACCAGAAA (SEQ ID NO: 51) | TCTTCTCGTCCCCTAAGCAAACAACATCCGCTTGCTTCTGTCTGTGTAACCACAGTGAATGGGTGTGCACGCTTGGTGGGCCTCTGAGCCCTGTTGCACAAACCAGAAA (SEQ ID NO: 52) | TCTTCTCGTCCCCTAAGCAA (rs2182957_c13_1_F: SEQ ID NO: 107) | TTTCTGGTTTGTGCAACAGG (rs2182957_c13_1_R; SEQ ID NO: 108) |
| rs3739005 | 2 | CACATGGGGCATTAAGAATCGCCCAGGGAGGAGGAGGGAGAACGCGTGCTTTTCACATTTGCATTTGAATTTTCGAGTTCCAGGATGTGTTTTTGTGCTCATCGATGT (SEQ ID NO: 53) | CACATGGGGCATTAAGAATCGCCCAGGGAGGAGGGGAGAACGCGTGCTTTTCACATTTGCATTTGAATTTTTGAGTTCCCAGGATGTGTGT (SEQ ID NO: 54) | CACATGGGGCATTAAGAAT (rs3739005_c2_2_F; SEQ ID NO: 109) | ACATCGATGAGCACAAAAACAC (rs3739005_c2_2_R; SEQ ID NO: 110) |
| rs530022 | 1 | GGGCTCTGAGGTGTGTGAAATAAAAACAAATGTCCATGTCTGTCCTTTTATGGCATTTTGGGACTTTACATTTCAAACATTTCAGACATGTATCACAACACGAAGGAATAACAGTTCCAGGGATATCT (SEQ ID NO: 55) | GGGCTCTGAGGTGTGTGAAATAAAAACAAATGTCCATGTCTGTCCTTTATGGCATTTTGGGACTTTACATTTCAAACATTTCAGACATGTATCACAACACGAGGGAATAACAGTTCCAGGGATATCT (SEQ ID NO: 56) | GGGCTCTGAGGTGTGTGAAA (rs530022_c1_2_F; SEQ ID NO: 111) | AGATATCCCTGAACTGTTATTCC (rs530022_c1_2_R; SEQ ID NO: 112) |

Example 4

Determination of Fetal Fraction by Massively Parallel Sequencing of a Target Library To determine the fraction of fetal cfDNA in a maternal sample, target polymorphic nucleic acid sequences each comprising a SNP were amplified and used for preparing a target library for sequencing in a massively parallel fashion.

cfDNA was extracted as described in Example 1. A target sequencing library was prepared as follows. cfDNA contained in 5 μl of purified cfDNA was amplified in a reaction volume of 50 μl containing 7.5 μl of a 1 μM primer mix (Table 1), 10 μl of NEB 5× Mastermix and 27 μl water. Thermal cycling was performed with the Gene Amp9700 (Applied Biosystems) using the following cycling conditions: incubating at 95° C. for 1 minute, followed by 20-30 cycles at 95° C. for 20 seconds, 68° C. for 1 minute, and 68° C. for 30s, which was followed by a final incubation at 68° C. for 5 minutes. A final hold at 4° C. was added until the samples were removed for combining with the unamplified portion of the purified cfDNA sample. The amplified product was purified using the Agencourt AMPure XP PCR purification system (Part No. A63881; Beckman Coulter Genomics, Danvers, MA). A final hold at 4° C. was added until the samples were removed for preparing the target library. The amplified product was analyzed with a 2100 Bioanalyzer (Agilent Technologies, Sunnyvale, CA), and the concentration of amplified product determined. A sequencing library of amplified target nucleic acids was prepared as described in Example 2, and was sequenced in a massively parallel fashion using sequencing-by-synthesis with reversible dye terminators and according to the Illumina protocol (BioTechniques® Protocol Guide 2007 Published December 2006: p 29, and on the world wide web at biotechniques.com/default.asp?page=protocol&subsection=article_display& id=112378). Analysis and counting of tags mapped to a reference genome consisting of 26 sequences (13 pairs each representing two alleles) comprising a SNP i.e. SEQ ID NO:1-26 was performed as described.

Table 3 provides the tag counts obtained from sequencing the target library, and the calculated fetal fraction derived from sequencing data.

TABLE 3

Determination of Fetal Fraction by Massively Parallel Sequencing of a Library of Polymorphic Nucleic Acids

| SNP | SNP TAG COUNTS | Fetal Fraction (%) |
|---|---|---|
| rs10773760.1\|Chr.12\|length = 128\|allele = A | 236590 | 1.98 |
| rs10773760.2\|Chr.12\|length = 128\|allele = G | 4680 | |
| rs13182883.1\|Chr.5\|length = 111\|allele = A | 3607 | 4.99 |
| rs13182883.2\|Chr.5\|length = 111\|allele = G | 72347 | |
| rs4530059.1\|Chr.14\|length = 110\|allele = A | 3698 | 1.54 |
| rs4530059.1\|Chr.14\|length = 110\|allele = G | 239801 | |
| rs8078417.1\|Chr.17\|length = 110\|allele = C | 1E+06 | 3.66 |
| rs8078417.2\|Chr.17\|length = 110\|allele = T | 50565 | |

Fetal Fraction (Mean ± S.D.) = 12.4 ± 6.6

The results show that polymorphic nucleic acid sequences each comprising at least one SNP can be amplified from cfDNA derived from a maternal plasma sample to construct a library that can be sequenced in a massively parallel fashion to determine the fraction of fetal nucleic acids in the maternal sample.

Example 5

Determination of Fetal Fraction Following Enrichment of Fetal and Maternal Nucleic Acids in a cfDNA Sequencing Library Sample To enrich the fetal and maternal cfDNA contained in a primary sequencing library constructed using purified fetal and maternal cfDNA, a portion of a purified cfDNA sample was used for amplifying polymorphic target nucleic acid sequences, and for preparing a sequencing library of amplified polymorphic target nucleic acids, which was used to enrich the fetal and maternal nucleic acid sequences comprised in the primary library.

The method corresponds to workflow 3 diagrammed in FIG. 3. A target sequencing library was prepared from a portion of the purified cfDNA as described in Example 2. A primary sequencing library was prepared using the remaining portion of the purified cfDNA as described in Example 2. Enrichment of the primary library for the amplified polymorphic nucleic acids comprised in the target library was obtained by diluting the primary and the target sequencing libraries to 10 nM, and combining the target library with the primary library at a ratio of 1:9 to provide an enriched sequencing library. Sequencing of the enriched library and analysis of the sequencing data was performed as described in Example 2.

Table 4 provides the number of sequence tags that mapped to the SNP genome for the informative SNPs identified from sequencing an enriched library derived from plasma samples of pregnant women each carrying a T21, a T13, a T18 and a monosomy X fetus, respectively. Fetal fraction was calculated as follows:

% fetal fraction allele$_x$=(($\Sigma$Fetal sequence tags for allele$_x$)/($\Sigma$Maternal sequence tags for allele$_x$))×100

Table 4 also provides the number of the sequence tags mapped to the human reference genome. Tags mapped to the human reference genome were used to determine the presence or absence of aneuploidy using the same plasma sample that was utilized for determining the corresponding fetal fraction. Method for using sequence tags counts for determining aneuploidy are described in U.S. Provisional Applications 61/407,017 and 61/455,849778, which are herein incorporated by reference in their entirety.

TABLE 4

Determination of Fetal Fraction by Massively Parallel Sequencing of an Enriched Library of Polymorphic Nucleic Acids

| Sample ID (karyotype) | SNP | SNP TAG COUNTS | FETAL FRACTION (%) |
|---|---|---|---|
| 11409 (47, XY + 21) | rs13182883.1\|Chr.5\|length = 111\|allele = A | 261 | 4.41 |
| | rs13182883.2\|Chr.5\|length = 111\|allele = G | 5918 | |
| | rs740598.1\|Chr.10\|length = 114\|allele = A | 5545 | 7.30 |
| | rs740598.2\|Chr.10\|length = 114\|allele = G | 405 | |
| | rs8078417.1\|Chr.17\|length = 110\|allele = C | 8189 | 6.74 |
| | rs8078417.2\|Chr.17\|length = 110\|allele = T | 121470 | |
| | rs576261.1\|Chr.19\|length = 114\|allele = A | 58342 | 7.62 |
| | rs576261.2\|Chr.19\|length = 114\|allele = C | 4443 | |
| 95133 (47, XX + 18) | rs1109037.1\|Chr.2\|length = 126\|allele = A | 12229 | 2.15 |
| | rs1109037.2\|Chr.2\|length = 126\|allele = G | 263 | |
| | rs13218440.1\|Chr.6\|length = 139\|allele = A | 55949 | 3.09 |
| | rs13218440.2\|Chr.6\|length = 139\|allele = G | 1729 | |
| | rs7041158.1\|Chr.9\|length = 117\|allele = C | 7281 | 4.12 |
| | rs7041158.2\|Chr.9\|length = 117\|allele = T | 300 | |
| | rs7205345.1\|Chr.16\|length = 116\|allele = C | 53999 | 2.14 |
| | rs7205345.2\|Chr.16\|length = 116\|allele = G | 1154 | |

TABLE 4-continued

Determination of Fetal Fraction by Massively Parallel Sequencing
of an Enriched Library of Polymorphic Nucleic Acids

| Sample ID (karyotype) | SNP | SNP TAG COUNTS | FETAL FRACTION (%) |
|---|---|---|---|
| 51236 | rs13218440.1\|Chr.6\|length = 139\|allele = A | 1119 | 1.65 |
| (46, XY + 13) | rs13218440.2\|Chr.6\|length = 139\|allele = G | 67756 | |
| | rs560681.1\|Chr.1\|length = 111\|allele = A | 14123 | 5.18 |
| | rs560681.2\|Chr.1\|length = 111\|allele = G | 732 | |
| | rs7205345.1\|Chr.16\|length = 116\|allele = C | 18176 | 1.63 |
| | rs7205345.2\|Chr.16\|length = 116\|allele = G | 296 | |
| | rs9866013.1\|Chr.3\|length = 121\|allele = C | 117 | 2.33 |
| | rs9866013.2\|Chr.3\|length = 121\|allele = T | 5024 | |
| 54430 | rs1109037.1\|Chr.2\|length = 126\|allele = A | 19841 | 1.80 |
| (45, XO) | rs1109037.2\|Chr.2\|length = 126\|allele = G | 357 | |
| | rs9866013.1\|Chr.3\|length = 121\|allele = C | 12931 | 3.81 |
| | rs9866013.2\|Chr.3\|length = 121\|allele = T | 493 | |
| | rs7041158.1\|Chr.9\|length = 117\|allele = C | 2800 | 4.25 |
| | rs7041158.2\|Chr.9\|length = 117\|allele = T | 119 | |
| | rs740598.1\|Chr.10\|length = 114\|allele = A | 12903 | 4.87 |
| | rs740598.2\|Chr.10\|length = 114\|allele = G | 628 | |
| | rs10773760.1\|Chr.12\|length = 128\|allele = A | 46324 | 4.65 |
| | rs10773760.2\|Chr.12\|length = 128\|allele = G | 2154 | |

Fetal Fraction (Mean ± S.D.) = 6.5 ± 1.5
Fetal Fraction (Mean ± S.D.) = 2.9 ± 0.9
Fetal Fraction (Mean ± S.D.) = 2.7 ± 1.7
Fetal Fraction (Mean ± S.D.) = 3.9 ± 1.2

Example 6

Determination of Fetal Fraction by Massively Parallel Sequencing: Enrichment of Fetal and Maternal Nucleic Acids for Polymorphic Nucleic Acids in a Purified cfDNA Sample To enrich the fetal and maternal cfDNA contained in a purified sample of cfDNA extracted from a maternal plasma sample, a portion of the purified cfDNA was used for amplifying polymorphic target nucleic acid sequences each comprising one SNP chosen from the panel of SNPs given in Table 5.

The method corresponds to workflow 2 diagrammed in FIG. 3. Cell-free plasma was obtained from a maternal blood sample, and cfDNA was purified from the plasma sample as described in Example 1. The final concentration was determined to be 92.8 pg/μl. cfDNA contained in 5 μl of purified cfDNA was amplified in a reaction volume of 50 μl containing 7.5 μl of a 1 uM primer mix (Table 1), 10 μl of NEB 5× Mastermix and 27 μl water. Thermal cycling was performed with the Gene Amp9700 (Applied Biosystems). Using the following cycling conditions: incubating at 95° C. for 1 minute, followed by 30 cycles at 95° C. for 20 seconds, 68° C. for 1 minute, and 68° C. for 30s, which was followed by a final incubation at 68° C. for 5 minutes. A final hold at 4° C. was added until the samples were removed for combining with the unamplified portion of the purified cfDNA sample. The amplified product was purified using the Agencourt AMPure XP PCR purification system (Part No. A63881; Beckman Coulter Genomics, Danvers, MA), and the concentration quantified using the Nanodrop 2000 (Thermo Scientific, Wilmington, DE). The purified amplification product was diluted 1:10 in water and 0.9 μl (371 pg) added to 40 μl of purified cfDNA sample to obtain a 10% spike. The enriched fetal and maternal cfDNA present in the purified cfDNA sample was used for preparing a sequencing library, and was sequenced as described in Example 2.

Table 5 provides the tag counts obtained for each of chromosomes 21, 18, 13, X and Y i.e. sequence tag density, and the tag counts obtained for the informative polymorphic sequences contained in the SNP reference genome. i.e. SNP tag density. The data show that sequencing information can be obtained from sequencing a single library constructed from a purified maternal cfDNA sample that has been enriched for sequences comprising SNPs to simultaneously determine the presence or absence of aneuploidy and the fetal fraction. The presence or absence of aneuploidy was determined using the number of tags mapped to chromosomes as described in U.S. Provisional Applications 61/407,017 and 61/455,849. In the example given, the data show that the fraction of fetal DNA in plasma sample AFR105 was quantifiable from the sequencing results of five informative SNPs and determined to be 3.84%. Sequence tag densities are provided for chromosomes 21, 13, 18, X and Y.

The example shows that the enrichment protocol provides the requisite tag counts for determining aneuploidy and fetal fraction from a single sequencing process.

TABLE 5

Determination of Fetal Fraction by Massively Parallel Sequencing:
Enrichment of Fetal and Maternal Nucleic Acids for Polymorphic Nucleic Acids in a Purified cfDNA sample

| | Aneuploidy | | | | |
|---|---|---|---|---|---|
| | Chromosome 21 | Chromosome 18 | Chromosome 13 | Chromosome X | Chromosome Y |
| Sequence Tag Density | 178763 | 359529 | 388204 | 572330 | 2219 |
| Karyotype | Unaffected | Unaffected | Unaffected | Unaffected | Unaffected |

| Fetal Fraction SNP | SNP TAG DENSITY | FETAL FRACTION (%) |
|---|---|---|
| rs10773760.1\|Chr.12\|length = 128\|allele = A | 18903 | 2.81 |
| rs10773760.2\|Chr.12\|length = 128\|allele = G | 532 | |
| rs1109037.1\|Chr.2\|length = 126\|allele = A | 347 | 5.43 |
| rs1109037.2\|Chr.2\|length = 126\|allele = G | 6394 | |
| rs2567608.1\|Chr.20\|length = 110\|allele = A | 94503 | 1.74 |
| rs2567608.2\|Chr.20\|length = 110\|allele = G | 1649 | |
| rs7041158.1\|Chr.9\|length = 117\|allele = C | 107 | 5.61 |
| rs7041158.2\|Chr.9\|length = 117\|allele = T | 6 | |
| rs8078417.1\|Chr.17\|length = 110\|allele = C | 162668 | 3.61 |
| rs8078417.2\|Chr.17\|length = 110\|allele = T | 5877 | |

Fetal Fraction (Mean ± S.D.) = 3.8 ± 1.7

Example 7

Determination of Fetal Fraction by Massively Parallel Sequencing: Enrichment of Fetal and Maternal Nucleic Acids for Polymorphic Nucleic Acids in a Plasma Sample To enrich the fetal and maternal cfDNA contained in an original plasma sample derived from a pregnant woman, a portion the original plasma sample was used for amplifying polymorphic target nucleic acid sequences each comprising one SNP chosen from the panel of SNPs given in Table 1, and a portion of the amplified product was combined with the remaining original plasma sample.

The method corresponds to workflow 2 diagrammed in FIG. 3. cfDNA contained in 15 µl of cell-free plasma was amplified in a reaction volume of 50 µl containing 9 ul of a 1 µM mixture of primers (15 plexTable 1), 1 µl of Phusion blood DNA polymerase, 25 ul of the 2× Phusion blood PCR buffer containing deoxynucleotide triphosphates (dNTPs: dATP, dCTP, dGTP and dTTP). Thermal cycling was performed with the Gene Amp9700 (Applied Biosystems) using the following cycling conditions: incubating at 95° C. for 3 minutes, followed by 35 cycles at 95° C. for 20 seconds, 55° C. for 30s, and 70° C. for 1 minute, which was followed by a final incubation at 68° C. for 5 minutes. A final hold at 4° C. was added until the samples were removed for combining with the unamplified portion of the cell-free plasma. The amplified product was diluted 1:2 with water and analyzed using the Bioanalyzer. An additional 3 µl of amplified product was diluted with 11.85 µl of water to obtain a final concentration of 2 ng/µl. 2.2 µl of the diluted amplified product was combined with the remaining plasma sample. The enriched fetal and maternal cfDNA present in the plasma sample was purified as described in Example 1, and used for preparing a sequencing library. Sequencing and analysis of the sequencing data was performed as described in Example 2.

The results are given in Table 6. In the example given, the data show that the fraction of fetal DNA in plasma sample SAC2517 was quantifiable from the sequencing results of one informative SNP and determined to be 9.5%. In the example given, sample SAC2517 was shown by karyotyping to be unaffected for aneuploidies of chromosomes 21, 13, 18, X and Y. Sequence tag densities are provided for chromosomes 21, 13, 18, X and Y. The presence or absence of aneuploidy was determined using tag counts as described in U.S. Provisional Applications 61/407,017 and 61/455,849, which are herein incorporated by reference in their entirety.

The example demonstrates that enriching the mixture of fetal and maternal cfDNA present in a plasma sample for nucleic acid sequences that comprise at least one informative SNP can be used to provide the requisite sequence and SNP tag counts for determining aneuploidy and fetal fraction from a single sequencing process by massively parallel sequencing a library prepared from cfDNA contained in a plasma sample that is enriched for polymorphic nucleic acids.

TABLE 6

Determination of Fetal Fraction by Massively Parallel Sequencing:
Enrichment of Fetal and Maternal Nucleic Acids for Polymorphic Nucleic Acids Comprising a SNP in a Plasma Sample

| | Aneuploidy | | | | |
|---|---|---|---|---|---|
| | Chromosome 21 | Chromosome 18 | Chromosome 13 | Chromosome X | Chromosome Y |
| Sequence Tag Density | 183851 | 400582 | 470526 | 714055 | 2449 |
| Karyotype | Unaffected | Unaffected | Unaffected | Unaffected | Unaffected |

| | Fetal Fraction | |
|---|---|---|
| SNP | TAG COUNTS | FETAL FRACTION (%) |
| rs10773760.1\|Chr.12\|length = 128\|allele = A | 8536 | 9.5 |
| rs10773760.2\|Chr.12\|length = 128\|allele = G | 89924 | |

Example 8

Determination of Fetal Fraction by Massively Parallel Sequencing of Samples Comprising Amplified Polymorphic Sequences: Tandem SNPs To determine the fraction of fetal cfDNA in a maternal sample, target polymorphic nucleic acid sequences each comprising a pair of tandem SNPs are amplified and used for preparing a target library for sequencing in a massively parallel fashion. Pairs of tandem SNPs can be selected from rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The primers used for amplifying the target sequences comprising the tandem SNPs are designed to encompass both SNP sites. For example, the forward primer is designed to encompass the first SNP, and the reverse primer is designed to encompass the second of the tandem SNP pair i.e. each of the SNP sites in the tandem pair is encompassed within the 36 bp generated by the sequencing method. Paired-end sequencing can be used to identify all sequences encompassing the tandem SNP sites. Exemplary sets of primers that are used to amplify the tandem SNPs disclosed herein are rs7277033-rs2110153_F (SEQ ID NOS 312 & 313): TCCTGGAAACAAAAGTATT (SEQ ID NO:197) and rs7277033-rs2110153_R (SEQ ID NOS 312 & 313): AACCTTACAACAAAGCTAGAA (SEQ ID NO:198), set rs2822654-rs1882882_F (SEQ ID NOS 314 & 315): ACTAAGCCTTGGGGATCCAG (SEQ ID NO:199) and rs2822654-rs1882882_R (SEQ ID NOS 314 & 315): TGCTGTGGAAATACTAAAAGG (SEQ ID NO:200), set rs368657-rs376635_F (SEQ ID NOS 316 & 317): CTCCAGAGGTAATCCTGTGA (SEQ ID NO:201) and rs368657-rs376635_R (SEQ ID NOS 316 & 317): TGGTGTGAGATGGTATCTAGG (SEQ ID NO:202), rs2822731-rs2822732_F (SEQ ID NOS 318 & 319): GTATAATCCATGAATCTTGTTT (SEQ ID NO:203) and rs2822731-rs2822732_R (SEQ ID NOS 318 & 319): TTCAAATTGTATATAAGAGAGT (SEQ ID NO:204), rs1475881-rs7275487_F (SEQ ID NOS 320 & 321): GCAGGAAAGTTATTTTTAAT (SEQ ID NO:205) and rs1475881-rs7275487_R (SEQ ID NOS 320 & 321): TGCTTGAGAAAGCTAACACTT (SEQ ID NO:206), rs1735976-rs2827016F (SEQ ID NOS 322 & 323):

CAGTGTTTGGAAATTGTCTG (SEQ ID NO:207) and rs1735976-rs2827016_R (SEQ ID NOS 322 & 323): GGCACTGGGAGATTATTGTA (SEQ ID NO:208), rs447349-rs2824097_F (SEQ ID NOS 324 & 325): TCCTGTTGTTAAGTACACAT (SEQ ID NO:209) and rs447349-rs2824097_R (SEQ ID NOS 324 & 325): GGGCCGTAATTACTTTTG (SEQ ID NO:210), rs418989-rs13047336_F (SEQ ID NOS 326 & 327): ACTCAGTAGGCACTTTGTGTC (SEQ ID NO:211) and rs418989-rs13047336_R (SEQ ID NOS 326 & 327): TCTTCCACCACACCAATC (SEQ ID NO:212), rs987980-rs987981_F (SEQ ID NOS 328 & 329): TGGCTTTT-CAAAGGTAAAA (SEQ ID NO:213) and rs987980-rs987981_R (SEQ ID NOS 328 & 329): GCAACGTTAACATCTGAATTT (SEQ ID NO:214), rs4143392-rs4143391_F (SEQ ID NOS 330 & 331): rs4143392-rs4143391 (SEQ ID NO:215) and rs4143392-rs4143391_R (SEQ ID NOS 330 & 331): ATTTTATATGT-CATGATCTAAG (SEQ ID NO:216), rs1691324-rs13050434_F (SEQ ID NOS 332 & 333): AGAGATTACAGGTGTGAGC (SEQ ID NO:217) and rs1691324-rs13050434_R (SEQ ID NOS 332 & 333): ATGATCCTCAACTGCCTCT (SEQ ID NO:218), rs11909758-rs9980111_F (SEQ ID NOS 334 & 335): TGAAACTCAAAAGAGAAAAG (SEQ ID NO:219) and rs11909758-rs9980111_R (SEQ ID NOS 334 & 335): ACA-GATTTCTACTTAAAATT (SEQ ID NO:220), rs2826842-rs232414_F (SEQ ID NOS 336 & 337): TGAAACT-CAAAAGAGAAAAG (SEQ ID NO:221) and rs2826842-rs232414_R (SEQ ID NOS 336 & 337): ACAGATTTCTACTTAAAATT (SEQ ID NO:222), rs2826842-rs232414_F (SEQ ID NOS 336 & 337): GCAAAGGGGTACTCTATGTA (SEQ ID NO:223) and rs2826842-rs232414_R (SEQ ID NOS 336 & 337): TATCGGGTCATCTTGTTAAA (SEQ ID NO:224), rs1980969-rs1980970_F (SEQ ID NOS 338 & 339): TCTAACAAAGCTCTGTCCAAAA (SEQ ID NO:225) and rs1980969-rs1980970_R (SEQ ID NOS 338 & 339): CCACACTGAATAACTGGAACA (SEQ ID NO:226), rs9978999-rs9979175_F (SEQ ID NOS 340 & 341): GCAAGCAAGCTCTCTACCTTC (SEQ ID NO:227) and rs9978999-rs9979175_R (SEQ ID NOS 340 & 341): TGTTCTTCCAAAATTCACATGC (SEQ ID NO:228), rs1034346-rs12481852_F (SEQ ID NOS 342 & 343): ATTTCACTATTCCTTCATTTT (SEQ ID NO:229) and rs1034346-rs12481852_R (SEQ ID NOS 342 & 343): TAATTGTTGCACACTAAATTAC (SEQ ID NO:230), rs4817013-rs7277036_F: (SEQ ID NOS 346 & 347) AAAAAGCCACAGAAATCAGTC (SEQ ID NO:231) and rs4817013-rs7277036_R (SEQ ID NOS 346 & 347): TTCT-TATATCTCACTGGGCATT (SEQ ID NO:232), rs9981121-rs2829696_F (SEQ ID NOS 348 & 349): GGATGGTAGAAGAGAAGAAAGG (SEQ ID NO:233) and rs9981121-rs2829696_R (SEQ ID NOS 348 & 349): GGATGGTAGAAGAGAAGAAAGG (SEQ ID NO:234), rs455921-rs2898102_F (SEQ ID NOS 350 & 351): TGCAAAGATGCAGAACCAAC (SEQ ID NO:235) and rs455921-rs2898102_R (SEQ ID NOS 350 & 351): TTTTGTTCCTTGTCCTGGCTGA (SEQ ID NO:236), rs2898102-rs458848_F (SEQ ID NOS 352 & 353): TGCAAAGATGCAGAACCAAC (SEQ ID NO:237) and rs2898102-rs458848_R (SEQ ID NOS 352 & 353): GCCTCCAGCTCTATCCAAGTT (SEQ ID NO:238), rs961301-rs2830208_F (SEQ ID NOS 354 & 355): CCT-TAATATCTTCCCATGTCCA (SEQ ID NO:239) and rs961301-rs2830208_R (SEQ ID NOS 354 & 355): ATTGT-TAGTGCCTCTTCTGCTT (SEQ ID NO:240), rs2174536-rs458076_F (SEQ ID NOS 356 & 357): GAGAAGT-GAGGTCAGCAGCT (SEQ ID NO:241) and rs2174536-rs458076_R (SEQ ID NOS 356 & 357): TTTCTAAATTTCCATTGAACAG (SEQ ID NO:242), rs11088023-rs11088024_F (SEQ ID NOS 358 & 359): GAAATTGGCAATCTGATTCT (SEQ ID NO:243) and rs11088023-rs11088024_R (SEQ ID NOS 358 & 359): CAACTTGTCCTTTATTGATGT (SEQ ID NO:244), rs1011734-rs1011733_F (SEQ ID NOS 360 & 361): CTATGTTGATAAAACATTGAAA (SEQ ID NO:245) and rs1011734-rs1011733_R (SEQ ID NOS 360 & 361): GCCTGTCTGGAATATAGTTT (SEQ ID NO:246), rs2831244-rs9789838_F (SEQ ID NOS 362 & 363): CAGGGCATATAATCTAAGCTGT (SEQ ID NO:247) and rs2831244-rs9789838_R (SEQ ID NOS 362 & 363): CAATGACTCTGAGTTGAGCAC (SEQ ID NO:248), rs8132769-rs2831440_F (SEQ ID NOS 364 & 365): ACTCTCTCCCTCCCCTCT (SEQ ID NO:249) and rs8132769-rs2831440_R (SEQ ID NOS 364 & 365): TATGGCCCCAAAACTATTCT (SEQ ID NO:250), rs8134080-rs2831524_F (SEQ ID NOS 366 & 367): ACAAGTACTGGGCAGATTGA (SEQ ID NO:251) and rs8134080-rs2831524_R (SEQ ID NOS 366 & 367): GCCAGGTTTAGCTTTCAAGT (SEQ ID NO:252), rs4817219-rs4817220_F (SEQ ID NOS 368 & 369): TTT-TATATCAGGAGAAACACTG (SEQ ID NO:253) and rs4817219-rs4817220_R (SEQ ID NOS 368 & 369): CCAGAATTTTGGAGGTTTAAT (SEQ ID NO:254), rs2250911-rs2250997_F (SEQ ID NOS 370 & 371): TGT-CATTCCTCCTTTATCTCCA (SEQ ID NO:255) and rs2250911-rs2250997_R (SEQ ID NOS 370 & 371): TTCTTTTGCCTCTCCCAAAG (SEQ ID NO:256), rs2831899-rs2831900_F (SEQ ID NOS 372 & 373): ACCCTGGCACAGTGTTGACT (SEQ ID NO:257) and rs2831899-rs2831900_R (SEQ ID NOS 372 & 373): TGGGCCTGAGTTGAGAAGAT (SEQ ID NO:258), rs2831902-rs2831903_F (SEQ ID NOS 374 & 375): AAT-TTGTAAGTATGTGCAACG (SEQ ID NO:259) and rs2831902-rs2831903_R (SEQ ID NOS 374 & 375): TTTTTCCCATTTCCAACTCT (SEQ ID NO:260), rs11088086-rs2251447_F (SEQ ID NOS 376 & 377): AAAAGATGAGACAGGCAGGT (SEQ ID NO:261) and rs11088086-rs2251447_R (SEQ ID NOS 376 & 377): ACCCTGTGAATCTCAAAAT (SEQ ID NO:262), rs2832040-rs11088088_F (SEQ ID NOS 378 & 379): GCACTTGCTTCTATTGTTTGT (SEQ ID NO:263) and rs2832040-rs11088088_R (SEQ ID NOS 378 & 379): CCCTTCCTCTCTTCCATTCT (SEQ ID NO:264), rs2832141-rs2246777_F (SEQ ID NOS 380 & 381): AGCACTGCAGGTA (SEQ ID NO:265) and rs2832141-rs2246777_R (SEQ ID NOS 380 & 381): ACAGATAC-CAAAGAACTGCAA (SEQ ID NO:266), rs2832959-rs9980934_F (SEQ ID NOS 382 & 383): TGGACACCTTTCAACTTAGA (SEQ ID NO:267) and rs2832959-rs9980934_R (SEQ ID NOS 382 & 383): GAACAGTAATGTTGAACTTTTT (SEQ ID NO:268), rs2833734-rs2833735_F (SEQ ID NOS 384 & 385): TCTTGCAAAAAGCTTAGCACA (SEQ ID NO:269) and rs2833734-rs2833735_R (SEQ ID NOS 384 & 385): AAAAAGATCTCAAAGGGTCCA (SEQ ID NO:270), rs933121-rs933122_F (SEQ ID NOS 386 & 387): GCTTTTGCTGAACATCAAGT (SEQ ID NO:271) and rs933121-rs933122_R (SEQ ID NOS 386 & 387): CCTTCCAGCAGCATAGTCT (SEQ ID NO:272), rs2834140-rs12626953_F (SEQ ID NOS 388 & 389): AAATCCAGGATGTGCAGT (SEQ ID NO:273) and rs2834140-rs12626953_R (SEQ ID NOS 388 & 389):

ATGATGAGGTCAGTGGTGT (SEQ ID NO:274), rs2834485-rs3453_F (SEQ ID NOS 390 & 391): CATCACAGATCATAGTAAATGG (SEQ ID NO:275) and rs2834485-rs3453_R (SEQ ID NOS 390 & 391): AATTATTATTTTGCAGGCAAT (SEQ ID NO:276), rs9974986-rs2834703_F (SEQ ID NOS 392 & 393): CATGAGGCAAACACCTTTCC (SEQ ID NO:277) and rs9974986-rs2834703_R (SEQ ID NOS 392 & 393): GCTGGACTCAGGATAAAGAACA (SEQ ID NO:278), rs2776266-rs2835001_F (SEQ ID NOS 394 & 395): TGGAAGCCTGAGCTGACTAA (SEQ ID NO:279) and rs2776266-rs2835001_R (SEQ ID NOS 394 & 395): CCTTCTTTTCCCCCAGAATC (SEQ ID NO:280), rs1984014-rs1984015_F (SEQ ID NOS 396 & 397): TAGGAGAACAGAAGATCAGAG (SEQ ID NO:281) and rs1984014-rs1984015_R (SEQ ID NOS 396 & 397): AAAGACTATTGCTAAATGCTTG (SEQ ID NO:282), rs7281674-rs2835316_F (SEQ ID NOS 398 & 399): TAAGCGTAGGGCTGTGTGTG (SEQ ID NO:283) and rs7281674-rs2835316_R (SEQ ID NOS 398 & 399): GGACGGATAGACTCCAGAAGG (SEQ ID NO:284), rs13047304-rs13047322_F (SEQ ID NOS 400 & 401): GAATGACCTTGGCACTTTTATCA (SEQ ID NO:285) and rs13047304-rs13047322_R (SEQ ID NOS 400 & 401): AAGGATAGAGATATACAGATGAATGGA (SEQ ID NO:286), rs2835735-rs2835736_F (SEQ ID NOS 404 & 405): CATGCACCGCGCAAATAC (SEQ ID NO:287) and rs2835735-rs2835736_R (SEQ ID NOS 404 & 405): ATGCCTCACCCACAAACAC (SEQ ID NO:288), rs13047608-rs2835826_F (SEQ ID NOS 406 & 407): TCCAAGCCCTTCTCACTCAC (SEQ ID NO:289) and rs13047608-rs2835826_R (SEQ ID NOS 406 & 407): CTGGGACGGTGACATTTTCT (SEQ ID NO:290), rs2836550-rs2212596_F (SEQ ID NOS 408 & 409): CCCAGGAAGAGTGGAAAGATT (SEQ ID NO:291) and rs2836550-rs2212596_R (SEQ ID NOS 408 & 409): TTAGCTTGCATGTACCTGTGT (SEQ ID NO:292), rs2836660-rs2836661_F (SEQ ID NOS 410 & 411): AGCTAGATGGGGTGAATTTT (SEQ ID NO:293) and _R: TGGGCTGAGGGGAGATTC (SEQ ID NO:294), rs465612-rs8131220_F (SEQ ID NOS 412 & 413): ATCAAGCTAATTAATGTTATCT (SEQ ID NO:295) and rs465612-rs8131220_R (SEQ ID NOS 412 & 413): AATGAATAAGGTCCTCAGAG (SEQ ID NO:296), rs9980072-rs8130031_F (SEQ ID NOS 414 & 415): TTTAATCTGATCATTGCCCTA (SEQ ID NO:297) and rs9980072-rs8130031_R (SEQ ID NOS 414 & 415): AGCTGTGGGTGACCTTGA (SEQ ID NO:298), rs418359-rs2836926_F (SEQ ID NOS 416 & 417): TGTCCCACCATTGTGTATTA (SEQ ID NO:299) and rs418359-rs2836926_R (SEQ ID NOS 416 & 417): TCAGACTTGAAGTCCAGGAT (SEQ ID NO:300), rs7278447-rs7278858_F (SEQ ID NOS 418 & 419): GCTTCAGGGGTGTTAGTTTT (SEQ ID NO:301) and rs7278447-rs7278858_R (SEQ ID NOS 418 & 419): CTTTGTGAAAAGTCGTCCAG (SEQ ID NO:302), rs385787-rs367001_F (SEQ ID NOS 420 & 421): CCATCATGGAAAGCATGG (SEQ ID NO:303) and rs385787-rs367001_R (SEQ ID NOS 420 & 421): TCATCTCCATGACTGCACTA (SEQ ID NO:304), rs367001-rs386095_F (SEQ ID NOS 422 & 423): GAGATGACGGAGTAGCTCAT (SEQ ID NO:305) and rs367001-rs386095_R (SEQ ID NOS 422 & 423): CCCAGCTGCACTGTCTAC (SEQ ID NO:306), rs2837296-rs2837297_F (SEQ ID NOS 424 & 425): TCTTGTTCCAATCACAGGAC (SEQ ID NO:307) and rs2837296-rs2837297_R (SEQ ID NOS 424 & 425): ATGCTGTTAGCTGAAGCTCT (SEQ ID NO:308), and rs2837381-rs4816672_F (SEQ ID NOS 426 & 427): TGAAAGCTCCTAAAGCAGAG (SEQ ID NO:309) and rs2837381-rs4816672_R (SEQ ID NOS 426 & 427): TTGAAGAGATGTGCTATCAT (SEQ ID NO:310). Polynucleotide sequences e.g. GC clamp sequences, can be included to ensure specific hybridization of AT-rich primers (Ghanta et al., PLOS ONE 5(10): doi10.1371/journal.pone.0013184 [2010], available on the world wide web at plosone.org). An example of a GC clamp sequence that can be included either 5' of the forward primer or 3' of the reverse primer is GCCGCCTGCAGCCCGCGCCCCCGTGCCCCCGCCCCGCCGCCGGCCCGGGCGCC (SEQ ID NO:311). Polymorphic sequences can be used alone or in combination with unamplified cfDNA to determine either fetal fraction or the presence or absence of aneuploidy and fetal fraction in a maternal sample as described for polymorphic SNP sequences. Sample preparation and enrichment of cfDNA sequencing library, a purified cfDNA sample, and a plasma sample is performed according to the method described in Examples 5, 6, and 7, respectively. All sequencing libraries are prepared as described in Example 2a., and sequencing is performed as described in Example 2b. Analysis of the sequencing data for the determination of fetal aneuploidy is performed as described in Example 5. Concomitant to the analysis for determining aneuploidy, the sequencing data is analyzed to determine the fetal fraction as follows. Following the transfer of the image and base call files to the Unix server running the Illumina "Genome Analyzer Pipeline" software version 1.51 as described in Example 3a., the 36 bp reads are aligned to a 'tandem SNP genome' using the BOWTIE program. The tandem SNP genome is identified as the grouping of the DNA sequences that encompass the alleles of the 58 tandem SNP pairs disclosed above. Only reads that mapped uniquely to the tandem SNP genome are used for the analysis of fetal fraction. Reads that match perfectly to the tandem SNP genome are counted as tags and filtered. Of the remaining reads, only reads having one or two mismatches are counted as tags and included in the analysis. Tags mapped to each of the tandem SNP alleles are counted, and the fetal fraction is determined essentially as described in Example 6 above but accounting for tags mapped to the two tandem SNP alleles x and y present on each of the amplified polymorphic target nucleic acid sequences that are amplified to enrich the samples i.e.

% fetal fraction allele$_{x+y}$=(($\Sigma$Fetal sequence tags for allele$_{x+y}$)/($\Sigma$Maternal sequence tags for allele$_{x+y}$))×100

Only informative tandem SNPs are used to determine the fetal fraction.

Optionally, the fraction of fetal nucleic acids in the mixture of fetal and maternal nucleic acids is calculated for each of the informative allele (allele$_{x,y}$) as follows:

% fetal fraction allele$_{x+y}$=((2×$\Sigma$Fetal sequence tags for allele$_{x+y}$)/($\Sigma$Maternal sequence tags for allele$_{x+y}$))×100, to compensate for the presence of 2 sets of tandem fetal alleles, one being masked by the maternal background.

The percent fetal fraction is calculated for at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or more informative sets of tandem alleles. In one embodiment, the fetal fraction is the average fetal fraction determined for at least 3 informative sets of tandem alleles.

Example 9

Determination of Fetal Fraction by Massively Parallel Sequencing of Samples Comprising Amplified Polymorphic Sequences: STRs To determine the fraction of fetal cfDNA in a maternal sample, target polymorphic nucleic acid sequences each comprising an STR are amplified and used for preparing a target library for sequencing in a massively parallel fashion.

Peripheral blood samples are obtained from pregnant subjects, and cfDNA is purified from the plasma fraction as described in Examples 1 and 2 STRs that are amplified are chosen from the codis and non-codis STRs disclosed in Table 7, and amplification of the polymorphic STR sequences is obtained using the corresponding sets of primers provided. For example, the STRs listed in Table 7 are amplified using the corresponding primers (SEQ ID NOs: 113-197), and the amplified product is used to generate a target sequencing library. The STR target sequencing library is prepared as described for the preparation of the SNP target library as described in Example 8. STRs CSF1PO, D13S317, D16S539, D18S51, D21S11, D2S1338D7S820, and FGA have been analyzed previously for determining fetal fraction, and are disclosed in U.S. Provisional applications 61/296,358 and 61/360,837.

TABLE 7

CODIS and NON-CODIS miniSTRs

| STR Locus (Marker Name) | Chromosome Location | Size Range (bp) | GenBank Accession | Primer Sequences (Forward/Reverse) |
|---|---|---|---|---|
| Codis miniSTR loci* | | | | |
| CSF1PO | 5q33.1 | 89-129 | X14720 | ACAGTAACTGCCTTCATAGATAG (CSF1PO_F; SEQ ID NO: 113) GTGTCAGACCCTGTTCTAAGTA (CSF1PO_R; SEQ ID NO: 114) |
| FGA | 4q31.3 | 125-281 | M64982 | AAATAAAATTAGGCATATTTACAAGC (FGA_F; SEQ ID NO: 115) GCTGAGTGATTTGTCTGTAATTG (FGA_R; SEQ ID NO: 116) |
| TH01 | 11p15.5 | 51-98 | D00269 | CCTGTTCCTCCCTTATTTCCC (TH01_F; SEQ ID NO: 117) GGGAACACAGACTCCATGGTG (TH01_R; SEQ ID NO: 118) |
| TPOX | 2p25.3 | 65-101 | M68651 | CTTAGGGAACCCTCACTGAATG (TPOX_F; SEQ ID NO: 119) GTCCTTGTCAGCGTTTATTTGC (TPOX_R; SEQ ID NO: 120) |
| vWA | 12p13.31 | 88-148 | M25858 | AATAATCAGTATGTGACTTGGATTGA (vWA_F; SEQ ID NO: 121) ATAGGATGGATGGATAGATGGA (vWA_R; SEQ ID NO: 122) |
| D3S1358 | 3p21.31 | 72-120 | NT_005997 | CAGAGCAAGACCCTGTCTCAT (D3S1358_F; SEQ ID NO: 123) TCAACAGAGGCTTGCATGTAT (D3S1358_R; SEQ ID NO: 124) |
| D5S818 | 5q23.2 | 81-117 | AC008512 | GGGTGATTTTCCTCTTTGGT (D5S818_F; SEQ ID NO: 125) AACATTTGTATCTTTATCTGTATCCTTAT TTAT (D5S818_R; SEQ ID NO: 126) |
| D7S820 | 7q21.11 | 136-176 | AC004848 | GAACACTTGTCATAGTTTAGAACGAAC (D7S820_F; SEQ ID NO: 127) TCATTGACAGAATTGCACCA (D7S820_R; SEQ ID NO: 128) |
| D8S1179 | 8q24.13 | 86-134 | AF216671 | TTTGTATTTCATGTGTACATTCGTATC (D7S820_F; SEQ ID NO: 129) ACCTATCCTGTAGATTATTTTCACTGTG (D7S820_R; SEQ ID NO: 130) |
| D13S317 | 13q31.1 | 88-132 | AL353628 | TCTGACCCATCTAACGCCTA (D13S317_F; SEQ ID NO: 131) CAGACAGAAAGATAGATAGATGATTGA (D13S317_R; SEQ ID NO: 132) |

TABLE 7-continued

CODIS and NON-CODIS miniSTRs

| STR Locus (Marker Name) | Chromosome Location | Size Range (bp) | GenBank Accession | Primer Sequences (Forward/Reverse) |
|---|---|---|---|---|
| D16S539 | 16q24.1 | 81-121 | AC024591 | ATACAGACAGACAGACAGGTG(D16S539_F; SEQ ID NO: 133) GCATGTATCTATCATCCATCTCT(D16S539_R; SEQ ID NO: 134) |
| D18S51 | 18q21.33 | 113-193 | AP001534 | TGAGTGACAAATTGAGACCTT(D18S51_F; SEQ ID NO: 135) GTCTTACAATAACAGTTGCTACTATT (D18S51_R; SEQ ID NO: 136) |
| D21S11 | 21q21.1 | 153-221 | AP000433 | ATTCCCCAAGTGAATTGC(D21S11_F; SEQ ID NO: 137) GGTAGATAGACTGGATAGATAGACGA (D21S11_R; SEQ ID NO: 138) |
| D2S1338 | 2q35 | 90-142 | AC01036 | TGGAAACAGAAATGGCTTGG(D2S1338_F; SEQ ID NO: 139) GATTGCAGGAGGGAAGGAAG(D2S1338_R; SEQ ID NO: 140) |
| Penta D | 21q22.3 | 94-167 | AP001752 | GAGCAAGACACCATCTCAAGAA(Penta D_F; SEQ ID NO: 141) GAAATTTTACATTTATGTTTATGATTCTCT (Penta D_R; SEQ ID NO: 142) |
| Penta E | 15q26.2 | 80-175 | AC027004 | GGCGACTGAGCAAGACTC(Penta E_F; SEQ ID NO: 143) GGTTATTAATTGAGAAAACTCCTTACA (Penta E_R; SEQ ID NO: 144) |

Non-Codis miniSTR loci*

| STR Locus (Marker Name) | Chromosome Location | Size Range (bp) | GenBank Accession | Primer Sequences (Forward/Reverse) |
|---|---|---|---|---|
| D22S1045 | 22q12.3 | 82-115 | AL022314 (17) | ATTTTCCCCGATGATAGTAGTCT(D22S1045_F; SEQ ID NO: 145) GCGAATGTATGATTGGCAATATTTTT (D22S1045_R; SEQ ID NO: 146) |
| D20S1082 | 20q13.2 | 73-101 | AL158015 | ACATGTATCCCAGAACTTAAAGTAAAC (D20S1082_F; SEQ ID NO: 147) GCAGAAGGGAAAATTGAAGCTG(D20S1082_R; SEQ ID NO: 148) |
| D20S482 | 20p13 | 85-126 | AL121781 (14) | CAGAGACACCGAACCAATAAGA(D20S482_F; SEQ ID NO: 149) GCCACATGAATCAATTCCTATAATAAA (D20S482_R; SEQ ID NO: 150) |
| D18S853 | 18p11.31 | 82-104 | AP005130 (11) | GCACATGTACCCTAAAACTTAAAAT (D18S853_F; SEQ ID NO: 151) GTCAACCAAAACTCAACAAGTAGTAA (D18S853_R; SEQ ID NO: 152) |
| D17S1301 | 17q25.1 | 114-139 | AC016888 (12) | AAGATGAAATTGCCATGTAAAAATA (D17S1301_F; SEQ ID NO: 153) GTGTGTATAACAAAATTCCTATGATGG (D17S1301_R; SEQ ID NO: 154) |
| D17S974 | 17p13.1 | 114-139 | AC034303 (10) | GCACCCAAAACTGAATGTCATA(D17S974_F; SEQ ID NO: 155) GGTGAGAGTGAGACCCTGTC(D17S974_R; SEQ ID NO: 156) |
| D14S1434 | 14q2.13 | 70-98 | AL121612 (13) | TGTAATAACTCTACGACTGTCTGTCTG (D14S1434_F; SEQ ID NO: 157) GAATAGGAGGTGGATGGATGG (D14S1434_R; SEQ ID NO: 158) |
| D12ATA63 | 12q23.3 | 76-106 | AC009771 (13) | GAGCGAGACCCTGTCTCAAG(D12ATA63_F; SEQ ID NO: 159) GGAAAAGACATAGGATAGCAATTT (D12ATA63_R; SEQ ID NO: 160) |

TABLE 7-continued

CODIS and NON-CODIS miniSTRs

| STR Locus (Marker Name) | Chromosome Location | Size Range (bp) | GenBank Accession | Primer Sequences (Forward/Reverse) |
|---|---|---|---|---|
| D11S4463 | 11q25 | 88-116 | AP002806 (14) | TCTGGATTGATCTGTCTGTCC (D11S4463_F; SEQ ID NO: 161) GAATTAAATACCATCTGAGCACTGAA (D11S4463_R; SEQ ID NO: 162) |
| D10S1435 | 10p15.3 | 82-139 | AL354747 (11) | TGTTATAATGCATTGAGTTTTATTCTG (D10S1435_F; SEQ ID NO: 163) GCCTGTCTCAAAAATAAAGAGATAGACA (D10S1435_R; SEQ ID NO: 164) |
| D10S1248 | 10q26.3 | 79-123 | AL391869 (13) | TTAATGAATTGAACAAATGAGTGAG (D10S1248_F; SEQ ID NO: 165) GCAACTCTGGTTGTATTGTCTTCAT (D10S1248_R; SEQ ID NO: 166) |
| D9S2157 | 9q34.2 | 71-107 | AL162417 (10) | CAAAGCGAGACTCTGTCTCAA (D9S2157_F; SEQ ID NO: 167) GAAAATGCTATCCTCTTTGGTATAAAT (D9S2157_R; SEQ ID NO: 168) |
| D9S1122 | 9q21.2 | 93-125 | AL161789 (12) | GGGTATTTCAAGATAACTGTAGATAGG (D9S1122_F; SEQ ID NO: 169) GCTTCTGAAAGCTTCTAGTTTACC (D9S1122_R; SEQ ID NO: 170) |
| D8S1115 | 8p11.21 | 63-96 | AC090739 (9) | TCCACATCCTCACCAACAC (D8S1115_F; SEQ ID NO: 171) GCCTAGGAAGGCTACTGTCAA (D8S1115_R; SEQ ID NO: 172) |
| D6S1017 | 6p21.1 | 81-110 | AL035588 (10) | CCACCCGTCCATTTAGGC (D6S1017_F; SEQ ID NO: 173) GTGAAAAAGTAGATATAATGGTTGGTG (D6S1017_R; SEQ ID NO: 174) |
| D6S474 | 6q21 | 107-136 | AL357514 (17) | GGTTTTCCAAGAGATAGACCAATTA (D6S474_F; SEQ ID NO: 175) GTCCTCTCATAAATCCCTACTCATATC (D6S474_R; SEQ ID NO: 176) |
| D5S2500 | 5q11.2 | 85-126 | AC008791 (17) | CTGTTGGTACATAATAGGTAGGTAGGT (D5S2500_F; SEQ ID NO: 177) GTCGTGGGCCCCATAAATC (D5S2500_R; SEQ ID NO: 178) |
| D4S2408 | 4p15.1 | 85-109 | AC110763 (9) | AAGGTACATAACAGTTCAATAGAAAGC (D4S2408_F; SEQ ID NO: 179) GTGAAATGACTGAAAAATAGTAACCA (D4S2408_R; SEQ ID NO: 180) |
| D4S2364 | 4q22.3 | 67-83 | AC022317 (9) | CTAGGAGATCATGTGGGTATGATT (D4S2364U_F; SEQ ID NO: 181) GCAGTGAATAAATGAACGAATGGA (D4S2364_R; SEQ ID NO: 182) |
| D3S4529 | 3p12.1 | 111-139 | AC117452 (13) | CCCAAAATTACTTGAGCCAAT (D3S452_F; SEQ ID NO: 183) GAGACAAAATGAAGAAACAGACAG (D3S452_R; SEQ ID NO: 184) |
| DS3053 | 3q26.31 | 84-108 | AC069259 (9) | TCTTTGCTCTCATGAATAGATCAGT (D3S3053_F; SEQ ID NO: 185) GTTTGTGATAATGAACCCACTCAG (D3S3053_R; SEQ ID NO: 186) |
| D2S1776 | 2q24.3 | 127-161 | AC009475 (11) | TGAACACAGATGTTAAGTGTGTATATG (D2S1776_F; SEQ ID NO: 187) GTCTGAGGTGGACAGTTATGAAA (D2S1776_R; SEQ ID NO: 188) |

TABLE 7-continued

CODIS and NON-CODIS miniSTRs

| STR Locus (Marker Name) | Chromosome Location | Size Range (bp) | GenBank Accession | Primer Sequences (Forward/Reverse) |
|---|---|---|---|---|
| D2S441 | 2p14 | 78-110 | AC079112 (12) | CTGTGGCTCATCTATGAAAACTT (D2S441_F; SEQ ID NO: 189) GAAGTGGCTGTGGTGTTATGAT (D2S441_R; SEQ ID NO: 190) |
| D1S1677 | 1q23.3 | 81-117 | AL513307 (15) | TTCTGTTGGTATAGAGCAGTGTTT (D1S1677_F; SEQ ID NO: 191) GTGACAGGAAGGACGGAATG (D1S1677_R; SEQ ID NO: 192) |
| D1S1627 | 1p21.1 | 81-100 | AC093119 (13) | CATGAGGTTTGCAAATACTATCTTAAC (D1S1627_F; SEQ ID NO: 193) GTTTTAATTTTCTCCAAATCTCCA (D1S1627_R; SEQ ID NO: 194) |
| D1GATA113 | 1p36.23 | 81-105 | Z97987 (11) | TCTTAGCCTAGATAGATACTTGCTTCC (D1GATA113_F; SEQ ID NO: 195) GTCAACCTTTGAGGCTATAGGAA (D1GATA113_R; SEQ ID NO: 196) |

*(Butler et al., J Forensic Sci 5:1054-1064; Hill et al., Poster #44-17th International Symposium on Human Identification-2006)

Sequencing of the library enriched for polymorphic STR sequences is performed using a NGS technology e.g. sequencing by synthesis. Sequence reads of lengths that encompass the STRs e g miniSTRs of at least 100 bp, to a reference STR genome consisting of the polymorphic sequences which were amplified in the sample. Informative STR alleles are identified by differences in the length of the repeats, and the number of STR sequence tags are counted, and used to determine the fetal fraction. Optionally, amplification of the polymorphic STR sequences is performed to enrich a plasma sample, a purified cfDNA sample or a cfDNA sequencing library sample, as described in Examples 5, 6, and 7, respectively.

Example 10

Determination of Fetal Fraction by Capillary Electrophoresis of Polymorphic Sequences Comprising STRs To determine fetal fraction in maternal samples comprising fetal and maternal cfDNA, peripheral blood samples were collected from volunteer pregnant women carrying either male or female fetuses. Peripheral blood samples were obtained and processed to provide purified cfDNA as described in Example 1

Ten microliters of cfDNA samples were analyzed using the AmpFlSTR® MiniFiler™ PCR amplification kit (Applied Biosystems, Foster City, CA) according to the manufacturer's instructions. Briefly, cfDNA contained in 10 μl was amplified in a reaction volume of 25 μl containing 5 μL fluorescently labeled primers (AmpF/STR® MiniFiler™ Primer Set), and the AmpF/STR® MiniFiler™ Master Mix, which includes AmpliTaq Gold® DNA polymerase and associated buffer, salt (1.5 mM MgCl2), and 200 μM deoxynucleotide triphosphates (dNTPs: dATP, dCTP, dGTP and dTTP). The fluorescently labeled primers are forward primers that are labeled with 6FAM™, VIC™, NED™, and PET™ dyes. Thermal cycling was performed with the Gene Amp9700 (Applied Biosystems) using the following cycling conditions: incubating at 95° C. for 10 minutes, followed by 30 cycles at 94° C. for 20 seconds, 59° C. for 2 minute, and 72° C. for 1 minute, which was followed by a final incubation at 60° C. for 45 minutes. A final hold at 4° C. was added until the samples were removed for analysis. The amplified product was prepared by diluting 1 ul of amplified product in 8.7 ul Hi-Di™ formamide (Applied Biosystems) and 0.3 μl GeneScan™-500 LIZ_ internal size standard (Applied Biosystems), and analyzed with an ABI PRISM3130xl Genetic Analyzer (Applied Biosystems) using Data Collection HID_G5_POP4 (Applied Biosystems), and a 36-cm capillary array. All genotyping was performed with GeneMapper_ID v3.2 software (Applied Biosystems) using manufacturer provided allelic ladders and bins and panels.

All genotyping measurement were performed on the Applied Biosystems 3130xl Genetic Analyzer, using a ±0.5-nt "window" around the size obtained for each allele to allow for detection and correct assignment of alleles. Any sample allele whose size was outside the ±0.5-nt window was determined to be OL i.e. "Off Ladder". OL alleles are alleles of a size that is not represented in the AmpF/STR® MiniFiler™ Allelic Ladder or an allele that does not correspond to an allelic ladder, but whose size is just outside a window because of measurement error. The minimum peak height threshold of >50 RFU was set based on validation experiments performed to avoid typing when stochastic effects are likely to interfere with accurate interpretation of mixtures. The calculation of fetal fraction is based on averaging all informative markers. Informative markers are identified by the presence of peaks on the electropherogram that fall within the parameters of preset bins for the STRs that are analyzed.

Calculations of fetal fraction were performed using the average peak height for major and minor alleles at every STR locus determined from triplicate injections. The rules applied to the calculation are:

1. off-ladder allele (OL) data for alleles are not included in the calculation; and 2. only peak heights derived from >50 RFU (relative fluorescence units) are included in the calculation 3. if only one bin is present the marker is deemed non-informative; and 4. if a second bin is called but the peaks of the first and second bins are within 50-70% of their relative fluorescence units (RFU) in peak height, the minority fraction is not measured and the marker is deemed not informative.

The fraction of the minor allele for any given informative marker is calculated by dividing the peak height of the minor component by the sum of the peak height for the major component, and expressed as a percent was first calculated for each informative locus as fetal fraction=(Σpeak height of minor allele/Σpeak height of major allele(s))×100, The fetal fraction for a sample comprising two or more informative STRs, would be calculated as the average of the fetal fractions calculated for the two or more informative markers.

Table 8 provides the data obtained from analyzing cfDNA of a subject pregnant with a male fetus.

TABLE 8

Fetal Fraction Determined in cfDNA of a Pregnant Subject by Analysis of STRs

| STR | Allele 1 | Allele 2 | Allele 3 | Allele 1 Height | Allele 2 Height | Allele 3 Height | Fetal Fraction | Fetal Fraction (Mean/STR) |
|---|---|---|---|---|---|---|---|---|
| AMEL | X | Y | | 3599 | 106 | | 2.9 | |
| AMEL | X | Y | | 3602 | 110 | | 3.1 | |
| AMEL | X | Y | | 3652 | 109 | | 3.0 | 3.0 |
| CSF1PO | 11 | 12 | | 2870 | 2730 | | | |
| CSF1PO | 11 | 12 | | 2924 | 2762 | | | |
| CSF1PO | 11 | 12 | | 2953 | 2786 | | | |
| D13S317 | 11 | 12 | | 2621 | 2588 | | | |
| D13S317 | 11 | 12 | | 2680 | 2619 | | | |
| D13S317 | 11 | 12 | | 2717 | 2659 | | | |
| D16S539 | 9 | 11 | | 1056 | 1416 | | | |
| D16S539 | 9 | 11 | | 1038 | 1394 | | | |
| D16S539 | 9 | 11 | | 1072 | 1437 | | | |
| D18S51 | 13 | 15 | | 2026 | 1555 | | | |
| D18S51 | 13 | 15 | | 2006 | 1557 | | | |
| D18S51 | 13 | 15 | | 2050 | 1578 | | | |
| D21S11 | 28 | 31.2 | | 2450 | 61 | | 2.5 | |
| D21S11 | 28 | 31.2 | | 2472 | 62 | | 2.5 | |
| D21S11 | 28 | 31.2 | | 2508 | 67 | | 2.7 | 2.6 |
| D2S1338 | 20 | 23 | | 3417 | 3017 | | | |
| D2S1338 | 20 | 23 | | 3407 | 3020 | | | |
| D2S1338 | 20 | 23 | | 3493 | 3055 | | | |
| D7S820 | 9 | 12 | 13 | 2373 | 178 | 1123 | 5.1 | |
| D7S820 | 9 | 12 | 13 | 2411 | 181 | 1140 | 5.1 | |
| D7S820 | 9 | 12 | 13 | 2441 | 182 | 1156 | 5.1 | 5.1 |
| FGA | 17.2 | 22 | 25 | 68 | 1140 | 896 | 3.3 | |
| FGA | 17.2 | 22 | 25 | 68 | 1144 | 909 | 3.1 | |
| FGA | 17.2 | 22 | 25 | 68 | 1151 | 925 | 3.3 | 3.2 |

Fetal Fraction = 3.5

The results show that cfDNA can be used for determining the presence or absence of fetal DNA as indicated by the detection of a minor component at one or more STR alleles, for determining the percent fetal fraction, and for determining fetal gender as indicated by the presence or absence of the Amelogenin allele.

Example 11

Preamplification of cfDNA for Determining Fetal Fraction by Capillary Electrophoresis of Polymorphic Sequences Comprising STRs To improve the sensitivity of the STR assay in detecting and quantifying the STR alleles in the minor contributor of the cfDNA sample, the number of starting genomes in the artificial samples was increased by a modified whole genome amplification strategy.

Peripheral blood samples were collected and processed as described in Example 2. Cell-free DNA was extracted from 1 ml cell-free plasma using the Roche MagNA Pure Compact Nucleic Acid Isolation Kit I—Large Volume (Roche Applied Science, IN) using the MagNA Pure Compact Instrument, and eluted in 50 μl of elution buffer. Ten microliters of the extracted cfDNA were used to quantify the cfDNA, and the remainder was stored (see storage instructions WI0035 Clinical Sample Storage). The concentration of the plasma extracted cfDNA was determined by fluorescence-based quantitation with UV absorbance measurements using the Qubit™ Quantitation Platform (Invitrogen).

The concentration of cfDNA quantified in plasma samples prepared using the MagnaPure Nucleic Acid Isolation Kit I from 16 pregnant subjects was determined to range between 20 and 100 pg/μl. As the fetal component of plasma cfDNA is known to contribute 3-10% of the total plasma cfDNA, artificial plasma samples were created by spiking aliquots of cfDNA derived from plasma of female volunteer subjects with cfDNA extracted from plasma of male volunteer subjects to mimic the ratios of fetal to maternal cfDNA found in the pregnant subjects. Artificial samples were created to contain 200-1000 pg of extracted female cfDNA that was spiked with 45-150 pg of extracted male cfDNA in a total volume of 10 μl. Each artificial sample was spiked to contain 3%, 5% and 10% male cfDNA.

Artificial samples having concentrations of total cfDNA of less than approximately 50 pg/μl, were preamplified using the modified improved primer extension amplification PCR (mIPEP) amplification according to the method of Hanson and Ballantyne, (Hanson and Ballantyne, Analytical Biochem 346:246-257 [2005]) as follows. Ten microliters of spiked plasma cfDNA were amplified in a 25 μl reaction volume containing 1 mM dNTPs, 2.5 mM MgCl$_2$ (Applied Biosystems), 1× Expand High Fidelity Buffer (No. 3), 10.5 U Expand High Fidelity Enzyme Mix (Roche Diagnostics), and 40 μM PEP primer (5'-NNNNNNNNNNNNNNN-3', Qiagen). The amplification was performed in a GeneAmp PCR System 9700 Thermocycler under the following conditions: (1) 20 and 30 cycles of 94° C. for 1 minute, 37° C. for 2 minutes, and 0.1° C./s ramp to 55° C. for 4 minutes. The amplification product was purified using a Qiagen column. The concentration of the amplification product was determined using the Qubit™ Quantitation Platform as described above. STR analysis was performed as described in Example 9 above, except that only peak heights >100 RFU were included in the calculations.

The results are shown in Tables 9, 10 and 11. The results provided in Table 9 show that the cfDNA contained in 10 µl cfDNA of artificial samples ART23 and ART24 having a starting concentration of cfDNA of 46.2 and 50.2 pg/µl, respectively, was amplified by approximately 5 and 10 fold following 20 and 30 cycles of PCR amplification, respectively.

These data indicate that a pre-amplification of cfDNA using the mIPEP method provided enhanced levels of total cfDNA rendering the level of the minor component more amenable to the STR analysis.

TABLE 9

Preamplification with mIPEP

| SAMPLE | cfDNA without mIPEP (pg/µl) | cfDNA with mIPEP:20 PCR cycles (pg/50 µl) | cfDNA with mIPEP:30 PCR cycles (pg/50 µl) |
|---|---|---|---|
| ART23 | 46.2 | 2265 | 4125 |
| ART24 | 50.2 | 2085 | 3875 |

Table 10 shows triplicate measurements profiling 9 loci of the cfDNA of spiked samples ART23 and ART24 following the mIPEP procedure with 20 and 30 cycles of amplification, as described above.

The data in Table 11 indicate that pre-amplification of cfDNA enables the detection and quantification of the minor component at most loci tested in artificially mixed samples having a starting cfDNA concentration that would otherwise not permit an accurate analysis of the minor STR alleles.

TABLE 10 mIPEP Preamplification and Detection of Minor Component

| STR Locus | Allele | ART23 (453 pg) mIPEP amplified 20 cycles Allele Height | ART23 (825 pg) mIPEP amplified 20 cycles Allele Height | ART23 (462 pg) Extracted unamplified cfDNA Allele Height | Allele | ART24 (417 pg) mIPEP amplified 30 cycles Allele Height | ART24 (775 pg) mIPEP amplified 30 cycles Allele Height | ART24 (502 pg) Extracted unamplified cfDNA Allele Height |
|---|---|---|---|---|---|---|---|---|
| AMEL | X/Y | 291/95 | 397/170 | 535/832 | X/Y | 695/359 | 1878/1148 | 1564/1959 |
| AMEL | X/Y | 425/147 | 428/188 | 675/1048 | X/Y | 1216/619 | 1551/954 | 1573/1943 |
| AMEL | X/Y | 267/94 | 455/203 | 664/1043 | X/Y | 718/363 | 1479/924 | 1621/2024 |
| CSF1PO | 10/11 | 800/979 | 725/1009 | 1429/1325 | 11/12 | 2029/1317 | 4159/2317 | 2990/3083 |
| CSF1PO | 10/11 | 1147/1432 | 789/1102 | 1779/1650 | 11/12 | 3449/2223 | 3460/113/1890 | 2996/3118 |
| CSF1PO | 10/11 | 729/906 | 831/1162 | 1783/1657 | 11/12 | 2006/1309 | 3362/1840 | 3072/3183 |
| D13S317 | 12 | 743 | 515 | 1229 | 11 | 955 | 1490 | 3634 |
| D13S317 | 12 | 1079 | 563 | 1534 | 11 | 1631 | 1198 | 3631 |
| D13S317 | 12 | 668 | 583 | 1520 | 11 | 968 | 1170 | 3795 |
| D16S539 | 9/10 | 239/140 | 370/466 | 835/676 | 10/11 | 513/512 | 1173/1472 | 1678/973 |
| D16S539 | 9/10 | 347/203 | 64*(OL)/391/489 | 1046/864 | 10/11 | 859/870 | 973/1212 | 1730/999 |
| D16S539 | 9/10 | 227/134 | 441/515 | 1055/860 | 10/11 | 530/513 | 960/1183 | 1784/1044 |
| D18S51 | 14/15 | 359/464 | 363/220 | 785/541 | 12/18 | 1044/576 | 1840/786 | 2559/1507 |
|  |  | 512/645 | 391/226 | 999/672 | 12/18 | 1769/994 | 1511/643 | 2565/1469 |
|  |  | 313/402 | 409/245 | 994/685 | 12/18 | 1033/567 | 1496/631 | 2643/1523 |
| D21S11 | 29/32 | 103/104 | 114/173 | 605/413 | 31.2 | 381 | 661 | 3276 |
|  |  | 149/153 | 130/182 | 759/523 | 31.2 | 650 | 536 | 3028 |
|  |  | 85/86 | 131/196 | 760/525 | 31.2 | 380 | 520 | 3282 |
| D2S1338 | 18/20 | 572/383 | 428/363 | 1116/1013 | 19/20 | 1066/433 | 2315/1243 | 2962/2968 |
|  |  | 827/553 | 454/386 | 1428/1279 | 19/20 | 1821/757 | 1901/101 | 2942/2942 |
|  |  | 530/351 | 482/408 | 1431/1275 | 19/20 | 1063/444 | 1859/1012 | 3072/3067 |
| D7S820 | 11/12 | 262/167 | 149/270 | 557/627 | 11/12 | 256/138 | 520/322 | 1550/1548 |
|  |  | 62/366/231 | 162/292 | 699/775 | 11/12 | 448/236 | 419/258 | 1484/1466 |
|  |  | 224/146 | 169/307 | 689/779 | 11/12 | 253/141 | 406/250 | 1579/1573 |
| FGA | 21/23 | 263/146 | 181/88 | 596/365 | 22/24 | 228/244 | 375/429 | 1272/1064 |
|  |  | 384/215 | 191/92 | 762/450 | 22/24 | 409/425 | 303/345 | 1221/1023 |
|  |  | 230/136 | 202/102 | 749/456 | 22/24 | 232/250 | 297/348 | 1298/1087 |

*"OL" means "Off Ladder measurement"

TABLE 11

Fetal Fraction Determined in a Sample Following Preamplification Using mIPEP

| STR marker | Allele 1/ Height | Allele 2/ Height | Allele 3/ Height | Allele 4/ Height | Percent minor fraction/STR - minor >100 RFU | Percent minor fraction/STR - minor <100 RFU |
|---|---|---|---|---|---|---|
| Amelogenin | X/2799 | Y/207 | | | | |
| Amelogenin | X/2751 | Y/198 | | | | |
| Amelogenin | X/3109 | Y/232 | | | | |
| | X/2886 | Y/212 | | | 7 | |
| CSF1PO | 10/2377 | 11/1869 | 12/508 | | | |
| CSF1PO | 10/2299 | 11/1814 | 12/498 | | | |
| CSF1PO | 10/2616 | 11/206 | 12/562 | | | |
| | 10/2431 | 11/1917 | 12/523 | | 12 | |
| D13S317 | 10/1232 | 11/1600 | 13/186 | | | |
| D13S317 | 10/1208 | 11/1548 | 13/182 | | | |
| D13S317 | 10/1386 | 11/1758 | 13/212 | | | |
| | 10/1275 | 11/1635 | 13/193 | | 12 | |
| D16S539 | 11/757 | 12/933 | | | | |
| D16S539 | 11/729 | 12/885 | | | | |
| D16S539 | 11/836 | 12/1031 | | | | |
| | 11/774 | 12/950 | | | 12 | |
| D18S51 | OL/80 | 14/3137 | 15/371 | | | |
| D18S51 | 11/73 | 14/3082 | 15/362 | | | |
| D18S51 | OL/83 | 14/3488 | 15/413 | | | |
| | OL | 14/3236 | 15/382 | | | |
| D21S11 | 29/953 | 30/941 | | | | |
| D21S11 | 29/921 | 30/908 | | | | |
| D21S11 | 29/1046 | 30/1045 | | | | |
| | 29/973 | 30/965 | | | | |
| D2S1338 | 17/461 | 18/366 | 20/2280 | 24/1760 | | |
| D2S1338 | 17/460 | 18/360 | 20/2240 | 24/1712 | | |
| D2S1338 | 17/508 | 18/409 | 20/2563 | 24/1971 | | |
| | 17/476 | 18/378 | 20/2361 | 24/1814 | 20 | |
| D7S820 | 8/1409 | 9/60 | 12/1059 | | | |
| D7S820 | 8/1380 | 9/60 | 12/1036 | | | |
| D7S820 | 8/1561 | 9/69 | 12/1166 | | | |
| | 8/1450 | 9/63 | 12/1087 | | | 2 |
| FGA | 19/825 | 21/850 | 25/279 | | | |
| FGA | 19/807 | 21/841 | 25/265 | | | |
| FGA | 19/913 | 21/958 | 25/306 | | | |
| | 19/848 | 21/883 | 25/283 | | 16 | |
| % fetal fraction >100 RFU for minor allele → 12 | | | | | 12 | |
| % fetal fraction including <100 RFU for minor allele → 11 | | | | | | 11 |

Example 12

Correlation of Fetal Fraction Determined by Analysis of Fetal and Maternal SNPs and STRs To verify that the calculated fetal fraction i.e. fraction of minor nucleic acid component, determined using the SNP and STR assay as described in the preceding Examples provided an accurate measurement of the fetal fraction, the percent fetal fraction of cfDNA in the plasma from the same pregnant subjects was compared.

Peripheral blood samples were obtained from 48 volunteer subjects, 24 of the subjects were pregnant with male fetuses, and 24 were pregnant with female fetuses. cfDNA was prepared as described in Example 1, Fetal fraction using SNPs was determined by massively parallel sequencing by synthesis as described in Example 5, and fetal fraction using STRs was determined using capillary electrophoresis as described in Example 10

Figure 6:
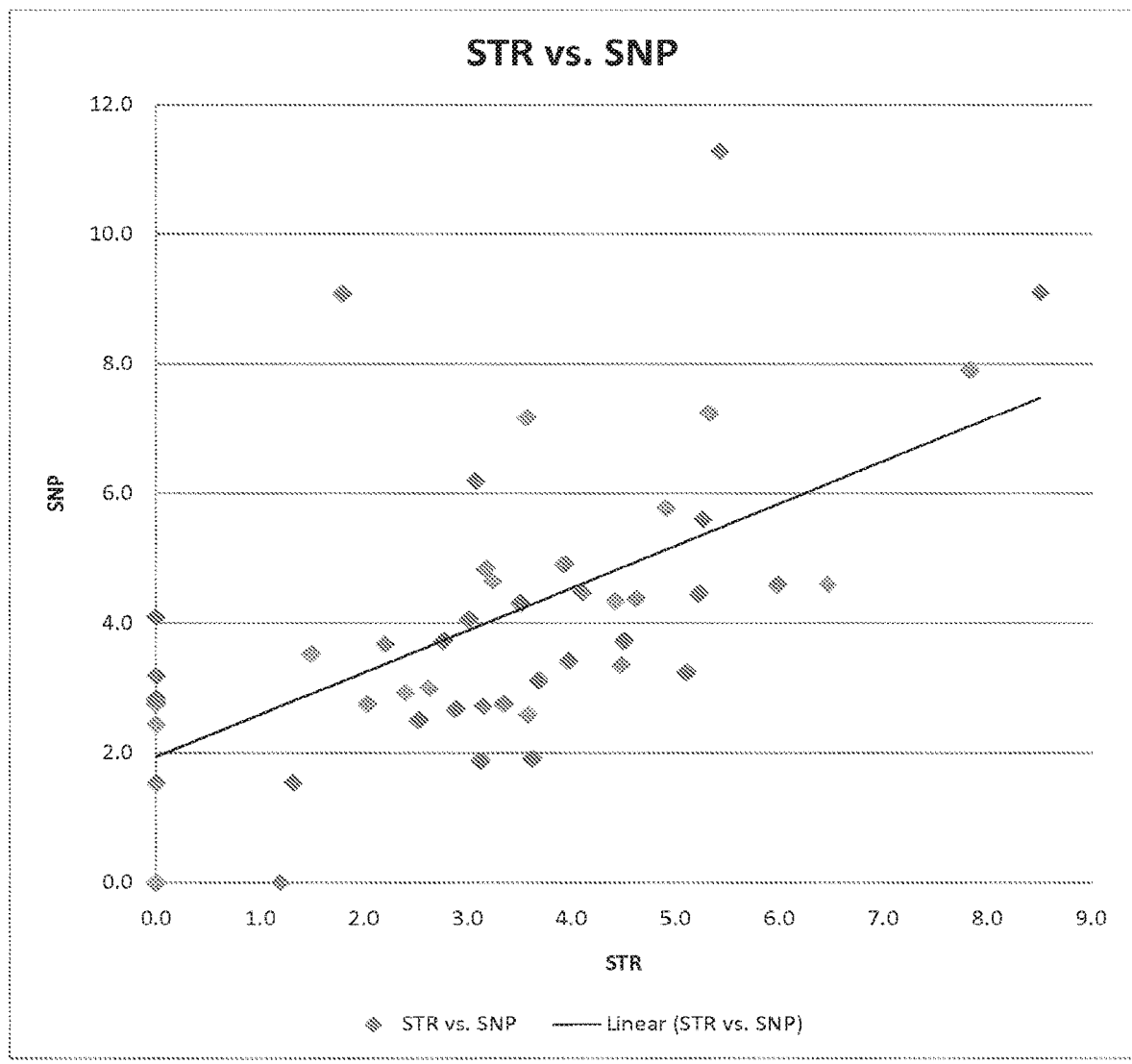
FIG. 6 illustrates the correlation of fetal fraction determined by massively parallel sequencing size separation of polymorphic sequences comprising SNPs and STRs.

The results shown in FIG. 6 indicate that a positive correlation exists between the fraction determined using the STR assay and the fraction determined using the SNP sequencing. These data further validate the use of polymorphic sequences comprising STRs or SNPs for determining the fraction of fetal cfDNA in a plasma sample.

Example 13

Use of Fetal Fraction to Set Thresholds and Estimate Minimum Sample Size in Aneuploidy Detection Counts of sequence matches to different chromosomes are manipulated to generate a score which will vary with chromosomal copy number that can be interpreted to identify chromosomal amplification or deletion. For example, such a score could be generated by comparing the relative amount of a sequence tags on a chromosome undergoing copy number changes to a chromosome known to be a euploid. Examples of scores that can be used to identify amplification or deletion include but are not limited to: counts for the chromosome of interest divided by counts of another chromosome from the same experimental run, the counts for the chromosome of interest divided by the total number of counts from the experimental run, comparison of counts from the sample of interest versus a separate control sample. Without loss of generality, it can be assumed that scores will increase as copy number increases. Knowledge of fetal fraction can be used to set "cutoff" thresholds to call "aneuploidy", "normal", or "marginal" (uncertain) states. Then, calculations are performed to estimate the minimum number of sequences required to achieve adequate sensitivity (i.e. probability of correctly identifying an aneuploidy state).

Figure 7:
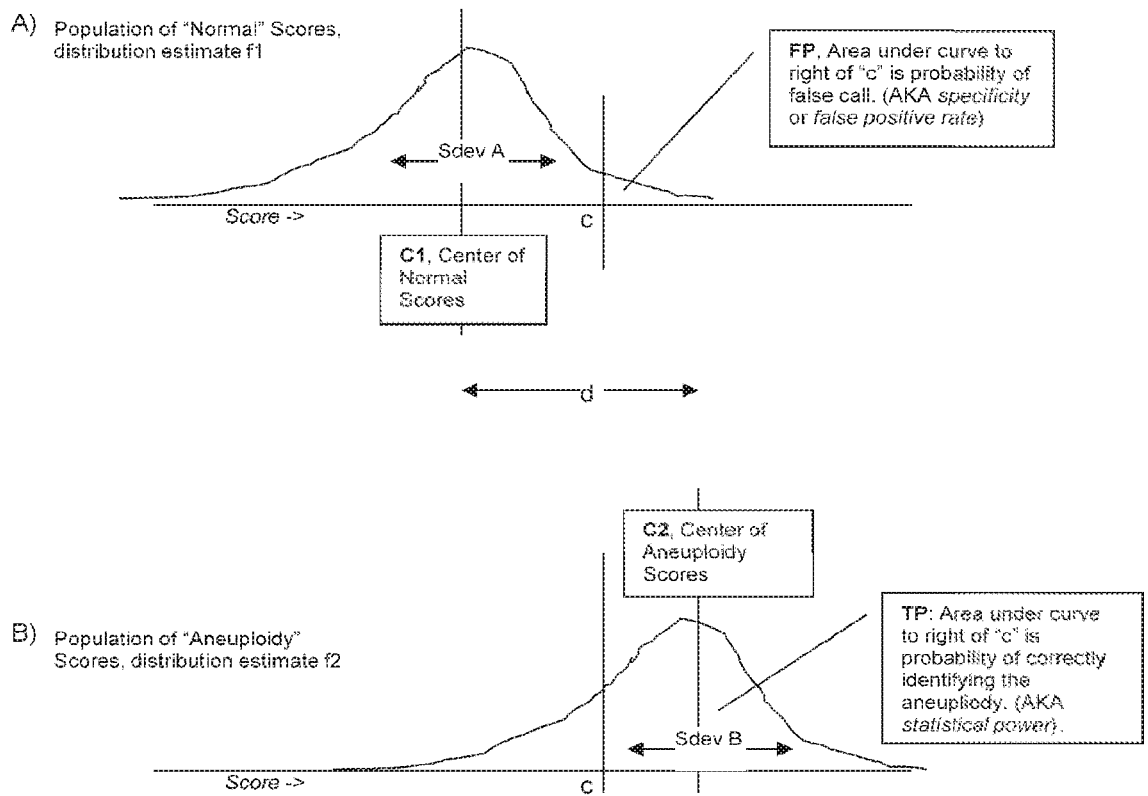
FIG. 7 illustrates an embodiment of use of fetal fraction for determining cutoff thresholds for aneuploidy detection.

FIG. 7 is a plot of two different populations of scores. The x-axis is score and the y-axis is frequency. Scores on samples of chromosomes without aneuploidy can have a distribution shown in FIG. 7A. FIG. 7B illustrates a hypothetical distribution of a population of scores on samples with an amplified chromosome. Without loss of generality, the graphs and equations show the case of a univariate score where the aneuploidy condition represents an amplification of copy number. Multivariate cases and/or reduction/deletion abnormalities are simple extensions or rearrangements of the given descriptions and are intend to fall within the scope of this art.

The amount of "overlap" between the populations can determine how well normal and aneuploidy cases can be discriminated. In general, increasing fetal fraction, ff, increases discrimination power by separating the two population centers (by moving "C2," the "Center of Aneuploidy Scores", and increasing "d," causing the populations to overlap less. Furthermore, an increase in the absolute value of the magnitude, m, (for example having four copies of the chromosome instead of a trisomy) of the amplification will also increase separation of population centers leading to higher power (i.e. higher probability of correctly identifying aneuploidy states).

Increasing the number of sequences generated, N, reduces standard deviations "sdevA" and/or "sdevB," the spread of the two populations of scores, which also causes the populations to overlap less.

Setting Thresholds and Estimating Sample Size

The following procedure can be used to set "c", the critical value for calling "aneuploidy", "normal", or "marginal" (uncertain) states. Without loss of generality, one sided statistical tests are used below.

First, an acceptable false positive rate, FP (sometimes also called "type I error" or "specificity"), is decided, which is the probability of a false positive or falsely calling aneuploidy. For example, FP can be at least, or about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, or 0.1.

Second, the value of "c" can be determined by solving the equation: FP=integral from c to infinity of (f1(x)dx).

$$FP = \int_c^\infty f1(x)dx \quad \text{(Equation 1)}$$

Once a critical value, c, has been determined, the minimum number sequences required to achieve a certain TP=True positive rate can be estimated. The true positive rate can be, for example, about 0.5, 0.6, 0.7, 0.8, or 0.9. In one embodiment, the true positive rate can be 0.8. In other words, N is the minimum number of sequences required to identify aneuploidy 100*TP percent of the time. N=minimum number such that TP=integral from c to infinity of f2(x,ff)dx>0.8. N is determined by solving $$\min_N \text{ s.t. } \left\{ TB \geq \int_c^\infty f2(x, N)dx \right\} \quad \text{(Equation 2)}$$

In classical statistical tests f1 and f2 are often F, non-central F distributions (a special case oft and non-central t distributions) although that is not a necessary condition for this application.

Setting "Levels" of Thresholds to Give More Control of Errors

Thresholds can also be set in stages using the above methods. For example, a threshold can be set for high confidence calling of "aneuploidy", say ca, using FP 0.001 and a "marginal" threshold, say cb, using FP 0.05. In this case if Score, S:

| | |
|---|---|
| (S > ca) | then call "Trisomy" |
| (cb > S <= ca) | then call "Marginal" |
| (S < cb) | then call "Normal" |

Some Trivial Generalizations Falling within Scope of this Art

Different values for thresholds such as TP, FP, etc can be used. Procedures can be run in any order. For example, one can start with N and solve for c, etc. Distributions can depend on ff so that f1(x,N,ff), f2(x,N,ff), and/or other variables. The above integral equations can be solved by reference to tables or by iterative computer methods. A non-centrality parameter can be estimated and power can be read from standard statistical tables. Statistical power and sample sizes may be derived from calculation or estimation of expected mean squares. Closed form theoretical distributions such as f, t, non-central t, normal, etc. or estimates (kernel or other) can be used to model the distributions f1, f2. Empirical threshold setting and parameter selection using Receiver Operator Characteristic Curves (ROC) can be used and collated with fetal fraction. Various estimates of distribution spread (variance, mean absolute deviation, inter quartile range, etc.) may be used. Various estimates of distribution center (mean, median, etc.) can be used. Two sided as opposed to one sided statistical tests can be used. The simple hypothesis test can be reformulated as linear or non-linear regression. Combinatorial methods, simulation (e.g., monte carlo), maximization (e.g., expectation maximization), iterative, or other methods can be used independently or in conjunction with the above to establish statistical power or thresholds.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for determining the fraction of fetal cell-free DNA (cfDNA) in a maternal sample comprising a mixture of fetal and maternal cfDNA, said method comprising:
(a) isolating said mixture of cfDNA from said sample;
(b) amplifying a plurality of predetermined polymorphic target nucleic acids in said mixture, wherein each of said predetermined polymorphic target nucleic acids comprises at least one single nucleotide polymorphism (SNP);
(c) preparing a sequencing library using at least a portion of the amplified product obtained in step (b);
(d) performing massively parallel sequencing of at least a portion of said library obtained in step (c) to provide sequence information for a plurality of sequence tags;
(e) using said sequence information to provide a number of sequence tags aligning to a reference sequence, wherein said reference sequence comprises allelic sequences for said at least one SNP in each of said plurality of predetermined target nucleic acids;
(f) counting the number of sequence tags aligned to said allelic sequences;
(g) identifying a plurality of informative SNPs from the number of sequence tags obtained in step (f), wherein said informative SNPs are identified by the difference in allelic sequences and the number of sequence tags aligned to each of the possible allelelic sequences for each SNP; and
(h) for each of said informative SNPs, calculating said fraction of fetal cfDNA from the number of sequence tags aligned to said possible allelic sequences for said informative SNPs.

2. The method of claim 1, wherein amplifying said plurality of predetermined polymorphic target nucleic acids in step (b) comprises performing PCR.

3. The method of claim 1, wherein said massively parallel sequencing is sequencing-by-synthesis with reversible dye terminators.

4. The method of claim 1, wherein said massively parallel sequencing is sequencing-by-ligation.

5. The method of claim 1, wherein said sequencing is single molecule sequencing.

6. The method of claim 1, wherein said sequencing comprises an amplification.

7. The method of claim 1, wherein said maternal sample is selected from blood, plasma, serum, urine and saliva.

8. The method of claim 1, wherein said method is a fetal gender-independent method.

9. The method of claim 1, wherein said plurality of polymorphic nucleic acids are located on a plurality of different chromosomes.

10. The method of claim 1, wherein said plurality of polymorphic sites are located on a chromosome other than chromosome 13, 18, 21, X or Y.

11. The method of claim 10, wherein said plurality of different chromosomes are selected from chromosomes 1-22.

12. The method of claim 1, wherein said plurality of polymorphic nucleic acids comprises at least 3 informative polymorphic sites.

13. The method of claim 1, wherein said plurality of polymorphic nucleic acids comprises at least 10 informative polymorphic sites.

14. The method of claim 1, wherein said at least one SNP is a single SNP selected from rs560681, rs1109037, rs9866013, rs13182883, rs13218440, rs7041158, rs740598, rs10773760, rs4530059, rs7205345, rs8078417, rs576261, rs2567608, rs430046, rs9951171, rs338882, rs10776839, rs9905977, rs1277284, rs258684, rs1347696, rs508485, rs9788670, rs8137254, rs3143, rs2182957, rs3739005, and rs530022.

15. The method of claim 1, further comprising using the calculated fraction of fetal cfDNA obtained in step (h) to set thresholds for calling an aneuploidy, a normal or a no call state.

16. The method of claim 1, further comprising using the calculated fraction of fetal cfDNA obtained in step (h) to estimate the probability of correctly identifying an aneuploidy.

* * * * *

UNITED STATES PATENT AND TRADEMARK OFFICE
CERTIFICATE OF CORRECTION

PATENT NO. : 12,139,760 B2  
APPLICATION NO. : 16/840103  
DATED : November 12, 2024  
INVENTOR(S) : Richard P. Rava et al.

Page 1 of 1

It is certified that error appears in the above-identified patent and that said Letters Patent is hereby corrected as shown below:

In the Claims

In Column 337, Line 36 (Claim 1), delete "allelelic" and insert -- allelic -- therefor.

Signed and Sealed this  
Fifteenth Day of April, 2025

Coke Morgan Stewart  
*Acting Director of the United States Patent and Trademark Office*